US009249233B2

(12) United States Patent
Champion et al.

(10) Patent No.: US 9,249,233 B2
(45) Date of Patent: Feb. 2, 2016

(54) IGE CH3 PEPTIDE VACCINE

(71) Applicant: Pfizer Vaccines LLC, New York, NY (US)

(72) Inventors: Brian Robert Champion, Kent (GB); David Robert Stead, Del Mar, CA (US); Paul Andrew Wright, San Diego, CA (US)

(73) Assignee: Pfizer Vaccines LLC, New York, NY (US)

( * ) Notice: Subject to any disclaimer, the term of this patent is extended or adjusted under 35 U.S.C. 154(b) by 126 days.

(21) Appl. No.: 14/225,258

(22) Filed: Mar. 25, 2014

(65) Prior Publication Data

US 2015/0118256 A1 Apr. 30, 2015

Related U.S. Application Data

(62) Division of application No. 13/152,032, filed on Jun. 2, 2011, now Pat. No. 8,722,053.

(60) Provisional application No. 61/352,127, filed on Jun. 7, 2010.

(51) Int. Cl.
| | |
|---|---|
| *A61K 39/395* | (2006.01) |
| *C07K 17/06* | (2006.01) |
| *A61K 39/00* | (2006.01) |
| *C07K 16/42* | (2006.01) |
| *A61K 39/44* | (2006.01) |
| *A61K 47/48* | (2006.01) |
| *A61K 38/10* | (2006.01) |
| *A61K 39/385* | (2006.01) |
| *C07K 4/12* | (2006.01) |
| *C07K 7/08* | (2006.01) |

(52) U.S. Cl.
CPC ............ *C07K 17/06* (2013.01); *A61K 39/0005* (2013.01); *A61K 39/44* (2013.01); *A61K 47/48023* (2013.01); *C07K 16/4291* (2013.01); *A61K 38/10* (2013.01); *A61K 39/385* (2013.01); A61K 2039/55505 (2013.01); A61K 2039/55561 (2013.01); A61K 2039/55566 (2013.01); A61K 2039/6037 (2013.01); A61K 2039/6075 (2013.01); A61K 2039/6081 (2013.01); A61K 2039/70 (2013.01); A61K 2300/00 (2013.01); *C07K 4/12* (2013.01); *C07K 7/08* (2013.01); C07K 2316/52 (2013.01); C07K 2317/52 (2013.01); C07K 2317/526 (2013.01); C07K 2317/528 (2013.01); C07K 2319/55 (2013.01); Y10S 424/805 (2013.01); Y10S 424/81 (2013.01); Y10S 530/806 (2013.01); Y10S 530/862 (2013.01); Y10S 530/866 (2013.01); Y10S 530/868 (2013.01)

(58) Field of Classification Search
None
See application file for complete search history.

(56) References Cited

U.S. PATENT DOCUMENTS

| | | | |
|---|---|---|---|
| 4,469,863 A | 9/1984 | Ts'o et al. | |
| 4,722,840 A | 2/1988 | Valenzuela et al. | |
| 5,023,243 A | 6/1991 | Tullis | |
| 5,071,651 A | 12/1991 | Sabara et al. | |
| 5,374,426 A | 12/1994 | Sabara et al. | |
| 5,614,382 A | 3/1997 | Metcalf | |
| 5,653,980 A * | 8/1997 | Hellman ............ | C07K 16/4291 424/184.1 |
| 5,658,738 A | 8/1997 | Nadeau et al. | |
| 5,668,265 A | 9/1997 | Nadeau et al. | |
| 5,792,463 A | 8/1998 | Valenzuela et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,231,864 B1 | 5/2001 | Birkett | |
| 6,239,116 B1 | 5/2001 | Krieg et al. | |
| 6,339,068 B1 | 1/2002 | Krieg et al. | |
| 6,610,297 B1 * | 8/2003 | Kricek ................ | C07K 16/00 424/131.1 |
| 6,949,520 B1 | 9/2005 | Hartmann et al. | |
| 8,475,801 B2 * | 7/2013 | Brown ................ | A61K 39/00 424/185.1 |
| 8,722,053 B2 * | 5/2014 | Champion ......... | A61K 39/0005 424/185.1 |
| 2002/0064525 A1 | 5/2002 | Morsey et al. | |
| 2004/0146504 A1 | 7/2004 | Morsey et al. | |
| 2004/0176283 A1 | 9/2004 | Robinson et al. | |
| 2005/0250934 A1 | 11/2005 | Wang et al. | |
| 2006/0062782 A1 | 3/2006 | Morsey et al. | |

FOREIGN PATENT DOCUMENTS

| | | |
|---|---|---|
| EP | 0 263 655 | 4/1988 |
| EP | 0 421 635 | 9/1990 |
| EP | 0 761 231 | 6/1993 |
| EP | 0 735 898 | 3/1999 |

(Continued)

OTHER PUBLICATIONS

Sasnauskas K. et al. "Generation of Recombinant Virus-Like Particles of Human and Non-Human Polyomaviruses in Yeast *Saccharomyces cerevisiae*" Intervirology 2002 vol. 45 308-317.

(Continued)

*Primary Examiner* — Michael Szperka

(74) *Attorney, Agent, or Firm* — Austin W. Zhang

(57) ABSTRACT

The present invention relates to the provision of novel immunogens comprising an antigenic IgE peptide preferably linked to an immunogenic carrier, compositions comprising the immunogens, and methods for the prevention, treatment or alleviation of IgE-mediated disorders. The invention further relates to methods for production of these medicaments, immunogenic compositions and pharmaceutical compositing thereof and their use in medicine.

17 Claims, 12 Drawing Sheets

(56) References Cited

FOREIGN PATENT DOCUMENTS

| | | | |
|---|---|---|---|
| EP | 1195161 A2 * | 4/2002 | ......... A61K 39/0008 |
| EP | 0 689 454 | 2/2005 | |
| EP | 1 736 538 | 6/2005 | |
| GB | 2 220 221 | 4/1990 | |
| WO | WO 90/03184 | 4/1990 | |
| WO | WO 90/14837 | 12/1990 | |
| WO | WO 91/18926 | 12/1991 | |
| WO | WO 92/11291 | 7/1992 | |
| WO | WO 93/05810 | 4/1993 | |
| WO | WO 94/21292 | 9/1994 | |
| WO | WO 95/01363 | 1/1995 | |
| WO | WO 96/02555 | 2/1996 | |
| WO | WO 96/11711 | 4/1996 | |
| WO | WO 9612740 A1 * | 5/1996 | ......... A61K 39/0008 |
| WO | WO 96/30523 | 10/1996 | |
| WO | WO 97/01640 | 1/1997 | |
| WO | WO 97/31948 | 9/1997 | |
| WO | WO 98/07705 | 2/1998 | |
| WO | WO 98/15631 | 4/1998 | |
| WO | WO 98/16247 | 4/1998 | |
| WO | WO 98/18810 | 5/1998 | |
| WO | WO 98/36772 | 8/1998 | |
| WO | WO 98/37919 | 9/1998 | |
| WO | WO 98/40100 | 9/1998 | |
| WO | WO 98/52581 | 11/1998 | |
| WO | WO 98/55495 | 12/1998 | |
| WO | WO 98/57659 | 12/1998 | |
| WO | WO 99/10375 | 3/1999 | |
| WO | WO 99/11241 | 3/1999 | |
| WO | WO 99/44636 | 9/1999 | |
| WO | WO 99/52549 | 10/1999 | |
| WO | WO 99/67293 | 12/1999 | |
| WO | WO 00/07621 | 2/2000 | |
| WO | WO 00/23105 | 4/2000 | |
| WO | WO 00/23955 | 4/2000 | |
| WO | WO 00/25722 | 5/2000 | |
| WO | WO 00/26385 | 5/2000 | |
| WO | WO 00/32227 | 6/2000 | |
| WO | WO 00/41720 | 7/2000 | |
| WO | WO 00/48630 | 8/2000 | |
| WO | WO 00/50461 | 8/2000 | |
| WO | WO 00/56358 | 9/2000 | |
| WO | WO 00/62800 | 10/2000 | |
| WO | WO 01/21152 | 3/2001 | |
| WO | WO 01/21207 | 3/2001 | |
| WO | WO 01/22990 | 4/2001 | |
| WO | WO 01/77158 | 10/2001 | |
| WO | WO 01/85208 | 11/2001 | |
| WO | WO 01/98333 | 12/2001 | |
| WO | WO 02/10416 | 2/2002 | |
| WO | WO 02/14478 | 2/2002 | |
| WO | WO 02/34288 | 5/2002 | |
| WO | WO 02/056905 | 7/2002 | |
| WO | WO 03/024480 | 3/2003 | |
| WO | WO 03/024481 | 3/2003 | |
| WO | WO 03/092714 | 11/2003 | |
| WO | WO 03/102165 | 12/2003 | |
| WO | WO 2004/007538 | 1/2004 | |
| WO | WO 2004/053091 | 6/2004 | |
| WO | WO 2004/058799 | 7/2004 | |
| WO | WO 2005/075504 | 8/2005 | |
| WO | WO 2006/134423 | 12/2006 | |
| WO | WO 2007/026190 | 3/2007 | |
| WO | WO 2007/095316 | 8/2007 | |
| WO | WO2007113224 | 10/2007 | |
| WO | WO 2007113224 A2 * | 10/2007 | .......... A61K 39/085 |
| WO | WO 2008/020331 | 2/2008 | |
| WO | WO 2008/123999 | 10/2008 | |
| WO | WO 2010/067286 | 6/2010 | |

OTHER PUBLICATIONS

Sasnauskas K. et al. "Yeast Cells Allow High-level Expression and Formation of Polyomavirus-Like Particles" Biological Chemistry 1999 vol. 380 381-386.

Schafmeister C. et al. "An All-Hydrocarbon Cross-Linking System for Enhancing the Helicity and Metabolic Stability of Peptides" Journal of the American Chemical Society 2000 vol. 122 5891-5892.

Seliger H. et al. "Oligonucleotide Analogues With Terminal 3'-3'- and 5'-5'-internucleotidic Linkages As Antisense Inhibitors of Viral Gene Expression" Nucleosides & Nucleotides 1991 vol. 10 Nos. 1-3 469-477.

Sjölander A. et al. "ISCOMs: An Adjuvant with Multiple Functions" Journal of Leukocyte Biology 1998 vol. 64 713-723.

Smiley B. et al. "Enhanced Read through of Opal (UGA) Stop Codons and Production of Mycoplasma pneumoniae P1 Epitopes in *Escherichia coli*" Gene 1993 vol. 134 33-40.

Speigelberg, H. et al., "Primary and Secondary Immune Response to Human IgE by Rabbits Immunized with Synthetic Ige Peptides" 1987, vol. 3988, No. 1, 251-261.

Späth J. et al. "Stabilization of a β-Hairpin Conformation in a Cyclic Peptide Using the Templating Effect of a Heterochiral Diproline Unit" Helvetica Chimica Acta 1998 vol. 81 1726-1738.

Stacey K. et al. "Macrophages Ingest and Are Activated by Bacterial DNA" The Journal of Immunology 1996 vol. 157 2116-2122.

Stirchak E. et al. "Uncharged Stereoregular Nucleic Acid Analogs: 2. Morpholino Nucleoside Oligomers With Carbomate Internucleoside Linkages" Nucleic Acids Research 1989 vol. 17 No. 15 6129-6141.

Tarköy M. et al. "Nucleic-acid Analogues With Constraint Conformational Flexibility in the Sugar-phosphate Backbone ('Bicyclo-DNA')" Helvetica Chimica Acta 1993 vol. 76 481-510.

Timmerman P. et al. "Rapid and Quantitative Cyclization of Multiple Peptide Loops Onto Synthetic Scaffolds for Structural Mimicry of Protein Surfaces" ChemBioChem 2005 vol. 6 821-824.

Twomey T. et al. "Structure and Immunogenicity of Experimental Foot-and-mouth Disease and Poliomyelitis Vaccines" Vaccine 1995 vol. 13 No. 16 1603-1610.

Uchida T. et al. "Mutation in the Structural Gene for Diptheria Toxin carried by Temperate Phageβ" Nature New Biology 1971 vol. 233 8-11.

Uchida T. "Diphtheria Toxin and Related Proteins" The Journal of Biological Chemistry 1973 vol. 248 No. 11 3838-3844.

Uhlmann E. et al. "Antisense Oligonucleotides: A New Therapeutic Principle" Chemical Reviews 1990 vol. 90 No. 4 543-584.

Ulrich R. et al. "Core Particles of Hepatitis B Virus As Carrier for Foreign Epitopes" Advances in Virus Research 1998. vol. 50 141-182.

Vandendriessche F. et al. "Acyclic Oligonucleotides: Possibilities and Limitations" Tetrahedron 1993 vol. 49 No. 33 7223-7238.

Wagner R. et al. "Potent and Selective Inhibition of Gene Expression by an Antisense Heptanucleotide" Nature Biotechnology 1996 vol. 14 840-844.

Warnes A. et al. "Expression of the Measles Virus Nucleoprotein Gene in *Escherichia coli* and Assembly of Nucleocapsid-like Structures" Gene 1995 vol. 160 173-178.

Wang C., et al., Synthetic IgE peptide vaccine for immunotherapy of allergy, Vaccine, Elsevier Ltd, 2003, vol. 21, No. 15, pp. 1580-1590.

Weiner G. et al. "Immunostimulatory Oligodeoxynucleotides Containing the CpG Motif Are Effective As Immune Adjuvants in Tumor Antigen Immunization" Proceedings of the National Academy of Science USA 1997 vol. 94 10833-10837.

Wurzburg B. et al. "Structure of the Human IgE-Fc Cε3-Cε4 Reveals Conformational Flexibility in the Antibody Effector Domains" Immunity 2000 vol. 13, pp. 375-385.

Yamamoto S. et al. "In Vitro Augmentation of Natural Killer Cell Activity and Production of Interferon-α/β and -γ With Deoxyribonucleic Acid Fraction From *Mycobacterium bovis* BCG" Japanese Journal of Cancer Research 1988 vol. 79 866-873.

Yamamoto S. et al. "Unique Palindromic Sequences in Synthetic Oligonucleotides Are Required to Induce IFN and Augment IFN-Mediated Natural Killer Activity" The Journal of Immunology 1992 vol. 148 No. 12 4072-4076.

Yi A. et al. "CpG DNA Rescue of Murine B Lymphoma Cells From Anti-IgM-Induced Growth Arrest and Programmed Cell Death Is Associated With Increased Expression of c-myc and bcl-xL" The Journal of Immunology 1996 vol. 157 4918-4925.

(56) References Cited

OTHER PUBLICATIONS

Yi A. et al. "CpG Motifs in Bacterial DNA Activate Leukocytes Through the pH-Dependent Generation of Reactive Oxygen Species" The Journal of Immunology 1998 vol. 160 4755-4761.

Yi A. et al. "CpG Oligodeoxyribonucleotides Rescue Mature Spleen B Cells From Spontaneous Apoptosis and Promote Cell Cycle Entry" The Journal of Immunology 1998 vol. 160 5898-5906.

Yi A. et al. "Rapid Immune Activation by CpG Motifs in Bacterial DNA. Systemic Induction of IL-6 Transcription Through an Antioxidant-Sensitive Pathway" The Journal of Immunology 1996 vol. 157 5394-5402.

Yuan T. et al. "Subtype-Independent Immature Secretion and Subtype-Dependent Replication Deficiency of a Highly Frequent Naturally Occurring Mutation of Human Hepatitis B Virus Core Antigen" Journal of Virology 1999 vol. 73 No. 12 10122-10128.

Zhang W. et al. "Novel Cyclic Analogs of Angiotensin II With Cyclization Between Positions 5 and 7: Conformational and Biological Implications" Journal of Medicinal Chemistry 1996 vol. 39 2738-2744.

Hartmann G. et al. "Delineation of a CpG Phosphorothioate Oligodeoxynucleotide for Activating Primate Immune Responses In Vitro and In Vivo" The Journal of Immunology 2000 vol. 164 1617-1624.

Van Der Heijden et al. "Manipulation of intestinal immune responses against ovalbumin by cholera toxin and its B subunit in mice" Immunology 1991 72 89-93.

Altschul S. et al. "Basic Local Alignment Search Tool" Journal of Molecular Biology 1990 vol. 215 403-410.

Altschul S. et al. "Gapped Blast and Psi-Blast: a new generation of protein database search programs" Nucleic Acids Research 1997 vol. 25 No. 17 3389-3402.

Andreu D. et al. "Formation of Disulfide Bonds in Synthetic Peptides and Proteins" Methods in Molecular Biology 1994 vol. 35 91-169.

Ballas Z. et al "Induction of NK Activity in Murine and Human Cells by CpG Motifs in Oligodeoxynucleotides and Bacterial DNA" The Journal of Immunology 1996 vol. 157 1840-1845.

Chen S. et al. "Protection of IgE-mediated Allergic Sensitization by Active Immunization With IgE Loops Constrained in GFP Protein Scaffold" Journal of Immunological Methods 2008 vol. 333 10-23.

Chu R. et al. "CpG Oligodeoxynucleotides Act As Adjuvants That Switch on T Helper 1 (Th1) Immunity" Journal of Experimental Medicine 1997 vol. 186 No. 10 1623-1631.

Cowdery J. et al. "Bacterial DNA Induces NK Cells to Produce IFN-γ In Vivo and Increases the Toxicity of Lipopolysaccharides" The Journal of Immunology 1996 vol. 156 4570-4575.

Coyle A. et al. "Central Role of Immunoglobulin (Ig) E in the Induction of Lung Eosinophil Infiltration and T Helper 2 Cell Cytokine Production: Inhibition by a Non-anaphylactogenic Anti-IgE Antibody" Journal of Experimental Medicine 1996 vol. 183 1303-1310.

Crooke S. et al. "Progress in Antisense Oligonucleotide Therapeutics" Annual Review of Pharmacology and Toxicology 1996 vol. 36 107-129.

Davis H. et al. "CpG DNA Is a Potent Enhancer of Specific Immunity in Mice Immunized With Recombinant Hepatitis B Surface Antigen" The Journal of Immunology 1998 vol. 160 870-876.

Froehler B. et al. "Triple-helix Formation by Oligodeoxynucleotides Containing the Carbocyclic Analogs of Thymidine and 5-Methyl-2'-deoxycytidine" Journal of the American Chemical Society 1992 vol. 114 8320-8322.

Garman S. et al. "Structure of the Fc Fragment of Human IgE Bound to Its High-affinity Receptor FcεRIα" Nature 2000 vol. 406 No. 6793 259-266.

Golmohammadi R. et al. "The Crystal Structure of Bacteriophage Qβ At 3.5 Å Resolution" Structure 1996 vol. 4 543-554.

Goodchild J. "Conjugates of Oligonucleotides and Modified Oligonucleotides: A review of their Synthesis and Properties" Bioconjugate Chemistry 1990 vol. 1 No. 3 165-187.

Halpern M. et al. "Bacterial DNA Induces Murine Interferon-γ Production by Stimulation of Interleukin-12 and Tumor Necrosis Factor-α" Cellular Immunology 1996 vol. 167 72-78.

Hartmann G. et al. "Mechanism and Function of a Newly Identified CpG DNA Motif in Human Primary B Cells" The Journal of Immunology 2000 vol. 164 944-953.

Hellman L. "Therapeutic Vaccines Against IgE-mediated Allergies" Expert Reviews Vaccines 2008 vol. 7 No. 2 193-208.

Hunziker J. et al "Nucleic Acid Analogues: Synthesis and Properties" Modern Synthesis Methods 1995 vol. 7 331-417.

Jiang X. et al. "Norwalk Virus Genome Cloning and Characterization" Science 1990 vol. 250 1580-1583.

Jiang Z. et al. "Pseudo-Cyclic Oligonucleotides: In Vitro and In Vivo Properties" Bioorganic & Medicinal Chemistry 1999 vol. 7 No. 12 2727-2735.

Jones L. et al. "Active Immunization With a Glycolipid Transition State Analogue Protects Against Endotoxic Shock" Angew. Chem. Int. Ed. 2002 vol. 41 No. 22 4241-4244.

Kanzler H. et al. "Therapeutic Targeting of Innate Immunity With Toll-like Receptor Agonists and Antagonists" Nature Medicine 2007 vol. 13 No. 5 552-559.

Kelso M. et al. "A Cyclic Metallopeptide Induces α Helicity in Short Peptide Fragments of Thermolysin" Angew. Chem. Int. Ed. 2003 vol. 42 No. 4 421-424.

Klinman D. et al. "CpG Motifs Present in Bacterial DNA Rapidly Induce Lymphocytes to Secrete Interleukin 6 Interleukin 12 and Interferon γ" Proceedings of the National Academy of Science 1996 vol. 93 2879-2883.

Klinman D. et al. "Hierarchical Recognition of CpG Motifs Expressed by Immunostimulatory Oligodeoxynucelotides" Clinical Exp. Immunology 2003 vol. 133 227-232.

Kolb H. et al. "The Growing Impact of Click Chemistry on Drug Discovery" Drug Discovery Today 2003 vol. 8 No. 24 1128-1137.

Kozlovska T. et al. "Recombinant RNA Phage Qβ Capsid Particles Synthesized and Self-assembled in *Escherichia coli*" Gene 1993 vol. 137 No. 1 133-137.

Kozlovska T. et al. "RNA Phage Qβ Coat Protein As a Carrier for Foreign Epitopes" Intervirology 1996 vol. 39 9-15.

Krieg A. "Immune Effects and Mechanisms of Action of CpG Motifs" Vaccine 2001 vol. 19 618-622.

Krieg A. et al. "CpG Motifs in Bacterial DNA Trigger Direct B-cell Activation" Nature 1995 vol. 374 546-549.

Krieg A. et al. "Enhancing Vaccines With Immune Stimulatory CpG DNA" Current Opinion in Molecular Therapeutics 2001 vol. 3 No. 1 15-24.

Krieg A. et al. "Sequence Motifs in Adenoviral DNA Block Immune Activation by Stimulatory CpG Motifs" Proceedings of the National Academy of Science 1998 vol. 95 12631-12636.

Lipford G. et al. "CpG-containing Synthetic Oligonucleotides Promote B and Cytotoxic T Cell Responses to Protein Antigen: A New Class of Vaccine Adjuvants" European Journal of Immunology 1997 vol. 27 2340-2344.

Litovchick A. et al. "Selection of Cyclic Peptide Aptamers to HCV IRES RNA Using mRNA Display" Proceedings of the National Academy of Science 2008 vol. 105 No. 40 15293-15298.

Lloyd C. et al. "Resolution of Bronchial Hyperresponsiveness and Pulmonary Inflammation Is Associated With IL-3 and Tissue Leukocyte Apoptosis" The Journal of Immunology 2001 vol. 166 2033-2040.

Matsuda S. et al. "Conjugates of a Dinuclear Zinc(II) Complex and DNA Oligomers as novel Sequence-Selective Artificial Ribonucleases" Angewandte Chemie International 1998 vol. 37 No. 23 3284-3286.

Matsui S. et al. "The Isolation and Characterization of a Norwalk Virus-specific cDNA" The Journal of Clinical Investigation 1991 vol. 87 1456-1461.

May J. et al. "Intraannular Savige-Fontana Reaction: One-step Conversion of One Class of Monocyclic Peptides Into Another Class of Bicyclic Peptides" Chemistry A European Journal 2008 vol. 14 3404-3409.

Messina J. et al. "Stimulation of In Vitro Murine Lymphocyte Proliferation by Bacterial DNA" The Journal of Immunology 1991 vol. 147 1759-1764.

Moldoveanu Z. et al. "CpG DNA a Novel Immune Enhancer for Systemic and Mucosal Immunization With Influenza Virus" Vaccine 1998 vol. 16 No. 11/12 1216-1224.

(56) References Cited

OTHER PUBLICATIONS

Neirynck S. et al. "A Universal Influenza a Vaccine Based on the Extracellular Domain of the M2 Protein" Nature Medicine 1999 vol. 5 No. 10 1157-1163.

Nicholls P. et al. "The Structure of Diphtheria Toxin as a Guide to Rational Design" Targeted Diagnosis and Therapies 1992 vol. 17 339-363.

Nielsen P. et al. "Peptide Nucleic Acid (PNA). A DNA Mimic With a Peptide Backbone" Bioconjugate Chemistry 1994 vol. 5 3-7.

Ott G. et al. "MF59 Design and Evaluation of a Safe and Potent Adjuvant for Human Vaccines" Vaccine Design: The Subunit and Adjuvant Approach 1995 Chapter 10 277-296.

Peng Z., et al., "Novel IgE peptide-based vaccine prevents the increase of IgE and down-regulates elevated IgE in rodents", Clinical & Experimental Allergy, 2007, vol. 27, No. 7, pp. 1040-1048.

Pfeifer M. et al. "Stabilisation of β-hairpin Conformations in a Protein Surface Mimetic Using a Bicyclic Template Derived From (2S3R4R)-diaminoproline" Chemistry Communications 1998 1977-1978.

Presta L. et al. "Humanization of an Antibody Directed Against IgE" The Journal of Immunology 1993 vol. 151 No. 5 2623-2632.

Pumpens P. et al. "HBV Core Particles As a Carrier for B Cell/T Cell Epitopes" Intervirology 2001 vol. 44 98-114.

Rodziewicz-Motowidł o S. et al. "Conformation-activity Relationships of Cyclo-constrained μ/δ Opioid Agonists Derived From the N-Terminal Tetrapeptide Segment of Dermorphin/deltorphin" Journal of Peptide Science 2008 vol. 14 898-902.

Roman M. et al. "Immunostimulatory DNA Sequences Function As T Helper-1-promoting Adjuvants" Nature Medicine 1997 vol. 3 No. 8 849-854.

\* cited by examiner

Figure 4
A. SMPH Conjugates
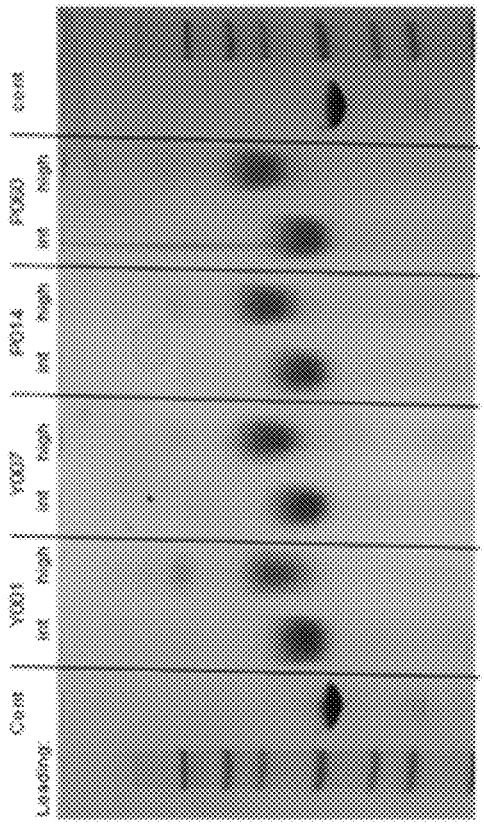
B. BAANS Conjugates
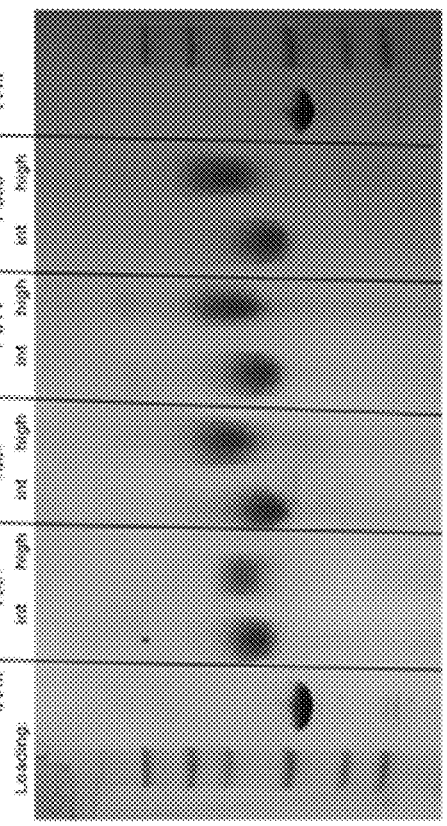

SEQUENCE LISTING

<160> NUMBER OF SEQ ID NOS: 459

<210> SEQ ID NO 1
<211> LENGTH: 20
<212> TYPE: PRT
<213> ORGANISM: Artificial
<220> FEATURE:
<223> OTHER INFORMATION: Synthetic Construct

<400> SEQUENCE: 1

Ser Thr Arg Lys Glu Glu Lys Gln Arg Asn Gly Thr Leu Thr Val Thr
1               5                   10                  15

Ser Thr Leu Pro
            20

<210> SEQ ID NO 2
<211> LENGTH: 19
<212> TYPE: PRT
<213> ORGANISM: Artificial
<220> FEATURE:
<223> OTHER INFORMATION: Synthetic Construct

<400> SEQUENCE: 2

```
Thr Arg Lys Glu Glu Lys Gln Arg Asn Gly Thr Leu Thr Val Thr Ser
1               5                   10                  15

Thr Leu Pro

<210> SEQ ID NO 3
<211> LENGTH: 18
<212> TYPE: PRT
<213> ORGANISM: Artificial
<220> FEATURE:
<223> OTHER INFORMATION: Synthetic Construct

<400> SEQUENCE: 3

Arg Lys Glu Glu Lys Gln Arg Asn Gly Thr Leu Thr Val Thr Ser Thr
1               5                   10                  15

Leu Pro

<210> SEQ ID NO 4
<211> LENGTH: 17
<212> TYPE: PRT
<213> ORGANISM: Artificial
<220> FEATURE:
<223> OTHER INFORMATION: Synthetic Construct

<400> SEQUENCE: 4

Lys Glu Glu Lys Gln Arg Asn Gly Thr Leu Thr Val Thr Ser Thr Leu
1               5                   10                  15

Pro

<210> SEQ ID NO 5
<211> LENGTH: 16
<212> TYPE: PRT
<213> ORGANISM: Artificial
<220> FEATURE:
<223> OTHER INFORMATION: Synthetic Construct

<400> SEQUENCE: 5

Glu Glu Lys Gln Arg Asn Gly Thr Leu Thr Val Thr Ser Thr Leu Pro
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic Construct

<400> SEQUENCE: 6

Glu Lys Gln Arg Asn Gly Thr Leu Thr Val Thr Ser Thr Leu Pro
1               5                   10                  15

<210> SEQ ID NO 7
<211> LENGTH: 14
<212> TYPE: PRT
<213> ORGANISM: Artificial
<220> FEATURE:
<223> OTHER INFORMATION: Synthetic Construct

<400> SEQUENCE: 7

Lys Gln Arg Asn Gly Thr Leu Thr Val Thr Ser Thr Leu Pro
1               5                   10

<210> SEQ ID NO 8
<211> LENGTH: 13
<212> TYPE: PRT
<213> ORGANISM: Artificial
```

```
<220> FEATURE:
<223> OTHER INFORMATION: Synthetic Construct

<400> SEQUENCE: 8

Gln Arg Asn Gly Thr Leu Thr Val Thr Ser Thr Leu Pro
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic Construct

<400> SEQUENCE: 9

Arg Asn Gly Thr Leu Thr Val Thr Ser Thr Leu Pro
1               5                   10

<210> SEQ ID NO 10
<211> LENGTH: 11
<212> TYPE: PRT
<213> ORGANISM: Artificial
<220> FEATURE:
<223> OTHER INFORMATION: Synthetic Construct

<400> SEQUENCE: 10

Asn Gly Thr Leu Thr Val Thr Ser Thr Leu Pro
1               5                   10

<210> SEQ ID NO 11
<211> LENGTH: 10
<212> TYPE: PRT
<213> ORGANISM: Artificial
<220> FEATURE:
<223> OTHER INFORMATION: Synthetic Construct

<400> SEQUENCE: 11

Gly Thr Leu Thr Val Thr Ser Thr Leu Pro
1               5                   10

<210> SEQ ID NO 12
<211> LENGTH: 9
<212> TYPE: PRT
<213> ORGANISM: Artificial
<220> FEATURE:
<223> OTHER INFORMATION: Synthetic Construct

<400> SEQUENCE: 12

Thr Leu Thr Val Thr Ser Thr Leu Pro
1               5

<210> SEQ ID NO 13
<211> LENGTH: 8
<212> TYPE: PRT
<213> ORGANISM: Artificial
<220> FEATURE:
<223> OTHER INFORMATION: Synthetic Construct

<400> SEQUENCE: 13

Leu Thr Val Thr Ser Thr Leu Pro
1               5

<210> SEQ ID NO 14
<211> LENGTH: 7
<212> TYPE: PRT
<213> ORGANISM: Artificial
<220> FEATURE:
```

```
<223> OTHER INFORMATION: Synthetic Construct

<400> SEQUENCE: 14

Thr Val Thr Ser Thr Leu Pro
1               5

<210> SEQ ID NO 15
<211> LENGTH: 6
<212> TYPE: PRT
<213> ORGANISM: Artificial
<220> FEATURE:
<223> OTHER INFORMATION: Synthetic Construct

<400> SEQUENCE: 15

Val Thr Ser Thr Leu Pro
1               5

<210> SEQ ID NO 16
<211> LENGTH: 5
<212> TYPE: PRT
<213> ORGANISM: Artificial
<220> FEATURE:
<223> OTHER INFORMATION: Synthetic Construct

<400> SEQUENCE: 16

Thr Ser Thr Leu Pro
1               5

<210> SEQ ID NO 17
<211> LENGTH: 4
<212> TYPE: PRT
<213> ORGANISM: Artificial
<220> FEATURE:
<223> OTHER INFORMATION: Synthetic Construct

<400> SEQUENCE: 17

Ser Thr Leu Pro
1

<210> SEQ ID NO 18
<211> LENGTH: 19
<212> TYPE: PRT
<213> ORGANISM: Artificial
<220> FEATURE:
<223> OTHER INFORMATION: Synthetic Construct

<400> SEQUENCE: 18

Ser Thr Arg Lys Glu Glu Lys Gln Arg Asn Gly Thr Leu Thr Val Thr
1               5                   10                  15

Ser Thr Leu

<210> SEQ ID NO 19
<211> LENGTH: 18
<212> TYPE: PRT
<213> ORGANISM: Artificial
<220> FEATURE:
<223> OTHER INFORMATION: Synthetic Construct

<400> SEQUENCE: 19

Thr Arg Lys Glu Glu Lys Gln Arg Asn Gly Thr Leu Thr Val Thr Ser
1               5                   10                  15

Thr Leu

<210> SEQ ID NO 20
<211> LENGTH: 17
```

```
<212> TYPE: PRT
<213> ORGANISM: Artificial
<220> FEATURE:
<223> OTHER INFORMATION: Synthetic Construct

<400> SEQUENCE: 20

Arg Lys Glu Glu Lys Gln Arg Asn Gly Thr Leu Thr Val Thr Ser Thr
1               5                   10                  15
Leu

<210> SEQ ID NO 21
<211> LENGTH: 16
<212> TYPE: PRT
<213> ORGANISM: Artificial
<220> FEATURE:
<223> OTHER INFORMATION: Synthetic Construct

<400> SEQUENCE: 21

Lys Glu Glu Lys Gln Arg Asn Gly Thr Leu Thr Val Thr Ser Thr Leu
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthetic Construct

<400> SEQUENCE: 22

Glu Glu Lys Gln Arg Asn Gly Thr Leu Thr Val Thr Ser Thr Leu
1               5                   10                  15

<210> SEQ ID NO 23
<211> LENGTH: 14
<212> TYPE: PRT
<213> ORGANISM: Artificial
<220> FEATURE:
<223> OTHER INFORMATION: Synthetic Construct

<400> SEQUENCE: 23

Glu Lys Gln Arg Asn Gly Thr Leu Thr Val Thr Ser Thr Leu
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic Construct

<400> SEQUENCE: 24

Lys Gln Arg Asn Gly Thr Leu Thr Val Thr Ser Thr Leu
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic Construct

<400> SEQUENCE: 25

Gln Arg Asn Gly Thr Leu Thr Val Thr Ser Thr Leu
1               5                   10

<210> SEQ ID NO 26
```

```
<211> LENGTH: 11
<212> TYPE: PRT
<213> ORGANISM: Artificial
<220> FEATURE:
<223> OTHER INFORMATION: Synthetic Construct

<400> SEQUENCE: 26

Arg Asn Gly Thr Leu Thr Val Thr Ser Thr Leu
1               5                   10

<210> SEQ ID NO 27
<211> LENGTH: 10
<212> TYPE: PRT
<213> ORGANISM: Artificial
<220> FEATURE:
<223> OTHER INFORMATION: Synthetic Construct

<400> SEQUENCE: 27

Asn Gly Thr Leu Thr Val Thr Ser Thr Leu
1               5                   10

<210> SEQ ID NO 28
<211> LENGTH: 9
<212> TYPE: PRT
<213> ORGANISM: Artificial
<220> FEATURE:
<223> OTHER INFORMATION: Synthetic Construct

<400> SEQUENCE: 28

Gly Thr Leu Thr Val Thr Ser Thr Leu
1               5

<210> SEQ ID NO 29
<211> LENGTH: 8
<212> TYPE: PRT
<213> ORGANISM: Artificial
<220> FEATURE:
<223> OTHER INFORMATION: Synthetic Construct

<400> SEQUENCE: 29

Thr Leu Thr Val Thr Ser Thr Leu
1               5

<210> SEQ ID NO 30
<211> LENGTH: 7
<212> TYPE: PRT
<213> ORGANISM: Artificial
<220> FEATURE:
<223> OTHER INFORMATION: Synthetic Construct

<400> SEQUENCE: 30

Leu Thr Val Thr Ser Thr Leu
1               5

<210> SEQ ID NO 31
<211> LENGTH: 6
<212> TYPE: PRT
<213> ORGANISM: Artificial
<220> FEATURE:
<223> OTHER INFORMATION: Synthetic Construct

<400> SEQUENCE: 31

Thr Val Thr Ser Thr Leu
1               5

<210> SEQ ID NO 32
<211> LENGTH: 5
```

```
<212> TYPE: PRT
<213> ORGANISM: Artificial
<220> FEATURE:
<223> OTHER INFORMATION: Synthetic Construct

<400> SEQUENCE: 32

Val Thr Ser Thr Leu
1               5

<210> SEQ ID NO 33
<211> LENGTH: 4
<212> TYPE: PRT
<213> ORGANISM: Artificial
<220> FEATURE:
<223> OTHER INFORMATION: Synthetic Construct

<400> SEQUENCE: 33

Thr Ser Thr Leu
1

<210> SEQ ID NO 34
<211> LENGTH: 18
<212> TYPE: PRT
<213> ORGANISM: Artificial
<220> FEATURE:
<223> OTHER INFORMATION: Synthetic Construct

<400> SEQUENCE: 34

Ser Thr Arg Lys Glu Glu Lys Gln Arg Asn Gly Thr Leu Thr Val Thr
1               5                   10                  15

Ser Thr

<210> SEQ ID NO 35
<211> LENGTH: 17
<212> TYPE: PRT
<213> ORGANISM: Artificial
<220> FEATURE:
<223> OTHER INFORMATION: Synthetic Construct

<400> SEQUENCE: 35

Thr Arg Lys Glu Glu Lys Gln Arg Asn Gly Thr Leu Thr Val Thr Ser
1               5                   10                  15

Thr

<210> SEQ ID NO 36
<211> LENGTH: 16
<212> TYPE: PRT
<213> ORGANISM: Artificial
<220> FEATURE:
<223> OTHER INFORMATION: Synthetic Construct

<400> SEQUENCE: 36

Arg Lys Glu Glu Lys Gln Arg Asn Gly Thr Leu Thr Val Thr Ser Thr
1               5                   10                  15

<210> SEQ ID NO 37
<211> LENGTH: 15
<212> TYPE: PRT
<213> ORGANISM: Artificial
<220> FEATURE:
<223> OTHER INFORMATION: Synthetic Construct

<400> SEQUENCE: 37

Lys Glu Glu Lys Gln Arg Asn Gly Thr Leu Thr Val Thr Ser Thr
1               5                   10                  15
```

<210> SEQ ID NO 38
<211> LENGTH: 14
<212> TYPE: PRT
<213> ORGANISM: Artificial
<220> FEATURE:
<223> OTHER INFORMATION: Synthetic Construct

<400> SEQUENCE: 38

Glu Glu Lys Gln Arg Asn Gly Thr Leu Thr Val Thr Ser Thr
1               5                   10

<210> SEQ ID NO 39
<211> LENGTH: 13
<212> TYPE: PRT
<213> ORGANISM: Artificial
<220> FEATURE:
<223> OTHER INFORMATION: Synthetic Construct

<400> SEQUENCE: 39

Glu Lys Gln Arg Asn Gly Thr Leu Thr Val Thr Ser Thr
1               5                   10

<210> SEQ ID NO 40
<211> LENGTH: 12
<212> TYPE: PRT
<213> ORGANISM: Artificial
<220> FEATURE:
<223> OTHER INFORMATION: Synthetic Construct

<400> SEQUENCE: 40

Lys Gln Arg Asn Gly Thr Leu Thr Val Thr Ser Thr
1               5                   10

<210> SEQ ID NO 41
<211> LENGTH: 11
<212> TYPE: PRT
<213> ORGANISM: Artificial
<220> FEATURE:
<223> OTHER INFORMATION: Synthetic Construct

<400> SEQUENCE: 41

Gln Arg Asn Gly Thr Leu Thr Val Thr Ser Thr
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic Construct

<400> SEQUENCE: 42

Arg Asn Gly Thr Leu Thr Val Thr Ser Thr
1               5                   10

<210> SEQ ID NO 43
<211> LENGTH: 9
<212> TYPE: PRT
<213> ORGANISM: Artificial
<220> FEATURE:
<223> OTHER INFORMATION: Synthetic Construct

<400> SEQUENCE: 43

Asn Gly Thr Leu Thr Val Thr Ser Thr
1               5

```
<210> SEQ ID NO 44
<211> LENGTH: 8
<212> TYPE: PRT
<213> ORGANISM: Artificial
<220> FEATURE:
<223> OTHER INFORMATION: Synthetic Construct

<400> SEQUENCE: 44

Gly Thr Leu Thr Val Thr Ser Thr
1               5

<210> SEQ ID NO 45
<211> LENGTH: 7
<212> TYPE: PRT
<213> ORGANISM: Artificial
<220> FEATURE:
<223> OTHER INFORMATION: Synthetic Construct

<400> SEQUENCE: 45

Thr Leu Thr Val Thr Ser Thr
1               5

<210> SEQ ID NO 46
<211> LENGTH: 6
<212> TYPE: PRT
<213> ORGANISM: Artificial
<220> FEATURE:
<223> OTHER INFORMATION: Synthetic Construct

<400> SEQUENCE: 46

Leu Thr Val Thr Ser Thr
1               5

<210> SEQ ID NO 47
<211> LENGTH: 5
<212> TYPE: PRT
<213> ORGANISM: Artificial
<220> FEATURE:
<223> OTHER INFORMATION: Synthetic Construct

<400> SEQUENCE: 47

Thr Val Thr Ser Thr
1               5

<210> SEQ ID NO 48
<211> LENGTH: 4
<212> TYPE: PRT
<213> ORGANISM: Artificial
<220> FEATURE:
<223> OTHER INFORMATION: Synthetic Construct

<400> SEQUENCE: 48

Val Thr Ser Thr
1

<210> SEQ ID NO 49
<211> LENGTH: 17
<212> TYPE: PRT
<213> ORGANISM: Artificial
<220> FEATURE:
<223> OTHER INFORMATION: Synthetic Construct

<400> SEQUENCE: 49

Ser Thr Arg Lys Glu Glu Lys Gln Arg Asn Gly Thr Leu Thr Val Thr
1               5                   10                  15

Ser
```

<210> SEQ ID NO 50
<211> LENGTH: 16
<212> TYPE: PRT
<213> ORGANISM: Artificial
<220> FEATURE:
<223> OTHER INFORMATION: Synthetic Construct

<400> SEQUENCE: 50

Thr Arg Lys Glu Glu Lys Gln Arg Asn Gly Thr Leu Thr Val Thr Ser
1               5                   10                  15

<210> SEQ ID NO 51
<211> LENGTH: 15
<212> TYPE: PRT
<213> ORGANISM: Artificial
<220> FEATURE:
<223> OTHER INFORMATION: Synthetic Construct

<400> SEQUENCE: 51

Arg Lys Glu Glu Lys Gln Arg Asn Gly Thr Leu Thr Val Thr Ser
1               5                   10                  15

<210> SEQ ID NO 52
<211> LENGTH: 14
<212> TYPE: PRT
<213> ORGANISM: Artificial
<220> FEATURE:
<223> OTHER INFORMATION: Synthetic Construct

<400> SEQUENCE: 52

Lys Glu Glu Lys Gln Arg Asn Gly Thr Leu Thr Val Thr Ser
1               5                   10

<210> SEQ ID NO 53
<211> LENGTH: 13
<212> TYPE: PRT
<213> ORGANISM: Artificial
<220> FEATURE:
<223> OTHER INFORMATION: Synthetic Construct

<400> SEQUENCE: 53

Glu Glu Lys Gln Arg Asn Gly Thr Leu Thr Val Thr Ser
1               5                   10

<210> SEQ ID NO 54
<211> LENGTH: 12
<212> TYPE: PRT
<213> ORGANISM: Artificial
<220> FEATURE:
<223> OTHER INFORMATION: Synthetic Construct

<400> SEQUENCE: 54

Glu Lys Gln Arg Asn Gly Thr Leu Thr Val Thr Ser
1               5                   10

<210> SEQ ID NO 55
<211> LENGTH: 11
<212> TYPE: PRT
<213> ORGANISM: Artificial
<220> FEATURE:
<223> OTHER INFORMATION: Synthetic Construct

<400> SEQUENCE: 55

Lys Gln Arg Asn Gly Thr Leu Thr Val Thr Ser
1               5                   10

```
<210> SEQ ID NO 56
<211> LENGTH: 10
<212> TYPE: PRT
<213> ORGANISM: Artificial
<220> FEATURE:
<223> OTHER INFORMATION: Synthetic Construct

<400> SEQUENCE: 56

Gln Arg Asn Gly Thr Leu Thr Val Thr Ser
1               5                   10

<210> SEQ ID NO 57
<211> LENGTH: 9
<212> TYPE: PRT
<213> ORGANISM: Artificial
<220> FEATURE:
<223> OTHER INFORMATION: Synthetic Construct

<400> SEQUENCE: 57

Arg Asn Gly Thr Leu Thr Val Thr Ser
1               5

<210> SEQ ID NO 58
<211> LENGTH: 8
<212> TYPE: PRT
<213> ORGANISM: Artificial
<220> FEATURE:
<223> OTHER INFORMATION: Synthetic Construct

<400> SEQUENCE: 58

Asn Gly Thr Leu Thr Val Thr Ser
1               5

<210> SEQ ID NO 59
<211> LENGTH: 7
<212> TYPE: PRT
<213> ORGANISM: Artificial
<220> FEATURE:
<223> OTHER INFORMATION: Synthetic Construct

<400> SEQUENCE: 59

Gly Thr Leu Thr Val Thr Ser
1               5

<210> SEQ ID NO 60
<211> LENGTH: 6
<212> TYPE: PRT
<213> ORGANISM: Artificial
<220> FEATURE:
<223> OTHER INFORMATION: Synthetic Construct

<400> SEQUENCE: 60

Thr Leu Thr Val Thr Ser
1               5

<210> SEQ ID NO 61
<211> LENGTH: 5
<212> TYPE: PRT
<213> ORGANISM: Artificial
<220> FEATURE:
<223> OTHER INFORMATION: Synthetic Construct

<400> SEQUENCE: 61

Leu Thr Val Thr Ser
1               5

<210> SEQ ID NO 62
```

```
<211> LENGTH: 4
<212> TYPE: PRT
<213> ORGANISM: Artificial
<220> FEATURE:
<223> OTHER INFORMATION: Synthetic Construct

<400> SEQUENCE: 62

Thr Val Thr Ser
1

<210> SEQ ID NO 63
<211> LENGTH: 16
<212> TYPE: PRT
<213> ORGANISM: Artificial
<220> FEATURE:
<223> OTHER INFORMATION: Synthetic Construct

<400> SEQUENCE: 63

Ser Thr Arg Lys Glu Glu Lys Gln Arg Asn Gly Thr Leu Thr Val Thr
1               5                   10                  15

<210> SEQ ID NO 64
<211> LENGTH: 15
<212> TYPE: PRT
<213> ORGANISM: Artificial
<220> FEATURE:
<223> OTHER INFORMATION: Synthetic Construct

<400> SEQUENCE: 64

Thr Arg Lys Glu Glu Lys Gln Arg Asn Gly Thr Leu Thr Val Thr
1               5                   10                  15

<210> SEQ ID NO 65
<211> LENGTH: 14
<212> TYPE: PRT
<213> ORGANISM: Artificial
<220> FEATURE:
<223> OTHER INFORMATION: Synthetic Construct

<400> SEQUENCE: 65

Arg Lys Glu Glu Lys Gln Arg Asn Gly Thr Leu Thr Val Thr
1               5                   10

<210> SEQ ID NO 66
<211> LENGTH: 13
<212> TYPE: PRT
<213> ORGANISM: Artificial
<220> FEATURE:
<223> OTHER INFORMATION: Synthetic Construct

<400> SEQUENCE: 66

Lys Glu Glu Lys Gln Arg Asn Gly Thr Leu Thr Val Thr
1               5                   10

<210> SEQ ID NO 67
<211> LENGTH: 12
<212> TYPE: PRT
<213> ORGANISM: Artificial
<220> FEATURE:
<223> OTHER INFORMATION: Synthetic Construct

<400> SEQUENCE: 67

Glu Glu Lys Gln Arg Asn Gly Thr Leu Thr Val Thr
1               5                   10

<210> SEQ ID NO 68
<211> LENGTH: 11
```

```
<212> TYPE: PRT
<213> ORGANISM: Artificial
<220> FEATURE:
<223> OTHER INFORMATION: Synthetic Construct

<400> SEQUENCE: 68

Glu Lys Gln Arg Asn Gly Thr Leu Thr Val Thr
1               5                   10

<210> SEQ ID NO 69
<211> LENGTH: 10
<212> TYPE: PRT
<213> ORGANISM: Artificial
<220> FEATURE:
<223> OTHER INFORMATION: Synthetic Construct

<400> SEQUENCE: 69

Lys Gln Arg Asn Gly Thr Leu Thr Val Thr
1               5                   10

<210> SEQ ID NO 70
<211> LENGTH: 9
<212> TYPE: PRT
<213> ORGANISM: Artificial
<220> FEATURE:
<223> OTHER INFORMATION: Synthetic Construct

<400> SEQUENCE: 70

Gln Arg Asn Gly Thr Leu Thr Val Thr
1               5

<210> SEQ ID NO 71
<211> LENGTH: 8
<212> TYPE: PRT
<213> ORGANISM: Artificial
<220> FEATURE:
<223> OTHER INFORMATION: Synthetic Construct

<400> SEQUENCE: 71

Arg Asn Gly Thr Leu Thr Val Thr
1               5

<210> SEQ ID NO 72
<211> LENGTH: 7
<212> TYPE: PRT
<213> ORGANISM: Artificial
<220> FEATURE:
<223> OTHER INFORMATION: Synthetic Construct

<400> SEQUENCE: 72

Asn Gly Thr Leu Thr Val Thr
1               5

<210> SEQ ID NO 73
<211> LENGTH: 6
<212> TYPE: PRT
<213> ORGANISM: Artificial
<220> FEATURE:
<223> OTHER INFORMATION: Synthetic Construct

<400> SEQUENCE: 73

Gly Thr Leu Thr Val Thr
1               5

<210> SEQ ID NO 74
<211> LENGTH: 5
<212> TYPE: PRT
```

```
<213> ORGANISM: Artificial
<220> FEATURE:
<223> OTHER INFORMATION: Synthetic Construct

<400> SEQUENCE: 74

Thr Leu Thr Val Thr
1               5

<210> SEQ ID NO 75
<211> LENGTH: 4
<212> TYPE: PRT
<213> ORGANISM: Artificial
<220> FEATURE:
<223> OTHER INFORMATION: Synthetic Construct

<400> SEQUENCE: 75

Leu Thr Val Thr
1

<210> SEQ ID NO 76
<211> LENGTH: 15
<212> TYPE: PRT
<213> ORGANISM: Artificial
<220> FEATURE:
<223> OTHER INFORMATION: Synthetic Construct

<400> SEQUENCE: 76

Ser Thr Arg Lys Glu Glu Lys Gln Arg Asn Gly Thr Leu Thr Val
1               5                   10                  15

<210> SEQ ID NO 77
<211> LENGTH: 14
<212> TYPE: PRT
<213> ORGANISM: Artificial
<220> FEATURE:
<223> OTHER INFORMATION: Synthetic Construct

<400> SEQUENCE: 77

Thr Arg Lys Glu Glu Lys Gln Arg Asn Gly Thr Leu Thr Val
1               5                   10

<210> SEQ ID NO 78
<211> LENGTH: 13
<212> TYPE: PRT
<213> ORGANISM: Artificial
<220> FEATURE:
<223> OTHER INFORMATION: Synthetic Construct

<400> SEQUENCE: 78

Arg Lys Glu Glu Lys Gln Arg Asn Gly Thr Leu Thr Val
1               5                   10

<210> SEQ ID NO 79
<211> LENGTH: 12
<212> TYPE: PRT
<213> ORGANISM: Artificial
<220> FEATURE:
<223> OTHER INFORMATION: Synthetic Construct

<400> SEQUENCE: 79

Lys Glu Glu Lys Gln Arg Asn Gly Thr Leu Thr Val
1               5                   10

<210> SEQ ID NO 80
<211> LENGTH: 11
<212> TYPE: PRT
<213> ORGANISM: Artificial
```

```
<220> FEATURE:
<223> OTHER INFORMATION: Synthetic Construct

<400> SEQUENCE: 80

Glu Glu Lys Gln Arg Asn Gly Thr Leu Thr Val
1               5                   10

<210> SEQ ID NO 81
<211> LENGTH: 10
<212> TYPE: PRT
<213> ORGANISM: Artificial
<220> FEATURE:
<223> OTHER INFORMATION: Synthetic Construct

<400> SEQUENCE: 81

Glu Lys Gln Arg Asn Gly Thr Leu Thr Val
1               5                   10

<210> SEQ ID NO 82
<211> LENGTH: 9
<212> TYPE: PRT
<213> ORGANISM: Artificial
<220> FEATURE:
<223> OTHER INFORMATION: Synthetic Construct

<400> SEQUENCE: 82

Lys Gln Arg Asn Gly Thr Leu Thr Val
1               5

<210> SEQ ID NO 83
<211> LENGTH: 8
<212> TYPE: PRT
<213> ORGANISM: Artificial
<220> FEATURE:
<223> OTHER INFORMATION: Synthetic Construct

<400> SEQUENCE: 83

Gln Arg Asn Gly Thr Leu Thr Val
1               5

<210> SEQ ID NO 84
<211> LENGTH: 7
<212> TYPE: PRT
<213> ORGANISM: Artificial
<220> FEATURE:
<223> OTHER INFORMATION: Synthetic Construct

<400> SEQUENCE: 84

Arg Asn Gly Thr Leu Thr Val
1               5

<210> SEQ ID NO 85
<211> LENGTH: 6
<212> TYPE: PRT
<213> ORGANISM: Artificial
<220> FEATURE:
<223> OTHER INFORMATION: Synthetic Construct

<400> SEQUENCE: 85

Asn Gly Thr Leu Thr Val
1               5

<210> SEQ ID NO 86
<211> LENGTH: 5
<212> TYPE: PRT
<213> ORGANISM: Artificial
<220> FEATURE:
```

```
<223> OTHER INFORMATION: Synthetic Construct

<400> SEQUENCE: 86

Gly Thr Leu Thr Val
1               5

<210> SEQ ID NO 87
<211> LENGTH: 4
<212> TYPE: PRT
<213> ORGANISM: Artificial
<220> FEATURE:
<223> OTHER INFORMATION: Synthetic Construct

<400> SEQUENCE: 87

Thr Leu Thr Val
1

<210> SEQ ID NO 88
<211> LENGTH: 14
<212> TYPE: PRT
<213> ORGANISM: Artificial
<220> FEATURE:
<223> OTHER INFORMATION: Synthetic Construct

<400> SEQUENCE: 88

Ser Thr Arg Lys Glu Glu Lys Gln Arg Asn Gly Thr Leu Thr
1               5                   10

<210> SEQ ID NO 89
<211> LENGTH: 13
<212> TYPE: PRT
<213> ORGANISM: Artificial
<220> FEATURE:
<223> OTHER INFORMATION: Synthetic Construct

<400> SEQUENCE: 89

Thr Arg Lys Glu Glu Lys Gln Arg Asn Gly Thr Leu Thr
1               5                   10

<210> SEQ ID NO 90
<211> LENGTH: 12
<212> TYPE: PRT
<213> ORGANISM: Artificial
<220> FEATURE:
<223> OTHER INFORMATION: Synthetic Construct

<400> SEQUENCE: 90

Arg Lys Glu Glu Lys Gln Arg Asn Gly Thr Leu Thr
1               5                   10

<210> SEQ ID NO 91
<211> LENGTH: 11
<212> TYPE: PRT
<213> ORGANISM: Artificial
<220> FEATURE:
<223> OTHER INFORMATION: Synthetic Construct

<400> SEQUENCE: 91

Lys Glu Glu Lys Gln Arg Asn Gly Thr Leu Thr
1               5                   10

<210> SEQ ID NO 92
<211> LENGTH: 10
<212> TYPE: PRT
<213> ORGANISM: Artificial
<220> FEATURE:
<223> OTHER INFORMATION: Synthetic Construct
```

<400> SEQUENCE: 92

Glu Glu Lys Gln Arg Asn Gly Thr Leu Thr
1               5                   10

<210> SEQ ID NO 93
<211> LENGTH: 9
<212> TYPE: PRT
<213> ORGANISM: Artificial
<220> FEATURE:
<223> OTHER INFORMATION: Synthetic Construct

<400> SEQUENCE: 93

Glu Lys Gln Arg Asn Gly Thr Leu Thr
1               5

<210> SEQ ID NO 94
<211> LENGTH: 8
<212> TYPE: PRT
<213> ORGANISM: Artificial
<220> FEATURE:
<223> OTHER INFORMATION: Synthetic Construct

<400> SEQUENCE: 94

Lys Gln Arg Asn Gly Thr Leu Thr
1               5

<210> SEQ ID NO 95
<211> LENGTH: 7
<212> TYPE: PRT
<213> ORGANISM: Artificial
<220> FEATURE:
<223> OTHER INFORMATION: Synthetic Construct

<400> SEQUENCE: 95

Gln Arg Asn Gly Thr Leu Thr
1               5

<210> SEQ ID NO 96
<211> LENGTH: 6
<212> TYPE: PRT
<213> ORGANISM: Artificial
<220> FEATURE:
<223> OTHER INFORMATION: Synthetic Construct

<400> SEQUENCE: 96

Arg Asn Gly Thr Leu Thr
1               5

<210> SEQ ID NO 97
<211> LENGTH: 5
<212> TYPE: PRT
<213> ORGANISM: Artificial
<220> FEATURE:
<223> OTHER INFORMATION: Synthetic Construct

<400> SEQUENCE: 97

Asn Gly Thr Leu Thr
1               5

<210> SEQ ID NO 98
<211> LENGTH: 4
<212> TYPE: PRT
<213> ORGANISM: Artificial
<220> FEATURE:
<223> OTHER INFORMATION: Synthetic Construct

```
<400> SEQUENCE: 98

Gly Thr Leu Thr
1

<210> SEQ ID NO 99
<211> LENGTH: 13
<212> TYPE: PRT
<213> ORGANISM: Artificial
<220> FEATURE:
<223> OTHER INFORMATION: Synthetic Construct

<400> SEQUENCE: 99

Ser Thr Arg Lys Glu Glu Lys Gln Arg Asn Gly Thr Leu
1               5                   10

<210> SEQ ID NO 100
<211> LENGTH: 12
<212> TYPE: PRT
<213> ORGANISM: Artificial
<220> FEATURE:
<223> OTHER INFORMATION: Synthetic Construct

<400> SEQUENCE: 100

Thr Arg Lys Glu Glu Lys Gln Arg Asn Gly Thr Leu
1               5                   10

<210> SEQ ID NO 101
<211> LENGTH: 11
<212> TYPE: PRT
<213> ORGANISM: Artificial
<220> FEATURE:
<223> OTHER INFORMATION: Synthetic Construct

<400> SEQUENCE: 101

Arg Lys Glu Glu Lys Gln Arg Asn Gly Thr Leu
1               5                   10

<210> SEQ ID NO 102
<211> LENGTH: 10
<212> TYPE: PRT
<213> ORGANISM: Artificial
<220> FEATURE:
<223> OTHER INFORMATION: Synthetic Construct

<400> SEQUENCE: 102

Lys Glu Glu Lys Gln Arg Asn Gly Thr Leu
1               5                   10

<210> SEQ ID NO 103
<211> LENGTH: 9
<212> TYPE: PRT
<213> ORGANISM: Artificial
<220> FEATURE:
<223> OTHER INFORMATION: Synthetic Construct

<400> SEQUENCE: 103

Glu Glu Lys Gln Arg Asn Gly Thr Leu
1               5

<210> SEQ ID NO 104
<211> LENGTH: 8
<212> TYPE: PRT
<213> ORGANISM: Artificial
<220> FEATURE:
<223> OTHER INFORMATION: Synthetic Construct

<400> SEQUENCE: 104
```

```
Glu Lys Gln Arg Asn Gly Thr Leu
1               5

<210> SEQ ID NO 105
<211> LENGTH: 7
<212> TYPE: PRT
<213> ORGANISM: Artificial
<220> FEATURE:
<223> OTHER INFORMATION: Synthetic Construct

<400> SEQUENCE: 105

Lys Gln Arg Asn Gly Thr Leu
1               5

<210> SEQ ID NO 106
<211> LENGTH: 6
<212> TYPE: PRT
<213> ORGANISM: Artificial
<220> FEATURE:
<223> OTHER INFORMATION: Synthetic Construct

<400> SEQUENCE: 106

Gln Arg Asn Gly Thr Leu
1               5

<210> SEQ ID NO 107
<211> LENGTH: 5
<212> TYPE: PRT
<213> ORGANISM: Artificial
<220> FEATURE:
<223> OTHER INFORMATION: Synthetic Construct

<400> SEQUENCE: 107

Arg Asn Gly Thr Leu
1               5

<210> SEQ ID NO 108
<211> LENGTH: 4
<212> TYPE: PRT
<213> ORGANISM: Artificial
<220> FEATURE:
<223> OTHER INFORMATION: Synthetic Construct

<400> SEQUENCE: 108

Asn Gly Thr Leu
1

<210> SEQ ID NO 109
<211> LENGTH: 12
<212> TYPE: PRT
<213> ORGANISM: Artificial
<220> FEATURE:
<223> OTHER INFORMATION: Synthetic Construct

<400> SEQUENCE: 109

Ser Thr Arg Lys Glu Glu Lys Gln Arg Asn Gly Thr
1               5                   10

<210> SEQ ID NO 110
<211> LENGTH: 11
<212> TYPE: PRT
<213> ORGANISM: Artificial
<220> FEATURE:
<223> OTHER INFORMATION: Synthetic Construct

<400> SEQUENCE: 110
```

Thr Arg Lys Glu Glu Lys Gln Arg Asn Gly Thr
1               5                   10

<210> SEQ ID NO 111
<211> LENGTH: 10
<212> TYPE: PRT
<213> ORGANISM: Artificial
<220> FEATURE:
<223> OTHER INFORMATION: Synthetic Construct

<400> SEQUENCE: 111

Arg Lys Glu Glu Lys Gln Arg Asn Gly Thr
1               5                   10

<210> SEQ ID NO 112
<211> LENGTH: 9
<212> TYPE: PRT
<213> ORGANISM: Artificial
<220> FEATURE:
<223> OTHER INFORMATION: Synthetic Construct

<400> SEQUENCE: 112

Lys Glu Glu Lys Gln Arg Asn Gly Thr
1               5

<210> SEQ ID NO 113
<211> LENGTH: 8
<212> TYPE: PRT
<213> ORGANISM: Artificial
<220> FEATURE:
<223> OTHER INFORMATION: Synthetic Construct

<400> SEQUENCE: 113

Glu Glu Lys Gln Arg Asn Gly Thr
1               5

<210> SEQ ID NO 114
<211> LENGTH: 7
<212> TYPE: PRT
<213> ORGANISM: Artificial
<220> FEATURE:
<223> OTHER INFORMATION: Synthetic Construct

<400> SEQUENCE: 114

Glu Lys Gln Arg Asn Gly Thr
1               5

<210> SEQ ID NO 115
<211> LENGTH: 6
<212> TYPE: PRT
<213> ORGANISM: Artificial
<220> FEATURE:
<223> OTHER INFORMATION: Synthetic Construct

<400> SEQUENCE: 115

Lys Gln Arg Asn Gly Thr
1               5

<210> SEQ ID NO 116
<211> LENGTH: 5
<212> TYPE: PRT
<213> ORGANISM: Artificial
<220> FEATURE:
<223> OTHER INFORMATION: Synthetic Construct

<400> SEQUENCE: 116

Gln Arg Asn Gly Thr

```
1               5

<210> SEQ ID NO 117
<211> LENGTH: 4
<212> TYPE: PRT
<213> ORGANISM: Artificial
<220> FEATURE:
<223> OTHER INFORMATION: Synthetic Construct

<400> SEQUENCE: 117

Arg Asn Gly Thr
1

<210> SEQ ID NO 118
<211> LENGTH: 11
<212> TYPE: PRT
<213> ORGANISM: Artificial
<220> FEATURE:
<223> OTHER INFORMATION: Synthetic Construct

<400> SEQUENCE: 118

Ser Thr Arg Lys Glu Glu Lys Gln Arg Asn Gly
1               5                   10

<210> SEQ ID NO 119
<211> LENGTH: 10
<212> TYPE: PRT
<213> ORGANISM: Artificial
<220> FEATURE:
<223> OTHER INFORMATION: Synthetic Construct

<400> SEQUENCE: 119

Thr Arg Lys Glu Glu Lys Gln Arg Asn Gly
1               5                   10

<210> SEQ ID NO 120
<211> LENGTH: 9
<212> TYPE: PRT
<213> ORGANISM: Artificial
<220> FEATURE:
<223> OTHER INFORMATION: Synthetic Construct

<400> SEQUENCE: 120

Arg Lys Glu Glu Lys Gln Arg Asn Gly
1               5

<210> SEQ ID NO 121
<211> LENGTH: 8
<212> TYPE: PRT
<213> ORGANISM: Artificial
<220> FEATURE:
<223> OTHER INFORMATION: Synthetic Construct

<400> SEQUENCE: 121

Lys Glu Glu Lys Gln Arg Asn Gly
1               5

<210> SEQ ID NO 122
<211> LENGTH: 7
<212> TYPE: PRT
<213> ORGANISM: Artificial
<220> FEATURE:
<223> OTHER INFORMATION: Synthetic Construct

<400> SEQUENCE: 122

Glu Glu Lys Gln Arg Asn Gly
1               5
```

```
<210> SEQ ID NO 123
<211> LENGTH: 6
<212> TYPE: PRT
<213> ORGANISM: Artificial
<220> FEATURE:
<223> OTHER INFORMATION: Synthetic Construct

<400> SEQUENCE: 123

Glu Lys Gln Arg Asn Gly
1               5

<210> SEQ ID NO 124
<211> LENGTH: 5
<212> TYPE: PRT
<213> ORGANISM: Artificial
<220> FEATURE:
<223> OTHER INFORMATION: Synthetic Construct

<400> SEQUENCE: 124

Lys Gln Arg Asn Gly
1               5

<210> SEQ ID NO 125
<211> LENGTH: 4
<212> TYPE: PRT
<213> ORGANISM: Artificial
<220> FEATURE:
<223> OTHER INFORMATION: Synthetic Construct

<400> SEQUENCE: 125

Gln Arg Asn Gly
1

<210> SEQ ID NO 126
<211> LENGTH: 10
<212> TYPE: PRT
<213> ORGANISM: Artificial
<220> FEATURE:
<223> OTHER INFORMATION: Synthetic Construct

<400> SEQUENCE: 126

Ser Thr Arg Lys Glu Glu Lys Gln Arg Asn
1               5                   10

<210> SEQ ID NO 127
<211> LENGTH: 9
<212> TYPE: PRT
<213> ORGANISM: Artificial
<220> FEATURE:
<223> OTHER INFORMATION: Synthetic Construct

<400> SEQUENCE: 127

Thr Arg Lys Glu Glu Lys Gln Arg Asn
1               5

<210> SEQ ID NO 128
<211> LENGTH: 8
<212> TYPE: PRT
<213> ORGANISM: Artificial
<220> FEATURE:
<223> OTHER INFORMATION: Synthetic Construct

<400> SEQUENCE: 128

Arg Lys Glu Glu Lys Gln Arg Asn
1               5
```

<210> SEQ ID NO 129
<211> LENGTH: 7
<212> TYPE: PRT
<213> ORGANISM: Artificial
<220> FEATURE:
<223> OTHER INFORMATION: Synthetic Construct

<400> SEQUENCE: 129

Lys Glu Glu Lys Gln Arg Asn
1               5

<210> SEQ ID NO 130
<211> LENGTH: 6
<212> TYPE: PRT
<213> ORGANISM: Artificial
<220> FEATURE:
<223> OTHER INFORMATION: Synthetic Construct

<400> SEQUENCE: 130

Glu Glu Lys Gln Arg Asn
1               5

<210> SEQ ID NO 131
<211> LENGTH: 5
<212> TYPE: PRT
<213> ORGANISM: Artificial
<220> FEATURE:
<223> OTHER INFORMATION: Synthetic Construct

<400> SEQUENCE: 131

Glu Lys Gln Arg Asn
1               5

<210> SEQ ID NO 132
<211> LENGTH: 4
<212> TYPE: PRT
<213> ORGANISM: Artificial
<220> FEATURE:
<223> OTHER INFORMATION: Synthetic Construct

<400> SEQUENCE: 132

Lys Gln Arg Asn
1

<210> SEQ ID NO 133
<211> LENGTH: 9
<212> TYPE: PRT
<213> ORGANISM: Artificial
<220> FEATURE:
<223> OTHER INFORMATION: Synthetic Construct

<400> SEQUENCE: 133

Ser Thr Arg Lys Glu Glu Lys Gln Arg
1               5

<210> SEQ ID NO 134
<211> LENGTH: 8
<212> TYPE: PRT
<213> ORGANISM: Artificial
<220> FEATURE:
<223> OTHER INFORMATION: Synthetic Construct

<400> SEQUENCE: 134

Thr Arg Lys Glu Glu Lys Gln Arg
1               5

-continued

```
<210> SEQ ID NO 135
<211> LENGTH: 7
<212> TYPE: PRT
<213> ORGANISM: Artificial
<220> FEATURE:
<223> OTHER INFORMATION: Synthetic Construct

<400> SEQUENCE: 135

Arg Lys Glu Glu Lys Gln Arg
1               5

<210> SEQ ID NO 136
<211> LENGTH: 6
<212> TYPE: PRT
<213> ORGANISM: Artificial
<220> FEATURE:
<223> OTHER INFORMATION: Synthetic Construct

<400> SEQUENCE: 136

Lys Glu Glu Lys Gln Arg
1               5

<210> SEQ ID NO 137
<211> LENGTH: 5
<212> TYPE: PRT
<213> ORGANISM: Artificial
<220> FEATURE:
<223> OTHER INFORMATION: Synthetic Construct

<400> SEQUENCE: 137

Glu Glu Lys Gln Arg
1               5

<210> SEQ ID NO 138
<211> LENGTH: 4
<212> TYPE: PRT
<213> ORGANISM: Artificial
<220> FEATURE:
<223> OTHER INFORMATION: Synthetic Construct

<400> SEQUENCE: 138

Glu Lys Gln Arg
1

<210> SEQ ID NO 139
<211> LENGTH: 8
<212> TYPE: PRT
<213> ORGANISM: Artificial
<220> FEATURE:
<223> OTHER INFORMATION: Synthetic Construct

<400> SEQUENCE: 139

Ser Thr Arg Lys Glu Glu Lys Gln
1               5

<210> SEQ ID NO 140
<211> LENGTH: 7
<212> TYPE: PRT
<213> ORGANISM: Artificial
<220> FEATURE:
<223> OTHER INFORMATION: Synthetic Construct

<400> SEQUENCE: 140

Thr Arg Lys Glu Glu Lys Gln
1               5

<210> SEQ ID NO 141
```

```
<211> LENGTH: 6
<212> TYPE: PRT
<213> ORGANISM: Artificial
<220> FEATURE:
<223> OTHER INFORMATION: Synthetic Construct

<400> SEQUENCE: 141

Arg Lys Glu Glu Lys Gln
1               5

<210> SEQ ID NO 142
<211> LENGTH: 5
<212> TYPE: PRT
<213> ORGANISM: Artificial
<220> FEATURE:
<223> OTHER INFORMATION: Synthetic Construct

<400> SEQUENCE: 142

Lys Glu Glu Lys Gln
1               5

<210> SEQ ID NO 143
<211> LENGTH: 4
<212> TYPE: PRT
<213> ORGANISM: Artificial
<220> FEATURE:
<223> OTHER INFORMATION: Synthetic Construct

<400> SEQUENCE: 143

Glu Glu Lys Gln
1

<210> SEQ ID NO 144
<211> LENGTH: 7
<212> TYPE: PRT
<213> ORGANISM: Artificial
<220> FEATURE:
<223> OTHER INFORMATION: Synthetic Construct

<400> SEQUENCE: 144

Ser Thr Arg Lys Glu Glu Lys
1               5

<210> SEQ ID NO 145
<211> LENGTH: 6
<212> TYPE: PRT
<213> ORGANISM: Artificial
<220> FEATURE:
<223> OTHER INFORMATION: Synthetic Construct

<400> SEQUENCE: 145

Thr Arg Lys Glu Glu Lys
1               5

<210> SEQ ID NO 146
<211> LENGTH: 5
<212> TYPE: PRT
<213> ORGANISM: Artificial
<220> FEATURE:
<223> OTHER INFORMATION: Synthetic Construct

<400> SEQUENCE: 146

Arg Lys Glu Glu Lys
1               5

<210> SEQ ID NO 147
<211> LENGTH: 4
```

```
<212> TYPE: PRT
<213> ORGANISM: Artificial
<220> FEATURE:
<223> OTHER INFORMATION: Synthetic Construct

<400> SEQUENCE: 147

Lys Glu Glu Lys
1

<210> SEQ ID NO 148
<211> LENGTH: 6
<212> TYPE: PRT
<213> ORGANISM: Artificial
<220> FEATURE:
<223> OTHER INFORMATION: Synthetic Construct

<400> SEQUENCE: 148

Ser Thr Arg Lys Glu Glu
1               5

<210> SEQ ID NO 149
<211> LENGTH: 5
<212> TYPE: PRT
<213> ORGANISM: Artificial
<220> FEATURE:
<223> OTHER INFORMATION: Synthetic Construct

<400> SEQUENCE: 149

Thr Arg Lys Glu Glu
1               5

<210> SEQ ID NO 150
<211> LENGTH: 4
<212> TYPE: PRT
<213> ORGANISM: Artificial
<220> FEATURE:
<223> OTHER INFORMATION: Synthetic Construct

<400> SEQUENCE: 150

Arg Lys Glu Glu
1

<210> SEQ ID NO 151
<211> LENGTH: 5
<212> TYPE: PRT
<213> ORGANISM: Artificial
<220> FEATURE:
<223> OTHER INFORMATION: Synthetic Construct

<400> SEQUENCE: 151

Ser Thr Arg Lys Glu
1               5

<210> SEQ ID NO 152
<211> LENGTH: 4
<212> TYPE: PRT
<213> ORGANISM: Artificial
<220> FEATURE:
<223> OTHER INFORMATION: Synthetic Construct

<400> SEQUENCE: 152

Thr Arg Lys Glu
1

<210> SEQ ID NO 153
<211> LENGTH: 4
<212> TYPE: PRT
```

```
<213> ORGANISM: Artificial
<220> FEATURE:
<223> OTHER INFORMATION: Synthetic Construct

<400> SEQUENCE: 153

Ser Thr Arg Lys
1

<210> SEQ ID NO 154
<211> LENGTH: 14
<212> TYPE: PRT
<213> ORGANISM: Artificial
<220> FEATURE:
<223> OTHER INFORMATION: Synthetic Construct

<400> SEQUENCE: 154

Cys Leu Val Val Asp Leu Ala Pro Ser Lys Gly Thr Val Asn
1               5                   10

<210> SEQ ID NO 155
<211> LENGTH: 13
<212> TYPE: PRT
<213> ORGANISM: Artificial
<220> FEATURE:
<223> OTHER INFORMATION: Synthetic Construct

<400> SEQUENCE: 155

Cys Leu Val Val Asp Leu Ala Pro Ser Lys Gly Thr Val
1               5                   10

<210> SEQ ID NO 156
<211> LENGTH: 12
<212> TYPE: PRT
<213> ORGANISM: Artificial
<220> FEATURE:
<223> OTHER INFORMATION: Synthetic Construct

<400> SEQUENCE: 156

Cys Leu Val Val Asp Leu Ala Pro Ser Lys Gly Thr
1               5                   10

<210> SEQ ID NO 157
<211> LENGTH: 11
<212> TYPE: PRT
<213> ORGANISM: Artificial
<220> FEATURE:
<223> OTHER INFORMATION: Synthetic Construct

<400> SEQUENCE: 157

Cys Leu Val Val Asp Leu Ala Pro Ser Lys Gly
1               5                   10

<210> SEQ ID NO 158
<211> LENGTH: 10
<212> TYPE: PRT
<213> ORGANISM: Artificial
<220> FEATURE:
<223> OTHER INFORMATION: Synthetic Construct

<400> SEQUENCE: 158

Cys Leu Val Val Asp Leu Ala Pro Ser Lys
1               5                   10

<210> SEQ ID NO 159
<211> LENGTH: 9
<212> TYPE: PRT
<213> ORGANISM: Artificial
```

```
<220> FEATURE:
<223> OTHER INFORMATION: Synthetic Construct

<400> SEQUENCE: 159

Cys Leu Val Val Asp Leu Ala Pro Ser
1               5

<210> SEQ ID NO 160
<211> LENGTH: 8
<212> TYPE: PRT
<213> ORGANISM: Artificial
<220> FEATURE:
<223> OTHER INFORMATION: Synthetic Construct

<400> SEQUENCE: 160

Cys Leu Val Val Asp Leu Ala Pro
1               5

<210> SEQ ID NO 161
<211> LENGTH: 7
<212> TYPE: PRT
<213> ORGANISM: Artificial
<220> FEATURE:
<223> OTHER INFORMATION: Synthetic Construct

<400> SEQUENCE: 161

Cys Leu Val Val Asp Leu Ala
1               5

<210> SEQ ID NO 162
<211> LENGTH: 6
<212> TYPE: PRT
<213> ORGANISM: Artificial
<220> FEATURE:
<223> OTHER INFORMATION: Synthetic Construct

<400> SEQUENCE: 162

Cys Leu Val Val Asp Leu
1               5

<210> SEQ ID NO 163
<211> LENGTH: 5
<212> TYPE: PRT
<213> ORGANISM: Artificial
<220> FEATURE:
<223> OTHER INFORMATION: Synthetic Construct

<400> SEQUENCE: 163

Cys Leu Val Val Asp
1               5

<210> SEQ ID NO 164
<211> LENGTH: 4
<212> TYPE: PRT
<213> ORGANISM: Artificial
<220> FEATURE:
<223> OTHER INFORMATION: Synthetic Construct

<400> SEQUENCE: 164

Cys Leu Val Val
1

<210> SEQ ID NO 165
<211> LENGTH: 13
<212> TYPE: PRT
<213> ORGANISM: Artificial
<220> FEATURE:
```

<223> OTHER INFORMATION: Synthetic Construct

<400> SEQUENCE: 165

Leu Val Val Asp Leu Ala Pro Ser Lys Gly Thr Val Asn
1               5                   10

<210> SEQ ID NO 166
<211> LENGTH: 12
<212> TYPE: PRT
<213> ORGANISM: Artificial
<220> FEATURE:
<223> OTHER INFORMATION: Synthetic Construct

<400> SEQUENCE: 166

Leu Val Val Asp Leu Ala Pro Ser Lys Gly Thr Val
1               5                   10

<210> SEQ ID NO 167
<211> LENGTH: 11
<212> TYPE: PRT
<213> ORGANISM: Artificial
<220> FEATURE:
<223> OTHER INFORMATION: Synthetic Construct

<400> SEQUENCE: 167

Leu Val Val Asp Leu Ala Pro Ser Lys Gly Thr
1               5                   10

<210> SEQ ID NO 168
<211> LENGTH: 10
<212> TYPE: PRT
<213> ORGANISM: Artificial
<220> FEATURE:
<223> OTHER INFORMATION: Synthetic Construct

<400> SEQUENCE: 168

Leu Val Val Asp Leu Ala Pro Ser Lys Gly
1               5                   10

<210> SEQ ID NO 169
<211> LENGTH: 9
<212> TYPE: PRT
<213> ORGANISM: Artificial
<220> FEATURE:
<223> OTHER INFORMATION: Synthetic Construct

<400> SEQUENCE: 169

Leu Val Val Asp Leu Ala Pro Ser Lys
1               5

<210> SEQ ID NO 170
<211> LENGTH: 8
<212> TYPE: PRT
<213> ORGANISM: Artificial
<220> FEATURE:
<223> OTHER INFORMATION: Synthetic Construct

<400> SEQUENCE: 170

Leu Val Val Asp Leu Ala Pro Ser
1               5

<210> SEQ ID NO 171
<211> LENGTH: 7
<212> TYPE: PRT
<213> ORGANISM: Artificial
<220> FEATURE:
<223> OTHER INFORMATION: Synthetic Construct

<400> SEQUENCE: 171

Leu Val Val Asp Leu Ala Pro
1               5

<210> SEQ ID NO 172
<211> LENGTH: 6
<212> TYPE: PRT
<213> ORGANISM: Artificial
<220> FEATURE:
<223> OTHER INFORMATION: Synthetic Construct

<400> SEQUENCE: 172

Leu Val Val Asp Leu Ala
1               5

<210> SEQ ID NO 173
<211> LENGTH: 5
<212> TYPE: PRT
<213> ORGANISM: Artificial
<220> FEATURE:
<223> OTHER INFORMATION: Synthetic Construct

<400> SEQUENCE: 173

Leu Val Val Asp Leu
1               5

<210> SEQ ID NO 174
<211> LENGTH: 4
<212> TYPE: PRT
<213> ORGANISM: Artificial
<220> FEATURE:
<223> OTHER INFORMATION: Synthetic Construct

<400> SEQUENCE: 174

Leu Val Val Asp
1

<210> SEQ ID NO 175
<211> LENGTH: 12
<212> TYPE: PRT
<213> ORGANISM: Artificial
<220> FEATURE:
<223> OTHER INFORMATION: Synthetic Construct

<400> SEQUENCE: 175

Val Val Asp Leu Ala Pro Ser Lys Gly Thr Val Asn
1               5                   10

<210> SEQ ID NO 176
<211> LENGTH: 11
<212> TYPE: PRT
<213> ORGANISM: Artificial
<220> FEATURE:
<223> OTHER INFORMATION: Synthetic Construct

<400> SEQUENCE: 176

Val Val Asp Leu Ala Pro Ser Lys Gly Thr Val
1               5                   10

<210> SEQ ID NO 177
<211> LENGTH: 10
<212> TYPE: PRT
<213> ORGANISM: Artificial
<220> FEATURE:
<223> OTHER INFORMATION: Synthetic Construct

```
<400> SEQUENCE: 177

Val Val Asp Leu Ala Pro Ser Lys Gly Thr
1               5                   10

<210> SEQ ID NO 178
<211> LENGTH: 9
<212> TYPE: PRT
<213> ORGANISM: Artificial
<220> FEATURE:
<223> OTHER INFORMATION: Synthetic Construct

<400> SEQUENCE: 178

Val Val Asp Leu Ala Pro Ser Lys Gly
1               5

<210> SEQ ID NO 179
<211> LENGTH: 8
<212> TYPE: PRT
<213> ORGANISM: Artificial
<220> FEATURE:
<223> OTHER INFORMATION: Synthetic Construct

<400> SEQUENCE: 179

Val Val Asp Leu Ala Pro Ser Lys
1               5

<210> SEQ ID NO 180
<211> LENGTH: 7
<212> TYPE: PRT
<213> ORGANISM: Artificial
<220> FEATURE:
<223> OTHER INFORMATION: Synthetic Construct

<400> SEQUENCE: 180

Val Val Asp Leu Ala Pro Ser
1               5

<210> SEQ ID NO 181
<211> LENGTH: 6
<212> TYPE: PRT
<213> ORGANISM: Artificial
<220> FEATURE:
<223> OTHER INFORMATION: Synthetic Construct

<400> SEQUENCE: 181

Val Val Asp Leu Ala Pro
1               5

<210> SEQ ID NO 182
<211> LENGTH: 5
<212> TYPE: PRT
<213> ORGANISM: Artificial
<220> FEATURE:
<223> OTHER INFORMATION: Synthetic Construct

<400> SEQUENCE: 182

Val Val Asp Leu Ala
1               5

<210> SEQ ID NO 183
<211> LENGTH: 4
<212> TYPE: PRT
<213> ORGANISM: Artificial
<220> FEATURE:
<223> OTHER INFORMATION: Synthetic Construct

<400> SEQUENCE: 183
```

```
Val Val Asp Leu
1

<210> SEQ ID NO 184
<211> LENGTH: 11
<212> TYPE: PRT
<213> ORGANISM: Artificial
<220> FEATURE:
<223> OTHER INFORMATION: Synthetic Construct

<400> SEQUENCE: 184

Val Asp Leu Ala Pro Ser Lys Gly Thr Val Asn
1               5                   10

<210> SEQ ID NO 185
<211> LENGTH: 10
<212> TYPE: PRT
<213> ORGANISM: Artificial
<220> FEATURE:
<223> OTHER INFORMATION: Synthetic Construct

<400> SEQUENCE: 185

Val Asp Leu Ala Pro Ser Lys Gly Thr Val
1               5                   10

<210> SEQ ID NO 186
<211> LENGTH: 9
<212> TYPE: PRT
<213> ORGANISM: Artificial
<220> FEATURE:
<223> OTHER INFORMATION: Synthetic Construct

<400> SEQUENCE: 186

Val Asp Leu Ala Pro Ser Lys Gly Thr
1               5

<210> SEQ ID NO 187
<211> LENGTH: 8
<212> TYPE: PRT
<213> ORGANISM: Artificial
<220> FEATURE:
<223> OTHER INFORMATION: Synthetic Construct

<400> SEQUENCE: 187

Val Asp Leu Ala Pro Ser Lys Gly
1               5

<210> SEQ ID NO 188
<211> LENGTH: 7
<212> TYPE: PRT
<213> ORGANISM: Artificial
<220> FEATURE:
<223> OTHER INFORMATION: Synthetic Construct

<400> SEQUENCE: 188

Val Asp Leu Ala Pro Ser Lys
1               5

<210> SEQ ID NO 189
<211> LENGTH: 6
<212> TYPE: PRT
<213> ORGANISM: Artificial
<220> FEATURE:
<223> OTHER INFORMATION: Synthetic Construct

<400> SEQUENCE: 189
```

```
Val Asp Leu Ala Pro Ser
1               5

<210> SEQ ID NO 190
<211> LENGTH: 5
<212> TYPE: PRT
<213> ORGANISM: Artificial
<220> FEATURE:
<223> OTHER INFORMATION: Synthetic Construct

<400> SEQUENCE: 190

Val Asp Leu Ala Pro
1               5

<210> SEQ ID NO 191
<211> LENGTH: 4
<212> TYPE: PRT
<213> ORGANISM: Artificial
<220> FEATURE:
<223> OTHER INFORMATION: Synthetic Construct

<400> SEQUENCE: 191

Val Asp Leu Ala
1

<210> SEQ ID NO 192
<211> LENGTH: 10
<212> TYPE: PRT
<213> ORGANISM: Artificial
<220> FEATURE:
<223> OTHER INFORMATION: Synthetic Construct

<400> SEQUENCE: 192

Asp Leu Ala Pro Ser Lys Gly Thr Val Asn
1               5                   10

<210> SEQ ID NO 193
<211> LENGTH: 9
<212> TYPE: PRT
<213> ORGANISM: Artificial
<220> FEATURE:
<223> OTHER INFORMATION: Synthetic Construct

<400> SEQUENCE: 193

Asp Leu Ala Pro Ser Lys Gly Thr Val
1               5

<210> SEQ ID NO 194
<211> LENGTH: 8
<212> TYPE: PRT
<213> ORGANISM: Artificial
<220> FEATURE:
<223> OTHER INFORMATION: Synthetic Construct

<400> SEQUENCE: 194

Asp Leu Ala Pro Ser Lys Gly Thr
1               5

<210> SEQ ID NO 195
<211> LENGTH: 7
<212> TYPE: PRT
<213> ORGANISM: Artificial
<220> FEATURE:
<223> OTHER INFORMATION: Synthetic Construct

<400> SEQUENCE: 195

Asp Leu Ala Pro Ser Lys Gly
```

```
1               5

<210> SEQ ID NO 196
<211> LENGTH: 6
<212> TYPE: PRT
<213> ORGANISM: Artificial
<220> FEATURE:
<223> OTHER INFORMATION: Synthetic Construct

<400> SEQUENCE: 196

Asp Leu Ala Pro Ser Lys
1               5

<210> SEQ ID NO 197
<211> LENGTH: 5
<212> TYPE: PRT
<213> ORGANISM: Artificial
<220> FEATURE:
<223> OTHER INFORMATION: Synthetic Construct

<400> SEQUENCE: 197

Asp Leu Ala Pro Ser
1               5

<210> SEQ ID NO 198
<211> LENGTH: 4
<212> TYPE: PRT
<213> ORGANISM: Artificial
<220> FEATURE:
<223> OTHER INFORMATION: Synthetic Construct

<400> SEQUENCE: 198

Asp Leu Ala Pro
1

<210> SEQ ID NO 199
<211> LENGTH: 9
<212> TYPE: PRT
<213> ORGANISM: Artificial
<220> FEATURE:
<223> OTHER INFORMATION: Synthetic Construct

<400> SEQUENCE: 199

Leu Ala Pro Ser Lys Gly Thr Val Asn
1               5

<210> SEQ ID NO 200
<211> LENGTH: 8
<212> TYPE: PRT
<213> ORGANISM: Artificial
<220> FEATURE:
<223> OTHER INFORMATION: Synthetic Construct

<400> SEQUENCE: 200

Leu Ala Pro Ser Lys Gly Thr Val
1               5

<210> SEQ ID NO 201
<211> LENGTH: 7
<212> TYPE: PRT
<213> ORGANISM: Artificial
<220> FEATURE:
<223> OTHER INFORMATION: Synthetic Construct

<400> SEQUENCE: 201

Leu Ala Pro Ser Lys Gly Thr
1               5
```

```
<210> SEQ ID NO 202
<211> LENGTH: 6
<212> TYPE: PRT
<213> ORGANISM: Artificial
<220> FEATURE:
<223> OTHER INFORMATION: Synthetic Construct

<400> SEQUENCE: 202

Leu Ala Pro Ser Lys Gly
1               5

<210> SEQ ID NO 203
<211> LENGTH: 5
<212> TYPE: PRT
<213> ORGANISM: Artificial
<220> FEATURE:
<223> OTHER INFORMATION: Synthetic Construct

<400> SEQUENCE: 203

Leu Ala Pro Ser Lys
1               5

<210> SEQ ID NO 204
<211> LENGTH: 4
<212> TYPE: PRT
<213> ORGANISM: Artificial
<220> FEATURE:
<223> OTHER INFORMATION: Synthetic Construct

<400> SEQUENCE: 204

Leu Ala Pro Ser
1

<210> SEQ ID NO 205
<211> LENGTH: 8
<212> TYPE: PRT
<213> ORGANISM: Artificial
<220> FEATURE:
<223> OTHER INFORMATION: Synthetic Construct

<400> SEQUENCE: 205

Ala Pro Ser Lys Gly Thr Val Asn
1               5

<210> SEQ ID NO 206
<211> LENGTH: 7
<212> TYPE: PRT
<213> ORGANISM: Artificial
<220> FEATURE:
<223> OTHER INFORMATION: Synthetic Construct

<400> SEQUENCE: 206

Ala Pro Ser Lys Gly Thr Val
1               5

<210> SEQ ID NO 207
<211> LENGTH: 6
<212> TYPE: PRT
<213> ORGANISM: Artificial
<220> FEATURE:
<223> OTHER INFORMATION: Synthetic Construct

<400> SEQUENCE: 207

Ala Pro Ser Lys Gly Thr
1               5
```

```
<210> SEQ ID NO 208
<211> LENGTH: 5
<212> TYPE: PRT
<213> ORGANISM: Artificial
<220> FEATURE:
<223> OTHER INFORMATION: Synthetic Construct

<400> SEQUENCE: 208

Ala Pro Ser Lys Gly
1               5

<210> SEQ ID NO 209
<211> LENGTH: 4
<212> TYPE: PRT
<213> ORGANISM: Artificial
<220> FEATURE:
<223> OTHER INFORMATION: Synthetic Construct

<400> SEQUENCE: 209

Ala Pro Ser Lys
1

<210> SEQ ID NO 210
<211> LENGTH: 7
<212> TYPE: PRT
<213> ORGANISM: Artificial
<220> FEATURE:
<223> OTHER INFORMATION: Synthetic Construct

<400> SEQUENCE: 210

Pro Ser Lys Gly Thr Val Asn
1               5

<210> SEQ ID NO 211
<211> LENGTH: 6
<212> TYPE: PRT
<213> ORGANISM: Artificial
<220> FEATURE:
<223> OTHER INFORMATION: Synthetic Construct

<400> SEQUENCE: 211

Pro Ser Lys Gly Thr Val
1               5

<210> SEQ ID NO 212
<211> LENGTH: 5
<212> TYPE: PRT
<213> ORGANISM: Artificial
<220> FEATURE:
<223> OTHER INFORMATION: Synthetic Construct

<400> SEQUENCE: 212

Pro Ser Lys Gly Thr
1               5

<210> SEQ ID NO 213
<211> LENGTH: 4
<212> TYPE: PRT
<213> ORGANISM: Artificial
<220> FEATURE:
<223> OTHER INFORMATION: Synthetic Construct

<400> SEQUENCE: 213

Pro Ser Lys Gly
1
```

```
<210> SEQ ID NO 214
<211> LENGTH: 6
<212> TYPE: PRT
<213> ORGANISM: Artificial
<220> FEATURE:
<223> OTHER INFORMATION: Synthetic Construct

<400> SEQUENCE: 214

Ser Lys Gly Thr Val Asn
1               5

<210> SEQ ID NO 215
<211> LENGTH: 5
<212> TYPE: PRT
<213> ORGANISM: Artificial
<220> FEATURE:
<223> OTHER INFORMATION: Synthetic Construct

<400> SEQUENCE: 215

Ser Lys Gly Thr Val
1               5

<210> SEQ ID NO 216
<211> LENGTH: 4
<212> TYPE: PRT
<213> ORGANISM: Artificial
<220> FEATURE:
<223> OTHER INFORMATION: Synthetic Construct

<400> SEQUENCE: 216

Ser Lys Gly Thr
1

<210> SEQ ID NO 217
<211> LENGTH: 5
<212> TYPE: PRT
<213> ORGANISM: Artificial
<220> FEATURE:
<223> OTHER INFORMATION: Synthetic Construct

<400> SEQUENCE: 217

Lys Gly Thr Val Asn
1               5

<210> SEQ ID NO 218
<211> LENGTH: 4
<212> TYPE: PRT
<213> ORGANISM: Artificial
<220> FEATURE:
<223> OTHER INFORMATION: Synthetic Construct

<400> SEQUENCE: 218

Lys Gly Thr Val
1

<210> SEQ ID NO 219
<211> LENGTH: 4
<212> TYPE: PRT
<213> ORGANISM: Artificial
<220> FEATURE:
<223> OTHER INFORMATION: Synthetic Construct

<400> SEQUENCE: 219

Gly Thr Val Asn
1

<210> SEQ ID NO 220
```

```
<211> LENGTH: 16
<212> TYPE: PRT
<213> ORGANISM: Artificial
<220> FEATURE:
<223> OTHER INFORMATION: Synthetic Construct

<400> SEQUENCE: 220

Gln Cys Arg Val Thr His Pro His Leu Pro Arg Ala Leu Met Arg Ser
1               5                   10                  15

<210> SEQ ID NO 221
<211> LENGTH: 15
<212> TYPE: PRT
<213> ORGANISM: Artificial
<220> FEATURE:
<223> OTHER INFORMATION: Synthetic Construct

<400> SEQUENCE: 221

Cys Arg Val Thr His Pro His Leu Pro Arg Ala Leu Met Arg Ser
1               5                   10                  15

<210> SEQ ID NO 222
<211> LENGTH: 14
<212> TYPE: PRT
<213> ORGANISM: Artificial
<220> FEATURE:
<223> OTHER INFORMATION: Synthetic Construct

<400> SEQUENCE: 222

Arg Val Thr His Pro His Leu Pro Arg Ala Leu Met Arg Ser
1               5                   10

<210> SEQ ID NO 223
<211> LENGTH: 13
<212> TYPE: PRT
<213> ORGANISM: Artificial
<220> FEATURE:
<223> OTHER INFORMATION: Synthetic Construct

<400> SEQUENCE: 223

Val Thr His Pro His Leu Pro Arg Ala Leu Met Arg Ser
1               5                   10

<210> SEQ ID NO 224
<211> LENGTH: 12
<212> TYPE: PRT
<213> ORGANISM: Artificial
<220> FEATURE:
<223> OTHER INFORMATION: Synthetic Construct

<400> SEQUENCE: 224

Thr His Pro His Leu Pro Arg Ala Leu Met Arg Ser
1               5                   10

<210> SEQ ID NO 225
<211> LENGTH: 11
<212> TYPE: PRT
<213> ORGANISM: Artificial
<220> FEATURE:
<223> OTHER INFORMATION: Synthetic Construct

<400> SEQUENCE: 225

His Pro His Leu Pro Arg Ala Leu Met Arg Ser
1               5                   10

<210> SEQ ID NO 226
<211> LENGTH: 10
```

```
<212> TYPE: PRT
<213> ORGANISM: Artificial
<220> FEATURE:
<223> OTHER INFORMATION: Synthetic Construct

<400> SEQUENCE: 226

Pro His Leu Pro Arg Ala Leu Met Arg Ser
1               5                   10

<210> SEQ ID NO 227
<211> LENGTH: 9
<212> TYPE: PRT
<213> ORGANISM: Artificial
<220> FEATURE:
<223> OTHER INFORMATION: Synthetic Construct

<400> SEQUENCE: 227

His Leu Pro Arg Ala Leu Met Arg Ser
1               5

<210> SEQ ID NO 228
<211> LENGTH: 8
<212> TYPE: PRT
<213> ORGANISM: Artificial
<220> FEATURE:
<223> OTHER INFORMATION: Synthetic Construct

<400> SEQUENCE: 228

Leu Pro Arg Ala Leu Met Arg Ser
1               5

<210> SEQ ID NO 229
<211> LENGTH: 7
<212> TYPE: PRT
<213> ORGANISM: Artificial
<220> FEATURE:
<223> OTHER INFORMATION: Synthetic Construct

<400> SEQUENCE: 229

Pro Arg Ala Leu Met Arg Ser
1               5

<210> SEQ ID NO 230
<211> LENGTH: 6
<212> TYPE: PRT
<213> ORGANISM: Artificial
<220> FEATURE:
<223> OTHER INFORMATION: Synthetic Construct

<400> SEQUENCE: 230

Arg Ala Leu Met Arg Ser
1               5

<210> SEQ ID NO 231
<211> LENGTH: 5
<212> TYPE: PRT
<213> ORGANISM: Artificial
<220> FEATURE:
<223> OTHER INFORMATION: Synthetic Construct

<400> SEQUENCE: 231

Ala Leu Met Arg Ser
1               5

<210> SEQ ID NO 232
<211> LENGTH: 4
<212> TYPE: PRT
```

```
<213> ORGANISM: Artificial
<220> FEATURE:
<223> OTHER INFORMATION: Synthetic Construct

<400> SEQUENCE: 232

Leu Met Arg Ser
1

<210> SEQ ID NO 233
<211> LENGTH: 15
<212> TYPE: PRT
<213> ORGANISM: Artificial
<220> FEATURE:
<223> OTHER INFORMATION: Synthetic Construct

<400> SEQUENCE: 233

Gln Cys Arg Val Thr His Pro His Leu Pro Arg Ala Leu Met Arg
1               5                   10                  15

<210> SEQ ID NO 234
<211> LENGTH: 14
<212> TYPE: PRT
<213> ORGANISM: Artificial
<220> FEATURE:
<223> OTHER INFORMATION: Synthetic Construct

<400> SEQUENCE: 234

Cys Arg Val Thr His Pro His Leu Pro Arg Ala Leu Met Arg
1               5                   10

<210> SEQ ID NO 235
<211> LENGTH: 13
<212> TYPE: PRT
<213> ORGANISM: Artificial
<220> FEATURE:
<223> OTHER INFORMATION: Synthetic Construct

<400> SEQUENCE: 235

Arg Val Thr His Pro His Leu Pro Arg Ala Leu Met Arg
1               5                   10

<210> SEQ ID NO 236
<211> LENGTH: 12
<212> TYPE: PRT
<213> ORGANISM: Artificial
<220> FEATURE:
<223> OTHER INFORMATION: Synthetic Construct

<400> SEQUENCE: 236

Val Thr His Pro His Leu Pro Arg Ala Leu Met Arg
1               5                   10

<210> SEQ ID NO 237
<211> LENGTH: 11
<212> TYPE: PRT
<213> ORGANISM: Artificial
<220> FEATURE:
<223> OTHER INFORMATION: Synthetic Construct

<400> SEQUENCE: 237

Thr His Pro His Leu Pro Arg Ala Leu Met Arg
1               5                   10

<210> SEQ ID NO 238
<211> LENGTH: 10
<212> TYPE: PRT
<213> ORGANISM: Artificial
```

```
<220> FEATURE:
<223> OTHER INFORMATION: Synthetic Construct

<400> SEQUENCE: 238

His Pro His Leu Pro Arg Ala Leu Met Arg
1               5                   10

<210> SEQ ID NO 239
<211> LENGTH: 9
<212> TYPE: PRT
<213> ORGANISM: Artificial
<220> FEATURE:
<223> OTHER INFORMATION: Synthetic Construct

<400> SEQUENCE: 239

Pro His Leu Pro Arg Ala Leu Met Arg
1               5

<210> SEQ ID NO 240
<211> LENGTH: 8
<212> TYPE: PRT
<213> ORGANISM: Artificial
<220> FEATURE:
<223> OTHER INFORMATION: Synthetic Construct

<400> SEQUENCE: 240

His Leu Pro Arg Ala Leu Met Arg
1               5

<210> SEQ ID NO 241
<211> LENGTH: 7
<212> TYPE: PRT
<213> ORGANISM: Artificial
<220> FEATURE:
<223> OTHER INFORMATION: Synthetic Construct

<400> SEQUENCE: 241

Leu Pro Arg Ala Leu Met Arg
1               5

<210> SEQ ID NO 242
<211> LENGTH: 6
<212> TYPE: PRT
<213> ORGANISM: Artificial
<220> FEATURE:
<223> OTHER INFORMATION: Synthetic Construct

<400> SEQUENCE: 242

Pro Arg Ala Leu Met Arg
1               5

<210> SEQ ID NO 243
<211> LENGTH: 5
<212> TYPE: PRT
<213> ORGANISM: Artificial
<220> FEATURE:
<223> OTHER INFORMATION: Synthetic Construct

<400> SEQUENCE: 243

Arg Ala Leu Met Arg
1               5

<210> SEQ ID NO 244
<211> LENGTH: 4
<212> TYPE: PRT
<213> ORGANISM: Artificial
<220> FEATURE:
```

<223> OTHER INFORMATION: Synthetic Construct

<400> SEQUENCE: 244

Ala Leu Met Arg
1

<210> SEQ ID NO 245
<211> LENGTH: 14
<212> TYPE: PRT
<213> ORGANISM: Artificial
<220> FEATURE:
<223> OTHER INFORMATION: Synthetic Construct

<400> SEQUENCE: 245

Gln Cys Arg Val Thr His Pro His Leu Pro Arg Ala Leu Met
1               5                   10

<210> SEQ ID NO 246
<211> LENGTH: 13
<212> TYPE: PRT
<213> ORGANISM: Artificial
<220> FEATURE:
<223> OTHER INFORMATION: Synthetic Construct

<400> SEQUENCE: 246

Cys Arg Val Thr His Pro His Leu Pro Arg Ala Leu Met
1               5                   10

<210> SEQ ID NO 247
<211> LENGTH: 12
<212> TYPE: PRT
<213> ORGANISM: Artificial
<220> FEATURE:
<223> OTHER INFORMATION: Synthetic Construct

<400> SEQUENCE: 247

Arg Val Thr His Pro His Leu Pro Arg Ala Leu Met
1               5                   10

<210> SEQ ID NO 248
<211> LENGTH: 11
<212> TYPE: PRT
<213> ORGANISM: Artificial
<220> FEATURE:
<223> OTHER INFORMATION: Synthetic Construct

<400> SEQUENCE: 248

Val Thr His Pro His Leu Pro Arg Ala Leu Met
1               5                   10

<210> SEQ ID NO 249
<211> LENGTH: 10
<212> TYPE: PRT
<213> ORGANISM: Artificial
<220> FEATURE:
<223> OTHER INFORMATION: Synthetic Construct

<400> SEQUENCE: 249

Thr His Pro His Leu Pro Arg Ala Leu Met
1               5                   10

<210> SEQ ID NO 250
<211> LENGTH: 9
<212> TYPE: PRT
<213> ORGANISM: Artificial
<220> FEATURE:
<223> OTHER INFORMATION: Synthetic Construct

```
<400> SEQUENCE: 250

His Pro His Leu Pro Arg Ala Leu Met
1               5

<210> SEQ ID NO 251
<211> LENGTH: 8
<212> TYPE: PRT
<213> ORGANISM: Artificial
<220> FEATURE:
<223> OTHER INFORMATION: Synthetic Construct

<400> SEQUENCE: 251

Pro His Leu Pro Arg Ala Leu Met
1               5

<210> SEQ ID NO 252
<211> LENGTH: 7
<212> TYPE: PRT
<213> ORGANISM: Artificial
<220> FEATURE:
<223> OTHER INFORMATION: Synthetic Construct

<400> SEQUENCE: 252

His Leu Pro Arg Ala Leu Met
1               5

<210> SEQ ID NO 253
<211> LENGTH: 6
<212> TYPE: PRT
<213> ORGANISM: Artificial
<220> FEATURE:
<223> OTHER INFORMATION: Synthetic Construct

<400> SEQUENCE: 253

Leu Pro Arg Ala Leu Met
1               5

<210> SEQ ID NO 254
<211> LENGTH: 5
<212> TYPE: PRT
<213> ORGANISM: Artificial
<220> FEATURE:
<223> OTHER INFORMATION: Synthetic Construct

<400> SEQUENCE: 254

Pro Arg Ala Leu Met
1               5

<210> SEQ ID NO 255
<211> LENGTH: 4
<212> TYPE: PRT
<213> ORGANISM: Artificial
<220> FEATURE:
<223> OTHER INFORMATION: Synthetic Construct

<400> SEQUENCE: 255

Arg Ala Leu Met
1

<210> SEQ ID NO 256
<211> LENGTH: 13
<212> TYPE: PRT
<213> ORGANISM: Artificial
<220> FEATURE:
<223> OTHER INFORMATION: Synthetic Construct
```

<400> SEQUENCE: 256

Gln Cys Arg Val Thr His Pro His Leu Pro Arg Ala Leu
1               5                   10

<210> SEQ ID NO 257
<211> LENGTH: 12
<212> TYPE: PRT
<213> ORGANISM: Artificial
<220> FEATURE:
<223> OTHER INFORMATION: Synthetic Construct

<400> SEQUENCE: 257

Cys Arg Val Thr His Pro His Leu Pro Arg Ala Leu
1               5                   10

<210> SEQ ID NO 258
<211> LENGTH: 11
<212> TYPE: PRT
<213> ORGANISM: Artificial
<220> FEATURE:
<223> OTHER INFORMATION: Synthetic Construct

<400> SEQUENCE: 258

Arg Val Thr His Pro His Leu Pro Arg Ala Leu
1               5                   10

<210> SEQ ID NO 259
<211> LENGTH: 10
<212> TYPE: PRT
<213> ORGANISM: Artificial
<220> FEATURE:
<223> OTHER INFORMATION: Synthetic Construct

<400> SEQUENCE: 259

Val Thr His Pro His Leu Pro Arg Ala Leu
1               5                   10

<210> SEQ ID NO 260
<211> LENGTH: 9
<212> TYPE: PRT
<213> ORGANISM: Artificial
<220> FEATURE:
<223> OTHER INFORMATION: Synthetic Construct

<400> SEQUENCE: 260

Thr His Pro His Leu Pro Arg Ala Leu
1               5

<210> SEQ ID NO 261
<211> LENGTH: 8
<212> TYPE: PRT
<213> ORGANISM: Artificial
<220> FEATURE:
<223> OTHER INFORMATION: Synthetic Construct

<400> SEQUENCE: 261

His Pro His Leu Pro Arg Ala Leu
1               5

<210> SEQ ID NO 262
<211> LENGTH: 7
<212> TYPE: PRT
<213> ORGANISM: Artificial
<220> FEATURE:
<223> OTHER INFORMATION: Synthetic Construct

<400> SEQUENCE: 262

```
Pro His Leu Pro Arg Ala Leu
1               5
```

<210> SEQ ID NO 263
<211> LENGTH: 6
<212> TYPE: PRT
<213> ORGANISM: Artificial
<220> FEATURE:
<223> OTHER INFORMATION: Synthetic Construct

<400> SEQUENCE: 263

```
His Leu Pro Arg Ala Leu
1               5
```

<210> SEQ ID NO 264
<211> LENGTH: 5
<212> TYPE: PRT
<213> ORGANISM: Artificial
<220> FEATURE:
<223> OTHER INFORMATION: Synthetic Construct

<400> SEQUENCE: 264

```
Leu Pro Arg Ala Leu
1               5
```

<210> SEQ ID NO 265
<211> LENGTH: 4
<212> TYPE: PRT
<213> ORGANISM: Artificial
<220> FEATURE:
<223> OTHER INFORMATION: Synthetic Construct

<400> SEQUENCE: 265

```
Pro Arg Ala Leu
1
```

<210> SEQ ID NO 266
<211> LENGTH: 12
<212> TYPE: PRT
<213> ORGANISM: Artificial
<220> FEATURE:
<223> OTHER INFORMATION: Synthetic Construct

<400> SEQUENCE: 266

```
Gln Cys Arg Val Thr His Pro His Leu Pro Arg Ala
1               5                   10
```

<210> SEQ ID NO 267
<211> LENGTH: 11
<212> TYPE: PRT
<213> ORGANISM: Artificial
<220> FEATURE:
<223> OTHER INFORMATION: Synthetic Construct

<400> SEQUENCE: 267

```
Cys Arg Val Thr His Pro His Leu Pro Arg Ala
1               5                   10
```

<210> SEQ ID NO 268
<211> LENGTH: 10
<212> TYPE: PRT
<213> ORGANISM: Artificial
<220> FEATURE:
<223> OTHER INFORMATION: Synthetic Construct

<400> SEQUENCE: 268

Arg Val Thr His Pro His Leu Pro Arg Ala
1               5                   10

<210> SEQ ID NO 269
<211> LENGTH: 9
<212> TYPE: PRT
<213> ORGANISM: Artificial
<220> FEATURE:
<223> OTHER INFORMATION: Synthetic Construct

<400> SEQUENCE: 269

Val Thr His Pro His Leu Pro Arg Ala
1               5

<210> SEQ ID NO 270
<211> LENGTH: 8
<212> TYPE: PRT
<213> ORGANISM: Artificial
<220> FEATURE:
<223> OTHER INFORMATION: Synthetic Construct

<400> SEQUENCE: 270

Thr His Pro His Leu Pro Arg Ala
1               5

<210> SEQ ID NO 271
<211> LENGTH: 7
<212> TYPE: PRT
<213> ORGANISM: Artificial
<220> FEATURE:
<223> OTHER INFORMATION: Synthetic Construct

<400> SEQUENCE: 271

His Pro His Leu Pro Arg Ala
1               5

<210> SEQ ID NO 272
<211> LENGTH: 6
<212> TYPE: PRT
<213> ORGANISM: Artificial
<220> FEATURE:
<223> OTHER INFORMATION: Synthetic Construct

<400> SEQUENCE: 272

Pro His Leu Pro Arg Ala
1               5

<210> SEQ ID NO 273
<211> LENGTH: 5
<212> TYPE: PRT
<213> ORGANISM: Artificial
<220> FEATURE:
<223> OTHER INFORMATION: Synthetic Construct

<400> SEQUENCE: 273

His Leu Pro Arg Ala
1               5

<210> SEQ ID NO 274
<211> LENGTH: 4
<212> TYPE: PRT
<213> ORGANISM: Artificial
<220> FEATURE:
<223> OTHER INFORMATION: Synthetic Construct

<400> SEQUENCE: 274

Leu Pro Arg Ala

```
<210> SEQ ID NO 275
<211> LENGTH: 11
<212> TYPE: PRT
<213> ORGANISM: Artificial
<220> FEATURE:
<223> OTHER INFORMATION: Synthetic Construct

<400> SEQUENCE: 275

Gln Cys Arg Val Thr His Pro His Leu Pro Arg
1               5                   10

<210> SEQ ID NO 276
<211> LENGTH: 10
<212> TYPE: PRT
<213> ORGANISM: Artificial
<220> FEATURE:
<223> OTHER INFORMATION: Synthetic Construct

<400> SEQUENCE: 276

Cys Arg Val Thr His Pro His Leu Pro Arg
1               5                   10

<210> SEQ ID NO 277
<211> LENGTH: 9
<212> TYPE: PRT
<213> ORGANISM: Artificial
<220> FEATURE:
<223> OTHER INFORMATION: Synthetic Construct

<400> SEQUENCE: 277

Arg Val Thr His Pro His Leu Pro Arg
1               5

<210> SEQ ID NO 278
<211> LENGTH: 8
<212> TYPE: PRT
<213> ORGANISM: Artificial
<220> FEATURE:
<223> OTHER INFORMATION: Synthetic Construct

<400> SEQUENCE: 278

Val Thr His Pro His Leu Pro Arg
1               5

<210> SEQ ID NO 279
<211> LENGTH: 7
<212> TYPE: PRT
<213> ORGANISM: Artificial
<220> FEATURE:
<223> OTHER INFORMATION: Synthetic Construct

<400> SEQUENCE: 279

Thr His Pro His Leu Pro Arg
1               5

<210> SEQ ID NO 280
<211> LENGTH: 6
<212> TYPE: PRT
<213> ORGANISM: Artificial
<220> FEATURE:
<223> OTHER INFORMATION: Synthetic Construct

<400> SEQUENCE: 280

His Pro His Leu Pro Arg
1               5
```

```
<210> SEQ ID NO 281
<211> LENGTH: 5
<212> TYPE: PRT
<213> ORGANISM: Artificial
<220> FEATURE:
<223> OTHER INFORMATION: Synthetic Construct

<400> SEQUENCE: 281

Pro His Leu Pro Arg
1               5

<210> SEQ ID NO 282
<211> LENGTH: 4
<212> TYPE: PRT
<213> ORGANISM: Artificial
<220> FEATURE:
<223> OTHER INFORMATION: Synthetic Construct

<400> SEQUENCE: 282

His Leu Pro Arg
1

<210> SEQ ID NO 283
<211> LENGTH: 10
<212> TYPE: PRT
<213> ORGANISM: Artificial
<220> FEATURE:
<223> OTHER INFORMATION: Synthetic Construct

<400> SEQUENCE: 283

Gln Cys Arg Val Thr His Pro His Leu Pro
1               5                   10

<210> SEQ ID NO 284
<211> LENGTH: 9
<212> TYPE: PRT
<213> ORGANISM: Artificial
<220> FEATURE:
<223> OTHER INFORMATION: Synthetic Construct

<400> SEQUENCE: 284

Cys Arg Val Thr His Pro His Leu Pro
1               5

<210> SEQ ID NO 285
<211> LENGTH: 8
<212> TYPE: PRT
<213> ORGANISM: Artificial
<220> FEATURE:
<223> OTHER INFORMATION: Synthetic Construct

<400> SEQUENCE: 285

Arg Val Thr His Pro His Leu Pro
1               5

<210> SEQ ID NO 286
<211> LENGTH: 7
<212> TYPE: PRT
<213> ORGANISM: Artificial
<220> FEATURE:
<223> OTHER INFORMATION: Synthetic Construct

<400> SEQUENCE: 286

Val Thr His Pro His Leu Pro
1               5
```

```
<210> SEQ ID NO 287
<211> LENGTH: 6
<212> TYPE: PRT
<213> ORGANISM: Artificial
<220> FEATURE:
<223> OTHER INFORMATION: Synthetic Construct

<400> SEQUENCE: 287

Thr His Pro His Leu Pro
1               5

<210> SEQ ID NO 288
<211> LENGTH: 5
<212> TYPE: PRT
<213> ORGANISM: Artificial
<220> FEATURE:
<223> OTHER INFORMATION: Synthetic Construct

<400> SEQUENCE: 288

His Pro His Leu Pro
1               5

<210> SEQ ID NO 289
<211> LENGTH: 4
<212> TYPE: PRT
<213> ORGANISM: Artificial
<220> FEATURE:
<223> OTHER INFORMATION: Synthetic Construct

<400> SEQUENCE: 289

Pro His Leu Pro
1

<210> SEQ ID NO 290
<211> LENGTH: 9
<212> TYPE: PRT
<213> ORGANISM: Artificial
<220> FEATURE:
<223> OTHER INFORMATION: Synthetic Construct

<400> SEQUENCE: 290

Gln Cys Arg Val Thr His Pro His Leu
1               5

<210> SEQ ID NO 291
<211> LENGTH: 8
<212> TYPE: PRT
<213> ORGANISM: Artificial
<220> FEATURE:
<223> OTHER INFORMATION: Synthetic Construct

<400> SEQUENCE: 291

Cys Arg Val Thr His Pro His Leu
1               5

<210> SEQ ID NO 292
<211> LENGTH: 7
<212> TYPE: PRT
<213> ORGANISM: Artificial
<220> FEATURE:
<223> OTHER INFORMATION: Synthetic Construct

<400> SEQUENCE: 292

Arg Val Thr His Pro His Leu
1               5
```

```
<210> SEQ ID NO 293
<211> LENGTH: 6
<212> TYPE: PRT
<213> ORGANISM: Artificial
<220> FEATURE:
<223> OTHER INFORMATION: Synthetic Construct

<400> SEQUENCE: 293

Val Thr His Pro His Leu
1               5

<210> SEQ ID NO 294
<211> LENGTH: 5
<212> TYPE: PRT
<213> ORGANISM: Artificial
<220> FEATURE:
<223> OTHER INFORMATION: Synthetic Construct

<400> SEQUENCE: 294

Thr His Pro His Leu
1               5

<210> SEQ ID NO 295
<211> LENGTH: 4
<212> TYPE: PRT
<213> ORGANISM: Artificial
<220> FEATURE:
<223> OTHER INFORMATION: Synthetic Construct

<400> SEQUENCE: 295

His Pro His Leu
1

<210> SEQ ID NO 296
<211> LENGTH: 8
<212> TYPE: PRT
<213> ORGANISM: Artificial
<220> FEATURE:
<223> OTHER INFORMATION: Synthetic Construct

<400> SEQUENCE: 296

Gln Cys Arg Val Thr His Pro His
1               5

<210> SEQ ID NO 297
<211> LENGTH: 7
<212> TYPE: PRT
<213> ORGANISM: Artificial
<220> FEATURE:
<223> OTHER INFORMATION: Synthetic Construct

<400> SEQUENCE: 297

Cys Arg Val Thr His Pro His
1               5

<210> SEQ ID NO 298
<211> LENGTH: 6
<212> TYPE: PRT
<213> ORGANISM: Artificial
<220> FEATURE:
<223> OTHER INFORMATION: Synthetic Construct

<400> SEQUENCE: 298

Arg Val Thr His Pro His
1               5

<210> SEQ ID NO 299
```

```
<211> LENGTH: 5
<212> TYPE: PRT
<213> ORGANISM: Artificial
<220> FEATURE:
<223> OTHER INFORMATION: Synthetic Construct

<400> SEQUENCE: 299

Val Thr His Pro His
1               5

<210> SEQ ID NO 300
<211> LENGTH: 4
<212> TYPE: PRT
<213> ORGANISM: Artificial
<220> FEATURE:
<223> OTHER INFORMATION: Synthetic Construct

<400> SEQUENCE: 300

Thr His Pro His
1

<210> SEQ ID NO 301
<211> LENGTH: 7
<212> TYPE: PRT
<213> ORGANISM: Artificial
<220> FEATURE:
<223> OTHER INFORMATION: Synthetic Construct

<400> SEQUENCE: 301

Gln Cys Arg Val Thr His Pro
1               5

<210> SEQ ID NO 302
<211> LENGTH: 6
<212> TYPE: PRT
<213> ORGANISM: Artificial
<220> FEATURE:
<223> OTHER INFORMATION: Synthetic Construct

<400> SEQUENCE: 302

Cys Arg Val Thr His Pro
1               5

<210> SEQ ID NO 303
<211> LENGTH: 5
<212> TYPE: PRT
<213> ORGANISM: Artificial
<220> FEATURE:
<223> OTHER INFORMATION: Synthetic Construct

<400> SEQUENCE: 303

Arg Val Thr His Pro
1               5

<210> SEQ ID NO 304
<211> LENGTH: 4
<212> TYPE: PRT
<213> ORGANISM: Artificial
<220> FEATURE:
<223> OTHER INFORMATION: Synthetic Construct

<400> SEQUENCE: 304

Val Thr His Pro
1

<210> SEQ ID NO 305
<211> LENGTH: 6
```

```
<212> TYPE: PRT
<213> ORGANISM: Artificial
<220> FEATURE:
<223> OTHER INFORMATION: Synthetic Construct

<400> SEQUENCE: 305

Gln Cys Arg Val Thr His
1               5

<210> SEQ ID NO 306
<211> LENGTH: 5
<212> TYPE: PRT
<213> ORGANISM: Artificial
<220> FEATURE:
<223> OTHER INFORMATION: Synthetic Construct

<400> SEQUENCE: 306

Cys Arg Val Thr His
1               5

<210> SEQ ID NO 307
<211> LENGTH: 4
<212> TYPE: PRT
<213> ORGANISM: Artificial
<220> FEATURE:
<223> OTHER INFORMATION: Synthetic Construct

<400> SEQUENCE: 307

Arg Val Thr His
1

<210> SEQ ID NO 308
<211> LENGTH: 5
<212> TYPE: PRT
<213> ORGANISM: Artificial
<220> FEATURE:
<223> OTHER INFORMATION: Synthetic Construct

<400> SEQUENCE: 308

Gln Cys Arg Val Thr
1               5

<210> SEQ ID NO 309
<211> LENGTH: 4
<212> TYPE: PRT
<213> ORGANISM: Artificial
<220> FEATURE:
<223> OTHER INFORMATION: Synthetic Construct

<400> SEQUENCE: 309

Cys Arg Val Thr
1

<210> SEQ ID NO 310
<211> LENGTH: 4
<212> TYPE: PRT
<213> ORGANISM: Artificial
<220> FEATURE:
<223> OTHER INFORMATION: Synthetic Construct

<400> SEQUENCE: 310

Gln Cys Arg Val
1

<210> SEQ ID NO 311
<211> LENGTH: 18
<212> TYPE: PRT
```

```
<213> ORGANISM: Artificial
<220> FEATURE:
<223> OTHER INFORMATION: Synthetic Construct

<400> SEQUENCE: 311

Cys Ala Asp Ser Asn Pro Arg Gly Val Ser Ala Tyr Leu Ser Arg Pro
1               5                   10                  15

Ser Pro

<210> SEQ ID NO 312
<211> LENGTH: 17
<212> TYPE: PRT
<213> ORGANISM: Artificial
<220> FEATURE:
<223> OTHER INFORMATION: Synthetic Construct

<400> SEQUENCE: 312

Ala Asp Ser Asn Pro Arg Gly Val Ser Ala Tyr Leu Ser Arg Pro Ser
1               5                   10                  15

Pro

<210> SEQ ID NO 313
<211> LENGTH: 16
<212> TYPE: PRT
<213> ORGANISM: Artificial
<220> FEATURE:
<223> OTHER INFORMATION: Synthetic Construct

<400> SEQUENCE: 313

Asp Ser Asn Pro Arg Gly Val Ser Ala Tyr Leu Ser Arg Pro Ser Pro
1               5                   10                  15

<210> SEQ ID NO 314
<211> LENGTH: 15
<212> TYPE: PRT
<213> ORGANISM: Artificial
<220> FEATURE:
<223> OTHER INFORMATION: Synthetic Construct

<400> SEQUENCE: 314

Ser Asn Pro Arg Gly Val Ser Ala Tyr Leu Ser Arg Pro Ser Pro
1               5                   10                  15

<210> SEQ ID NO 315
<211> LENGTH: 14
<212> TYPE: PRT
<213> ORGANISM: Artificial
<220> FEATURE:
<223> OTHER INFORMATION: Synthetic Construct

<400> SEQUENCE: 315

Asn Pro Arg Gly Val Ser Ala Tyr Leu Ser Arg Pro Ser Pro
1               5                   10

<210> SEQ ID NO 316
<211> LENGTH: 13
<212> TYPE: PRT
<213> ORGANISM: Artificial
<220> FEATURE:
<223> OTHER INFORMATION: Synthetic Construct

<400> SEQUENCE: 316

Pro Arg Gly Val Ser Ala Tyr Leu Ser Arg Pro Ser Pro
1               5                   10
```

```
<210> SEQ ID NO 317
<211> LENGTH: 12
<212> TYPE: PRT
<213> ORGANISM: Artificial
<220> FEATURE:
<223> OTHER INFORMATION: Synthetic Construct

<400> SEQUENCE: 317

Arg Gly Val Ser Ala Tyr Leu Ser Arg Pro Ser Pro
1               5                   10

<210> SEQ ID NO 318
<211> LENGTH: 11
<212> TYPE: PRT
<213> ORGANISM: Artificial
<220> FEATURE:
<223> OTHER INFORMATION: Synthetic Construct

<400> SEQUENCE: 318

Gly Val Ser Ala Tyr Leu Ser Arg Pro Ser Pro
1               5                   10

<210> SEQ ID NO 319
<211> LENGTH: 10
<212> TYPE: PRT
<213> ORGANISM: Artificial
<220> FEATURE:
<223> OTHER INFORMATION: Synthetic Construct

<400> SEQUENCE: 319

Val Ser Ala Tyr Leu Ser Arg Pro Ser Pro
1               5                   10

<210> SEQ ID NO 320
<211> LENGTH: 9
<212> TYPE: PRT
<213> ORGANISM: Artificial
<220> FEATURE:
<223> OTHER INFORMATION: Synthetic Construct

<400> SEQUENCE: 320

Ser Ala Tyr Leu Ser Arg Pro Ser Pro
1               5

<210> SEQ ID NO 321
<211> LENGTH: 8
<212> TYPE: PRT
<213> ORGANISM: Artificial
<220> FEATURE:
<223> OTHER INFORMATION: Synthetic Construct

<400> SEQUENCE: 321

Ala Tyr Leu Ser Arg Pro Ser Pro
1               5

<210> SEQ ID NO 322
<211> LENGTH: 7
<212> TYPE: PRT
<213> ORGANISM: Artificial
<220> FEATURE:
<223> OTHER INFORMATION: Synthetic Construct

<400> SEQUENCE: 322

Tyr Leu Ser Arg Pro Ser Pro
1               5

<210> SEQ ID NO 323
```

```
<211> LENGTH: 6
<212> TYPE: PRT
<213> ORGANISM: Artificial
<220> FEATURE:
<223> OTHER INFORMATION: Synthetic Construct

<400> SEQUENCE: 323

Leu Ser Arg Pro Ser Pro
1               5

<210> SEQ ID NO 324
<211> LENGTH: 5
<212> TYPE: PRT
<213> ORGANISM: Artificial
<220> FEATURE:
<223> OTHER INFORMATION: Synthetic Construct

<400> SEQUENCE: 324

Ser Arg Pro Ser Pro
1               5

<210> SEQ ID NO 325
<211> LENGTH: 4
<212> TYPE: PRT
<213> ORGANISM: Artificial
<220> FEATURE:
<223> OTHER INFORMATION: Synthetic Construct

<400> SEQUENCE: 325

Arg Pro Ser Pro
1

<210> SEQ ID NO 326
<211> LENGTH: 17
<212> TYPE: PRT
<213> ORGANISM: Artificial
<220> FEATURE:
<223> OTHER INFORMATION: Synthetic Construct

<400> SEQUENCE: 326

Cys Ala Asp Ser Asn Pro Arg Gly Val Ser Ala Tyr Leu Ser Arg Pro
1               5                   10                  15

Ser

<210> SEQ ID NO 327
<211> LENGTH: 16
<212> TYPE: PRT
<213> ORGANISM: Artificial
<220> FEATURE:
<223> OTHER INFORMATION: Synthetic Construct

<400> SEQUENCE: 327

Ala Asp Ser Asn Pro Arg Gly Val Ser Ala Tyr Leu Ser Arg Pro Ser
1               5                   10                  15

<210> SEQ ID NO 328
<211> LENGTH: 15
<212> TYPE: PRT
<213> ORGANISM: Artificial
<220> FEATURE:
<223> OTHER INFORMATION: Synthetic Construct

<400> SEQUENCE: 328

Asp Ser Asn Pro Arg Gly Val Ser Ala Tyr Leu Ser Arg Pro Ser
1               5                   10                  15
```

```
<210> SEQ ID NO 329
<211> LENGTH: 14
<212> TYPE: PRT
<213> ORGANISM: Artificial
<220> FEATURE:
<223> OTHER INFORMATION: Synthetic Construct

<400> SEQUENCE: 329

Ser Asn Pro Arg Gly Val Ser Ala Tyr Leu Ser Arg Pro Ser
1               5                   10

<210> SEQ ID NO 330
<211> LENGTH: 13
<212> TYPE: PRT
<213> ORGANISM: Artificial
<220> FEATURE:
<223> OTHER INFORMATION: Synthetic Construct

<400> SEQUENCE: 330

Asn Pro Arg Gly Val Ser Ala Tyr Leu Ser Arg Pro Ser
1               5                   10

<210> SEQ ID NO 331
<211> LENGTH: 12
<212> TYPE: PRT
<213> ORGANISM: Artificial
<220> FEATURE:
<223> OTHER INFORMATION: Synthetic Construct

<400> SEQUENCE: 331

Pro Arg Gly Val Ser Ala Tyr Leu Ser Arg Pro Ser
1               5                   10

<210> SEQ ID NO 332
<211> LENGTH: 11
<212> TYPE: PRT
<213> ORGANISM: Artificial
<220> FEATURE:
<223> OTHER INFORMATION: Synthetic Construct

<400> SEQUENCE: 332

Arg Gly Val Ser Ala Tyr Leu Ser Arg Pro Ser
1               5                   10

<210> SEQ ID NO 333
<211> LENGTH: 10
<212> TYPE: PRT
<213> ORGANISM: Artificial
<220> FEATURE:
<223> OTHER INFORMATION: Synthetic Construct

<400> SEQUENCE: 333

Gly Val Ser Ala Tyr Leu Ser Arg Pro Ser
1               5                   10

<210> SEQ ID NO 334
<211> LENGTH: 9
<212> TYPE: PRT
<213> ORGANISM: Artificial
<220> FEATURE:
<223> OTHER INFORMATION: Synthetic Construct

<400> SEQUENCE: 334

Val Ser Ala Tyr Leu Ser Arg Pro Ser
1               5

<210> SEQ ID NO 335
```

```
<211> LENGTH: 8
<212> TYPE: PRT
<213> ORGANISM: Artificial
<220> FEATURE:
<223> OTHER INFORMATION: Synthetic Construct

<400> SEQUENCE: 335

Ser Ala Tyr Leu Ser Arg Pro Ser
1               5

<210> SEQ ID NO 336
<211> LENGTH: 7
<212> TYPE: PRT
<213> ORGANISM: Artificial
<220> FEATURE:
<223> OTHER INFORMATION: Synthetic Construct

<400> SEQUENCE: 336

Ala Tyr Leu Ser Arg Pro Ser
1               5

<210> SEQ ID NO 337
<211> LENGTH: 6
<212> TYPE: PRT
<213> ORGANISM: Artificial
<220> FEATURE:
<223> OTHER INFORMATION: Synthetic Construct

<400> SEQUENCE: 337

Tyr Leu Ser Arg Pro Ser
1               5

<210> SEQ ID NO 338
<211> LENGTH: 5
<212> TYPE: PRT
<213> ORGANISM: Artificial
<220> FEATURE:
<223> OTHER INFORMATION: Synthetic Construct

<400> SEQUENCE: 338

Leu Ser Arg Pro Ser
1               5

<210> SEQ ID NO 339
<211> LENGTH: 4
<212> TYPE: PRT
<213> ORGANISM: Artificial
<220> FEATURE:
<223> OTHER INFORMATION: Synthetic Construct

<400> SEQUENCE: 339

Ser Arg Pro Ser
1

<210> SEQ ID NO 340
<211> LENGTH: 16
<212> TYPE: PRT
<213> ORGANISM: Artificial
<220> FEATURE:
<223> OTHER INFORMATION: Synthetic Construct

<400> SEQUENCE: 340

Cys Ala Asp Ser Asn Pro Arg Gly Val Ser Ala Tyr Leu Ser Arg Pro
1               5                   10                  15

<210> SEQ ID NO 341
<211> LENGTH: 15
```

```
<212> TYPE: PRT
<213> ORGANISM: Artificial
<220> FEATURE:
<223> OTHER INFORMATION: Synthetic Construct

<400> SEQUENCE: 341

Ala Asp Ser Asn Pro Arg Gly Val Ser Ala Tyr Leu Ser Arg Pro
1               5                   10                  15

<210> SEQ ID NO 342
<211> LENGTH: 14
<212> TYPE: PRT
<213> ORGANISM: Artificial
<220> FEATURE:
<223> OTHER INFORMATION: Synthetic Construct

<400> SEQUENCE: 342

Asp Ser Asn Pro Arg Gly Val Ser Ala Tyr Leu Ser Arg Pro
1               5                   10

<210> SEQ ID NO 343
<211> LENGTH: 13
<212> TYPE: PRT
<213> ORGANISM: Artificial
<220> FEATURE:
<223> OTHER INFORMATION: Synthetic Construct

<400> SEQUENCE: 343

Ser Asn Pro Arg Gly Val Ser Ala Tyr Leu Ser Arg Pro
1               5                   10

<210> SEQ ID NO 344
<211> LENGTH: 12
<212> TYPE: PRT
<213> ORGANISM: Artificial
<220> FEATURE:
<223> OTHER INFORMATION: Synthetic Construct

<400> SEQUENCE: 344

Asn Pro Arg Gly Val Ser Ala Tyr Leu Ser Arg Pro
1               5                   10

<210> SEQ ID NO 345
<211> LENGTH: 11
<212> TYPE: PRT
<213> ORGANISM: Artificial
<220> FEATURE:
<223> OTHER INFORMATION: Synthetic Construct

<400> SEQUENCE: 345

Pro Arg Gly Val Ser Ala Tyr Leu Ser Arg Pro
1               5                   10

<210> SEQ ID NO 346
<211> LENGTH: 10
<212> TYPE: PRT
<213> ORGANISM: Artificial
<220> FEATURE:
<223> OTHER INFORMATION: Synthetic Construct

<400> SEQUENCE: 346

Arg Gly Val Ser Ala Tyr Leu Ser Arg Pro
1               5                   10

<210> SEQ ID NO 347
<211> LENGTH: 9
<212> TYPE: PRT
```

```
<213> ORGANISM: Artificial
<220> FEATURE:
<223> OTHER INFORMATION: Synthetic Construct

<400> SEQUENCE: 347

Gly Val Ser Ala Tyr Leu Ser Arg Pro
1               5

<210> SEQ ID NO 348
<211> LENGTH: 8
<212> TYPE: PRT
<213> ORGANISM: Artificial
<220> FEATURE:
<223> OTHER INFORMATION: Synthetic Construct

<400> SEQUENCE: 348

Val Ser Ala Tyr Leu Ser Arg Pro
1               5

<210> SEQ ID NO 349
<211> LENGTH: 7
<212> TYPE: PRT
<213> ORGANISM: Artificial
<220> FEATURE:
<223> OTHER INFORMATION: Synthetic Construct

<400> SEQUENCE: 349

Ser Ala Tyr Leu Ser Arg Pro
1               5

<210> SEQ ID NO 350
<211> LENGTH: 6
<212> TYPE: PRT
<213> ORGANISM: Artificial
<220> FEATURE:
<223> OTHER INFORMATION: Synthetic Construct

<400> SEQUENCE: 350

Ala Tyr Leu Ser Arg Pro
1               5

<210> SEQ ID NO 351
<211> LENGTH: 5
<212> TYPE: PRT
<213> ORGANISM: Artificial
<220> FEATURE:
<223> OTHER INFORMATION: Synthetic Construct

<400> SEQUENCE: 351

Tyr Leu Ser Arg Pro
1               5

<210> SEQ ID NO 352
<211> LENGTH: 4
<212> TYPE: PRT
<213> ORGANISM: Artificial
<220> FEATURE:
<223> OTHER INFORMATION: Synthetic Construct

<400> SEQUENCE: 352

Leu Ser Arg Pro
1

<210> SEQ ID NO 353
<211> LENGTH: 15
<212> TYPE: PRT
<213> ORGANISM: Artificial
```

<220> FEATURE:
<223> OTHER INFORMATION: Synthetic Construct

<400> SEQUENCE: 353

Cys Ala Asp Ser Asn Pro Arg Gly Val Ser Ala Tyr Leu Ser Arg
1               5                   10                  15

<210> SEQ ID NO 354
<211> LENGTH: 14
<212> TYPE: PRT
<213> ORGANISM: Artificial
<220> FEATURE:
<223> OTHER INFORMATION: Synthetic Construct

<400> SEQUENCE: 354

Ala Asp Ser Asn Pro Arg Gly Val Ser Ala Tyr Leu Ser Arg
1               5                   10

<210> SEQ ID NO 355
<211> LENGTH: 13
<212> TYPE: PRT
<213> ORGANISM: Artificial
<220> FEATURE:
<223> OTHER INFORMATION: Synthetic Construct

<400> SEQUENCE: 355

Asp Ser Asn Pro Arg Gly Val Ser Ala Tyr Leu Ser Arg
1               5                   10

<210> SEQ ID NO 356
<211> LENGTH: 12
<212> TYPE: PRT
<213> ORGANISM: Artificial
<220> FEATURE:
<223> OTHER INFORMATION: Synthetic Construct

<400> SEQUENCE: 356

Ser Asn Pro Arg Gly Val Ser Ala Tyr Leu Ser Arg
1               5                   10

<210> SEQ ID NO 357
<211> LENGTH: 11
<212> TYPE: PRT
<213> ORGANISM: Artificial
<220> FEATURE:
<223> OTHER INFORMATION: Synthetic Construct

<400> SEQUENCE: 357

Asn Pro Arg Gly Val Ser Ala Tyr Leu Ser Arg
1               5                   10

<210> SEQ ID NO 358
<211> LENGTH: 10
<212> TYPE: PRT
<213> ORGANISM: Artificial
<220> FEATURE:
<223> OTHER INFORMATION: Synthetic Construct

<400> SEQUENCE: 358

Pro Arg Gly Val Ser Ala Tyr Leu Ser Arg
1               5                   10

<210> SEQ ID NO 359
<211> LENGTH: 9
<212> TYPE: PRT
<213> ORGANISM: Artificial
<220> FEATURE:

```
<223> OTHER INFORMATION: Synthetic Construct

<400> SEQUENCE: 359

Arg Gly Val Ser Ala Tyr Leu Ser Arg
1               5

<210> SEQ ID NO 360
<211> LENGTH: 8
<212> TYPE: PRT
<213> ORGANISM: Artificial
<220> FEATURE:
<223> OTHER INFORMATION: Synthetic Construct

<400> SEQUENCE: 360

Gly Val Ser Ala Tyr Leu Ser Arg
1               5

<210> SEQ ID NO 361
<211> LENGTH: 7
<212> TYPE: PRT
<213> ORGANISM: Artificial
<220> FEATURE:
<223> OTHER INFORMATION: Synthetic Construct

<400> SEQUENCE: 361

Val Ser Ala Tyr Leu Ser Arg
1               5

<210> SEQ ID NO 362
<211> LENGTH: 6
<212> TYPE: PRT
<213> ORGANISM: Artificial
<220> FEATURE:
<223> OTHER INFORMATION: Synthetic Construct

<400> SEQUENCE: 362

Ser Ala Tyr Leu Ser Arg
1               5

<210> SEQ ID NO 363
<211> LENGTH: 5
<212> TYPE: PRT
<213> ORGANISM: Artificial
<220> FEATURE:
<223> OTHER INFORMATION: Synthetic Construct

<400> SEQUENCE: 363

Ala Tyr Leu Ser Arg
1               5

<210> SEQ ID NO 364
<211> LENGTH: 4
<212> TYPE: PRT
<213> ORGANISM: Artificial
<220> FEATURE:
<223> OTHER INFORMATION: Synthetic Construct

<400> SEQUENCE: 364

Tyr Leu Ser Arg
1

<210> SEQ ID NO 365
<211> LENGTH: 14
<212> TYPE: PRT
<213> ORGANISM: Artificial
<220> FEATURE:
<223> OTHER INFORMATION: Synthetic Construct
```

<400> SEQUENCE: 365

Cys Ala Asp Ser Asn Pro Arg Gly Val Ser Ala Tyr Leu Ser
1               5                   10

<210> SEQ ID NO 366
<211> LENGTH: 13
<212> TYPE: PRT
<213> ORGANISM: Artificial
<220> FEATURE:
<223> OTHER INFORMATION: Synthetic Construct

<400> SEQUENCE: 366

Ala Asp Ser Asn Pro Arg Gly Val Ser Ala Tyr Leu Ser
1               5                   10

<210> SEQ ID NO 367
<211> LENGTH: 12
<212> TYPE: PRT
<213> ORGANISM: Artificial
<220> FEATURE:
<223> OTHER INFORMATION: Synthetic Construct

<400> SEQUENCE: 367

Asp Ser Asn Pro Arg Gly Val Ser Ala Tyr Leu Ser
1               5                   10

<210> SEQ ID NO 368
<211> LENGTH: 11
<212> TYPE: PRT
<213> ORGANISM: Artificial
<220> FEATURE:
<223> OTHER INFORMATION: Synthetic Construct

<400> SEQUENCE: 368

Ser Asn Pro Arg Gly Val Ser Ala Tyr Leu Ser
1               5                   10

<210> SEQ ID NO 369
<211> LENGTH: 10
<212> TYPE: PRT
<213> ORGANISM: Artificial
<220> FEATURE:
<223> OTHER INFORMATION: Synthetic Construct

<400> SEQUENCE: 369

Asn Pro Arg Gly Val Ser Ala Tyr Leu Ser
1               5                   10

<210> SEQ ID NO 370
<211> LENGTH: 9
<212> TYPE: PRT
<213> ORGANISM: Artificial
<220> FEATURE:
<223> OTHER INFORMATION: Synthetic Construct

<400> SEQUENCE: 370

Pro Arg Gly Val Ser Ala Tyr Leu Ser
1               5

<210> SEQ ID NO 371
<211> LENGTH: 8
<212> TYPE: PRT
<213> ORGANISM: Artificial
<220> FEATURE:
<223> OTHER INFORMATION: Synthetic Construct

```
<400> SEQUENCE: 371

Arg Gly Val Ser Ala Tyr Leu Ser
1               5

<210> SEQ ID NO 372
<211> LENGTH: 7
<212> TYPE: PRT
<213> ORGANISM: Artificial
<220> FEATURE:
<223> OTHER INFORMATION: Synthetic Construct

<400> SEQUENCE: 372

Gly Val Ser Ala Tyr Leu Ser
1               5

<210> SEQ ID NO 373
<211> LENGTH: 6
<212> TYPE: PRT
<213> ORGANISM: Artificial
<220> FEATURE:
<223> OTHER INFORMATION: Synthetic Construct

<400> SEQUENCE: 373

Val Ser Ala Tyr Leu Ser
1               5

<210> SEQ ID NO 374
<211> LENGTH: 5
<212> TYPE: PRT
<213> ORGANISM: Artificial
<220> FEATURE:
<223> OTHER INFORMATION: Synthetic Construct

<400> SEQUENCE: 374

Ser Ala Tyr Leu Ser
1               5

<210> SEQ ID NO 375
<211> LENGTH: 4
<212> TYPE: PRT
<213> ORGANISM: Artificial
<220> FEATURE:
<223> OTHER INFORMATION: Synthetic Construct

<400> SEQUENCE: 375

Ala Tyr Leu Ser
1

<210> SEQ ID NO 376
<211> LENGTH: 13
<212> TYPE: PRT
<213> ORGANISM: Artificial
<220> FEATURE:
<223> OTHER INFORMATION: Synthetic Construct

<400> SEQUENCE: 376

Cys Ala Asp Ser Asn Pro Arg Gly Val Ser Ala Tyr Leu
1               5                   10

<210> SEQ ID NO 377
<211> LENGTH: 12
<212> TYPE: PRT
<213> ORGANISM: Artificial
<220> FEATURE:
<223> OTHER INFORMATION: Synthetic Construct

<400> SEQUENCE: 377
```

```
Ala Asp Ser Asn Pro Arg Gly Val Ser Ala Tyr Leu
1               5                   10

<210> SEQ ID NO 378
<211> LENGTH: 11
<212> TYPE: PRT
<213> ORGANISM: Artificial
<220> FEATURE:
<223> OTHER INFORMATION: Synthetic Construct

<400> SEQUENCE: 378

Asp Ser Asn Pro Arg Gly Val Ser Ala Tyr Leu
1               5                   10

<210> SEQ ID NO 379
<211> LENGTH: 10
<212> TYPE: PRT
<213> ORGANISM: Artificial
<220> FEATURE:
<223> OTHER INFORMATION: Synthetic Construct

<400> SEQUENCE: 379

Ser Asn Pro Arg Gly Val Ser Ala Tyr Leu
1               5                   10

<210> SEQ ID NO 380
<211> LENGTH: 9
<212> TYPE: PRT
<213> ORGANISM: Artificial
<220> FEATURE:
<223> OTHER INFORMATION: Synthetic Construct

<400> SEQUENCE: 380

Asn Pro Arg Gly Val Ser Ala Tyr Leu
1               5

<210> SEQ ID NO 381
<211> LENGTH: 8
<212> TYPE: PRT
<213> ORGANISM: Artificial
<220> FEATURE:
<223> OTHER INFORMATION: Synthetic Construct

<400> SEQUENCE: 381

Pro Arg Gly Val Ser Ala Tyr Leu
1               5

<210> SEQ ID NO 382
<211> LENGTH: 7
<212> TYPE: PRT
<213> ORGANISM: Artificial
<220> FEATURE:
<223> OTHER INFORMATION: Synthetic Construct

<400> SEQUENCE: 382

Arg Gly Val Ser Ala Tyr Leu
1               5

<210> SEQ ID NO 383
<211> LENGTH: 6
<212> TYPE: PRT
<213> ORGANISM: Artificial
<220> FEATURE:
<223> OTHER INFORMATION: Synthetic Construct

<400> SEQUENCE: 383
```

Gly Val Ser Ala Tyr Leu
1               5

<210> SEQ ID NO 384
<211> LENGTH: 5
<212> TYPE: PRT
<213> ORGANISM: Artificial
<220> FEATURE:
<223> OTHER INFORMATION: Synthetic Construct

<400> SEQUENCE: 384

Val Ser Ala Tyr Leu
1               5

<210> SEQ ID NO 385
<211> LENGTH: 4
<212> TYPE: PRT
<213> ORGANISM: Artificial
<220> FEATURE:
<223> OTHER INFORMATION: Synthetic Construct

<400> SEQUENCE: 385

Ser Ala Tyr Leu
1

<210> SEQ ID NO 386
<211> LENGTH: 12
<212> TYPE: PRT
<213> ORGANISM: Artificial
<220> FEATURE:
<223> OTHER INFORMATION: Synthetic Construct

<400> SEQUENCE: 386

Cys Ala Asp Ser Asn Pro Arg Gly Val Ser Ala Tyr
1               5                   10

<210> SEQ ID NO 387
<211> LENGTH: 11
<212> TYPE: PRT
<213> ORGANISM: Artificial
<220> FEATURE:
<223> OTHER INFORMATION: Synthetic Construct

<400> SEQUENCE: 387

Ala Asp Ser Asn Pro Arg Gly Val Ser Ala Tyr
1               5                   10

<210> SEQ ID NO 388
<211> LENGTH: 10
<212> TYPE: PRT
<213> ORGANISM: Artificial
<220> FEATURE:
<223> OTHER INFORMATION: Synthetic Construct

<400> SEQUENCE: 388

Asp Ser Asn Pro Arg Gly Val Ser Ala Tyr
1               5                   10

<210> SEQ ID NO 389
<211> LENGTH: 9
<212> TYPE: PRT
<213> ORGANISM: Artificial
<220> FEATURE:
<223> OTHER INFORMATION: Synthetic Construct

<400> SEQUENCE: 389

Ser Asn Pro Arg Gly Val Ser Ala Tyr

```
1               5

<210> SEQ ID NO 390
<211> LENGTH: 8
<212> TYPE: PRT
<213> ORGANISM: Artificial
<220> FEATURE:
<223> OTHER INFORMATION: Synthetic Construct

<400> SEQUENCE: 390

Asn Pro Arg Gly Val Ser Ala Tyr
1               5

<210> SEQ ID NO 391
<211> LENGTH: 7
<212> TYPE: PRT
<213> ORGANISM: Artificial
<220> FEATURE:
<223> OTHER INFORMATION: Synthetic Construct

<400> SEQUENCE: 391

Pro Arg Gly Val Ser Ala Tyr
1               5

<210> SEQ ID NO 392
<211> LENGTH: 6
<212> TYPE: PRT
<213> ORGANISM: Artificial
<220> FEATURE:
<223> OTHER INFORMATION: Synthetic Construct

<400> SEQUENCE: 392

Arg Gly Val Ser Ala Tyr
1               5

<210> SEQ ID NO 393
<211> LENGTH: 5
<212> TYPE: PRT
<213> ORGANISM: Artificial
<220> FEATURE:
<223> OTHER INFORMATION: Synthetic Construct

<400> SEQUENCE: 393

Gly Val Ser Ala Tyr
1               5

<210> SEQ ID NO 394
<211> LENGTH: 4
<212> TYPE: PRT
<213> ORGANISM: Artificial
<220> FEATURE:
<223> OTHER INFORMATION: Synthetic Construct

<400> SEQUENCE: 394

Val Ser Ala Tyr
1

<210> SEQ ID NO 395
<211> LENGTH: 11
<212> TYPE: PRT
<213> ORGANISM: Artificial
<220> FEATURE:
<223> OTHER INFORMATION: Synthetic Construct

<400> SEQUENCE: 395

Cys Ala Asp Ser Asn Pro Arg Gly Val Ser Ala
1               5                   10
```

```
<210> SEQ ID NO 396
<211> LENGTH: 10
<212> TYPE: PRT
<213> ORGANISM: Artificial
<220> FEATURE:
<223> OTHER INFORMATION: Synthetic Construct

<400> SEQUENCE: 396

Ala Asp Ser Asn Pro Arg Gly Val Ser Ala
1               5                   10

<210> SEQ ID NO 397
<211> LENGTH: 9
<212> TYPE: PRT
<213> ORGANISM: Artificial
<220> FEATURE:
<223> OTHER INFORMATION: Synthetic Construct

<400> SEQUENCE: 397

Asp Ser Asn Pro Arg Gly Val Ser Ala
1               5

<210> SEQ ID NO 398
<211> LENGTH: 8
<212> TYPE: PRT
<213> ORGANISM: Artificial
<220> FEATURE:
<223> OTHER INFORMATION: Synthetic Construct

<400> SEQUENCE: 398

Ser Asn Pro Arg Gly Val Ser Ala
1               5

<210> SEQ ID NO 399
<211> LENGTH: 7
<212> TYPE: PRT
<213> ORGANISM: Artificial
<220> FEATURE:
<223> OTHER INFORMATION: Synthetic Construct

<400> SEQUENCE: 399

Asn Pro Arg Gly Val Ser Ala
1               5

<210> SEQ ID NO 400
<211> LENGTH: 6
<212> TYPE: PRT
<213> ORGANISM: Artificial
<220> FEATURE:
<223> OTHER INFORMATION: Synthetic Construct

<400> SEQUENCE: 400

Pro Arg Gly Val Ser Ala
1               5

<210> SEQ ID NO 401
<211> LENGTH: 5
<212> TYPE: PRT
<213> ORGANISM: Artificial
<220> FEATURE:
<223> OTHER INFORMATION: Synthetic Construct

<400> SEQUENCE: 401

Arg Gly Val Ser Ala
1               5
```

```
<210> SEQ ID NO 402
<211> LENGTH: 4
<212> TYPE: PRT
<213> ORGANISM: Artificial
<220> FEATURE:
<223> OTHER INFORMATION: Synthetic Construct

<400> SEQUENCE: 402

Gly Val Ser Ala
1

<210> SEQ ID NO 403
<211> LENGTH: 10
<212> TYPE: PRT
<213> ORGANISM: Artificial
<220> FEATURE:
<223> OTHER INFORMATION: Synthetic Construct

<400> SEQUENCE: 403

Cys Ala Asp Ser Asn Pro Arg Gly Val Ser
1               5                   10

<210> SEQ ID NO 404
<211> LENGTH: 9
<212> TYPE: PRT
<213> ORGANISM: Artificial
<220> FEATURE:
<223> OTHER INFORMATION: Synthetic Construct

<400> SEQUENCE: 404

Ala Asp Ser Asn Pro Arg Gly Val Ser
1               5

<210> SEQ ID NO 405
<211> LENGTH: 8
<212> TYPE: PRT
<213> ORGANISM: Artificial
<220> FEATURE:
<223> OTHER INFORMATION: Synthetic Construct

<400> SEQUENCE: 405

Asp Ser Asn Pro Arg Gly Val Ser
1               5

<210> SEQ ID NO 406
<211> LENGTH: 7
<212> TYPE: PRT
<213> ORGANISM: Artificial
<220> FEATURE:
<223> OTHER INFORMATION: Synthetic Construct

<400> SEQUENCE: 406

Ser Asn Pro Arg Gly Val Ser
1               5

<210> SEQ ID NO 407
<211> LENGTH: 6
<212> TYPE: PRT
<213> ORGANISM: Artificial
<220> FEATURE:
<223> OTHER INFORMATION: Synthetic Construct

<400> SEQUENCE: 407

Asn Pro Arg Gly Val Ser
1               5
```

```
<210> SEQ ID NO 408
<211> LENGTH: 5
<212> TYPE: PRT
<213> ORGANISM: Artificial
<220> FEATURE:
<223> OTHER INFORMATION: Synthetic Construct

<400> SEQUENCE: 408

Pro Arg Gly Val Ser
1               5

<210> SEQ ID NO 409
<211> LENGTH: 4
<212> TYPE: PRT
<213> ORGANISM: Artificial
<220> FEATURE:
<223> OTHER INFORMATION: Synthetic Construct

<400> SEQUENCE: 409

Arg Gly Val Ser
1

<210> SEQ ID NO 410
<211> LENGTH: 9
<212> TYPE: PRT
<213> ORGANISM: Artificial
<220> FEATURE:
<223> OTHER INFORMATION: Synthetic Construct

<400> SEQUENCE: 410

Cys Ala Asp Ser Asn Pro Arg Gly Val
1               5

<210> SEQ ID NO 411
<211> LENGTH: 8
<212> TYPE: PRT
<213> ORGANISM: Artificial
<220> FEATURE:
<223> OTHER INFORMATION: Synthetic Construct

<400> SEQUENCE: 411

Ala Asp Ser Asn Pro Arg Gly Val
1               5

<210> SEQ ID NO 412
<211> LENGTH: 7
<212> TYPE: PRT
<213> ORGANISM: Artificial
<220> FEATURE:
<223> OTHER INFORMATION: Synthetic Construct

<400> SEQUENCE: 412

Asp Ser Asn Pro Arg Gly Val
1               5

<210> SEQ ID NO 413
<211> LENGTH: 6
<212> TYPE: PRT
<213> ORGANISM: Artificial
<220> FEATURE:
<223> OTHER INFORMATION: Synthetic Construct

<400> SEQUENCE: 413

Ser Asn Pro Arg Gly Val
1               5

<210> SEQ ID NO 414
```

```
<211> LENGTH: 5
<212> TYPE: PRT
<213> ORGANISM: Artificial
<220> FEATURE:
<223> OTHER INFORMATION: Synthetic Construct

<400> SEQUENCE: 414

Asn Pro Arg Gly Val
1               5

<210> SEQ ID NO 415
<211> LENGTH: 4
<212> TYPE: PRT
<213> ORGANISM: Artificial
<220> FEATURE:
<223> OTHER INFORMATION: Synthetic Construct

<400> SEQUENCE: 415

Pro Arg Gly Val
1

<210> SEQ ID NO 416
<211> LENGTH: 8
<212> TYPE: PRT
<213> ORGANISM: Artificial
<220> FEATURE:
<223> OTHER INFORMATION: Synthetic Construct

<400> SEQUENCE: 416

Cys Ala Asp Ser Asn Pro Arg Gly
1               5

<210> SEQ ID NO 417
<211> LENGTH: 7
<212> TYPE: PRT
<213> ORGANISM: Artificial
<220> FEATURE:
<223> OTHER INFORMATION: Synthetic Construct

<400> SEQUENCE: 417

Ala Asp Ser Asn Pro Arg Gly
1               5

<210> SEQ ID NO 418
<211> LENGTH: 6
<212> TYPE: PRT
<213> ORGANISM: Artificial
<220> FEATURE:
<223> OTHER INFORMATION: Synthetic Construct

<400> SEQUENCE: 418

Asp Ser Asn Pro Arg Gly
1               5

<210> SEQ ID NO 419
<211> LENGTH: 5
<212> TYPE: PRT
<213> ORGANISM: Artificial
<220> FEATURE:
<223> OTHER INFORMATION: Synthetic Construct

<400> SEQUENCE: 419

Ser Asn Pro Arg Gly
1               5

<210> SEQ ID NO 420
<211> LENGTH: 4
```

```
<212> TYPE: PRT
<213> ORGANISM: Artificial
<220> FEATURE:
<223> OTHER INFORMATION: Synthetic Construct

<400> SEQUENCE: 420

Asn Pro Arg Gly
1

<210> SEQ ID NO 421
<211> LENGTH: 7
<212> TYPE: PRT
<213> ORGANISM: Artificial
<220> FEATURE:
<223> OTHER INFORMATION: Synthetic Construct

<400> SEQUENCE: 421

Cys Ala Asp Ser Asn Pro Arg
1               5

<210> SEQ ID NO 422
<211> LENGTH: 6
<212> TYPE: PRT
<213> ORGANISM: Artificial
<220> FEATURE:
<223> OTHER INFORMATION: Synthetic Construct

<400> SEQUENCE: 422

Ala Asp Ser Asn Pro Arg
1               5

<210> SEQ ID NO 423
<211> LENGTH: 5
<212> TYPE: PRT
<213> ORGANISM: Artificial
<220> FEATURE:
<223> OTHER INFORMATION: Synthetic Construct

<400> SEQUENCE: 423

Asp Ser Asn Pro Arg
1               5

<210> SEQ ID NO 424
<211> LENGTH: 4
<212> TYPE: PRT
<213> ORGANISM: Artificial
<220> FEATURE:
<223> OTHER INFORMATION: Synthetic Construct

<400> SEQUENCE: 424

Ser Asn Pro Arg
1

<210> SEQ ID NO 425
<211> LENGTH: 6
<212> TYPE: PRT
<213> ORGANISM: Artificial
<220> FEATURE:
<223> OTHER INFORMATION: Synthetic Construct

<400> SEQUENCE: 425

Cys Ala Asp Ser Asn Pro
1               5

<210> SEQ ID NO 426
<211> LENGTH: 5
<212> TYPE: PRT
```

```
<213> ORGANISM: Artificial
<220> FEATURE:
<223> OTHER INFORMATION: Synthetic Construct

<400> SEQUENCE: 426

Ala Asp Ser Asn Pro
1               5

<210> SEQ ID NO 427
<211> LENGTH: 4
<212> TYPE: PRT
<213> ORGANISM: Artificial
<220> FEATURE:
<223> OTHER INFORMATION: Synthetic Construct

<400> SEQUENCE: 427

Asp Ser Asn Pro
1

<210> SEQ ID NO 428
<211> LENGTH: 5
<212> TYPE: PRT
<213> ORGANISM: Artificial
<220> FEATURE:
<223> OTHER INFORMATION: Synthetic Construct

<400> SEQUENCE: 428

Cys Ala Asp Ser Asn
1               5

<210> SEQ ID NO 429
<211> LENGTH: 4
<212> TYPE: PRT
<213> ORGANISM: Artificial
<220> FEATURE:
<223> OTHER INFORMATION: Synthetic Construct

<400> SEQUENCE: 429

Ala Asp Ser Asn
1

<210> SEQ ID NO 430
<211> LENGTH: 4
<212> TYPE: PRT
<213> ORGANISM: Artificial
<220> FEATURE:
<223> OTHER INFORMATION: Synthetic Construct

<400> SEQUENCE: 430

Cys Ala Asp Ser
1

<210> SEQ ID NO 431
<211> LENGTH: 21
<212> TYPE: DNA
<213> ORGANISM: Artificial
<220> FEATURE:
<223> OTHER INFORMATION: Synthetic Construct

<400> SEQUENCE: 431
tcgtcgtttt tcggtgcttt t                                           21

<210> SEQ ID NO 432
<211> LENGTH: 21
<212> TYPE: DNA
<213> ORGANISM: Artificial
<220> FEATURE:
```

-continued

```
<223> OTHER INFORMATION: Synthetic Construct

<400> SEQUENCE: 432
tcgtcgtttt tcggtcgttt t                                              21

<210> SEQ ID NO 433
<211> LENGTH: 24
<212> TYPE: DNA
<213> ORGANISM: Artificial
<220> FEATURE:
<223> OTHER INFORMATION: Synthetic Construct

<400> SEQUENCE: 433
tcgtcgtttt gtcgttttgt cgtt                                           24

<210> SEQ ID NO 434
<211> LENGTH: 18
<212> TYPE: PRT
<213> ORGANISM: Artificial
<220> FEATURE:
<223> OTHER INFORMATION: Synthetic Construct

<400> SEQUENCE: 434

Ala Asp Ser Asn Pro Arg Gly Val Ser Ala Tyr Leu Ser Arg Pro Ser
1               5                   10                  15

Pro Cys

<210> SEQ ID NO 435
<211> LENGTH: 133
<212> TYPE: PRT
<213> ORGANISM: Artificial
<220> FEATURE:
<223> OTHER INFORMATION: Synthetic Construct

<400> SEQUENCE: 435

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
                20                  25                  30

Val Ala Ser Leu Ser Gln Ala Gly Ala Val Pro Ala Leu Glu Lys Arg
            35                  40                  45

Val Thr Val Ser Val Ser Gln Pro Ser Arg Asn Arg Lys Asn Tyr Lys
        50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
            115                 120                 125

Leu Asn Pro Ala Tyr
        130

<210> SEQ ID NO 436
<211> LENGTH: 21
<212> TYPE: PRT
<213> ORGANISM: Artificial
<220> FEATURE:
<223> OTHER INFORMATION: Synthetic Construct

<400> SEQUENCE: 436
```

```
Ser Thr Arg Lys Glu Glu Lys Gln Arg Asn Gly Thr Leu Thr Val Thr
1               5                   10                  15

Ser Thr Leu Pro Cys
            20
```

<210> SEQ ID NO 437
<211> LENGTH: 14
<212> TYPE: PRT
<213> ORGANISM: Artificial
<220> FEATURE:
<223> OTHER INFORMATION: Synthetic Construct

<400> SEQUENCE: 437

```
Leu Val Val Asp Leu Ala Pro Ser Lys Gly Thr Val Asn Cys
1               5                   10
```

<210> SEQ ID NO 438
<211> LENGTH: 20
<212> TYPE: PRT
<213> ORGANISM: Artificial
<220> FEATURE:
<223> OTHER INFORMATION: Synthetic Construct

<400> SEQUENCE: 438

```
Cys Leu Val Val Asp Leu Ala Pro Ser Lys Gly Thr Val Asn Gly Gly
1               5                   10                  15

Gly Gly Gly Cys
            20
```

<210> SEQ ID NO 439
<211> LENGTH: 19
<212> TYPE: PRT
<213> ORGANISM: Artificial
<220> FEATURE:
<223> OTHER INFORMATION: Synthetic Construct

<400> SEQUENCE: 439

```
Cys Ala Asp Ser Asn Pro Arg Gly Val Ser Ala Tyr Leu Ser Arg Pro
1               5                   10                  15

Ser Pro Cys
```

<210> SEQ ID NO 440
<211> LENGTH: 21
<212> TYPE: DNA
<213> ORGANISM: Artificial
<220> FEATURE:
<223> OTHER INFORMATION: Synthetic Construct

<400> SEQUENCE: 440
ggggacgacg tcgtgggggg g                                           21

<210> SEQ ID NO 441
<211> LENGTH: 24
<212> TYPE: DNA
<213> ORGANISM: Artificial
<220> FEATURE:
<223> OTHER INFORMATION: Synthetic Construct

<400> SEQUENCE: 441
tcgtcgtttc gtcgttttgt cgtt                                        24

<210> SEQ ID NO 442
<211> LENGTH: 24
<212> TYPE: DNA

```
<213> ORGANISM: Artificial
<220> FEATURE:
<223> OTHER INFORMATION: Synthetic Construct

<400> SEQUENCE: 442
tcgtcgtttt gtcgtttttt tcga                                24

<210> SEQ ID NO 443
<211> LENGTH: 22
<212> TYPE: DNA
<213> ORGANISM: Artificial
<220> FEATURE:
<223> OTHER INFORMATION: Synthetic Construct

<400> SEQUENCE: 443
tcgcgtcgtt cggcgcgcgc cg                                  22

<210> SEQ ID NO 444
<211> LENGTH: 23
<212> TYPE: DNA
<213> ORGANISM: Artificial
<220> FEATURE:
<223> OTHER INFORMATION: Synthetic Construct

<400> SEQUENCE: 444
tcgtcgacgt tcggcgcgcg ccg                                 23

<210> SEQ ID NO 445
<211> LENGTH: 21
<212> TYPE: DNA
<213> ORGANISM: Artificial
<220> FEATURE:
<223> OTHER INFORMATION: Synthetic Construct

<400> SEQUENCE: 445
tcggacgttc ggcgcgcgcc g                                   21

<210> SEQ ID NO 446
<211> LENGTH: 19
<212> TYPE: DNA
<213> ORGANISM: Artificial
<220> FEATURE:
<223> OTHER INFORMATION: Synthetic Construct

<400> SEQUENCE: 446
tcggacgttc ggcgcgccg                                      19

<210> SEQ ID NO 447
<211> LENGTH: 20
<212> TYPE: DNA
<213> ORGANISM: Artificial
<220> FEATURE:
<223> OTHER INFORMATION: Synthetic Construct

<400> SEQUENCE: 447
tcgcgtcgtt cggcgcgccg                                     20

<210> SEQ ID NO 448
<211> LENGTH: 20
<212> TYPE: DNA
<213> ORGANISM: Artificial
<220> FEATURE:
<223> OTHER INFORMATION: Synthetic Construct

<400> SEQUENCE: 448
tcgacgttcg gcgcgcgccg                                     20
```

<210> SEQ ID NO 449
<211> LENGTH: 18
<212> TYPE: DNA
<213> ORGANISM: Artificial
<220> FEATURE:
<223> OTHER INFORMATION: Synthetic Construct

<400> SEQUENCE: 449
tcgacgttcg gcgcgccg                                                 18

<210> SEQ ID NO 450
<211> LENGTH: 18
<212> TYPE: DNA
<213> ORGANISM: Artificial
<220> FEATURE:
<223> OTHER INFORMATION: Synthetic Construct

<400> SEQUENCE: 450
tcgcgtcgtt cggcgccg                                                 18

<210> SEQ ID NO 451
<211> LENGTH: 22
<212> TYPE: DNA
<213> ORGANISM: Artificial
<220> FEATURE:
<223> OTHER INFORMATION: Synthetic Construct

<400> SEQUENCE: 451
tcgcgacgtt cggcgcgcgc cg                                            22

<210> SEQ ID NO 452
<211> LENGTH: 22
<212> TYPE: DNA
<213> ORGANISM: Artificial
<220> FEATURE:
<223> OTHER INFORMATION: Synthetic Construct

<400> SEQUENCE: 452
tcgtcgtttt cggcgcgcgc cg                                            22

<210> SEQ ID NO 453
<211> LENGTH: 22
<212> TYPE: DNA
<213> ORGANISM: Artificial
<220> FEATURE:
<223> OTHER INFORMATION: Synthetic Construct

<400> SEQUENCE: 453
tcgtcgtttt cggcggccgc cg                                            22

<210> SEQ ID NO 454
<211> LENGTH: 24
<212> TYPE: DNA
<213> ORGANISM: Artificial
<220> FEATURE:
<223> OTHER INFORMATION: Synthetic Construct

<400> SEQUENCE: 454
tcgtcgtttt acggcgccgt gccg                                          24

<210> SEQ ID NO 455
<211> LENGTH: 23
<212> TYPE: DNA
<213> ORGANISM: Artificial
<220> FEATURE:

```
<223> OTHER INFORMATION: Synthetic Construct

<400> SEQUENCE: 455
tcgtcgtttt cggcgcgcgc cgt                                              23

<210> SEQ ID NO 456
<211> LENGTH: 23
<212> TYPE: DNA
<213> ORGANISM: Artificial
<220> FEATURE:
<223> OTHER INFORMATION: Synthetic Construct

<400> SEQUENCE: 456
tcgtcgacga tcggcgcgcg ccg                                              23

<210> SEQ ID NO 457
<211> LENGTH: 20
<212> TYPE: PRT
<213> ORGANISM: Artificial
<220> FEATURE:
<223> OTHER INFORMATION: Synthetic Construct

<400> SEQUENCE: 457

Ala Asp Ser Asn Pro Arg Gly Val Ser Ala Tyr Leu Ser Arg Pro Ser
 1               5                  10                  15

Pro Gly Gly Cys
            20

<210> SEQ ID NO 458
<211> LENGTH: 16
<212> TYPE: PRT
<213> ORGANISM: Artificial
<220> FEATURE:
<223> OTHER INFORMATION: Synthetic Construct

<400> SEQUENCE: 458

Gln Cys Ile Val Asp His Pro Asp Phe Pro Lys Pro Ile Val Arg Ser
 1               5                  10                  15

<210> SEQ ID NO 459
<211> LENGTH: 18
<212> TYPE: PRT
<213> ORGANISM: Artificial
<220> FEATURE:
<223> OTHER INFORMATION: Synthetic Construct

<400> SEQUENCE: 459

Pro Asp His Glu Pro Arg Gly Val Ile Thr Tyr Leu Ile Pro Pro Ser
 1               5                  10                  15

Pro Cys
```

IGE CH3 PEPTIDE VACCINE

CROSS-REFERENCE TO RELATED APPLICATIONS

This application is a division of U.S. application Ser. No. 13/152,032 filed on Jun. 2, 2011, now allowed, which claims benefit of U.S. Provisional Application No. 61/352,127 filed on Jun. 7, 2010. The disclosure of each of U.S. application Ser. No. 13/152,032 and U.S. Provisional Application No. 61/352,127 is incorporated herein by reference in its entirety.

REFERENCE TO SEQUENCE LISTING

This application is being filed electronically via EFS-Web and includes an electronically submitted sequence listing in .txt format. The .txt file contains a sequence listing entitled "SeqPC71675B_ST25.txt" created on Mar. 25, 2014 and having a size of 84 KB. The sequence listing contained in the .txt file is part of the specification and is herein incorporated by reference in its entirety.

FIELD OF THE INVENTION

The present invention relates to the provision of novel immunogens comprising an antigenic IgE peptide preferably linked to an immunogenic carrier for the prevention, treatment or alleviation of IgE-mediated disorders. The invention further relates to methods for production of these medicaments, immunogenic compositions and pharmaceutical composition thereof and their use in medicine.

BACKGROUND

During the past few decades, allergic diseases have increased to almost epidemic proportions and estimates suggest that 20-30% of the total population in many Western countries is affected. The key role played by IgE in initiating the allergic responses is well documented. Upon release from B lymphocytes, IgE binds to the high affinity IgE receptor (FceRI) present on mast cells and basophils. The subsequent cross-linkage of adjacent IgE molecules on these cells by specific allergens then results in their activation, leading to the release of a number of pro-inflammatory mediators (e.g. histamine, leukotrinenes, prostaglandins), as well as key cytokines and chemokines. Consequently, acute local responses are followed by recruitment and activation of other inflammatory cells (e.g. eosinophils, T lymphocytes), thereby amplifying the allergic cascade. Dendritic cells, for example those present at sites of allergic inflammation (e.g. the lung), may also express FceR1 and can use this receptor to selectively and efficiently take up allergens present in immune complexes with IgE and process these allergens selectively for presentation to allergen-specific T-cells, thus providing a mechanism for persistent T-cell activation and pathologic inflammatory responses.

Most current treatment regimens aim at relieving symptoms rather than treating the cause of the disease and are based primarily on the use of antihistamines, antileukotrienes, cromoglycates, beta-agonists and on general anti-inflammatory compounds such as corticosteroids. Although some of the affected patients have their disease under relatively good control with these drugs, their frequency of administration (often daily or even several times a day) often leads to poor patient compliance and subsequent deterioration of the disease. In addition, in some cases such as severe asthma and severe atopic dermatitis, existing therapies are insufficient to control the disease.

Very recently, a monoclonal antibody (omalizumab, also termed E25, marketed under the trade name Xolair®; Presta et al. *J Immunol.* 1993 Sep. 1; 151(5):2623-32.) gained approval from several agencies around the world, primarily for treatment of severe asthma and rhinitis. Despite showing efficacy against severe asthma, this antibody still has some drawbacks. Firstly, this is a humanized murine monoclonal antibody, and as such, does not entirely preclude immunological reactions in human patients, thus possibly raising some safety concerns. Secondly, the dose of omalizumab used in treating severe asthma is based on both body weight and the level of circulating free IgE. Patients whose body weight and circulating free IgE that deviate from a specified range are recommended not to use this treatment. Those patients that can be treated may require to receive up to three subcutaneous injections once every two weeks. This heavily impacts on the costs of treatment (estimated to range at US$15,000-44,000 annually per patient), as well as on the quality of life of the patients, making it difficult to use as a general strategy for treatment of allergies.

To overcome the problems of high cost and frequent administrations, an alternative is to trigger our own immune system to produce the therapeutic antibodies by vaccination.

In the course of their investigations, previous workers in the allergy field have encountered a number of considerations, and problems, which have to be taken into account when designing new anti-allergy therapies. One of the most dangerous problems revolves around the involvement of IgE cross-linking in the histamine release signal. It is most often the case that the generation of anti-IgE antibodies during active vaccination, are capable of triggering histamine release per se, by the cross-linking of neighbouring IgE-receptor complexes in the absence of allergen. This phenomenon is termed anaphylactogenicity. Indeed many commercially available anti-IgE monoclonal antibodies which are normally used for IgE detection assays, are anaphylactogenic, and consequently useless and potentially dangerous if administered to a patient. Therefore, in order to be safe and effective, the passively administered, or vaccine induced, antibodies must bind in a region of IgE which is capable of inhibiting IgE activities without being anaphylactic per se.

It is therefore desirable to provide a composition, such as an antigenic IgE peptide, or the combination of several thereof, coupled to an immunogenic carrier, and optionally administered with one or more adjuvants, able to induce potent non anaphylactogenic anti-IgE antibodies in an individual capable of significantly reducing levels of circulating free IgE. Increased potency would typically result in the following benefits: lower doses required to achieve clinical benefits, lower volume of injection required e.g. for subcutaneous or intramuscular administration (compared to monoclonal antibody therapies, for example), lower cost of treatment, increased chances of treatment success, decreased frequency of administration in the treatment regimen, thus providing access to treatment to a wider population of patients, including patients with higher body weight and/or high levels of circulating IgE, and improving patients' quality of life.

SUMMARY OF THE INVENTION

The present invention relates to an immunogen comprising an antigenic IgE peptide preferably linked to an immunogenic carrier.

In an embodiment, the present invention relates to an immunogen comprising at least one antigenic IgE peptide linked to an immunogenic carrier, wherein said antigenic IgE peptide consists of an amino acid sequence selected from the group consisting of SEQ ID Nos: 1 to 430 and wherein said immunogenic carrier is selected in the group consisting of DT (Diphtheria toxoin), TT (tetanus toxoid) or fragment C of TT, PD (*Haemophilus influenzae* protein D), CRM197, CRM176, CRM228, CRM 45, CRM 9, CRM102, CRM 103 and CRM107 and wherein said antigenic IgE peptide is chemically cross linked to said immunogenic carrier. In an embodiment, said antigenic IgE peptide consists of an amino acid sequence selected from the group consisting of SEQ ID Nos: 220 to 310. In a further embodiment, said antigenic IgE peptide consists of an amino acid sequence selected from the group consisting of SEQ ID Nos:311 to 430.

In an embodiment, said antigenic IgE peptide further comprises either:
- at its C-terminus a peptide linker having the formula $(G)_nC$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0 said formula represents a cysteine) or;
- at its N-terminus a linker having the formula $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine) or;
- at its C-terminus a linker having the formula $(G)_nC$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n 0 or 1 (where n is equal to 0 said formula represents a cysteine) and at its N-terminus a linker having the formula $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine).

In an embodiment, said antigenic IgE peptide is chemically cross linked to said immunogenic carrier using a heterobifunctional cross-linker, preferably using SMPH (Succinimidyl-6-[β-maleimidopropionamido]hexanoate) or BAANS (bromoacetic acid N-hydroxysuccinimide ester) as cross linker.

In an embodiment, the invention relates to the above immunogens wherein the molar ratio of antigenic peptide to the immunogenic carrier is from about 1:1 to about 40:1, preferably the molar ratio of antigenic IgE peptide to the immunogenic carrier is from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

The invention also relates to a composition comprising at least two immunogens disclosed above, preferably wherein said antigenic IgE peptides are individually conjugated to said immunogenic carriers (i.e., all the antigenic IgE peptides that are linked to a given immunogenic carrier molecule have the same amino acid sequence). The invention also relates to immunogenic compositions comprising such immunogens or composition of immunogens, optionally comprising an adjuvant preferably selected from the group consisting of alum; CpG-containing oligonucleotides, preferably CpG7909 and CpG24555; and saponin-based adjuvants, preferably Iscomatrix.

Another aspect of the invention relates to pharmaceutical compositions comprising an immunogen or composition of immunogens according to the invention, or an immunogenic composition thereof, as well as to medical uses of said compositions.

In particular, the invention relates to an immunogen or composition of immunogens of the invention, or an immunogenic or pharmaceutical composition thereof, for use as a medicament, preferably in treatment, alleviation or prophylaxis of IgE-mediated disorders. The invention also relates to methods of inducing an immune response in an individual to self-IgE and to methods for treating, alleviating or preventing IgE-mediated disorders comprising administering an effective amount of said immunogen or composition of immunogens or immunogenic or pharmaceutical composition thereof.

DETAILED DESCRIPTION OF THE INVENTION

Definitions and General Techniques

Figure 1:
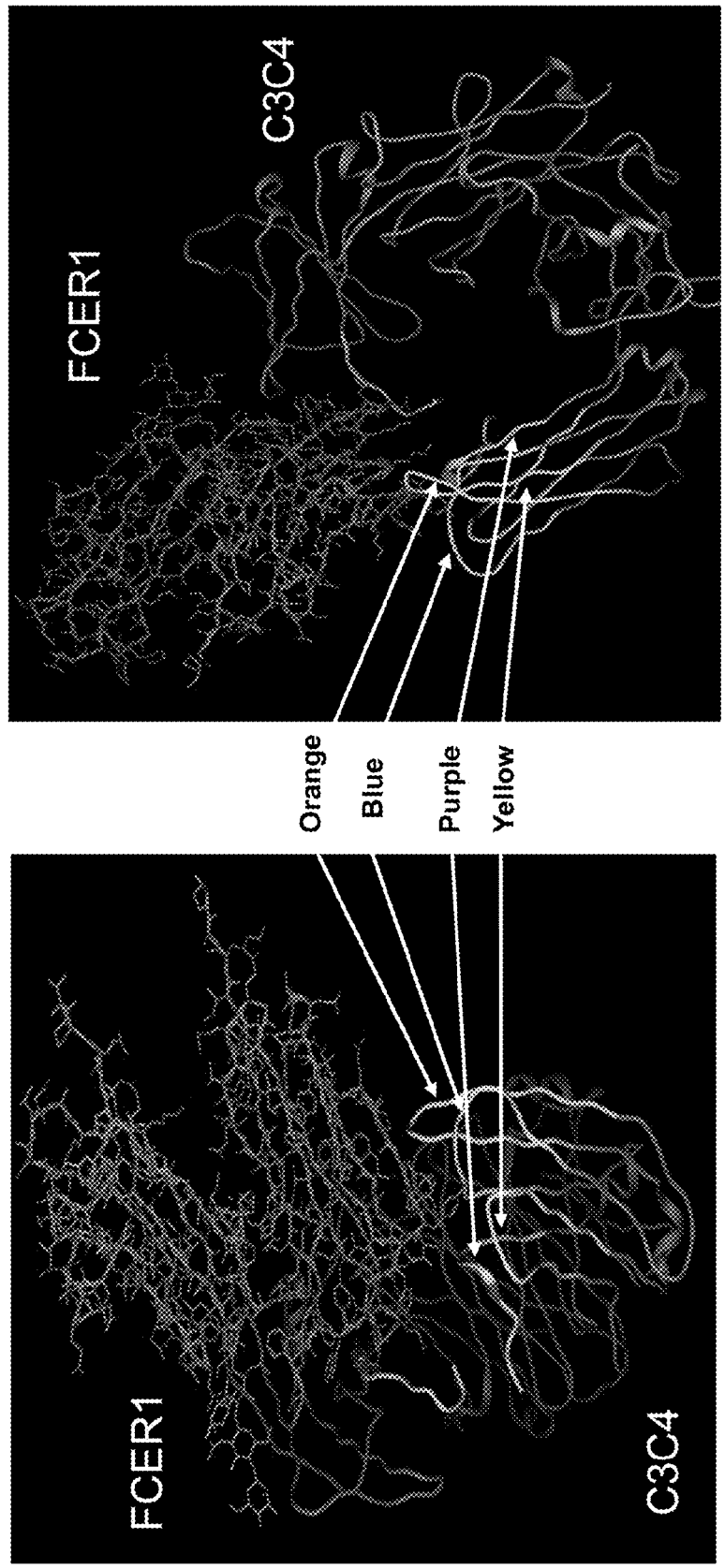
FIG. 1: Structural display of the interaction between the CH3-CH4 region of human IgE with its high affinity receptor FceRI. Displayed are 4 loops (blue, purple, orange and yellow) corresponding to the 4 peptides of SEQ ID Nos: 165, 312, 1 and 220 respectively.
Figure 2:
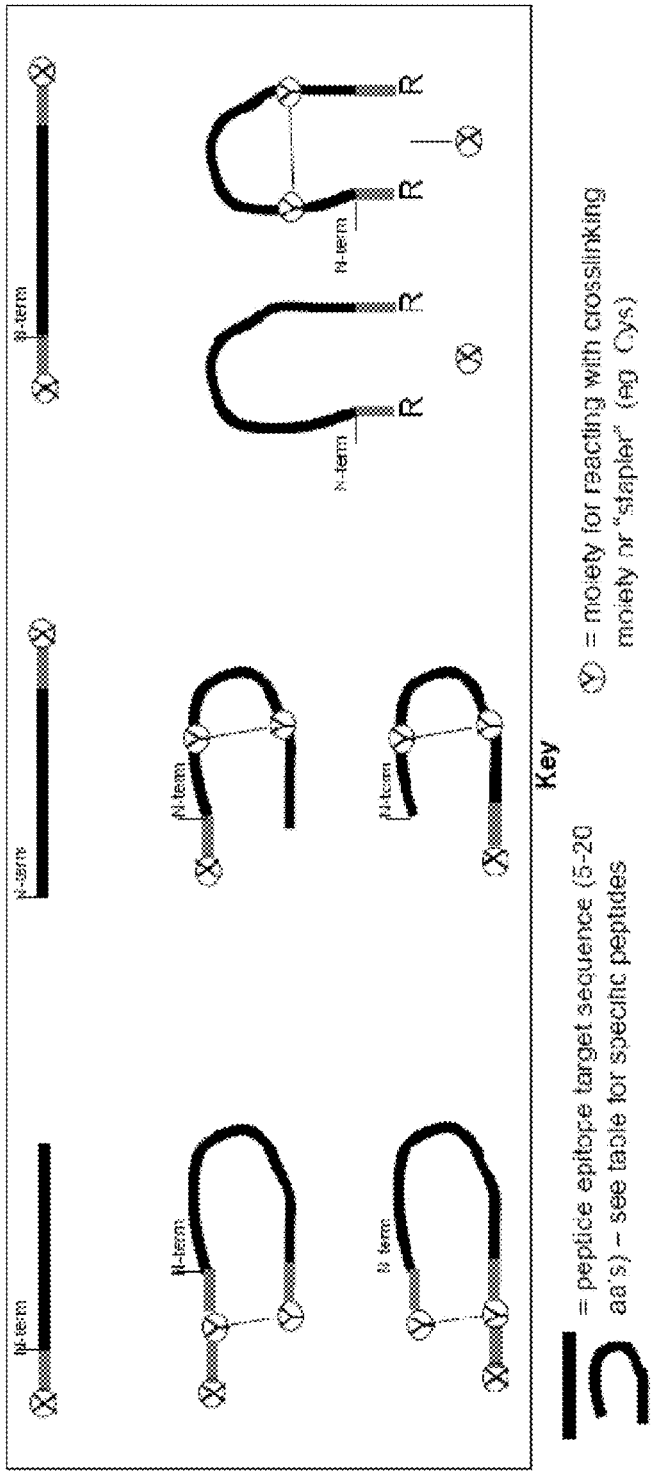
FIG. 2: Graphic depictions of peptide formats for inducing antibody responses to structurally defined epitopes of human IgE.

Unless otherwise defined herein, scientific and technical terms used in connection with the present invention shall have the meanings that are commonly understood by those of ordinary skill in the art. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). Enzymatic reactions and purification techniques are performed according to manufacturer's specifications, as commonly accomplished in the art or as described herein.

The nomenclature used in connection with, and the laboratory procedures and techniques of, analytical chemistry, synthetic organic chemistry, and medicinal and pharmaceutical chemistry described herein are those well known and commonly used in the art.

Throughout this specification and claims, the word "comprise," or variations such as "comprises" or "comprising," will be understood to imply the inclusion of a stated integer or group of integers but not the exclusion of any other integer or group of integers. When the terms "one," "a," or "an" are used in this disclosure, they mean "at least one" or "one or more,", unless otherwise indicated. Further, unless otherwise required by context, singular terms shall include pluralities and plural terms shall include the singular unless the content clearly dictates otherwise.

All publications, patents and patent applications cited herein, whether supra or infra, are hereby incorporated by reference in their entirety.

General Definitions

The term "peptide" or "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "isolated protein", "isolated polypeptide" or "isolated peptide" is a protein, polypeptide or peptide that by virtue of its origin or source of derivation (1) is not associated with naturally associated components that accompany it in its native state, (2) is free of other proteins from the same species, (3) is expressed by a cell from a different species, or (4) does not occur in nature. Thus, a peptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, when the term "purified" is used in reference to a molecule (e.g., a peptide, polypeptide or protein), it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified.

In some embodiments, a compound is substantially pure or purified when it is at least 20%, at least 30%, at least 40%, at least 50%, or at least 60%, by weight, free from organic molecules with which it is naturally associated or with which it is associated during manufacture. In some embodiments, the preparation is at least 70%, at least 75%, at least 90%, at least 95%, or at least 99%, by weight, of the compound of interest relative to its contaminants.

A substantially pure or purified compound can be obtained, for example, by extraction from a natural source (e.g., bacteria), by chemically synthesizing a compound, or by a combination of purification and chemical modification. A substantially pure or purified compound can also be obtained by, for example, enriching a sample having a compound that binds an antibody of interest. Purity can be measured by any appropriate method, e.g., chromatography, mass spectroscopy, high performance liquid chromatography analysis, etc.

The term "heterologous," as used herein in the context of an IgE peptide or polypeptide, where a IgE polypeptide fusion protein comprises an IgE peptide or polypeptide and a "heterologous" polypeptide, refers to a polypeptide that is other than an IgE peptide or polypeptide, e.g., a polypeptide that is not normally associated in nature with an IgE peptide or polypeptide. For example, a heterologous polypeptide bears no significant amino acid sequence identity to the IgE peptide or polypeptide, e.g., the heterologous polypeptide has less than about 50%, less than about 40%, less than about 30%, or less than about 20% amino acid sequence identity to the IgE peptide or polypeptide.

As used herein, the term "IgE-mediated disorder" or "IgE-related disorder" means a condition or disease which is characterized by the overproduction and/or hypersensitivity to the immunoglobulin IgE. Specifically it would be construed to include conditions associated with anaphylactic hypersensitivity and atopic allergies, including for example: asthma, allergic asthma, allergic rhinitis and conjunctivitis (hay fever), eczema, urticaria, atopic dermatitis, and food allergies including peanut allergy. The serious physiological condition of anaphylactic shock caused by, e. g., bee stings, snake bites, food or medication, is also encompassed under the scope of this term. Other IgE-mediated disorders include anaphylaxis, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, ulcerative colitis, indeterminate colitis and infectious colitis), urticaria, and psoriasis.

Antigenic IgE Peptide of the Invention

The present invention relates to IgE peptides, and peptides derived thereof, which have been identified as portions of the IgE CH3 domain able to form loops participating in the interaction of CH3-CH4 region with its high affinity receptor FceRI (cf FIG. 1). Such IgE peptides were shown to be immunogenic and non-anaphylactogenic.

Such antigenic IgE peptides may be used alone or in combination, preferably when conjugated to an immunogenic carrier, to induce auto anti-IgE antibodies in a subject in order to treat, prevent or ameliorate IgE-related disorders.

In particular, the present invention relates to an immunogen consisting of, consisting essentially of, or comprising an antigenic IgE peptide preferably linked to an immunogenic carrier.

In one embodiment, the antigenic IgE peptide of the invention consists of, consists essentially of, or comprises an amino acid sequence selected from the group consisting of SEQ ID Nos: 1 to 430.

In another embodiment, said antigenic IgE peptide consists of, consists essentially of, or comprises an amino acid sequence selected from the group consisting of SEQ ID Nos: 1 to 153.

In another embodiment, said antigenic IgE peptide consists of, consists essentially of, or comprises an amino acid sequence selected from the group consisting of SEQ ID Nos: 154 to 219.

In still another embodiment, said antigenic IgE peptide consists of, consists essentially of, or comprises an amino acid sequence selected from the group consisting of SEQ ID Nos: 220 to 310.

In still another embodiment, said antigenic IgE peptide consists of, consists essentially of, or comprises an amino acid sequence selected from the group consisting of SEQ ID Nos: 311 to 430.

In an embodiment, the antigenic IgE peptide of the invention consists of, or consists essentially of, an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430.

In another embodiment, the antigenic IgE peptide of the invention consists of, or consists essentially of, an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, and 153. Preferably, said antigenic IgE peptide consists of, or consists essentially of, an amino acid sequence selected from the group consisting of SEQ ID Nos: 1, 2, 3, 4, 5, 6, 7, 8, 9, 10, 11, 12, 13, 14, 15, 18, 19, 20, 21, 22, 23, 24, 25, 26, 27, 28, 29, 30, 31, 34, 35, 36, 37, 38, 39, 40, 41, 42, 43, 44, 45, 46, 49, 50, 51, 52, 53, 54, 55, 56, 57, 58, 59, 60, 63, 64, 65, 66, 67, 68, 69, 70, 71, 72, 73, 76, 77, 78, 79, 80, 81, 82, 83, 84, 85, 88, 89, 90, 91, 92, 93, 94, 95, 96, 99, 100, 101, 102, 103, 104, 105, 106, 109, 110, 111, 112, 113, 114, 115, 118, 119, 120, 121, 122, 123, 126, 127, 128, 129, 130, 133, 134, 135, 136, 139, 140, 141, 144, 145 and 148. More preferably, said antigenic IgE peptide consists of, or consists essentially of, an amino acid sequence selected from the group consisting of SEQ ID Nos: 1, 2, 3, 4, 5, 6, 7, 8, 9, 10, 11, 12, 18, 19, 20, 21, 22, 23, 24, 25, 26, 27, 28, 34, 35, 36, 37, 38, 39, 40, 41, 42, 43, 49, 50, 51, 52, 53, 54, 55, 56, 57, 63, 64, 65, 66, 67, 68, 69, 70, 76, 77, 78, 79, 80, 81, 82, 88, 89, 90, 91, 92, 93, 99, 100, 101, 102, 103, 109, 110, 111, 112, 118, 119, 120, 126, 127, 133, and 139. Even more preferably, said antigenic IgE peptide consists of, or consists essentially of, an amino acid sequence selected from the group consisting of SEQ ID Nos: 1, 2, 3, 4, 5, 6, 7, 8, 9, 18, 19, 20, 21, 22, 23, 24, 25, 34, 35, 36, 37, 38, 39, 40, 49, 50, 51, 52, 53, 54, 63, 64, 65, 66, 67, 76, 77, 78, 79, 88, 89, 90, 99, 100, 101 and 109. Even more preferably, said antigenic IgE peptide consists of, or consists essentially of, an amino acid sequence selected from the group consisting of SEQ ID Nos: 1, 2, 3, 4, 5, 6, 18, 19, 20, 21, 22, 34, 35, 36, 37, 49, 50, 51, 63, 64 and 76. Even more preferably, said antigenic IgE peptide consists of, or consists essentially of, an amino acid sequence selected from the group consisting of SEQ ID Nos: 1, 2, 3, 18, 19 and 34. Most preferably, said antigenic IgE peptide consists of, or consists essentially of, an amino acid sequence of SEQ ID Nos: 1 or 18.

In another embodiment, the antigenic IgE peptide of the invention consists of, or consists essentially of, an amino acid sequence selected from the group consisting of SEQ ID Nos: 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, and 219. Preferably, said antigenic IgE peptide consists of, or consists essentially of, an amino acid sequence selected from the group consisting of SEQ ID Nos: 154, 155, 156, 157, 158, 159, 160, 161, 162, 165, 166, 167, 168, 169, 170, 171, 172, 175, 176, 177, 178, 179, 180, 181, 184, 185, 186, 187, 188, 189, 192, 193, 194, 195, 196, 199, 200, 201, 202, 205, 206, 207, 210, 211, 214 and 217. More preferably, said antigenic IgE peptide consists of, or consists essentially of, an amino acid sequence selected from the group consisting of SEQ ID Nos: 154, 155, 156, 157, 158, 159, 165, 166, 167, 168, 169, 175, 176, 177, 178, 184, 185, 186, 192, 193, 199 and 200. Even more preferably, said antigenic IgE peptide consists of, or consists essentially of, an amino acid sequence selected from the group consisting of SEQ ID Nos: 154, 155, 156, 165, 166 and 175. Most preferably, said antigenic IgE peptide consists of, or consists essentially of, an amino acid sequence of SEQ ID Nos: 154 or 165.

In another embodiment, the antigenic IgE peptide of the invention consists of, or consists essentially of, an amino acid sequence selected from the group consisting of SEQ ID Nos: 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, and 310. Preferably, said antigenic IgE peptide consists of, or consists essentially of, an amino acid sequence selected from the group consisting of SEQ ID Nos: 220, 221, 222, 223, 224, 225, 226, 227, 228, 229, 230, 233, 234, 235, 236, 237, 238, 239, 240, 241, 242, 245, 246, 247, 248, 249, 250, 251, 252, 253, 256, 257, 258, 259, 260, 261, 262, 263, 266, 267, 268, 269, 270, 271, 272, 275, 276, 277, 278, 279, 280, 283, 284, 285, 286, 287, 290, 291, 292, 293, 296, 297, 298, 301, 302 and 305.

More preferably, said antigenic IgE peptide consists of, or consists essentially of, an amino acid sequence selected from the group consisting of SEQ ID Nos: 220, 221, 222, 223, 224, 225, 226, 227, 233, 234, 235, 236, 237, 238, 239, 245, 246, 247, 248, 249, 250, 256, 257, 258, 259, 260, 266, 267, 268, 269, 275, 276, 277, 283, 284 and 290. Even more preferably, said antigenic IgE peptide consists of, or consists essentially of, an amino acid sequence selected from the group consisting of SEQ ID Nos: 220, 221, 222, 223, 224, 233, 234, 235, 236, 245, 246, 247, 256, 257 and 266. Even more preferably, said antigenic IgE peptide consists of, or consists essentially of, an amino acid sequence selected from the group consisting of SEQ ID Nos: 220, 221, 222, 233, 234 and 245. Most preferably, said antigenic IgE peptide consists of, or consists essentially of, an amino acid sequence of SEQ ID Nos: 220 or 233.

In yet another embodiment, the antigenic IgE peptide of the invention consists of, or consists essentially of, an amino acid sequence selected from the group consisting of SEQ ID Nos: 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430. Preferably, said antigenic IgE peptide consists of, or consists essentially of, an amino acid sequence selected from the group consisting of SEQ ID Nos:311, 312, 313, 314, 315, 316, 317, 318, 319, 320, 321, 322, 323, 326, 327, 328, 329, 330, 331, 332, 333, 334, 335, 336, 337, 340, 341, 342, 343, 344, 345, 346, 347, 348, 349, 350, 353, 354, 355, 356, 357, 358, 359, 360, 361, 362, 365, 366, 367, 368, 369, 370, 371, 372, 373, 376, 377, 378, 379, 380, 381, 382, 383, 386, 387, 388, 389, 390, 391, 392, 395, 396, 397, 398, 399, 400, 403, 404, 405, 406, 407, 410, 411, 412, 413, 416, 417, 418, 421, 422 and 425. More preferably, said antigenic IgE peptide consists of, or consists essentially of, an amino acid sequence selected from the group consisting of SEQ ID Nos: 311, 312, 313, 314, 315, 316, 317, 318, 319, 320, 326, 327, 328, 329, 330, 331, 332, 333, 334, 340, 341, 342, 343, 344, 345, 346, 347, 353, 354, 355, 356, 357, 358, 359, 365, 366, 367, 368, 369, 370, 376, 377, 378, 379, 380, 386, 387, 388, 389, 395, 396, 397, 403, 404 and 410. Even more preferably, said antigenic IgE peptide consists of, or consists essentially of, an amino acid sequence selected from the group consisting of SEQ ID Nos: 311, 312, 313, 314, 315, 316, 317, 326, 327, 328, 329, 330, 331, 340, 341, 342, 343, 344, 353, 354, 355, 356, 365, 366, 367, 376, 377 and 386. Even more preferably, said antigenic IgE peptide consists of, or consists essentially of, an amino acid sequence selected from the group consisting of SEQ ID Nos: 311, 312, 313, 314, 326, 327, 328, 340, 341 and 353. Even more preferably, said antigenic IgE peptide consists of, or consists essentially of, an amino acid sequence selected from the group consisting of SEQ ID Nos: 311, 312 and 326. Most preferably, said antigenic IgE peptide consists of, or consists essentially of, an amino acid sequence of SEQ ID Nos:311 or 312.

The term "antigenic IgE peptide biological activity", when used herein, refers to the ability of the antigenic IgE peptides of the invention to induce auto anti-IgE antibodies in a patient, with an antagonistic profile, such auto-antibodies being able to decrease the level of circulating free IgE while not causing any significant IgE-mediated release of inflammatory mediators and while being substantially unable to bind to IgE bound to its high affinity receptor. It will be apparent to the man skilled in the art which techniques may be used to confirm whether a specific construct falls within the scope of the present invention. Such techniques include, but are not restricted to, the techniques described in the Example section of the present application, and also to the following. The putative peptide can be assayed to ascertain the immunogenicity of the construct, in that antisera raised by the putative peptide cross-react with the native IgE molecule, and are also functional in blocking allergic mediator release from allergic effector cells.

The specificity of these responses can be confirmed by functional assays where pulldown of IgE can be quantified and/or by inhibition of degranulation of cells expressing the IgE receptor, or by competition experiments by blocking the activity of the antiserum with the peptide itself or the native IgE, and/or specific monoclonal antibodies that are known to bind the epitope within IgE. Techniques to ascertain binding to IgE-FcRI are also well known to those skilled in the art.

In an embodiment the antigenic IgE peptides of the present invention are of a size such that they mimic a region selected from the whole IgE domain in which the native epitope is found. In a particular embodiment, the antigenic IgE peptides of the invention, are less than 100 amino acids in length, preferably shorter than 75 amino acids, more preferably less than 50 amino acids, even more preferably less than 40 amino acids. The antigenic IgE peptides of the invention are typically 4, 5, 6, 7, 8, 9, 10, 11, 12, 13, 14, 15, 16, 17, 18, 19, 20, 21, 22, 23, 24, 25, 26, 27, 28, 29 or 30 amino acids in length, preferably from 4 to 20 amino acids, for example 6 to 12, or 6 to 9 amino acids.

Specific examples of antigenic IgE peptides of the invention are provided in the sequence listing and include peptides ranging from 4 to 20 amino acids in length.

The antigenic peptides of the invention include an amino acid sequence derived from a portion of human IgE CH3, such derived portion of human CH3 either corresponding to the amino acid sequence of naturally occurring IgE or corresponding to variant IgE, i.e. the amino acid sequence of naturally occurring IgE in which a small number of amino acids have been substituted, added or deleted but which retains essentially the same immunological properties. In addition, such derived IgE CH3 portion can be further modified by amino acids, especially at the N- and C-terminal ends to allow the antigenic IgE peptide to be conformationally constrained and/or to allow coupling of the antigenic IgE peptide to an immunogenic carrier after appropriate chemistry has been carried out.

The antigenic IgE peptides of the present invention encompass functionally active variant peptides derived from the amino acid sequence of IgE CH3 in which amino acids have been deleted, inserted or substituted without essentially detracting from the immunological properties thereof, i.e. such functionally active variant peptides retain a substantial antigenic IgE peptide biological activity. Typically, such functionally variant peptides have an amino acid sequence homologous, preferably highly homologous, to an amino acid sequence selected from the group consisting of SEQ ID Nos: 1 to 430, more preferably to an amino acid sequence selected from the group consisting of SEQ ID Nos: 1 to 153 and 220 to 430, even more preferably to an amino acid sequence selected from the group consisting of SEQ ID Nos: 220 to 430.

In one embodiment, such functionally active variant peptides exhibit at least 60%, 65%, 70%, 75%, 80%, 85%, 90% or 95% identity to an amino acid sequence selected from the group consisting of SEQ ID Nos: 1 to 430, more preferably to an amino acid sequence selected from the group consisting of SEQ ID Nos: 1 to 153 and 220 to 430, even more preferably to an amino acid sequence selected from the group consisting of SEQ ID Nos: 220 to 430.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). An alternative algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997).

Functionally active variants comprise naturally occurring functionally active variants such as allelic variants and species variants and non-naturally occurring functionally active variants that can be produced by, for example, mutagenesis techniques or by direct synthesis.

A functionally active variant differs by about, for example, 1, 2, 3, 4, 5, 6, 7, 8, 9, or 10 amino acid residues from any of the peptide shown at SEQ ID Nos: 1 to 430, more preferably at SEQ ID Nos: 1 to 153 and 220 to 430, even more preferably at SEQ ID Nos: 220 to 430, and yet retain an antigenic IgE biological activity. Where this comparison requires alignment the sequences are aligned for maximum homology. The site of variation can occur anywhere in the peptide, as long as the biological activity is substantially similar to a peptide shown in SEQ ID Nos: 1 to 430, more preferably substantially similar to a peptide shown in SEQ ID Nos: 1 to 153 and 220 to 430, even more preferably substantially similar to a peptide shown in SEQ ID Nos: 220 to 430.

The antigenic IgE peptide of the invention may be used alone or preferably when conjugated to an immunogenic carrier, to induce auto anti-IgE antibodies in a subject in order to treat, prevent or ameliorate IgE-related disorders.

Peptide Linkers

In embodiments where the antigenic IgE peptide of the invention are either fused, conjugated or otherwise attached to an immunogenic carrier, spacer or linker sequences may be added at one or both ends of the antigenic IgE peptides.

Therefore the antigenic IgE peptide of the invention may comprise additional amino acids, either at their N-terminus, or at their C-terminus or at both the N-terminus and C-terminus. Preferably these additional amino acids are covalently linked by peptide bonds to either the N-terminus, or the C-terminus or both the N-terminus and C-terminus of the antigenic IgE peptide of the invention.

These additional amino acids may allow coupling of the antigenic IgE peptide to an immunogenic carrier after appropriate chemistry has been carried out. They are referred as peptide linkers in the present disclosure.

In an embodiment of the present invention the antigenic IgE peptide disclosed herein further comprises either at its N-terminus, or at its C-terminus or at both the N-terminus and C-terminus a peptide linker which is able to react with an attachment site of the immunogenic carrier in a chemical cross-linking reaction.

In an embodiment, the antigenic IgE peptide disclosed herein further comprise at its C-terminus a linker having the formula $(G)_nC$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0 said formula represents a cysteine). Preferably the antigenic IgE peptide disclosed herein further comprise at its C-terminus a linker having the formula GGGC, GGC, GC or C.

In another embodiment of the present invention the antigenic IgE peptide disclosed herein further comprise at its N-terminus a linker having the formula $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine). Preferably the antigenic IgE peptide disclosed herein further comprise at its N-terminus a linker having the formula CGGG, CGG, CG or C.

In another embodiment the antigenic IgE peptide disclosed herein further comprise at its N-terminus a linker having the formula GGGC, GGC, GC or C.

In another embodiment the antigenic IgE peptide disclosed herein further comprise at its C-terminus a linker having the formula $(G)_nC$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n 0 or 1 (where n is equal to 0 said formula represents a cysteine) and at its N-terminus a linker having the formula $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine). Preferably the antigenic IgE peptide disclosed herein further comprise at its N-terminus a linker having the formula GGGC, GGC, GC or C and at its C-terminus a linker having the formula GGGC, GGC, GC or C. More preferably the antigenic IgE peptide disclosed herein further comprise at its N-terminus a cysteine and at its C-terminus a cysteine.

Representative of said antigenic IgE peptides further comprising a peptide linker are disclosed at SEQ ID NO: 434, 436, 437, 438, 439 and 457. In an embodiment of the invention, the antigenic IgE peptide comprising a linker is any of the peptide disclosed at table 9.

In some embodiment, the antigenic IgE peptide disclosed herein further comprises either at its N-terminus, or at its C-terminus or at both the N-terminus and C-terminus a peptide linker selected from the group consisting of: (a) CGG; (b) N-terminal gamma 1-linker; (c) N-terminal gamma 3-linker; (d) Ig hinge regions; (e) N-terminal glycine linkers; (f) (G) kC (G) n with n=0-12 and k=0-5; (g) N-terminal glycine-serine linkers; (h) (G) kC (G) m (S) i (GGGGS) n with n=0-3, k=0-5, m=0-10, i=0-2; (i) GGC; (k) GGC-NH2; (1) C-terminal gamma 1-linker; (m) C-terminal gamma 3-linker; (n) C-terminal glycine linkers; (o) (G) nC (G) k with n=0-12 and k=0-5; (p) C-terminal glycine-serine linkers; (q) (G) m (S) t (GGGGS) n (G) oC (G) k with n=0-3, k=0-5, m=0-10, 1=0-2, and o=0-8. Further examples of peptide linkers are the hinge region of immunoglobulins, glycine serine linkers (GGGGS) n, and glycine linkers (G) n all further containing a cysteine residue as second attachment site and optionally further glycine residues. Typically preferred examples of said amino acid linkers are N-terminal gamma 1: CGDKTHTSPP; C-terminal gamma 1: DKTHTSPPCG; N-terminal gamma 3: CGGPKPSTPPGSSGGAP; C-terminal gamma 3: PKPSTPPGSSGGAPGGCG; N-terminal glycine linker: GCGGGG and C-terminal glycine linker: GGGGCG.

In one embodiment, the antigenic IgE peptides of the invention are expressed as fusion peptides with the peptide linkers. Fusion of the peptide linkers can be effected by fusion to either the N- or C-terminus of the antigenic IgE peptide.

Immunogenic Carrier of the Invention

In an embodiment of the present invention, the antigenic IgE peptide or polypeptide of the invention is linked to an immunogenic carrier molecule to form immunogens for vaccination protocols, preferably wherein the carrier molecule is not related to the native IgE molecule.

The term "immunogenic carrier" herein includes those materials which have the property of independently eliciting an immunogenic response in a host animal and which can be covalently coupled to a peptide, polypeptide or protein either directly or via a linker.

The types of carriers used in the immunogens of the present invention will be readily known to the person skilled in the art.

In an embodiment, the immunogenic carrier of the present invention is selected from the group consisting of DT (Diphtheria toxin), TT (tetanus toxid) or fragment C of TT, PD (*Haemophilus influenzae* protein D—see, e.g., EP 0 594 610 B), hemocyanins (particularly Keyhole Limpet Hemocyanin [KLH]), CRM197 (a nontoxic but antigenically identical variant of diphtheria toxin), other DT point mutants, such as CRM176, CRM228, CRM 45 (Uchida et al J. Biol. Chem. 218; 3838-3844, 1973); CRM 9, CRM102, CRM 103 and CRM107 and other mutations described by Nicholls and Youle in Genetically Engineered Toxins, Ed: Frankel, Maecel Dekker Inc, 1992.

In an embodiment, the immunogenic carrier is DT (Diphtheria toxoid). In another embodiment, the immunogenic carrier is TT (tetanus toxid). In yet another embodiment, the immunogenic carrier is PD (*Haemophilus influenzae* protein D—see, e.g., EP 0 594 610 B).

In a preferred embodiment, the immunogenic carrier is CRM197 protein (also known as CRM197). The CRM197 protein is a nontoxic form of diphtheria toxin but is immunologically indistinguishable from the diphtheria toxin. CRM197 is produced by *C. diphtheriae* infected by the nontoxigenic phage β197tox-created by nitrosoguanidine mutagenesis of the toxigenic corynephage beta (Uchida, T. et al. 1971, Nature New Biology 233:8-11). The CRM197 protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The CRM197 protein is a safe and effective T-cell dependent carrier for saccharides. Further details about CMR197 and production thereof can be found e.g. in U.S. Pat. No. 5,614,382.

Linking the Antigenic IgE Peptide and the Immunogenic Carrier, Either Directly or Via a Peptide Linker According to an embodiment of the present invention the antigenic IgE peptide disclosed herein are linked, preferably chemically cross linked, to an immunogenic carrier, either directly or via one of the peptide linker disclosed herein, to generate an immunogen. In an embodiment, the immunogenic carrier is CRM197.

The antigenic IgE peptides of the invention may be coupled to immunogenic carriers via chemical conjugation or by expression of genetically engineered fusion partners.

In an embodiment, the antigenic IgE peptide disclosed herein is linked to the immunogenic carrier, preferably CRM197, by way of chemical cross-linking as described herein and preferably by using a heterobifunctional cross-linker.

Therefore, in one aspect of the invention, the antigenic IgE peptide of the invention is bound to the immunogenic carrier (e.g. to CRM197) by way of chemical cross-linking preferably by using a heterobifunctional cross-linker.

In some embodiments, the hetero-bifunctional crosslinker contains a functional group which can react with first attachment sites, i.e. with the immunogenic carrier (e.g. CRM197), and a further functional group which can react with a preferred second attachment site, e.g. a cysteine residue either present in or fused to the antigenic IgE peptide made available for reaction by reduction.

The first step of the procedure, typically called the derivatization, is the reaction of the immunogenic carrier (e.g. CRM197) with the cross-linker. The product of this reaction is an activated carrier. In the second step, unreacted cross-linker is removed using usual methods such as gel filtration or dialysis. In the third step, the antigenic peptide (e.g. any of the antigenic IgE peptide disclosed herein optionally comprising, either at its N-terminus, or at its C-terminus or both a peptide linker disclosed herein) is reacted with the activated carrier, and this step is typically called the coupling step. Unreacted antigenic peptide may be optionally removed in a fourth step, for example by dialysis. Optionally, the unconjugated reactive linker sites on the carrier may be "capped" (e.g. with free Cysteine etc).

Several hetero-bifunctional crosslinkers are known to the art. These include the preferred cross-linkers BAANS (bromoacetic acid N-hydroxysuccinimide ester), SMPH (Succinimidyl-6-[β-maleimidopropionamido]hexanoate), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage. In a preferred embodiment of the present invention, the hetero-bifunctional crosslinker is BAANS (bromoacetic acid N-hydroxysuccinimide ester) or SMPH (Succinimidyl-6-[β-maleimidopropionamido]hexanoate).

Another class of cross-linkers suitable in the practice of the invention is characterized by the introduction of a disulfide linkage between the antigenic peptide and the immunogenic carrier (e.g. CRM197). Preferred cross-linkers belonging to this class include for example SPDP and Sulfo-LC-SPDP (Pierce).

The cysteine residue present on the antigenic peptide (e.g. on the antigenic IgE peptide disclosed herein or on the antigenic IgE peptide disclosed herein comprising, either at its N-terminus, or at its C-terminus or both a peptide linker disclosed herein) has to be in its reduced state to react with the hetero-bifunctional cross-linker on the activated carrier, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e. g. DTT, TCEP or p-mercaptoethanol is required. Low concentrations of reducing agent are compatible with coupling as described in WO02/05690, higher concentrations inhibit the coupling reaction, as a skilled artisan would know, in which case the reductand has to be removed or its concentration decreased prior to coupling, e. g. by dialysis, gel filtration or reverse phase HPLC.

In a particular embodiment, when the sequence of an antigenic IgE peptide disclosed herein comprises a cysteine, said antigenic IgE peptide is covalently linked to the immunogenic carrier (e.g. CRM197) directly via said cysteine without using a peptide linker. In said embodiment, the antigenic IgE peptide disclosed herein is linked to the immunogenic carrier, preferably CRM197, by way of chemical cross-linking as described herein and preferably by using a heterobifunctional cross-linker. An IgE peptide with a cysteine in it may have the cysteine at or near the N- or C-terminus or in any other position.

Binding of the antigenic peptide (e.g. any of the antigenic IgE peptide disclosed herein optionally comprising, either at its N-terminus, or at its C-terminus or both a peptide linker disclosed herein) to the immunogenic carrier by using a hetero-bifunctional cross-linker according to the methods described above, allows coupling of the antigenic peptide to the immunogenic carrier (e.g. to CRM197) in an oriented fashion.

In another embodiment, the antigenic IgE peptide of the present invention is expressed as a fusion protein with the immunogenic carrier to generate the immunogen. Fusion of the peptide can be effected by insertion into the immunogenic carrier primary sequence, or by fusion to either the N- or C-terminus of the immunogenic carrier. Hereinafter, when referring to fusion proteins of a peptide to an immunogenic carrier, the fusion to either ends of the subunit sequence or internal insertion of the peptide within the carrier sequence are encompassed. Fusion, as referred to hereinafter, may be effected by insertion of the antigenic peptide into the sequence of carrier, by substitution of part of the sequence of the carrier with the antigenic peptide, or by a combination of deletion, substitution or insertions.

In an embodiment, the antigenic IgE peptide of the invention are expressed as fusion peptides with both a peptide linker, to either the N- or C-terminus of the antigenic IgE peptide, and fusion of the immunogenic carrier to said peptide linker to generate the immunogen.

Preferred Immunogens of the Invention

In an embodiment, the invention relates to an immunogen comprising an antigenic IgE peptide consisting of, or consisting essentially of, an amino acid sequence of SEQ ID Nos: 220, 221, 222, 233, 234 or 245, most preferably, of SEQ ID Nos: 220 or 233, wherein said antigenic IgE further comprises at its C-terminus a cysteine which is chemically cross linked to an immunogenic carrier via a thioether linkage. In a preferred embodiment, said immunogenic carrier is selected from the group consisting of DT (Diphtheria toxin), TT (tetanus toxoid) or fragment C of TT, PD (*Haemophilus influenzae* protein D), CRM197, other DT point mutants, such as CRM176, CRM228, CRM 45, CRM 9, CRM102, CRM 103 and CRM107. Preferably said immunogenic carrier is CRM197.

In an embodiment, the invention relates to an immunogen comprising an antigenic IgE consisting of, or consisting essentially of, an amino acid sequence of SEQ ID Nos: 220, 221, 222, 233, 234 or 245, most preferably, of SEQ ID Nos: 220 or 233, wherein said antigenic IgE further comprises at its N-terminus a cysteine which is chemically cross linked to an immunogenic carrier via a thioether linkage. In a preferred embodiment, said immunogenic carrier is selected from the group consisting of DT (Diphtheria toxin), TT (tetanus toxoid) or fragment C of TT, PD (*Haemophilus influenzae* protein D, CRM197, other DT point mutants, such as CRM176, CRM228, CRM 45, CRM 9, CRM102, CRM 103 and CRM107. Preferably said immunogenic carrier is CRM197.

In an embodiment, the invention relates to an immunogen comprising an antigenic IgE peptide consisting of, or consisting essentially of, an amino acid sequence of SEQ ID Nos: 311, 312 or 326, most preferably, of SEQ ID Nos: 311 or 312. Preferably, said antigenic IgE peptide has at its C-terminus a GC linker, preferably a linker having the formula GGC (preferably said antigenic IgE peptide which comprises at its C-terminus a GC linker consists of, or consists essentially of amino acid sequence of SEQ ID No: 457) which is chemically cross linked to an immunogenic carrier via a thioether linkage using SMPH (Succinimidyl-6-[β-maleimidopropionamido]hexanoate) or BAANS (bromoacetic acid N-hydroxysuccinimide ester) as cross linker. In a preferred embodiment, said immunogenic carrier is selected from the group consisting of DT (Diphtheria toxin), TT (tetanus toxoid) or fragment C of TT, PD (*Haemophilus influenzae* protein D, CRM197, other DT point mutants, such as CRM176, CRM228, CRM 45, CRM 9, CRM102, CRM 103 and CRM107. Preferably said immunogenic carrier is CRM197.

In an embodiment, the invention relates to an immunogen comprising an antigenic IgE peptide consisting of SEQ ID Nos: 312, said antigenic IgE peptide further comprises at its C-terminus a GC linker having the sequence GGC, which is chemically cross linked to an immunogenic carrier via a thioether linkage using SMPH (Succinimidyl-6-[β-maleimidopropionamido]hexanoate) or BAANS (bromoacetic acid N-hydroxysuccinimide ester) as cross linker, said linkage being between a lysine residue of the immunogenic carrier and the cysteine residue of said GC linker and wherein said immunogenic carrier is CRM197.

In an embodiment, the invention relates to an immunogen comprising an antigenic peptide consisting of SEQ ID Nos: 457 which is chemically cross linked to CRM197 via a thioether linkage using SMPH (Succinimidyl-6-[β-maleimidopropionamido]hexanoate) or BAANS (bromoacetic acid N-hydroxysuccinimide ester) as cross linker, said linkage being between a lysine residue of CRM197 and the cysteine residue of said antigenic peptide.

In an embodiment, the invention relates to an immunogen comprising an antigenic IgE consisting of, or consisting essentially of, an amino acid sequence of SEQ ID Nos: 220, 221, 233, 234, 244 or 246, most preferably, of SEQ ID Nos: 220 or 233 which is chemically cross linked to an immunogenic carrier via a thioether linkage using SMPH (Succinimidyl-6-[β-maleimidopropionamido]hexanoate) or BAANS (bromoacetic acid N-hydroxysuccinimide ester) as cross linker, said linkage being between a lysine residue of the immunogenic carrier and the cysteine residue of said antigenic IgE peptide. In a preferred embodiment, said immunogenic carrier is selected from the group consisting of DT (Diphtheria toxin), TT (tetanus toxid) or fragment C of TT, PD (*Haemophilus influenzae* protein D, CRM197, other DT point mutants, such as CRM176, CRM228, CRM 45, CRM 9, CRM102, CRM 103 and CRM107. Preferably said immunogenic carrier is CRM197.

In an embodiment, the invention relates to an immunogen comprising an antigenic IgE peptide consisting of SEQ ID Nos: 220 which is chemically cross linked to an immunogenic carrier via a thioether linkage using SMPH (Succinimidyl-6-[β-maleimidopropionamido]hexanoate) or BAANS (bromoacetic acid N-hydroxysuccinimide ester) as cross linker, said linkage being between a lysine residue of the immunogenic carrier and the cysteine residue of said antigenic IgE peptide and wherein said immunogenic carrier is CRM197.

Conjugation Density

In an embodiment, in order to generate the immunogen of the invention, the antigenic IgE is chemically cross linked to an immunogenic carrier, either directly or via a peptide linker as disclosed herein, using for example an hetero-bifunctional crosslinker (e.g. SMPH or BAANS). In said embodiment, one or more than one antigenic IgE peptide can be linked to each immunogenic carrier molecule.

The goal of the antigenic peptide-carrier conjugation is to present the antigenic peptide in the best possible way to the immune system. In reaching this goal, the choice of conjugation chemistry may control the resultant titer, affinity, and specificity of the antibodies generated against the antigenic IgE peptide. It may be important in some cases to control the density of the antigenic IgE peptide on the surface of the carrier. Too little antigenic peptide substitution may result in little or no response.

An antigenic peptide density too high actually may cause immunological suppression and decrease the response, or might alter the conformation of the conjugated peptides such that they induce weaker antibody responses that cross-react with native IgE. In addition, the cross-linker itself may generate an undesired immune response. These issues may need to be taken into consideration in selecting not only the appropriate cross-linking reagents, but also the appropriate ratios of antigenic IgE peptide/immunogenic carrier.

Therefore in an embodiment of the present invention, in the immunogen disclosed herein the molar ratio of antigenic IgE peptide to the immunogenic carrier (e.g. CRM197) is from about 1:1 to about 40:1. Preferably, said molar ratio is from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

The extent of derivatization of the immunogenic carrier with cross-linker can be influenced by varying experimental conditions such as the concentration of each of the reaction partners, the excess of one reagent over the other, the pH, the temperature and the ionic strength. The degree of coupling, i.e. the amount of antigenic IgE peptide per immunogenic carrier can be adjusted by varying the experimental conditions described above to match the requirements of the vaccine.

The molar ratio of antigenic IgE peptide to the immunogenic carrier can be determined for example by using MALDI-MS. However a number of other methods are also available for determining peptide load depending on the type of conjugation chemistry used. So as well as MALDI-MS, similar ionization techniques can be employed such as SELDI-MS and IMS (ion mobility spectroscopy). For BAANS conjugates the CMC/CMCA method (described at example 15 and FIG. 3 of the present document) can be utilised to determine both peptide load and the extent of capping of unreacted BrAc groups. For the SMPH conjugates a similar method can be used, however with a slightly different version of the CMC product produced upon hydrolysis of a BAANS conjugate.

Composition of the Invention Comprising at Least Two Immunogens Described Herein In a further aspect the present invention relates to a composition comprising at least two immunogens described herein. In an embodiment, the present invention relates to a composition comprising at least two immunogen wherein each of these immunogen comprises an antigenic IgE peptide disclosed herein linked to an immunogenic carrier. In an embodiment said composition comprises two, three, four or five immunogens of the present invention wherein each of these immunogen comprises an antigenic IgE peptide disclosed herein linked to an immunogenic carrier.

Preferably, each antigenic IgE peptide is individually linked to different molecules of immunogenic carrier (each molecule of immunogenic carrier only having one type of antigenic IgE peptide conjugated to it). In said embodiment, the antigenic IgE peptide is said to be individually conjugated to the immunogenic carrier.

In an embodiment, the invention relates to a composition comprising or consisting of two immunogens each of these immunogen comprising an antigenic IgE peptide disclosed herein linked to an immunogenic carrier. Preferably, each antigenic IgE peptides are individually conjugated to the immunogenic carrier. In an embodiment, the antigenic IgE peptide of the first immunogen consists of an amino acid sequence selected from the group consisting of SEQ ID Nos: 220 to 310, preferably from the group consisting of SEQ ID Nos: 220, 221, 222, 223, 224, 225, 226, 227, 228, 229, 230, 233, 234, 235, 236, 237, 238, 239, 240, 241, 242, 245, 246, 247, 248, 249, 250, 251, 252, 253, 256, 257, 258, 259, 260, 261, 262, 263, 266, 267, 268, 269, 270, 271, 272, 275, 276, 277, 278, 279, 280, 283, 284, 285, 286, 287, 290, 291, 292, 293, 296, 297, 298, 301, 302 and 305, more preferably from the group consisting of SEQ ID Nos: 220, 221, 222, 223, 224, 225, 226, 227, 233, 234, 235, 236, 237, 238, 239, 245, 246, 247, 248, 249, 250, 256, 257, 258, 259, 260, 266, 267, 268, 269, 275, 276, 277, 283, 284 and 290, even more preferably from the group consisting of SEQ ID Nos: 220, 221, 222, 223, 224, 233, 234, 235, 236, 245, 246, 247, 256, 257 and 266, even more preferably from the group consisting of SEQ ID Nos:220, 221, 222, 233, 234 and 245, most preferably, said antigenic IgE peptide consists of an amino acid sequence of SEQ ID Nos: 220 or 233.

In an embodiment the antigenic IgE peptide of the second immunogen consists of an amino acid sequence selected from the group consisting of SEQ ID Nos:311 to 430, preferably from the group consisting of SEQ ID Nos:311, 312, 313, 314, 315, 316, 317, 318, 319, 320, 321, 322, 323, 326, 327, 328, 329, 330, 331, 332, 333, 334, 335, 336, 337, 340, 341, 342, 343, 344, 345, 346, 347, 348, 349, 350, 353, 354, 355, 356, 357, 358, 359, 360, 361, 362, 365, 366, 367, 368, 369, 370, 371, 372, 373, 376, 377, 378, 379, 380, 381, 382, 383, 386, 387, 388, 389, 390, 391, 392, 395, 396, 397, 398, 399, 400, 403, 404, 405, 406, 407, 410, 411, 412, 413, 416, 417, 418, 421, 422 and 425, more preferably from the group consisting of SEQ ID Nos: 311, 312, 313, 314, 315, 316, 317, 318, 319, 320, 326, 327, 328, 329, 330, 331, 332, 333, 334, 340, 341, 342, 343, 344, 345, 346, 347, 353, 354, 355, 356, 357, 358, 359, 365, 366, 367, 368, 369, 370, 376, 377, 378, 379, 380, 386, 387, 388, 389, 395, 396, 397, 403, 404 and 410, even more preferably from the group consisting of SEQ ID Nos: 311, 312, 313, 314, 315, 316, 317, 326, 327, 328, 329, 330, 331, 340, 341, 342, 343, 344, 353, 354, 355, 356, 365, 366, 367, 376, 377 and 386, even more preferably from the group consisting of SEQ ID Nos: 311, 312, 313, 314, 326, 327, 328, 340, 341 and 353, even more preferably from the group consisting of SEQ ID Nos: 311, 312 and 326, most preferably, said antigenic IgE peptide consists of an amino acid sequence of SEQ ID Nos:311 or 312.

In an embodiment, the invention relates to a composition comprising or consisting of two immunogens each of these immunogen comprising an antigenic IgE peptide linked to an immunogenic carrier wherein, the antigenic IgE peptide of the first immunogen consists of an amino acid sequence of SEQ ID Nos: 220 and the antigenic IgE peptide of the second immunogen consists of 312. Preferably, each antigenic IgE peptides are individually conjugated to the immunogenic carrier.

In an embodiment, the invention relates to a composition comprising or consisting of two immunogens each of these immunogen comprising an antigenic IgE peptide disclosed herein individually conjugated to an immunogenic carrier. In an embodiment the first immunogen consists of an immunogen comprising an antigenic IgE peptide consisting of, or consisting essentially of, an amino acid sequence of SEQ ID Nos: 220, 221, 233, 234, 244 and 246, most preferably, of SEQ ID Nos: 220 or 233. Preferably said first antigenic IgE peptide is chemically cross linked to CRM197 via a thioether linkage using SMPH (Succinimidyl-6-[β-maleimidopropionamido]hexanoate) or BAANS (bromoacetic acid N-hydroxysuccinimide ester) as cross linker, said linkage being between a residue of the immunogenic carrier and the cysteine residue of said antigenic IgE peptide. Preferably, the second immunogen consists of an immunogen comprising an antigenic IgE peptide consisting of, or consisting essentially of, an amino acid sequence of SEQ ID Nos: 311, 312 or 326, most preferably, of SEQ ID Nos: 311 or 312. Preferably, said second antigenic IgE peptide further comprises at its C-terminus a GC linker, preferably a linker having the formula GGC (preferably said second antigenic IgE peptide which comprises at its C-terminus a GC linker consists of, or consists essentially of amino acid sequence of SEQ ID No: 457) which is chemically cross linked to an immunogenic carrier via a thioether linkage using SMPH (Succinimidyl-6-[β-maleimidopropionamido]hexanoate) or BAANS (bromoacetic acid N-hydroxysuccinimide ester) as cross linker. In a preferred embodiment, said immunogenic carrier is CRM197.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using SMPH (Succinimidyl-6-[β-maleimidopropionamido]hexanoate) as cross linker, said linkage being between a lysine residue CRM197 and the cysteine residue of said antigenic IgE peptide and wherein said immunogenic carrier and;

the second immunogen consists of an antigenic peptide of SEQ ID NO: 457 chemically cross linked to CRM197 via a thioether linkage using SMPH (Succinimidyl-6-[β-maleimidopropionamido]hexanoate) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 3:1 to about 8:1, preferably from about 10:1 to about 15:1.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using BAANS (bromoacetic acid N-hydroxysuccinimide ester) as cross linker, said linkage being between a lysine residue CRM197 and the cysteine residue of said antigenic IgE peptide and wherein said immunogenic carrier and;

the second immunogen consists of an antigenic peptide of SEQ ID NO: 457 chemically cross linked to CRM197 via a thioether linkage using BAANS (bromoacetic acid N-hydroxysuccinimide ester) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using SMPH (Succinimidyl-6-[β-maleimidopropionamido]hexanoate) as cross linker, said linkage being between a lysine residue CRM197 and the cysteine residue of said antigenic IgE peptide and wherein said immunogenic carrier and;

the second immunogen consists of an antigenic peptide of SEQ ID NO: 457 chemically cross linked to CRM197 via a thioether linkage using SMPH (Succinimidyl-6-[β-maleimidopropionamido]hexanoate) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using BAANS (bromoacetic acid N-hydroxysuccinimide ester) as cross linker, said linkage being between a lysine residue CRM197 and the cysteine residue of said antigenic IgE peptide and wherein said immunogenic carrier and;

the second immunogen consists of an antigenic peptide of SEQ ID NO: 457 chemically cross linked to CRM197 via a thioether linkage using SMPH (Succinimidyl-6-[β-maleimidopropionamido]hexanoate) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using SMPH (Succinimidyl-6-[β-maleimidopropionamido]hexanoate) as cross linker, said linkage being between a lysine residue CRM197 and the cysteine residue of said antigenic IgE peptide and wherein said immunogenic carrier and;

the second immunogen consists of an antigenic IgE of SEQ ID NO: 312, further comprising at its C-terminus a linker having the sequence GGC, chemically cross linked to CRM197 via a thioether linkage using SMPH (Succinimidyl-6-[β-maleimidopropionamido]hexanoate) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using BAANS (bromoacetic acid N-hydroxysuccinimide ester) as cross linker, said linkage being between a lysine residue CRM197 and the cysteine residue of said antigenic IgE peptide and wherein said immunogenic carrier and;

the second immunogen consists of an antigenic IgE of SEQ ID NO: 312, further comprising at its C-terminus a linker having the sequence GGC, chemically cross linked to CRM197 via a thioether linkage using BAANS (bromoacetic acid N-hydroxysuccinimide ester) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using SMPH (Succinimidyl-6-[β-maleimidopropionamido]hexanoate) as cross linker, said linkage being between a lysine residue CRM197 and the cysteine residue of said antigenic IgE peptide and wherein said immunogenic carrier and;

the second immunogen consists of an antigenic IgE of SEQ ID NO: 312, further comprising at its C-terminus a linker having the sequence GGC, chemically cross linked to CRM197 via a thioether linkage using BAANS (bromoacetic acid N-hydroxysuccinimide ester) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

In an embodiment, the invention relates to a composition comprising two immunogens wherein each of these immunogens consists of an antigenic IgE peptide individually conjugated to CRM197 wherein:

the first immunogen consists an antigenic IgE peptide of SEQ ID NO: 220 chemically cross linked to an immunogenic carrier via a thioether linkage using BAANS (bromoacetic acid N-hydroxysuccinimide ester) as cross linker, said linkage being between a lysine residue CRM197 and the cysteine residue of said antigenic IgE peptide and wherein said immunogenic carrier and;

the second immunogen consists of an antigenic IgE of SEQ ID NO: 312, further comprising at its C-terminus a linker having the sequence GGC, chemically cross linked to CRM197 via a thioether linkage using SMPH (Succinimidyl-6-[β-maleimidopropionamido]hexanoate) as cross linker, said linkage being between a lysine residue of CRM197 and the cysteine residue of said antigenic peptide. In an embodiment, the molar ratio of antigenic peptide to the immunogenic carrier is from about 1:1 to about 40:1, preferably from about 2:1 to about 30:1, preferably about 3:1 to about 20:1, preferably about 5:1 to about 20:1, preferably about 5:1 to about 15:1, preferably about 10:1 to about 20:1, preferably about 15:1 to about 20:1, preferably from about 5:1 to about 10:1, preferably from about 10:1 to about 15:1.

In an embodiment, the invention relates to a process for the production of a composition comprising at least two immunogens disclosed herein, comprising the step of combining said at least two immunogens.

In an embodiment, the invention relates to a composition comprising, or consisting of, two, three, four or more immunogens wherein each of these immunogen comprise an antigenic IgE peptide linked to an immunogenic carrier and wherein, said antigenic IgE peptide consists of, or consists essentially of, an amino acid sequence selected from the group consisting of SEQ ID Nos: 1 to 430. In an embodiment, said antigenic IgE peptides are linked to the same immunogenic carrier. In another embodiment, said antigenic IgE peptides are individually conjugated to different immunogenic carrier and then mixed.

DNA

For any recombinantly expressed peptide or protein which forms part of the present invention, including an antigenic IgE peptide according to the invention coupled or not to an immunogenic carrier, the nucleic acid which encodes said peptide or protein also forms an aspect of the present invention, as does an expression vector comprising the nucleic acid, and a host cell containing the expression vector (autonomously or chromosomally inserted). A method of recombinantly producing the peptide or protein by expressing it in the above host cell and isolating the peptide or protein therefrom is a further aspect of the invention. The full-length native IgE molecule or the full-length native DNA sequence encoding it are not covered by the present invention.

Method of Production of the Immunogen of the Invention

The invention further relates to a process for the production of the immunogen disclosed herein. In an embodiment said immunogen comprises at least one antigenic IgE peptide disclosed herein linked to an immunogenic carrier disclosed herein. Therefore the invention further relates to a process for the production of an immunogen comprising the step of linking at least one antigenic IgE peptide disclosed herein to an immunogenic carrier disclosed herein. In an embodiment said linkage is performed by chemical cross linkage, either directly or via a peptide linker, in particular a GC linker (eg. a cysteine or GGC) as disclosed herein. In an embodiment, the invention relates to a process for the production of an immunogen comprising the step of linking at least one antigenic IgE peptide disclosed herein, optionally further comprising a peptide linker as disclosed herein, to an immunogenic carrier disclosed herein (e.g. CRM197), said linkage being performed by chemical cross linkage as disclosed herein.

In a particular embodiment, when the sequence of the antigenic IgE peptide disclosed herein comprises a cysteine, said antigenic IgE peptide is covalently linked to the immunogenic carrier (e.g. CRM197) directly via said cysteine without a peptide linker. In said embodiment, the process includes a step of chemical cross-linking as described herein and preferably using a heterobifunctional cross-linker (e.g. bromoacetic acid N-hydroxysuccinimide ester (BAANS) or Succinimidyl-6-[β-maleimidopropionamido]hexanoate (SMPH)). Therefore in some embodiments, the chemical cross-linking step results in the immunogenic carrier (e.g. CRM197) being cross linked via a thioether linkage via the cysteine residue of said antigenic IgE.

In an embodiment, when the sequence of the antigenic IgE peptide disclosed herein does not comprise a cysteine, a peptide linker comprising a cysteine, in particular a GC linker as disclosed herein (eg. a cysteine or GGC), is added at either the C-terminus, N-Terminus or both of said antigenic IgE peptide and said polypeptide (antigenic IgE peptide+peptide linker) is covalently linked to the immunogenic carrier (e.g. CRM197) via the cysteine of the peptide linker. In said embodiment, the process include a step of chemical cross-linking as described herein, preferably using a heterobifunctional cross-linker (e.g. bromoacetic acid N-hydroxysuccinimide ester (BAANS) or Succinimidyl-6-[β-maleimidopropionamido]hexanoate (SMPH)). Therefore in some embodiments, the chemical cross-linking step results in the immunogenic carrier (e.g. CRM197) being cross linked via a thioether linkage via the cysteine residue of a peptide linker comprising a cysteine.

The invention also relates to a process for the production of the immunogen disclosed herein. The first step of the procedure, typically called the derivatization, is the reaction of the immunogenic carrier (e.g. CRM197) with the cross-linker. The product of this reaction is an activated carrier. In the second step, unreacted cross-linker is removed using usual methods such as gel filtration or dialysis. In the third step, the antigenic peptide (e.g. any of the antigenic IgE peptide disclosed herein optionally comprising, either at its N-terminus, or at its C-terminus or both a peptide linker disclosed herein) is reacted with the activated carrier, and this step is typically called the coupling step. Unreacted antigenic peptide may be optionally removed in a fourth step, for example by dialysis. Optionally, in a further step, the unconjugated reactive linker sites on the carrier may be "capped" (e.g. with free Cysteine etc).

A further embodiment of the present invention relates to an immunogen obtainable by the process disclosed herein.

In one embodiment of the invention, a peptide, polypeptide or protein of the invention is derived from a natural source and isolated from a mammal, such as a human, a primate, a cat, a dog, a horse, a mouse, or a rat, preferably from a human source. A peptide, polypeptide or protein of the invention can thus be isolated from cells or tissue sources using standard protein purification techniques.

Alternatively, peptides, polypeptides and proteins of the invention can be synthesized chemically or produced using recombinant DNA techniques.

For example, a peptide, polypeptide or protein of the invention can be synthesized by solid phase procedures well known in the art. Suitable syntheses may be performed by utilising "T-boc" or "F-moc" procedures. Cyclic peptides can be synthesised by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in 'Solid Phase Peptide Synthesis: A Practical Approach' by E. Atherton and R. C. Sheppard, published by IRL at Oxford University Press (1989) and 'Methods in Molecular Biology, Vol. 35: Peptide Synthesis Protocols (ed. M. W. Pennington and B. M. Dunn), chapter 7, pp 91-171 by D. Andreau et al.

Alternatively, a polynucleotide encoding a peptide, polypeptide or protein of the invention can be introduced into an expression vector that can be expressed in a suitable expression system using techniques well known in the art, followed by isolation or purification of the expressed peptide, polypeptide, or protein of interest. A variety of bacterial, yeast, plant, mammalian, and insect expression systems are available in the art and any such expression system can be used. Optionally, a polynucleotide encoding a peptide, polypeptide or protein of the invention can be translated in a cell-free translation system.

Antigenic IgE peptides of the invention can also comprise those that arise as a result of the existence of multiple genes, alternative transcription events, alternative RNA splicing events, and alternative translational and postranslational events. A peptide can be expressed in systems, e.g. cultured cells, which result in substantially the same postranslational modifications present as when the peptide is expressed in a native cell, or in systems that result in the alteration or omission of postranslational modifications, e.g. glycosylation or cleavage, present when expressed in a native cell.

A peptide, polypeptide or protein of the invention, such as an antigenic IgE peptide, can be produced as a fusion protein that contains other non-IgE or non-IgE-derived amino acid sequences, such as amino acid linkers or signal sequences or immunogenic carriers as defined herein, as well as ligands useful in protein purification, such as glutathione-S-transferase, histidine tag, and staphylococcal protein A. More than one antigenic IgE peptide of the invention can be present in a fusion protein. The heterologous polypeptide can be fused, for example, to the N-terminus or C-terminus of the peptide, polypeptide or protein of the invention. A peptide, polypeptide or protein of the invention can also be produced as fusion proteins comprising homologous amino acid sequences, i.e., other IgE or IgE-derived sequences.

Compositions Comprising an Antigenic IgE Peptide of the Invention

The present invention further relates to compositions, particularly immunogenic compositions also referred to as "subject immunogenic compositions", comprising an immunogen disclosed herein and optionally at least one adjuvant. In an embodiment, said immunogen comprises or consists of an antigenic IgE peptide of the invention, preferably linked to an immunogenic carrier, more preferably CRM197. Such immunogenic compositions, particularly when formulated as pharmaceutical compositions, are deemed useful to prevent, treat or alleviate IgE-related disorders.

In some embodiments, a subject immunogenic composition according to the invention comprises an antigenic IgE peptide comprising an amino acid sequence selected from SEQ ID Nos: 1 to 430, and functionally active variants thereof, preferably from the group consisting of SEQ ID Nos: 1 to 430, more preferably from the group consisting of SEQ ID Nos: 1 to 153 and 220 to 430, even more preferably from the group consisting of SEQ ID Nos: 220 to 430. In some embodiment, said antigenic IgE peptide is linked to an immunogenic carrier, preferably CRM197.

A subject immunogenic composition comprising an antigenic IgE peptide according to the invention can be formulated in a number of ways, as described in more detail below. In some embodiments, a subject immunogenic composition comprises single species of antigenic IgE peptide, e.g., the immunogenic composition comprises a population of antigenic IgE peptides, substantially all of which have the same amino acid sequence. In other embodiments, a subject immunogenic composition comprises two or more different antigenic IgE peptides, e.g., the immunogenic composition comprises a population of antigenic IgE peptides, the members of which population can differ in amino acid sequence. A subject immunogenic composition can comprise from two to about 20 different antigenic IgE peptides, e.g., a subject immunogenic composition can comprise 2, 3, 4, 5, 6, 7, 8, 9, 10, 11-15, or 15-20 different antigenic IgE peptides, each having an amino acid that differs from the amino acid sequences of the other antigenic IgE peptides.

In some embodiments, a subject immunogenic composition comprises at least one adjuvant. Suitable adjuvants include those suitable for use in mammals, preferably in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjölander et al. (1998) *J. Leukocyte Biol.* 64:713; WO90/03184, WO96/11711, WO 00/48630, WO98/36772, WO00/41720, WO06/134423 and WO07/026190), LT/CT mutants, poly(D,L-lactide-co-glycolide) (PLG) microparticles, Quil A, interleukins, and the like. For veterinary applications including but not limited to animal experimentation, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg *Vaccine* 2000, 19, 618-622; Krieg *Curr opin Mol Ther* 2001 3:15-24; Roman et al., *Nat. Med.,* 1997, 3, 849-854; Weiner et al., *PNAS USA,* 1997, 94, 10833-10837; Davis et al, *J. Immunol,* 1998, 160, 870-876; Chu et al., *J. Exp. Med,* 1997, 186, 1623-1631; Lipford et al, *Eur. J. Immunol.,* 1997, 27, 2340-2344; Moldoveami et al., *Vaccine,* 1988, 16, 1216-1224, Krieg et al., *Nature,* 1995, 374, 546-549; Klinman et al., *PNAS USA,* 1996, 93, 2879-2883; Ballas et al, *J. Immunol,* 1996, 157, 1840-1845; Cowdery et al, *J. Immunol,* 1996, 156, 4570-4575; Halpern et al, *Cell Immunol,* 1996, 167, 72-78; Yamamoto et al, *Jpn. J. Cancer Res.,* 1988, 79, 866-873; Stacey et al, *J. Immunol.,* 1996, 157, 2116-2122; Messina et al, *J. Immunol,* 1991, 147, 1759-1764; Yi et al, *J. Immunol,* 1996, 157, 4918-4925; Yi et al, *J. Immunol,* 1996, 157, 5394-5402; Yi et al, *J. Immunol,* 1998, 160, 4755-4761; and Yi et al, *J. Immunol,* 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition, such as Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g. as described in Kanzler et al 2007, Nature Medicine 13, p 1552-9), including TLR3 ligands such as polyI:C and similar compounds such as Hiltonol and Ampligen.

In an embodiment, the immunogenic composition of the present invention comprises at least one adjuvant which is a CpG Oligonucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

Different classes of CpG immunostimulatory oligonucleotides have been identified. These are referred to as A, B, C and P class, and are described in greater detail below. Methods and compositions of the invention embrace the use of these different classes of CpG immunostimulatory oligonucleotides.

Any of the classes may be subjugated to an E modification which enhances its potency. An E modification may be a halogen substitution for the 5' terminal nucleotide; examples of such substitutions include but are not limited to bromo-uridine or iodo-uridine substitutions. An E modification can also include an ethyl-uridine substitution for the 5' terminal nucleotide.

The "A class" CpG immunostimulatory oligonucleotides are characterized functionally by the ability to induce high levels of interferon-alpha (IFN-α) from plasmacytoid dendritic cells (pDC) and inducing NK cell activation while having minimal effects on B cell activation. Structurally, this class typically has stabilized poly-G sequences at 5' and 3' ends. It also has a palindromic phosphodiester CpG dinucleotide-containing sequence of at least 6 nucleotides, for example but not necessarily, it contains one of the following hexamer palindromes: GACGTC, AGCGCT, or AACGTT described by Yamamoto and colleagues. Yamamoto S et al. J. Immunol 148:4072-6 (1992). A class CpG immunostimulatory oligonucleotides and exemplary sequences of this class have been described in U.S. Non-Provisional patent application Ser. No. 09/672,126 and published PCT application PCT/USOO/26527 (WO 01/22990), both filed on Sep. 27, 2000.

In an embodiment, the "A class" CpG oligonucleotide of the invention has the following nucleic acid sequence: 5'

GGGGACGACGTCGTGGGGGGG 3' (SEQ ID NO: 440). Some non-limiting examples of A-Class oligonucleotides include:

5' G*G*G_G_A_C_G_A_C_G_T_C_G_T_G_G*G*G*G*G*G 3'; wherein * refers to a phosphorothioate bond and _ refers to a phosphodiester bond.

The "B class" CpG immunostimulatory oligonucleotides are characterized functionally by the ability to activate B cells and pDC except are relatively weak in inducing IFN-α and NK cell activation. Structurally, this class typically may be fully stabilized with phosphorothioate linkages, but it may also have one or more phosphodiester linkages, preferably between the cytosine and guanine of the CpG motif(s), in which case the molecule is referred to as semi-soft. In one embodiment, the CpG Oligonucleotide of the present invention is a B class CpG oligonucleotide represented by at least the formula:

5' $X_1X_2CGX_3X_4$ 3', wherein X1, X2, X3, and X4 are nucleotides. In one embodiment, $X_2$ is adenine, guanine, or thymine. In another embodiment, $X_3$ is cytosine, adenine, or thymine.

In another embodiment, the CpG Oligonucleotide of the present invention is a B class CpG oligonucleotide represented by at least the formula:

5' $N_1X_1X_2CGX_3X_4N_2$ 3', wherein $X_1$, $X_2$, $X_3$, and $X_4$ are nucleotides and N is any nucleotide and $N_1$ and $N_2$ are nucleic acid sequences composed of from about 0-25 N's each. In one embodiment, $X_1X_2$ is a dinucleotide selected from the group consisting of GpT, GpG, GpA, ApA, ApT, ApG, CpT, CpA, CpG, TpA, TpT and TpG; and $X_3X_4$ is a dinucleotide selected from the group consisting of TpT, ApT, TpG, ApG, CpG, TpC, ApC, CpC, TpA, ApA and CpA. Preferably $X_1X_2$ is GpA or GpT and X3X4 is TpT. In other embodiments, $X_1$ or $X_2$ or both are purines and $X_3$ or $X_4$ or both are pyrimidines or $X_1X_2$ is GpA and $X_3$ or $X_4$ or both are pyrimidines. In one preferred embodiment, $X_1X_2$ is a dinucleotide selected from the group consisting of TpA, ApA, ApC, ApG and GpG. In yet another embodiment, $X_3X_4$ is a dinucleotide selected from the group consisting of TpT, TpA, TpG, ApA, ApG, GpA and CpA. $X_1X_2$, in another embodiment, is a dinucleotide selected from the group consisting of TpT, TpG, ApT, GpC, CpC, CpT, TpC, GpT and CpG; $X_3$ is a nucleotide selected from the group consisting of A and T, and $X_4$ is a nucleotide, but when $X_1X_2$ is TpC, GpT or CpG, $X_3X_4$ is not TpC, ApT or ApC.

In another preferred embodiment, the CpG oligonucleotide has the sequence 5' $TCN_1TX_1X_2CGX_3X_4$ 3'. The CpG oligonucleotides of the invention, in some embodiments, include $X_1X_2$ selected from the group consisting of GpT, GpG, GpA and ApA and X3X4 selected from the group consisting of TpT, CpT and TpC.

The B class CpG oligonucleotide sequences of the invention are those broadly described above as well as disclosed in published PCT Patent Applications PCT/US95/01570 and PCT/US97/19791, and in U.S. Pat. Nos. 6,194,388, 6,207, 646, 6,214,806, 6,218,371, 6,239,116 and 6,339,068. Exemplary sequences include but are not limited to those disclosed in these latter applications and patents.

In an embodiment, the "B class" CpG oligonucleotide of the invention has the following nucleic acid sequence:

(SEQ ID NO: 431)
5' TCGTCGTTTTTCGGTGCTTTT 3',
or (SEQ ID NO: 432)
5' TCGTCGTTTTTCGGTCGTTTT 3',
or (SEQ ID NO: 433)
5' TCGTCGTTTTGTCGTTTTGTCGTT 3',
or (SEQ ID NO: 441)
5' TCGTCGTTTCGTCGTTTTGTCGTT 3',
or (SEQ ID NO: 442)
5' TCGTCGTTTTGTCGTTTTTTCGA 3'.

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

5' T*C*G*T*C*G*T*T*T*T*T*C*G*G*T*G*C*T*T*T*T 3',
or

5' T*C*G*T*C*G*T*T*T*T*T*C*G*G*T*C*G*T*T*T*T 3',
or

5' T*C*G*T*C*G*T*T*T*T*G*T*C*G*T*T*T*T*G*T*C*G*T*T 3',
or

5' T*C*G*T*C*G*T*T*T*C*G*T*C*G*T*T*T*T*G*T*C*G*T*T 3',
or

5' T*C*G*T*C*G*T*T*T*T*G*T*C*G*T*T*T*T*T*T*C*G*A 3'.

wherein * refers to a phosphorothioate bond.

The "C class" of CpG immunostimulatory oligonucleotides is characterized functionally by the ability to activate B cells and NK cells and induce IFN-α. Structurally, this class typically includes a region with one or more B class-type immunostimulatory CpG motifs, and a GC-rich palindrome or near-palindrome region that allows the molecules to form secondary (e.g., stem-loop) or tertiary (e.g., dimer) type structures. Some of these oligonucleotides have both a traditional "stimulatory" CpG sequence and a "GC-rich" or "B-cell neutralizing" motif. These combination motif oligonucleotides have immune stimulating effects that fall somewhere between the effects associated with traditional B class CpG oligonucleotides (i.e., strong induction of B cell activation and dendritic cell (DC) activation), and the effects associated with A class CpG ODN (i.e., strong induction of IFN-α and NK cell activation but relatively poor induction of B cell and DC activation). Krieg A M et al. (1995) Nature 374:546-9; Ballas Z K et al. (1996) J Immunol 157:1840-5; Yamamoto S et al. (1992) J Immunol 148:4072-6.

The C class of combination motif immune stimulatory oligonucleotides may have either completely stabilized, (e.g., all phosphorothioate), chimeric (phosphodiester central region), or semi-soft (e.g., phosphodiester within CpG motif)

backbones. This class has been described in U.S. patent application U.S. Ser. No. 10/224,523 filed on Aug. 19, 2002.

One stimulatory domain or motif of the C class CpG oligonucleotide is defined by the formula: 5' $X_1DCGHX_2$ 3'. D is a nucleotide other than C. C is cytosine. G is guanine. H is a nucleotide other than G. $X_1$ and $X_2$ are any nucleic acid sequence 0 to 10 nucleotides long. $X_1$ may include a CG, in which case there is preferably a T immediately preceding this CG. In some embodiments, DCG is TCG. $X_1$ is preferably from 0 to 6 nucleotides in length. In some embodiments, $X_2$ does not contain any poly G or poly A motifs. In other embodiments, the immunostimulatory oligonucleotide has a poly-T sequence at the 5' end or at the 3' end. As used herein, "poly-A" or "poly-T" shall refer to a stretch of four or more consecutive A's or T's respectively, e.g., 5' AAAA 3' or 5' TTTT 3'. As used herein, "poly-G end" shall refer to a stretch of four or more consecutive G's, e.g., 5' GGGG 3', occurring at the 5' end or the 3' end of a nucleic acid. As used herein, "poly-G oligonucleotide" shall refer to an oligonucleotide having the formula 5' $X_1X_2GGGX_3X_4$ 3' wherein $X_1$, $X_2$, $X_3$, and $X_4$ are nucleotides and preferably at least one of $X_3$ and $X_4$ is a G. Some preferred designs for the B cell stimulatory domain under this formula comprise TTTTTCG, TCG, TTCG, TTTCG, TTTTCG, TCGT, TTCGT, TTTCGT, TCGTCGT.

The second motif of the C class CpG oligonucleotide is referred to as either P or N and is positioned immediately 5' to $X_1$ or immediately 3' to $X_2$.

N is a B cell neutralizing sequence that begins with a CGG trinucleotide and is at least 10 nucleotides long. A B cell neutralizing motif includes at least one CpG sequence in which the CG is preceded by a C or followed by a G (Krieg A M et al. (1998) Proc Natl Acad Sd USA 95:12631-12636) or is a CG containing DNA sequence in which the C of the CG is methylated. Neutralizing motifs or sequences have some degree of immunostimulatory capability when present in an otherwise non-stimulatory motif, but when present in the context of other immunostimulatory motifs serve to reduce the immunostimulatory potential of the other motifs.

P is a GC-rich palindrome containing sequence at least 10 nucleotides long.

As used herein, "palindrome" and equivalently "palindromic sequence" shall refer to an inverted repeat, i.e., a sequence such as ABCDEE'D'C'B'A' in which A and A', B and B', etc., are bases capable of forming the usual Watson-Crick base pairs.

As used herein, "GC-rich palindrome" shall refer to a palindrome having a base composition of at least two-thirds G's and Cs. In some embodiments the GC-rich domain is preferably 3' to the "B cell stimulatory domain". In the case of a 10-base long GC-rich palindrome, the palindrome thus contains at least 8 G's and Cs. In the case of a 12-base long GC-rich palindrome, the palindrome also contains at least 8 G's and Cs. In the case of a 14-mer GC-rich palindrome, at least ten bases of the palindrome are G's and Cs. In some embodiments the GC-rich palindrome is made up exclusively of G's and Cs.

In some embodiments the GC-rich palindrome has a base composition of at least 81% G's and Cs. In the case of such a 10-base long GC-rich palindrome, the palindrome thus is made exclusively of G's and Cs. In the case of such a 12-base long GC-rich palindrome, it is preferred that at least ten bases (83%) of the palindrome are G's and Cs. In some preferred embodiments, a 12-base long GC-rich palindrome is made exclusively of G's and Cs. In the case of a 14-mer GC-rich palindrome, at least twelve bases (86%) of the palindrome are G's and Cs. In some preferred embodiments, a 14-base long GC-rich palindrome is made exclusively of G's and Cs. The Cs of a GC-rich palindrome can be unmethylated or they can be methylated.

In general this domain has at least 3 Cs and Gs, more preferably 4 of each, and most preferably 5 or more of each. The number of Cs and Gs in this domain need not be identical. It is preferred that the Cs and Gs are arranged so that they are able to form a self-complementary duplex, or palindrome, such as CCGCGCGG. This may be interrupted by As or Ts, but it is preferred that the self-complementarity is at least partially preserved as for example in the motifs CGACGT-TCGTCG or CGGCGCCGTGCCG. When complementarity is not preserved, it is preferred that the non-complementary base pairs be TG. In a preferred embodiment there are no more than 3 consecutive bases that are not part of the palindrome, preferably no more than 2, and most preferably only 1. In some embodiments, the GC-rich palindrome includes at least one CGG trimer, at least one CCG trimer, or at least one CGCG tetramer. In other embodiments, the GC-rich palindrome is not CCCCCCGGGGGG or GGGGGGCCCCCC, CCCCCGGGGG or GGGGGCCCCC.

At least one of the G's of the GC rich region may be substituted with an inosine (I). In some embodiments, P includes more than one I.

In certain embodiments, the immunostimulatory oligonucleotide has one of the following formulas 5' $NX_1DCGHX_2$ 3', 5' $X_1DCGHX_2N$ 3', 5' $PX_1DCGHX_2$ 3', 5' $X_1DCGHX_2P$ 3', 5' $X_1DCGHX_2PX_3$ 3', 5' $X_1DCGHPX_3$ 3', 5' $DCGHX_2PX_3$ 3', 5' $TCGHX_2PX3$ 3', 5' $DCGHPX_3$ 3' or 5'$DCGHP$ 3'.

The invention provides other immune stimulatory oligonucleotides defined by a formula 5' $N_1PyGN_2P$ 3'. $N_1$ is any sequence 1 to 6 nucleotides long. Py is a pyrimidine. G is guanine. $N_2$ is any sequence 0 to 30 nucleotides long. P is a GC-rich palindrome containing a sequence at least 10 nucleotides long.

$N_1$ and $N_2$ may contain more than 50% pyrimidines, and more preferably more than 50% T. $N_1$ may include a CG, in which case there is preferably a T immediately preceding this CG. hi some embodiments, N1PyG is TCG, and most preferably a TCG$N_2$, where $N_2$ is not G.

$N_1PyGN_2P$ may include one or more inosine (I) nucleotides. Either the C or the G in $N_1$ may be replaced by inosine, but the CpI is preferred to the IpG. For inosine substitutions such as IpG, the optimal activity may be achieved with the use of a "semi-soft" or chimeric backbone, where the linkage between the IG or the CI is phosphodiester. N1 may include at least one CI, TCI, IG or TIG motif.

In certain embodiments $N_1PyGN_2$ is a sequence selected from the group consisting of TTTTTCG, TCG, TTCG, TTTCG, TTTTCG, TCGT, TTCGT, TTTCGT, and TCGTCGT. In an embodiment, the "C class" CpG oligonucleotides of the invention has the following nucleic acid sequence:

```
                                        (SEQ ID NO: 443)
    5' TCGCGTCGTTCGGCGCGCGCCG 3',
    or
                                        (SEQ ID NO: 444)
    5' TCGTCGACGTTCGGCGCGCGCCG 3',
    or
                                        (SEQ ID NO: 445)
    5' TCGGACGTTCGGCGCGCGCCG 3',
    or
```

```
                                       (SEQ ID NO: 446)
5' TCGGACGTTCGGCGCGCCG 3',
or (SEQ ID NO: 447)
5' TCGCGTCGTTCGGCGCGCCG 3',
or (SEQ ID NO: 448)
5' TCGACGTTCGGCGCGCGCCG 3',
or (SEQ ID NO: 449)
5' TCGACGTTCGGCGCGCCG 3',
or (SEQ ID NO: 450)
5' TCGCGTCGTTCGGCGCCG 3',
or (SEQ ID NO: 451)
5' TCGCGACGTTCGGCGCGCGCCG 3',
or (SEQ ID NO: 452)
5' TCGTCGTTTTCGGCGCGCGCCG 3',
or (SEQ ID NO: 453)
5' TCGTCGTTTTCGGCGGCCGCCG 3',
or (SEQ ID NO: 454)
5' TCGTCGTTTTACGGCGCCGTGCCG 3',
or (SEQ ID NO: 455)
5' TCGTCGTTTTCGGCGCGCGCCGT 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide.

Some non-limiting examples of C-Class oligonucleotides include:

```
5' T*C_G*C_G*T*C_G*T*T*C_G*G*C*G*C_G*C*G*C*C*G 3',
or

5' T*C_G*T*C_G*A*C_G*T*T*C_G*G*C*G*C_G*C*G*C*C*G 3',
or

5' T*C_G*G*A*C_G*T*T*C_G*G*C*G*C_G*C*G*C*C*G 3',
or

5' T*C_G*G*A*C_G*T*T*C_G*G*C*G*C*G*C*C*G 3',
or

5' T*C_G*C_G*T*C_G*T*T*C_G*G*C*G*C*G*C*C*G 3',
or

5' T*C_G*A*C_G*T*T*C_G*G*C*G*C_G*C*G*C*C*G 3',
or

5' T*C_G*A*C_G*T*T*C_G*G*C*G*C*G*C*C*G 3',
or

5' T*C_G*C_G*T*C_G*T*T*C_G*G*C*G*C*C*G 3',
or

5' T*C_G*C_G*A*C_G*T*T*C_G*G*C*G*C_G*C*G*C*C*G 3',
or

5' T*C*G*T*C*G*T*T*T*C*G*G*C*G*C*G*C*C*G 3',
or

5' T*C*G*T*C*G*T*T*T*T*C*G*G*C*G*G*C*C*G*C*C*G 3',
or

5' T*C*G*T*C_G*T*T*T*T*A*C_G*G*C*G*C*C_G*T*G*C*C*G 3',
or

5' T*C_G*T*C*G*T*T*T*T*C*G*G*C*G*C*G*C*G*C*C*G*T 3'
``` wherein * refers to a phosphorothioate bond and _ refers to a phosphodiester bond.

In any of these sequences, an ethyl-uridine or a halogen may substitute for the 5' T; examples of halogen substitutions include but are not limited to bromo-uridine or iodo-uridine substitutions.

The "P class" CpG immunostimulatory oligonucleotides have been described in WO2007/095316 and are characterized by the fact that they contain duplex forming regions such as, for example, perfect or imperfect palindromes at or near both the 5' and 3' ends, giving them the potential to form higher ordered structures such as concatamers. These oligonucleotides referred to as P-Class oligonucleotides have the ability in some instances to induce much high levels of IFN-α secretion than the C-Class. The P-Class oligonucleotides have the ability to spontaneously self-assemble into concatamers either in vitro and/or in vivo. Without being bound by any particular theory for the method of action of these molecules, one potential hypothesis is that this property endows the P-Class oligonucleotides with the ability to more highly crosslink TLR9 inside certain immune cells, inducing a distinct pattern of immune activation compared to the previously described classes of CpG oligonucleotides.

In an embodiment, the CpG Oligonucleotide of the present invention is a P class CpG oligonucleotide containing a 5' TLR activation domain and at least two palindromic regions, one palindromic region being a 5' palindromic region of at least 6 nucleotides in length and connected to a 3' palindromic region of at least 8 nucleotides in length either directly or through a spacer, wherein the oligonucleotide includes at least one YpR dinucleotide. In an embodiment, said oligonucleotide is not T*C_G*T*C_G*A* C_G*T*T*C_G*G*C*G*C_G*C*G*C*C*G. In one embodiment the P class CpG oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In yet another embodiment the TLR activation domain is within the 5' palindromic region. In another embodiment the TLR activation domain is immediately 5' to the 5' palindromic region. In still another embodiment the 5' palindromic region is at least 8 nucleotides in length. In another embodiment the 3' palindromic region is at least 10 nucleotides in length. In another embodiment the 5' palindromic region is at least 10 nucleotides in length. In yet another embodiment the 3' palindromic region includes an unmethylated CpG dinucleotide. In another embodiment the 3' palindromic region includes two unmethylated CpG dinucleotides. In another embodiment the 5' palindromic region includes an unmethylated CpG dinucleotide. In yet another embodiment the 5' palindromic region includes two unmethylated CpG dinucleotides. In another embodiment the 5' and 3' palindromic regions have a duplex stability value of at least 25. In another embodiment the 5' and 3' palindromic regions have a duplex stability value of at least 30. In another embodiment the 5' and 3' palindromic regions have a duplex stability value of at least 35. In another embodiment the 5' and 3' palindromic regions have a duplex stability value of at least 40. In another embodiment the 5' and 3' palindromic regions have a duplex stability value of at least 45. In another embodiment the 5' and 3' palindromic regions have a duplex stability value of at least 50. In another embodiment the 5' and 3' palindromic regions have a duplex stability value of at least 55. In another embodiment the 5' and 3' palindromic regions have a duplex stability value of at least 60. In another embodiment the 5' and 3' palindromic regions have a duplex stability value of at least 65.

In one embodiment the two palindromic regions are connected directly. In another embodiment the two palindromic regions are connected via a 3'-3' linkage. In another embodiment the two palindromic regions overlap by one nucleotide. In yet another embodiment the two palindromic regions overlap by two nucleotides. In another embodiment the two palindromic regions do not overlap. In another embodiment the two palindromic regions are connected by a spacer. In one embodiment the spacer is a nucleic acid having a length of 1-50 nucleotides. In another embodiment the spacer is a nucleic acid having a length of 1 nucleotide. In another embodiment the spacer is a non-nucleotide spacer. In one embodiment the non-nucleotide spacer is a D-spacer. In another embodiment the non-nucleotide spacer is a linker. In one embodiment the oligonucleotide has the formula 5' $XP_1SP_2T$ 3', wherein X is the TLR activation domain, $P_1$ is a palindrome, S is a spacer, $P_2$ is a palindrome, and T is a 3' tail of 0-100 nucleotides in length. In one embodiment X is TCG, TTCG, or TTTCG. In another embodiment T is 5-50 nucleotides in length. In yet another embodiment T is 5-10 nucleotides in length. In one embodiment S is a nucleic acid having a length of 1-50 nucleotides. In another embodiment S is a nucleic acid having a length of 1 nucleotide. In another embodiment S is a non-nucleotide spacer. In one embodiment the non-nucleotide spacer is a D-spacer. In another embodiment the non-nucleotide spacer is a linker. In another embodiment the oligonucleotide is not an antisense oligonucleotide or a ribozyme. In one embodiment $P_1$ is A and T rich. In another embodiment $P_1$ includes at least 4 Ts. In another embodiment $P_2$ is a perfect palindrome. In another embodiment P2 is G-C rich. In still another embodiment $P_2$ is $CGGCGCX_1GCGCCG$, where $X_1$ is T or nothing.

In one embodiment the oligonucleotide includes at least one phosphorothioate linkage. In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the CpG Oligonucleotide for use in the present invention is a P class CpG oligonucleotide with a 5' TLR activation domain and at least two complementarity-containing regions, a 5' and a 3' complementarity-containing region, each complementarity-containing region being at least 8 nucleotides in length and connected to one another either directly or through a spacer, wherein the oligonucleotide includes at least one pyrimidine-purine (YpR) dinucleotide, and wherein at least one of the complementarity-containing regions is not a perfect palindrome. In one embodiment the oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In another embodiment the TLR activation domain is within the 5' complementarity-containing region. In another embodiment the TLR activation domain is immediately 5' to the 5' complementarity-containing region. In another embodiment the 3' complementarity-containing region is at least 10 nucleotides in length. In yet another embodiment the 5' complementarity-containing region is at least 10 nucleotides in length. In one embodiment the 3' complementarity-containing region includes an unmethylated CpG dinucleotide. In another embodiment the 3' complementarity-containing region includes two unmethylated CpG dinucleotides. In yet another embodiment the 5' complementarity-containing region includes an unmethylated CpG dinucleotide. In another embodiment the 5' complementarity-containing region includes two unmethylated CpG dinucleotides. In another embodiment the complementarity-containing regions include at least one nucleotide analog. In another embodiment the complementarity-containing regions form an intramolecular duplex. In one embodiment the intramolecular duplex includes at least one non-Watson Crick base pair. In another embodiment the non-Watson Crick base pair is G-T, G-A, G-G, or C-A. In one embodiment the complementarity-containing regions form intermolecular duplexes. In another embodiment at least one of the intermolecular duplexes includes at least one non-Watson Crick base pair. In another embodiment the non-Watson Crick base pair is G-T, G-A, G-G, or C-A. In yet another embodiment the complementarity-containing regions contain a mismatch. In still another embodiment the complementarity-containing regions contain two mismatches. In another embodiment the complementarity-containing regions contain an intervening nucleotide. In another embodiment the complementarity-containing regions contain two intervening nucleotides.

In one embodiment the 5' and 3' complementarity-containing regions have a duplex stability value of at least 25. In another embodiment the 5' and 3' complementarity-containing regions have a duplex stability value of at least 30. In another embodiment the 5' and 3' complementarity-containing regions have a duplex stability value of at least 35. In another embodiment the complementarity-containing regions have a duplex stability value of at least 40. In another embodiment the complementarity-containing regions have a duplex stability value of at least 45. In another embodiment the complementarity-containing regions have a duplex stability value of at least 50. In another embodiment the complementarity-containing regions have a duplex stability value of at least 55. In another embodiment the complementarity-containing regions have a duplex stability value of at least 60. In another embodiment the complementarity-containing regions have a duplex stability value of at least 65.

In another embodiment the two complementarity-containing regions are connected directly. In another embodiment the two palindromic regions are connected via a 3'-3' linkage. In yet another embodiment the two complementarity-containing regions overlap by one nucleotide. In another embodiment the two complementarity-containing regions overlap by two nucleotides. In another embodiment the two complementarity-containing regions do not overlap. In another embodiment the two complementarity-containing regions are connected by a spacer. In another embodiment the spacer is a nucleic acid having a length of 1-50 nucleotides. In another embodiment the spacer is a nucleic acid having a length of 1 nucleotide. In one embodiment the spacer is a non-nucleotide spacer. In another embodiment the non-nucleotide spacer is a D-spacer. In yet another embodiment the non-nucleotide spacer is a linker.

In one embodiment the P-class oligonucleotide has the formula 5' XNSPT 3', wherein X is the TLR activation domain, N is a non-perfect palindrome, P is a palindrome, S is a spacer, and T is a 3' tail of 0-100 nucleotides in length. In another embodiment X is TCG, TTCG, or TTTCG. In another embodiment T is 5-50 nucleotides in length. In another embodiment T is 5-10 nucleotides in length. In another embodiment S is a nucleic acid having a length of 1-50 nucleotides. In another embodiment S is a nucleic acid having a length of 1 nucleotide. In another embodiment S is a non-nucleotide spacer. In another embodiment the non-nucleotide spacer is a D-spacer. In another embodiment the non-nucleotide spacer is a linker. In another embodiment the oligonucleotide is not an antisense oligonucleotide or a ribozyme. In another embodiment N is A and T rich. In another embodiment N is includes at least 4 Ts. In another embodiment P is a perfect palindrome. In another embodiment P is G-C rich. In another embodiment P is CGGCGCX$_1$GCGCCG, wherein X$_1$ is T or nothing. In another embodiment the oligonucleotide includes at least one phosphorothioate linkage. In another embodiment all interaucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the "P class" CpG oligonucleotides of the invention has the following nucleic acid sequence: 5' TCGTCGACGATCGGCGCGCGCCG 3' (SEQ ID NO: 456).

In said sequences, all of the linkages may be all phosphorothioate bonds. In another embodiment, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

A non-limiting example of P-Class oligonucleotides include:

5'T*C_G*T*C_G*A*C_G*A*T*C_G*G*C*G*C_G*C*G*C*C*G 3' wherein * refers to a phosphorothioate bond and _ refers to a phosphodiester bond.

In an embodiment, all the internucleotide linkage of the CpG oligonucleotides disclosed herein are phosphodiester bonds ("soft" oligonucleotides, as described in the PCT application WO2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in the PCT application WO2007/026190.

Other modified oligonucleotides include combinations of phosphodiester, phosphorothioate, methylphosphonate, methylphosphorothioate, phosphorodithioate, and/or p-ethoxy linkages.

Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could, in some embodiments, includes at least one phosphodiester (phosphodiester or phosphodiester-like) linkage and at least one boranophosphonate (stabilized) linkage. In other embodiments, a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation, peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165. Methods for preparing chimeric oligonucleotides are also known. For instance patents issued to Uhlmann et al have described such techniques.

Mixed backbone modified ODN may be synthesized as described in the PCT application WO2007/026190.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The size of the CpG oligonucleotide (i.e., the number of nucleotide residues along the length of the oligonucleotide) also may contribute to the stimulatory activity of the oligonucleotide. For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotide disclosed herein comprise substitutions or modifications, such as in the bases and/or sugars as described at paragraph 134 to 147 of WO2007/026190.

In an embodiment, the CpG oligonucleotide of the present invention is chemically modified. Examples of chemical modifications are known to the skilled person and are described, for example in Uhlmann E. et al. (1990), Chem. Rev. 90:543, S. Agrawal, Ed., Humana Press, Totowa, USA 1993; Crooke, S. T. et al. (1996) Annu. Rev. Pharmacol. Toxicol. 36:107-129; and Hunziker J. et al., (1995), Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In some embodiments of the invention, CpG-containing nucleic acids are simply mixed with immunogenic carriers according to methods known to those skilled in the art (see, e.g. WO03/024480).

In a particular embodiment of the present invention, any of the vaccine disclosed herein comprises from 2 µg to 100 mg of CpG oligonucleotide, preferably from 0.1 mg to 50 mg CpG oligonucleotide, preferably from 0.2 mg to 10 mg CpG oligonucleotide, preferably from 0.3 mg to 5 mg CpG oligonucleotide, preferably from 0.3 mg to 5 mg CpG oligonucleotide, even preferably from 0.5 to 2 mg CpG oligonucleotide, even preferably from 0.75 to 1.5 mg CpG oligonucleotide. In a preferred embodiment, any of the vaccine disclosed herein comprises approximately 1 mg CpG oligonucleotide.

In some embodiments of the invention, CpG-containing nucleic acids are simply mixed with the immunogen according to methods known to those skilled in the art (see for example WO03/024480). In other embodiments of the invention, CpG-containing nucleic acids are enclosed within VLPs (see e.g. WO03/024481).

Preferred adjuvants in the context of the present invention include alum; CpG-containing oligonucleotides, preferably CpG 7909 (SEQ ID NO: 433) and CpG24555 (SEQ ID NO: 431); and saponin-based adjuvants, preferably Iscomatrix, which could be used alone or in combination. Preferably, said CpG-containing nucleic acid comprises one or more modified linkages, preferably one or more phosphorothioate linkages, even more preferably all internucleotide linkages of the oligonucleotide are phosphorothioate linkages.

The invention therefore provides an immunogenic composition comprising an antigenic IgE peptide, preferably comprising an amino acid sequence selected from the group consisting of SEQ ID Nos: 1 to 430, more preferably an amino acid sequence selected from the group consisting of SEQ ID Nos: 1 to 153 and 220 to 430, even more preferably an amino acid sequence selected from the group consisting of SEQ ID Nos: 220 to 430 and at least one adjuvant. Said antigenic IgE peptide is preferably linked to an immunogenic carrier as disclosed herein, preferably CRM197. In one embodiment, said adjuvant is a saponin-based adjuvant, preferably Iscomatrix. In another embodiment, said adjuvant is Alum. In still another embodiment, said adjuvant is a CpG-containing nucleic acid. Preferably said adjuvant is CpG7909. More preferably said adjuvant is CpG24555. Preferably, said CpG-containing nucleic acid comprises one or more modified linkages, preferably one or more phosphorothioate linkages, even more preferably all internucleotide linkages of the oligonucleotide are phosphorothioate linkages.

In still another embodiment, the immunogenic composition comprises two adjuvants, preferably selected from the group consisting of aluminum salts (also collectively known as "Alum"), sapoinin-based adjuvants, and CpG-containing nucleic acids. Examples of aluminum salt adjuvants include aluminum hydroxide, aluminum phosphate, and potassium aluminum sulfate. In some embodiments the immunogenic composition comprises an aluminum hydroxide (such as Alhydrogel) or aluminum phosphate (such as AdjuPhos). In a preferred embodiment, said adjuvants are Alum and a CpG-containing nucleic acid, preferably CpG7909 or CpG24555, more preferably CpG24555. Preferably, said CpG-containing nucleic acid comprises one or more modified linkages, preferably one or more phosphorothioate linkages, even more preferably all internucleotide linkages of the oligonucleotide are phosphorothioate linkages. In another preferred embodiment, said adjuvants are a saponin-based adjuvant, preferably Iscomatrix, and a CpG-containing nucleic acid, preferably CpG7909, more preferably CpG24555. Preferably, said CpG-containing nucleic acid comprises one or more modified linkages, preferably one or more phosphorothioate linkages, even more preferably all internucleotide linkages of the oligonucleotide are phosphorothioate linkages. In another preferred embodiment, said adjuvants are Alum and a saponin-based adjuvant, preferably Iscomatrix.

In still another embodiment, the immunogenic composition comprises three adjuvants, preferably selected from the group consisting of Alum, a saponin-based adjuvant, preferably Iscomatrix, and CpG-containing nucleic acids, more preferably CpG7909, even more preferably CpG24555. Preferably, said CpG-containing nucleic acid comprises one or more modified linkages, preferably one or more phosphorothioate linkages, even more preferably all internucleotide linkages of the oligonucleotide are phosphorothioate linkages.

Pharmaceutical Compositions of the Invention

The invention also provides pharmaceutical compositions comprising an antigenic IgE peptide immunogen or a composition of immunogens of the invention, or an immunogenic composition thereof, in a formulation in association with one or more pharmaceutically acceptable excipient. In some embodiments the pharmaceutical composition further comprises one or more adjuvants (as adjuvant described described above). The term "excipient" is used herein to refer to any ingredient other than the active ingredients (i.e. the antigenic IgE peptide of the invention eventually coupled to an immunogenic carrier and optionally combined with one or more adjuvants). The choice of excipient(s) will to a large extent depend on factors such as the particular mode of administration, the effect of the excipient on solubility and stability, conformational integrity and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the active ingredient.

Pharmaceutical compositions of the present invention and methods for their preparation will be readily apparent to those skilled in the art. Such compositions and methods for their preparation may be found, for example, in *Remington's Pharmaceutical Sciences*, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, or proteins accepted in the art may suitably be employed for the peptides or proteins of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous, subcutaneous, intradermal and intramuscular routes, even more preferred embodiments are the intramuscular or the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-IgE peptide, preferably coupled to an immunogenic carrier, eventually in combination with one or more adjuvants, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 0.1 mg/mL to about 20 mg/mL of a peptide or immunogen of the invention, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

The immunogens described herein can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the immunogen of the invention per actuation and the actuation volume may for example vary from 1 µL to 100 µL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

A pharmaceutical composition comprising the immunogen disclosed herein or a composition of immunogens disclosed herein, or the immunogenic composition disclosed herein, may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compositions of the invention can be used to treat, alleviate or prevent IgE-mediated disorders or symptoms in a subject at risk or suffering from such disorder or symptom by stimulating an immune response in said subject by immunotherapy. Immunotherapy can comprise an initial immunization followed by additional, e. g. one, two, three, or more boosters.

An "immunologically effective amount" of an immunogen of the invention, or a composition of immunogens of the invention is an amount that is delivered to a mammalian subject, either in a single dose or as part of a series, which is effective for inducing an immune response against IgE in said subject. This amount varies depending upon the health and physical condition of the individual to be treated, the taxonomic group of individual to be treated, the capacity of the individual's immune system to synthesize antibodies, the formulation of the vaccine, and other relevant factors. It is expected that the amount will fall in a relatively broad range that can be determined through routine trials.

The term "pharmaceutically effective dose," "therapeutically effective dose," "pharmaceutically effective amount" or "therapeutically effective amount" refers to that amount or dose required to treat or prevent, or alleviate one or more IgE-related disorder or symptom in a subject. The pharmaceutically effective amount or dose depends on inter alia the specific compound to administer, the severity of the symptoms, the susceptibility of the subject to side effects, the type of disease, the composition used, the route of administration, the type of mammal being treated, the physical characteristics of the specific mammal under consideration such as health and physical condition, concurrent medication, the capacity of the individual's immune system to synthesize antibodies, the degree of protection desired, and other factors that those skilled in the medical arts will recognize. For prophylaxis purposes, the amount of immunogen in each dose is selected as an amount which induces an immunoprotective response without significant adverse side effects in typical vaccinees. Following an initial vaccination, subjects may receive one or several booster immunisations adequately spaced.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For example, immunogens or a composition of immunogens of the invention or pharmaceutical composition of the invention can be administered to a subject at a dose of about 0.1 µg to about 200 mg, e.g., from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg, with optional boosters given at, for example, 1 week, 2 weeks, 3 weeks, 4 weeks, two months, three months, 6 months and/or a year later.

In an embodiment the immunogens or a composition of immunogens disclosed herein are administered to a subject at a dose of about 0.1 µg to about 200 mg, e.g., from about 0.1 µg to about 5 µg, from about 5 µg to about 10 µg, from about 10 µg to about 25 µg, from about 25 µg to about 50 µg, from about 50 µg to about 100 µg, from about 100 µg to about 200 µg, from about 100 µg to about 500 µg, from about 500 µg to about 1 mg, from about 1 mg to about 2 mg. In a particular embodiment, the amount of the immunogen administered to a subject is from about 1 µg to about 15 µg. In another particular embodiment, the amount of the immunogen administered to a subject is from about 1 µg to about 10 µg.

In some embodiments, a single dose of an immunogen or a composition of immunogens of the invention, or immunogenic or pharmaceutical composition thereof is administered. In other embodiments, multiple doses are administered. The frequency of administration can vary depending on any of a variety of factors, e.g., severity of the symptoms, degree of immunoprotection desired, whether the composition is used for prophylactic or curative purposes, etc. For example, in some embodiments, an immunogen or a composition of immunogens of the invention, or immunogenic or pharmaceutical composition thereof is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). When the composition of the invention is used for prophylaxis purposes, they will be generally administered for both priming and boosting doses. It is expected that the boosting doses will be adequately spaced, or preferably given yearly or at such times where the levels of circulating antibody fall below a desired level. Boosting doses may consist of the antigenic IgE peptide in the absence of the original immunogenic carrier molecule. Such booster constructs may comprise an alternative immunogenic carrier or may be in the absence of any carrier. Such booster compositions may be formulated either with or without adjuvant.

The duration of administration of an immunogen or a composition of immunogens of the invention, e.g., the period of time over which an immunogen is administered, can vary, depending on any of a variety of factors, e.g., patient response, etc. For example, an immunogen can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A variety of treatment methods are also contemplated by the present disclosure, which methods comprise administering an immunogen or a composition of immunogens of the invention, or immunogenic or pharmaceutical composition thereof. Subject treatment methods include methods of inducing an immune response in an individual to self-IgE, and methods of preventing, alleviating or treating an IgE-mediated disorder or symptom in an individual.

In one aspect, the present invention provides a method for treating, preventing or alleviating an IgE-related disorder or symptom in a subject, comprising administering a therapeutically effective amount of an immunogen or a composition of immunogens of the invention, or immunogenic or pharmaceutical composition thereof, to said subject.

In another aspect, the present invention provides a method for inducing an immune response against self-IgE in a subject, comprising administering a therapeutically or immunogenically effective amount of an immunogen or a composition of immunogens of the invention, or immunogenic or pharmaceutical composition thereof, to said subject. "Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. Said subject is preferably human, and may be either male or female, of any age.

Other aspects of the invention relate to an immunogen or a composition of immunogens of the invention, or immunogenic or pharmaceutical composition thereof, for use as a medicament, preferably in treatment, alleviation or prophylaxis of IgE-related disorders. In yet another aspect, the present invention provides the use of an immunogen or a composition of immunogens of the invention, or immunogenic or pharmaceutical composition thereof, in the manufacture of a medicament, preferably for treating an IgE-mediated disorder.

In some aspects of the uses or methods of the invention, said IgE-mediated disorder is selected from the group consisting of conjunctivitis, allergic asthma, allergic rhinitis, atopic dermatitis, anaphylaxis, asthma, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, food allergies, ulcerative colitis, indeterminate colitis and infectious colitis), urticaria, psoriasis, preferably from the group consisting of asthma, allergic asthma, allergic rhinitis and food allergies.

Asthma is a chronic inflammatory disorder of the airways causing recurrent episodes of wheezing, breathlessness, chest tightness, and/or coughing in susceptible individuals. Those skilled in the art distinguish various types of asthma, including: allergic asthma, which is thought to arise in patients having developed a hypersensitivity to environmental allergens; drug-induced asthma, typically triggered by sensitivity to aspirin or other COX inhibitors; exercise-induced asthma; near-fatal and hyperacute asthma; nocturnal asthma; occupational asthma, generally caused by exposure to certain chemicals in the workplace. Thus asthma can be triggered by various stimuli, including: airborne allergens, such as dust-mites, pollens, animal dander, fungal spores, feathers . . . (extrinsic asthma); non specific irritants, such as tobacco smoke, chemical fumes, pollution, sulphur dioxide . . . (intrinsic asthma).

Allergic rhinitis generally involves a collection of symptoms, including inflammatory symptoms, predominantly in the nose, sinuses and eyes, which occur after exposure to airborne particles. Symptoms include sneezing; nasal obstruction; runny nose (and occasionally nosebleeds); coughing; headache; itching nose, mouth, eyes, throat, skin, or any area exposed to the allergen; impaired smell (and thus sensitivity to flavours); stuffy nose (nasal congestion); conjunctivitis; watering eyes; sore throat; and wheezing. Allergic rhinitis may be perennial and/or seasonal. Perennial allergic rhinitis is allergic rhinitis that lasts throughout the year. It is typically caused by continuous exposure to allergens such as animal dander, indoor mould spores, or house dust mites. Seasonal allergic rhinitis is allergic rhinitis that occurs only during certain times of the year. It is commonly caused by allergies to tree, grass, and weed pollen that are produced seasonally.

A food allergy is an exaggerated immune response triggered by eggs, peanuts, milk, or some other specific food. Any food can cause an allergic reaction, but a few foods are the main culprits. In children, the most common food allergies are to eggs, peanuts, milk, soy, tree nuts, wheat, shellfish (shrimp, crab, lobster, snails, clams). In older children and adults, the most common food allergies are: peanuts, tree nuts, shellfish, and fish. The symptoms may be confined mainly to the stomach and intestines, or may involve many parts of the body after the food is digested or absorbed. Symptoms may include: scratchy throat, anaphylaxis (a severe, whole-body allergic reaction that can result in death); abdominal pain; diarrhoea; nausea; vomiting; stomach cramps; itching of the mouth, throat, eyes, skin, or any area; hives; angioedema (swelling, especially of the eyelids, face, lips, and tongue); light-headedness or fainting; nasal congestion; runny nose; shortness of breath; wheezing; difficulty swallowing; oral allergy syndrome. The oral allergy syndrome generally comprises itching lips, tongue, and throat, and sometimes swollen lips.

In other aspects of the uses or methods of the invention, said subject is a mammal, preferably a human subject.

In still other aspects of the uses or methods of the invention, said subject suffers from said IgE-mediated disorder. Alternatively, said subject is at risk of suffering from said IgE-mediated disorder.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Selection of Antigenic IgE Peptides

The structure of the constant domains CH3-CH4 from human IgE interacting with the IgE high affinity receptor FceRI alpha subunit has been solved and published (Wurzburg B A et al., (2000) Immunity, I3 (3), 375-85; Garman S C et al., (2000) Nature 20, 406 (6793), 259-66). This structural information was used together with literature suggesting that are two regions where binding occurs to identify 4 potential loops as key interaction points and to design the following 4 peptides which would correspond to areas of importance for the IgE-FceRI interaction (see FIG. 1).

```
Purple:
                                          (SEQ ID No: 312)
ADSNPRGVSAYLSRPSP Blue:
                                          (SEQ ID No: 165)
LVVDLAPSKGTVN Orange:
                                          (SEQ ID No: 1)
STRKEEKQRNGTLTVTSTLP Yellow:
                                          (SEQ ID No: 220)
QCRVTHPHLPRALMRS (also referred to as "Yellow
001" or "Y001" in some other examples).
```

Example 2

Preparation of Purple-VLP Conjugates

The purple peptide (SEQ ID No: 312) in which a terminal cysteine residue was added for conjugation purposes (sequence ADSNPRGVSAYLSRPSPC (SEQ ID NO: 434)) was synthesised using a standard Fmoc protocol on CLEAR amide resin. The amino acid coupling reactions were carried out using 5 fold excess of Fmoc-protected amino acid activated with 1 eq of HBTU (2-(1H-Benzotriazole-1-yl)-1,1,3, 3-tetramethyluronium hexafluorophosphate) in the presence of HOBt (hydroxybenzotriazole) and NMM (N-methylmorpholine). The deprotection of Fmoc group was achieved with 20% piperidine/DMF. Resin-bound peptide was then cleaved and side chain protecting groups removed simultaneously with Reagent D (TFA/H2O/DODT: 89/3/8). The peptide was made with a free N-terminus and amidated C-terminus. The crude peptide was purified to homogeneity by HPLC using a BEH 130 C18 column and a water/acetonitrile gradient in the presence of 0.1% TFA. The purified peptide was vacuum-dried using a lyophilizer. The peptide was analyzed using mass-spectrometry (LC-MS) and gave satisfactory data (see below).

TABLE 1

| Peptide | Purity | Expected Mass (Da) | Observed Mass (Da) |
|---|---|---|---|
| Purple + Cyst (SEQ ID NO: 434) | 95% | 1877.1 | 1878.1 |

The Purple+Cyst (SEQ ID NO: 434) peptide was conjugated to the Virus-Like Particles (VLP) Qβ and Hepatitis B Surface Antigen (HBsAg) in two separate conjugation experiments. The Qβ used in this study was produced by bacterial *E. Coli* fermentation in a BL21 (DE3) strain incorporating a pET28 plasmid encoding the 14 kD monomer protein:

```
                                          (SEQ ID NO: 435)
MAKLETVTLGNIGKDGKQTLVLNPRGVNPTNGVASLSQAGAVPALEKRVT

VSVSQPSRNRKNYKVQVKIQNPTACTANGSCDPSVTRQAYADVTFSFTQY

STDEERAFVRTELAALLASPLLIDAIDQLNPAY.
```

The fermentation is induced at an OD600 of 0.8 with IPTG and allowed to proceed overnight in terrific broth (TB) with kanamycin. The VLP, which self-assembles in the host cell, was then purified from the fermentation cell pellet using the method described in the patent application EP20050105513 with the following differences: after cell disruption, the clarified homogenate was treated with ammonium sulphate at 50% saturation and the cell pellet recovered by centrifugation. Then, the pellet was redissolved in HEPES buffer and dialysed against HEPES buffer before proceeding to the first column step in the published method. After the ion-exchange column and hydroxylapatite column steps, the material was purified using a further anion-exchange column step and sterile filtered to make the final VLP bulk material, which was analysed by size-exclusion chromatography, SDS-PAGE and electron microscopy with acceptable results.

The HBsAg (subtype adw) used in this study was purchased from Aldevron (ND, USA). The HBsAg exists as spherical particles approximately 22 nm in diameter, which consist of multiple copies of a 24 kD monomeric protein embedded in a lipid bilayer vesicle. An *S. Cerevisiae* strain for production of HBsAg of this type is also available from the ATCC culture collection.

The VLPs (both Qβ and HBsAg) were activated using N-gamma-maleimido-butyryloxy-succinimide ester (GMBS) linking reagent. The GMBS reagent was dissolved in dimethyl sulphoxide (DMSO) and added to the VLP solution at a 0-fold molar excess. The activation reaction was allowed to proceed for 30 minutes and the solution was then desalted using a NAP-25 desalting column into Dulbeccos Phosphate Buffered Saline (DPBS) with 5 mM EDTA. If necessary, the protein solution was concentrated slightly using 10 kD spin microconcentrators prior to the next conjugation reaction.

Prior to the conjugation reaction, the purple peptide was dissolved in an aliquot of pH 7.4 DPBS, with 5 mM EDTA as an additive. The concentration of the peptide in solution was 10 mg/ml. The solubilised peptide was added to an aliquot of TCEP immobilised reducing agent (Pierce Chemical) which had been washed in DPBS containing 5 mM EDTA. The aliquot of peptides was incubated with mixing in the presence of the TCEP gel for approximately 1 hour, after which time the aliquot was spun down in a microfuge and the solid pellet discarded. The reduced peptide-containing supernatant was added directly to the activated VLP which had been prepared earlier.

The reaction between the VLPs and the reduced peptides was allowed to proceed for at least thirty minutes with very gentle mixing. At the end of the reaction time each sample was desalted into Dulbeccos PBS (DPBS) using NAP-10 or NAP-25 desalting columns (GE Healthcare). The desalted conjugated peptides were analysed for protein content using the Bradford (Coomassie Brilliant Blue, Pierce Chemical) assay as well as by SDS-PAGE and size-exclusion chromatography. The conjugate products were sterile filtered using a 0.22 µm filter and stored at 2-8° C. until use. Careful attention was paid to these samples during storage to prevent freezing or exposure to extremes in temperature.

The extent of the conjugation for the two VLP-peptide samples was measured using SDS-PAGE, and a molecular weight increase was observed for both samples which is consistent with the addition of the peptide to the VLP protein monomer. In addition, the Qβ-peptide sample was tested in the HPLC size-exclusion chromatography assay (using a Tosoh PWXL5000 HPLC column) and found to contain assembled VLP when compared to unconjugated samples of VLP. Furthermore, the Qβ-peptide sample was observed using electron microscopy using a JEOL 1230 TEM with 80 kV beam, and found to contain assembled, uniform particles. The integrity of the HBsAg-peptide conjugate particle was tested using non-reduced SDS-PAGE and since the protein did not enter the gel, the sample was deemed to contain high-molecular-mass species and to be suitable for in vivo use.

Example 3

Preparation of Orange, Purple, Yellow, and Blue-VLP Conjugates as Well as Purple-Constrained and Blue-Improved-VLP Conjugates The Yellow, Blue+Cyst, Purple+Cyst and Orange+Cyst peptides which amino acid sequences are indicated in Table 2 were synthesised according to methods known in the art and mainly according to the protocol in Example 2, as follows. The peptides were synthesized on a Symphony peptide synthesizer with a standard Fmoc protocol on CLEAR amide resin, except for peptide Yellow which was made on preloaded Fmoc-Ser(tBU)-Wang resin. See Example 2 for details about the coupling reactions and deprotection. All peptides were made with a free N-terminus and amidated C-terminus except for the peptide Yellow which was made with an acetylated N-terminus and carboxylated C-terminus. The crude peptides were purified on a HPLC system with a BEH 130 C18 column as in Example 2. The purified peptides were vacuum-dried using a lyophilizer. Finally, the peptides were analyzed with LC-MS and all peptides gave satisfactory data (see Table 3 below).

The Blue-Improved and Purple-Constrained peptides were manufactured by CEM Corporation (Matthews, N.C., USA). The peptides were manufactured using standard peptide chemistry techniques and purified using chromatography. The purified peptides were analysed using LC-MS and found to be of high purity (>95%) (see Table 3 below).

TABLE 2

Peptide Sequences

| Name | Sequence | SEQ ID No |
|---|---|---|
| Orange + Cyst | STRKEEKQRNGTLTVTSTLPC | 436 |
| Yellow | QCRVTHPHLPRALMRS | 220 |
| Blue + Cyst | LVVDLAPSKGTVNC | 437 |
| Purple + Cyst | ADSNPRGVSAYLSRPSPC | 434 |
| Blue-Improved | CLVVDLAPSKGTVNGGGGGC | 438 |
| Purple-Constrained | CADSNPRGVSAYLSRPSPC | 439 |

Underscore indicates cysteine residues assed for conjugation purposes and double underscore indicates a GC linker.

TABLE 3

LC-MS Data of Peptides.

| Peptide | Purity | Expected Mass (Da) | Observed Mass (Da) |
|---|---|---|---|
| Orange + Cyst | 97% | 2349.6 | 2352 |
| Yellow | 98.7% | 1944.3 | 1944 |
| Purple + Cyst | 95% | 1877.1 | 1878.1 |
| Blue + Cyst | 96.6% | 1415.7 | 1416 |
| Purple-Constrained | >95% | 1979.0 | 1979.4 |
| Blue-Improved | >95% | 1803.8 | 1803.2 |

Each peptide was conjugated to the Virus-Like Particle (VLP) Qβ in separate batches. The Qβ used in this study was produced by bacterial E. Coli fermentation and extensive purification as in Example 2.

The VLP (>1 mg/ml protein concentration by Bradford assay) was activated using N-gamma-maleimidobutyryloxysuccinimide ester (GMBS) linking reagent from Pierce Chemical as described in Example 2 above.

Prior to the conjugation reaction, each peptide was dissolved in an aliquot of pH 7.4 Dulbeccos Phosphate Buffered Saline (DPBS), with 5 mM EDTA as an additive. The concentration of each peptide in solution was in the range 8-12 mg/ml, see table 4 below for exact data. The solubilised peptide was added to an aliquot of TCEP immobilised reducing agent as described in Example 2 above. The reduced peptide-containing supernatant was added directly to the activated VLP which had been prepared earlier.

The reaction between the VLPs and the reduced peptides was allowed to proceed for at least thirty minutes with very gentle mixing. At the end of the reaction time each sample was desalted into Dulbeccos PBS (DPBS) using NAP-10 or NAP-25 desalting columns (GE Healthcare). The desalted conjugated peptides were then concentrated using 10 kD MWCO spin concentrators, and analysed for protein content using the Bradford (Coomassie Brilliant Blue, Pierce Chemical) assay as well as by SDS-PAGE and size-exclusion chromatography, see below for further details. The conjugate products were sterile filtered using a 0.22 µm filter and stored at 2-8° C. until use. Careful attention was paid to these samples during storage to prevent freezing or exposure to extremes in temperature. The VLP-peptide conjugates were analysed for extent of conjugation and particle assembly as described in Example 2 above (SDS-PAGE including densitometry, electron microscopy and size-exclusion HPLC).

TABLE 4

VLP-Peptide Conjugates

| Peptide | Amount of Peptide (mg) | Peptide Concentration in DPBS (mg/ml) | Approx amount of activated VLP added (mg) | Final Yield (mg) | Substitution* (μg peptide per mg protein) |
|---|---|---|---|---|---|
| Yellow | 4.5 | 11.3 | 5 | 3.2 | 54 |
| Orange + Cyst | 4.5 | 11.3 | 5 | 2.8 | 70 |
| Blue + Cyst | 3.5 | 8.8 | 4 | 1.9 | 47 |
| Purple + Cyst | 3.5 | 8.8 | 4 | 2.3 | 60 |
| Purple-Constrained | 3 | 10 | 3 | 1.3 | 62 |
| Blue-Improved | 3 | 10 | 3 | 1.5 | 48 |

*As determined by SDS-PAGE and densitometry calculations

Example 4

Preparation of Orange, Purple, Yellow, and Blue-KLH Conjugates as Well as Purple-Constrained and Blue-Improved-KLH Conjugates The peptides of Table 2 were conjugated to KLH purchased from Pierce Chemical (Rockford, Ill., USA) and purified as follows. The peptides were made as detailed in Examples 2 and 3 above. The KLH used was Imject Malemide-activated KLH supplied by Pierce Chemical as a lyophilised solid. Vials of this KLH were reconstituted with tissue-culture-grade water prior to addition of the peptides. The peptides were treated with TCEP gel as described in Examples 2 and 3 above and the reduced-peptide-containing supernatants were added directly to aliquots of the activated KLH solution and incubated with gentle mixing. The coupling reaction was allowed to proceed for two hours, at which time the solutions were centrifuged to remove solids and desalted using gravity drip desalting columns as previous. The desalted conjugates were analysed by SDS-PAGE, Bradford protein assay, and tryptic digest followed by MS-MALDI analysis. The conjugates were sterile filtered using a 0.22 μm filter and kept at 2-8° C. until use, as freezing KLH solutions is not recommended.

Example 5

IgE Peptide Identification

This study aimed to evaluate how efficacious peptides conjugated to a Qbeta VLP (as detailed in Examples 2 and 3 above) were in inducing an antibody response that can bind to human IgE. Female Balb/c (6-8 weeks) were injected by the intramuscular route (50 microliter volume injected into each Tibialis anterior muscle) on days 0, 19 and 34. Necropsy took place on day 46. At necropsy 400-600 microliter blood was sampled from euthanised mice by cardiac puncture. Blood was left to coagulate overnight and the next day, serum was collected.

Antibody responses from immunized animals were investigated for some or all of the following assays: a) IgG titer determination, b) binding to serum free IgE, c) binding to FceRI bound IgE, d) degranulation assay, and e) IgE quantification assays.

a) Total IgG Titer Determination

Summary: A colorimetric ELISA that generates a reciprocal titer (RT) to represent the levels of total IgG molecules which are specific to the vaccine. Serial dilutions were prepared from sera samples and tested in the assay. Serum sample prepared from pooled Ce3-vaccinated mice sera samples was used as positive control. Balb/c neg serum from Harlan Labs was used as negative control (pooled from 400 animals Harlan laboratories Code# R-0131D). Coating of assay plates: 384-well high bind assay plates (Corning International Cat#3700) were coated with 25 μL/well of Human Ce3Ce4 protein stock diluted to 1 μg/mL with 0.01 M PBS pH 7.4 and incubated on a shaker at RT for 3 hours. After washing ×2 with PBS pH 7.4, plates were blocked using 80 μL/well of 0.01 M PBS/1% BSA, incubated at RT for 1 hour before a final wash ×3 with 0.01 M PBS pH 7.4/0.05% Tween 20. Sample preparation and assay: The following day, an 8 point ½ log serial dilution of each sample was prepared starting at 1:100 dilution (PBS/1% BSA diluent), 25 μL/well of the serial dilution transferred in duplicate into the human Ce3Ce4 coated plate then incubated shaking at RT for 1.5 hours. After washing ×3 with 0.01 M PBS pH 7.4/0.05% Tween 20, added 25 μL/well of Total IgG detection antibody (Rabbit anti-mu IgG-Fc, Cat# A90-130A Bethyl Laboratories) 1:6000 with 0.01 M PBS pH 7.4/1% BSA, then incubated shaking at RT for 1 hour. After washing ×5 with 0.01 M PBS pH 7.4/0.05% Tween 20, added 25 μL/well Bio-Rad kit goat anti-rabbit horseradish peroxidase conjugate (Bio-Rad Cat#172-1019) 1:3000 with 0.01 M PBS pH 7.4/0.05% Tween 20 pH 7.4, then incubated shaking at RT for 1 hour. After washing ×4 with 0.01 M PBS pH 7.4/0.05% Tween 20 then ×1 with 0.01 M PBS pH 7.4 only, added 25 μL/well Mouse Typer HRP Substrate (Bio-Rad Cat#172-1064), then incubated at RT for 30 mins. Added 25 μL/well 2% oxalic acid, read at Abs 405 nm. Data analysis: A cut-off value (Abs 405 nm) was calculated by taking the mean of the duplicate reads generated by the lowest concentration of the appropriate study negative control group and multiplying this value by 2.5. Titration curves were plotted for each test sample (sample titer vs Abs 405 nm) and the sample titer (subsequently transformed into reciprocal titer) was predicted from the calculated cut-off value.

b) Free IgE Binding Titer

Summary: An electrochemiluminescence (ECL) assay that generates a reciprocal titer (RT) and max value to represent the levels of mouse IgG:human IgE complexes formed after incubation of serial dilutions of test sera overnight with a high concentration of human IgE. Serum sample prepared from pooled Ce3-vaccinated mice sera samples was used as positive control, along with a mouse antibody to a region of the human IgE Ce3 domain (AbDserotec 0100-0413 (E411 (5H2)) spiked at 50 μg/mL and 1 mg/mL into Balb/c neg serum from Harlan Labs (pooled from 400 animals Harlan laboratories Code# R-0131D), which was also used alone as a negative control. Incubation of samples with Human IgE: An 8 point ½ log serial dilution of each sample, including controls, was prepared starting at 1:3 dilution (0.01 M PBS pH 7.4/1% BSA diluent). 10 μL volumes of each sample concentration was mixed with 10 μL of 100 μg/mL Human IgE (diluted from stock using 0.01M PBS pH 7.4/1% BSA), then plates were sealed and incubated overnight at 4° C. Coating of assay plates: The following day, 384-well assay plates (Meso-Scale Diagnostics (MSD) standard bind Cat# L11XA-1, 0370PA) were coated with 12 μL/well of Sheep pAb to human IgE (Gentaur, ICL (Immunology Consultants Lab) Cat# SE-80A) diluted to 1 μg/mL with 0.01M PBS pH 7.4, then incubated on a shaker at RT for 2 hours. After washing ×3 with 0.01M PBS pH 7.4, plates were blocked using 25 μL/well of Pierce starting blocking buffer (Pierce Biotech. Cat#37538) and incubated on a shaker at RT for 40 mins, before a final wash ×3 with 0.01 M PBS pH 7.4. Sample preparation and assay: Volumes of 20 μL of the overnight incubation mix of sera with human IgE were diluted 1:5 with 80 μL/well 0.01 M PBS pH 7.4/1% BSA and then 12 μL/well transferred in duplicate into the coated MSD assay plates. After incubating on a shaker at RT for 2 hours, plates were washed ×3 with 0.01M PBS pH 7.4/0.05% Tween 20. Added 12 μL/well detection antibody (Donkey pAb to mouse IgG H+L Abcam Cat# ab6707, MSD SULFO-tagged using MSD Cat# R91AN-1) 1:5000 with 0.01M PBS pH 7.4/1% BSA, then incubated shaking at RT for 1 hour. After washing ×3 with 0.01 M PBS pH 7.4/0.05% Tween 20 added 50 μL/well MSD Read buffer T (4×) with surfactant (MSD Cat# R92TC) 1:2 with MQ Water. Plates were read using an MSD Sector Imager 6000.

Data analysis: A cut-off value (Pixels) was calculated by taking the mean of the duplicate reads generated by the lowest concentration of the appropriate study negative control group and multiplying this value by 5. Titration curves were plotted for each test sample (sample titer vs Pixels) and the sample titer (subsequently transformed into reciprocal titer) was predicted from the calculated cut off value. The max peak value of the titration curves was also recorded.

c) Binding to Receptor Bound IgE

This assay measures if antibodies in serum from vaccinated mice can bind to some human IgE bound to the FceRI receptor on the surface of RBL-THE cells, those antibodies are then detected by an anti-mouse Fc specific antibody conjugated to phycoerythrin and the fluorescence is measured by flow cytometry. An anti-human IgE antibody from Biodesign diluted in non-vaccinated BALBc serum has been used as a positive control. Assay: Frozen RBL-THE cells (p 12 $10 \times 10^6$ cells/ml) were thawed and washed once with assay buffer (PBS—5% goat serum). $2 \times 10^5$ cells/well in blocking buffer (PBS—5% goat serum-0.1 mg/ml mouse Fab (ChromPure Mouse IgG, Fab fragment—Jackson Immunoresearch)) were seeded in 96-well plates and incubated on the 4° C. shaker for 1 h30. 50 μl of 4 ug/ml human IgE were added per well (diluted in assay buffer) (except the control wells Biodesign no IgE, cells only and aMo-PE) and the plates were incubated for 1 h on the 4° C. shaker. The cells were washed once with assay buffer and resuspended in 30 μl of anti-human IgE (Biodesign 10 ug/ml, 5 ug/ml, 2.5 ug/ml—positive control) diluted in 5% BALBc serum or with serum samples from vaccinated mice diluted 1:20. 1:40 and 1:80 in assay buffer. The serum samples were plated in triplicate and the controls in duplicate. Plates were incubated on the 4° C. shaker for 1 h30 then washed with assay buffer, resuspended in 100 μl of goat anti-Mouse Fc specific-PE antibody (1:200 in assay buffer, Goat Jackson Immunoresearch) and incubated for 45 min on 4° C. shaker. Cells were washed 3 times with assay buffer, resuspended in 80 μl Paraformaldehyde 2% in PBS and incubated overnight at 4° C. Fluorescence intensity was measured by flow cytometry. Data analysis: The mean fluorescence intensity of each sample was used for analysis. The negative control (aMo-PE alone) was averaged and its value subtracted from each well. The positive control was averaged and each sample was expressed as a percentage of positive control (Biodesign) at its respective serum dilution. The 1:40 serum dilution was then extracted and an ANOVA was performed.

d) Degranulation Assay

This assay measures if the serum from vaccinated mice induces degranulation of RBL-THE cells by measuring the activity of b-hexosaminidase enzyme released by RBL-THE cells in media. E25 (Xolair) diluted in non-vaccinated BALBc serum was used as a negative control (40 ug/ml) and goat polyclonal antibody from Sigma diluted in non-vaccinated BALBc serum was used as a positive control. Cell Seeding: Frozen RBL-THE p 12 ($10 \times 10^6$ cells/vial; Rat basophil leukaemia cells stably transfected with human FceRI) were thawed, washed in RBL-P media (MEM-Earles supplement with 15% FCS and 2 mM L-Glutamine) and resuspended in RBL-P media at $8 \times 10^5$ cells/ml with 0.25 μg/ml Human IgE. $8 \times 10^4$ cells/well were seeded in flat bottom 96 well plate and incubated for 48 hours at 37° C./5% CO2. Samples and buffers preparation: On day 3, Tyrode's buffer 1× (NaCl 135 mM, KCl 5 mM, CaCl2 1.8 mM, MgCl2 1 mM, Glucose 5.6 mM, BSA 1 mg/ml, Hepes 20 mM, pH 7.4) was prepared. Tyrode's buffer-5% BALBc serum, Tyrode's buffer-2.5% BALBc serum and Triton 1% in Tyrode's-5% BALBc serum were also prepared. Positive control (Goat polyclonal anti-IgE antibody (82 mg/ml in PBS)—Sigma, I0632) was serially diluted in Tyrode's buffer-5% BALBc serum (1st well in Tyrode's buffer-5% BALBc serum and then in Tyrode's buffer) from 10 μg/ml to 2.5 μg/ml. The negative control (E25) was kept constant at 40 ug/ml in diluted Balbc serum (1:20, 1:40 and 1:80 serum dilution). Test serum samples from vaccinated mice were tested at 1:20, 1:40 and 1:80 serum dilution. All of the controls and test serum samples are tested in triplicate on each plate. Agonist assay: On day 3, cell plates were removed from incubator. 95 μl of media were remove from wells and cells were washed with 200 μl of Tyrode's buffer 1×, the wash buffer was removed and 70 μl of diluted antibodies (either positive control, negative control or test serum sample) were added. Cells were incubated at 37° C./5% CO2 for 1 hour. At the end of incubation, plates were removed from incubator and centrifuge at 1200 rpm for 5 minutes to sediment any detached cells. 65 μl of supernatant was removed and put into sterile 96-well plates. 25 ul of the supernatant was tested for β-hexosaminidase activity. β-hexosaminidase activity: 25 μl of supernatant was added to a 96-well plate. 25 μl of 4 mM NAGA in citrate buffer (4 mM N-acetyl-β-D-glucosaminide (NAGA) (Sigma, N9376) in 50 mM citrate buffer pH 4.5) was added to all wells (freshly prepared), the plates were incubated for 1 h at 37° C. and 150 μl of 0.2M glycine pH 10.7 was add to stop the reaction. Plates were read at at 405 nm with Envision. Data analysis: Degranulation was expressed as a percentage of the total β-hexosaminidase activity from values for Total wells (treated with 1% Triton X-100). The % of degranulation at dilution 1:40 was then extracted for analysis and an ANOVA is performed on the serum samples.

e) Reduction of Free Human IgE Assay

Summary: An electrochemiluminescence (ECL) assay that quantifies the levels of free human IgE that remain after overnight incubation of aliquots of test sera with a serial dilution of human IgE, during which time mouse IgG:human IgE complexes form. To ensure accuracy of the human IgE quantification assay, it is essential to firstly remove any mouse IgG:human IgE complexes using protein G coated magnetic Dynabeads, which bind out any complexes via the mouse IgG Fc region. A value for the % decrease in human IgE levels from that of the appropriate negative control groups can be calculated for each sample.

As a positive control, Xolair/E25 was spiked at 40 μg/mL (standard therapy dose) into Balb/c neg serum from Harlan Labs (pooled from 400 animals Harlan laboratories Code# R-0131D), which was also used alone as a negative control. Incubation of samples with Human IgE: 2 μL volumes of each concentration of an 8 point ½ log serial dilution of human IgE (0.01 M PBS pH 7.4/1% BSA diluent) were added to each of 8×10 μL volumes of test sera samples, including positive control Xolair/E25 (40 μg/mL), the IgE starting at a final concentration of 30 μg/mL. Plates were sealed and incubated overnight at 4° C. Coating of assay plates: The following day, 384-well assay plates (Meso-Scale Diagnostics (MSD) standard bind Cat# L11XA-1, 0370PA) were coated with 12 μL/well of Sheep pAb to human IgE (Gentaur, ICL (Immunology Consultants Lab) Cat# SE-80A) diluted to 5 μg/mL with 0.01M PBS pH 7.4, then incubated on a shaker at RT for 2 hours. After washing ×3 with 0.01M PBS pH 7.4, plates were blocked using 25 μL/well of Pierce starting blocking buffer (Pierce Biotech. Cat#37538) and incubated on a shaker at RT for 40 mins, before a final wash ×3 with 0.01 M PBS pH 7.4. Sample and Dynabead preparation: Volumes of 5 μL of the overnight incubation mix of sera with human IgE were diluted 1:20 with 95 μL/well 0.01M PBS pH 7.4/1% BSA. [Note: Also diluted 10 μL of the 1:20 dilution a further 1:2 with 0.01 PBS pH 7.4/1% BSA to test in the Free IgE binding assay to get a measurement of mu IgG:hu IgE complexes before the Protein G bead incubation]. The required volume of 1× concentration of Protein G Dynabeads (Invitrogen Cat#10004D) was washed and prepared as in pack insert, then concentrated ×4 by resuspending in 0.25× initial bead volume. Incubation of sample with Dynabeads: Mixed 30 μL of each 1:20 sample with 15 μL/well 4× beads, incubated shaking at RT for 1 hour. Removed beads from samples using a Dynal magnetic bar plate (Invitrogen Cat#12027) and mixed 40 μL of the remaining sample with 20 μL fresh 4× bead mix, incubated shaking at RT for 1 hour. Transferred 45 μL/well remaining sample into fresh wells and centrifuge 1 min at 1000 rpm, returned plates onto the magnetic bar plate and transferred 40 μL/well into fresh wells. [Note: Used 30 μL of remaining sample to test in the Free IgE binding assay to get a measurement of mu IgG:hu IgE complexes after the Protein G bead incubation to ensure all complexes have been removed]. Quantification assay: Prepared a 12 point ½ log serial dilution standard curve of human IgE in 80% MSD mouse serum assay diluent/20% 0.01 M PBS pH 7.4/1% BSA, starting at a concentration of 5 μg/mL. Diluted remaining sample from bead incubation 1:5 using MSD mouse serum assay diluent (MSD Cat# R52BB-2). Transferred serial dilutions of standard curve and samples in triplicate at 12 μL/well into coated MSD wells and incubate shaking at RT for 2 hours. After washing plates ×3 with 0.01 M PBS pH 7.4/0.05% Tween 20, added 12 μL/well detection antibody (Rabbit anti-Human IgE Antibody epsilon chain specific Bethyl Cat# A80-109A, MSD SULFO-tagged using MSD Cat# R91AN-1) 1:300 with 0.01 M PBS pH 7.4/1% BSA, then incubated shaking at RT for 1 hour. After washing ×3 with 0.01 M PBS pH 7.4/0.05% Tween 20 added 50 μL/well MSD Read buffer T (4×) with surfactant (MSD Cat# R92TC) 1:2 with MQ Water. Plates were read using an MSD Sector Imager 6000. [Note: A Free IgE binding assay was run in tandem with this quantification assay to test samples from before and after bead incubation using the same protocol as previously described, except using the donkey detection antibody at 1:2000 with 0.01 M PBS pH 7.4/1% BSA and using an anti-human detection antibody for the E25/Xolair positive control only (SULFO-tagged goat anti-human IgG MSD Cat# R32AJ-5) 1:4000 with 0.01M PBS pH 7.4/1% BSA]. Data analysis: Raw data (Pixels) was logged, standard curve plotted (Log human IgE concentration ng/mL vs. Log Pixels) and an asymmetric 5-parameter curve fit applied. Log IgE concentrations of the test samples were predicted from the standard curve and subsequently anti-logged and multiplied by 200 to derive the actual remaining free IgE concentrations in ng/mL. For each sample and control, the % decrease in human IgE levels was calculated compared to the appropriate control group and plotted vs. human IgE (ng/mL) originally added to serum sample, both axes on Log scale, to generate a titration curve.

Results: The results are summarised in Table 5 below. More specifically and surprisingly, this study showed that a combination of Yellow and Purple Qbeta conjugations when administered via the intramuscular route at a total dose of 25 microgram conjugate (i.e. 12.5 microgram individual conjugate) is the most effective, and was more effective than using either peptide conjugate as single antigen at double dose. We have shown in this study that this combination induce an antibody response with a high capacity to bind free IgE as well as that these antibodies are capable of reducing levels of IgE to up to 80% depending on the dose of IgE challenge. These antibody responses were not able to bind receptor engaged IgE and did not cause degranulation of receptor expressing target cells. Combining the Qbeta with the adjuvants Alum and CPG24555 (wherein all internucleotide linkages of the oligonucleotide are phosphorothioate linkages) were highly efficient in inducing these antibody responses. Overall it can be concluded that in terms of inducing mouse IgG antibodies with a strong ability to bind free human IgE, the Yellow peptide is the most promising peptide when administered individually or in combination with Purple or Orange peptide conjugates, or with both Purple and Orange peptide conjugates vaccinated at high dose and volume.

TABLE 5

Summary of data from Example 5

|  | Reciprocal IgG titer | IgE binding titer geomean (95% confidence interval) | IgE binding max Mean (±std dev) | % Degranuation (±std dev) | % Decrease in 9186 ng/mL IgE levels (±std dev) | % Decrease in 861 ng/mL IgE levels (±std dev) | % Decrease in 81 ng/mL IgE levels (±std dev) |
|---|---|---|---|---|---|---|---|
| Yellow | 34125* | 2706 (1801-4067) | 53698 (±15329) | 10 (±0.3) | 15.4% (±7.5%) | 6.4% (±8.0%) | 34.6% (±3.8%) |
| Blue | 100* | 30* | 6361* | 15 (±0.5) | | | |
| Orange | 100* | 95* | 11427* | 9 (±0.4) | 14.7% (±6.3%) | 10.8% (±7.1%) | 7.2% (±3.2%) |
| Purple | 29920* | 405 (118-1389) | 30514 (±12365) | 9 (±0.1) | 6.2% (±4.1%) | 0.1% (±10.4%) | 12.6% (±5.5%) |
| Blue improved | 1137* | 30* | 4228* | 9 (±0.6) | | | |

TABLE 5-continued

Summary of data from Example 5

| | Reciprocal IgG titer | IgE binding titer geomean (95% confidence interval) | IgE binding max Mean (±std dev) | % Degranuation (±std dev) | % Decrease in 9186 ng/mL IgE levels (±std dev) | % Decrease in 861 ng/mL IgE levels (±std dev) | % Decrease in 81 ng/mL IgE levels (±std dev) |
|---|---|---|---|---|---|---|---|
| Purple constrained | 6008* | 186 (63-546) | 26194 (±10443) | 9 (±0.1) | | | |
| Yellow + Orange | 13192* | 1048 (350-3136) | 41202 (±19176) | 10 (±0.3) | 14.3% (±2.0%) | 29.7% (±4.5%) | 14.8% (±6.4%) |
| Yellow + Purple | 7793* | 6823 (400-1165) | 48357 (±11888) | 10 (±0.4) | 34.8% (±2.6%) | 60.0% (±4.5%) | 80.3% (±2.7%) |
| Blue + Orange | 4424* | 30 (30-30) | 12259 (±3685) | 10 (±0.3) | | | |
| Blue + Purple | 7146* | 500 (266-939) | 32333 (±8934) | 11 (±1.6) | | | |
| Blue improved + Purple constrained | 384* | 30* | 10490* | 12 (±0.5) | | | |
| Orange, Yellow, Blue and Purple | 8825* | 202 (91-451) | 26745 (±10920) | 11 (±1.1) | | | |
| Blue improved + Purple constrained, Orange, Yellow | 228* | 30* | 8286* | 11 (±0.3) | | | |
| VLP control | 100* | 30 (30-30) | 3650 (±606) | 10 (±0.3) | 0.3% (±4.2%) | 0% (±2.9%) | 0% (±4.4%) |
| Blue improved ± Purple constrained, Orange, Yellow | 14427* | 96 (46-198) | 16712 (±4326) | 10 (±0.1) | | | |
| Blue improved + Purple constrained, Orange, Yellow (high dose) | 38128* | 316* | 24149* | 10 (±0.2) | | | |
| VLP control (high dose) | 100* | 30* | 2829* | 10 (±0.2) | | | |

N/A: Not applicable
Total conjugation dose is 25 microgram, unless high dose is administered where total dose is 50 microgram per injection
Doses on days 0, 19, 34
Conjugation partner = Qbeta VLP (Viral like particle)
Adjuvant: 20 μg CPG 24555 (all internucleotide linkages phosphorothioate linkages). Alum = ALhydrogel ™ at 20 % v/v
*n = 1 run on pooled samples Example 6

Hyperimmunisation Study

This study aimed to evaluate the effect of a rapid immunisation schedule for induction of high affinity antibodies against IgE. Groups of 8 female Balb/c mice (6-8 weeks old) were injected intraperitoneally and subcutaneously with the peptide KLH-conjugates (as detailed in Example 4 above) on days 0, 3, 8 and 11. A combination of CPG7909 and Alhydrogel (Alum 1.3% at 20% v/v) and Incomplete Freunds adjuvant (IFA) were used as adjuvants in this study. All peptides were conjugated to KLH. Necropsy was performed on day 22 and blood was collected as in Example 5.

Antibody responses from immunized animals were investigated for using either all or some of the following assays: a) IgG titer determination, b) binding to serum free IgE, c) binding to FceRI bound IgE, d) degranulation assay, and e) IgE quantification assays. All assays are described in detail under Example 5. Results Table 6 summarise the data from Example 6. Total titers in this study were approximately 10 fold less than in VRS-IgE-008-003. The data from this study shows that Purple, Purple constrained, Yellow and Orange peptides are immunogenic. Surprisingly, the Blue peptide was a very weak antigen, and constrining the peptide and increasing solubility showed an increased immunogenicity, showing that this peptide may need to be constrained to show acceptable immunogenicity.

TABLE 6

Summary of data from Example 6

|  | Reciprocal IgG titer geomean (95% confidence interval) | IgE binding titer | IgE binding max | % Bidning to IgE-FceRI (±std dev) | % Degranuation (±std dev) |
|---|---|---|---|---|---|
| Yellow | 3118 (475-20470) | 66* | 19740* | 4 (±1.3) | 7 (±0.3) |
| Blue | 100 (100-100) | 30* | 11337* | 4 (±1.1) | 7 (±0.3) |
| Blue-improved | 30 (0-6030) | 30* | 8709* | 3 (±0.6) | 5 (±0.1) |
| Orange | 719 (596-868) | 30* | 7287* | 4 (±0.7) | 4 (±0.2) |
| Purple | 1189 (673-2102) | 30* | 11103* | 3 (±0.4) | 8 (±0.1) |
| Purple constrained | 1996 (1670-2385) | 49* | 15789* | 3 (±0.7) | 8 (±0.3) |
| Orange, Yellow, Blue and Purple mix | 1665 (1606-1726) | 54* | 18349* | 5 (±0.7) | 8 (±0.2) |
| KLH control | 100 (100-100) | 30* | 6496* | 4 (±0.6) | 9 (±0.3) |

Total conjugation dose is 25 microgram per injection
Doses at days 0, 3, 8, 11
Conjugation partner = KLH
Adjuvant: 20 µg CPG 7909 (all internucleotide linkages phosphorothioate linkages), Alum = ALhydrogel™ at 20% v/v + IFA (incomplete Freunds adjuvant)
*n = 1 run on pooled samples

Example 7

Efficacy of Peptides Conjugated to KLH, HBsAg and Qbeta in Inducing Antibody Response that can Bind to Human IgE This study aimed to evaluate how efficacious peptides conjugated to KLH, HBsAg and Qbeta (as detailed in Examples 2, 3 and 4 above) were in inducing an antibody response that can bind to human IgE. Female Balb/c (6-8 weeks) were injected by the intramuscular route (50 microliter volume injected into each Tibialis anterior muscle) on days 0, 19 and 34. Necropsy took place on day 46. At necropsy 400-600 microliter blood was sampled from euthanised mice by cardiac puncture. Blood was left to coagulate overnight and the next day, serum was collected.

Antibody responses from immunized animals were investigated for using either all or some of the following assays: a) IgG titer determination, b) binding to serum free IgE, c) binding to FceRI bound IgE, d) degranulation assay, and e) IgE quantification assays. All assays are described in detail under Example 5.

A Summary of Data is Presented in Table 7.

This study showed that purple and yellow peptides were highly immunogenic. Conjugation of the purple peptide to KLH, Qbeta and HBsAg allowed induction of high antibody responses that were capable of binding to free IgE to a very high degree. These antibody responses were not able to bind receptor engaged IgE and did not cause degranulation of receptor expressing target cells. Both adjuvants (AbiSCO and CPG 7909 and Alum combination) were effective in inducing high levels of antibody responses.

TABLE 7

Summary of data from Example 7

|  | Reciprocal IgG titer geomean (95% confidence interval) | IgE binding titer (±std dev) | IgE binding max (±std dev) | % Bidning to IgE-FceRI (±std dev) | % Degranuation (±std dev) | % Decrease in 9186 ng/mL IgE levels (±std dev) |
|---|---|---|---|---|---|---|
| Yellow-KLH (AbISCO) | 4777 (3115-7327) | 175 (71-427) | 33914 (±17977) | 9 (±4) | 7 (±1) | 0% (±3.6%) |
| Blue-KLH (AbISCO) | 100* | 30 (30-30) | 4176 (±1220) | 9 (±3) | 7 (±1) | 0% (±4.3%) |
| Blue-improved (AbISCO) | 998* | 31 (28-35) | 5338 (±3226) | 12 (±2) | 7 (±0) | 0% (±7.3%) |
| Orange-KLH (AbISCO) | 3656* | 30 (30-30) | 6896 (±2078) | 10 (±2) | 7 (±1) | 0% (±2.6%) |
| Purple-KLH (AbISCO) | 2765 (1298-5891) | 86 (34-215) | 23738 (±16509) | 10 (±2) | 7 (±0) | 0% (±5.8%) |
| Purple constrained-KLH (AbISCO) | 3011 (1518-5972) | 100 (31-325) | 15716 (±9038) | 10 (±3) | 6 (±0.4) | 0.8% (±5.4%) |
| KLH control (AbISCO) | 100 (100-100) | 30 (30-30) | 3399 (±244) | 6 (±2) | 6 (±1) | 0% (±8.3%) |
| Purple-KLH (3 doses) (AbISCO) | 25964 (6713-100415) | 335 (80-1405) | 29032 (±18281) | 7 (±0.4) | 10 (±1) | 22.6% (±2.8%) |
| KLH control (3 doses) (AbISCO) | 424 (289-623) | 34 (25-47) | 8377 (±4475) | 9 (±3) | 8 (±1) | 0% (±4.1%) |
| Purple-KLH (CPG + Alum) | 3791 (1493-9626) | 113 (40-315) | 18207 (±14530) | 11 (±1) | 9 (±1) | 0% (±6.5%) |
| Purple - Qb VLP (CPG + Alum) | 11286 (4517-28197) | 137 (61-305) | 23288 (±16580) | 9 (±4) | 6 (±2) | 0% (±3.4%) |
| Purple - Qb VLP (CPG + AbISCO) | 3792 (2149-6690) | 478 (142-1608) | 39125 (±19461) | 7 (±3) | 7 (±1) | 15.3% (±3.8%) |
| Purple - HBsAg (CPG + Alum) | 36063 (9378-138680) | 2310 (921-5792) | 42383 (±16438) | 6 (±2) | 6 (±2) | 9% (±4.1%) |
| Qbeta control (CPG + Alum) | 100* | 30 (30-30) | 4425 (±650) | 11 (±1) | 8 (±1) | 0% (±0.5%) |

TABLE 7-continued

Summary of data from Example 7

|  | Reciprocal IgG titer geomean (95% confidence interval) | IgE binding titer (±std dev) | IgE binding max (±std dev) | % Bidning to IgE-FceRI (±std dev) | % Degranuation (±std dev) | % Decrease in 9186 ng/mL IgE levels (±std dev) |
|---|---|---|---|---|---|---|
| KLH control (CPG + Alum) | 100* | 30 (30-30) | 2981 (±357) | 5 (±1) | 7 (±1) | 0% (±1.6%) |
| Qbeta control (CPG + AbISCO) | 100 (100-100) | 30 (30-30) | 4234 (±278) | 13 (±3) | 7 (±2) | 0% (±12.1%) |
| CPG + AbISCO | 100 (100-100) | 30 (30-30) | 1941 (±588) | 2 (±1) | 5 (±1) | 0% (±7.8%) |

Total conjugation dose is 25 microgram per injection
Doses on days 0, 21
Conjugation partner = KLH, Q beta or HBsAg VLPAdjuvant: 20 µg CPG 24555 (all internucleotide linkages phosphorothioate linkages) + Alum = ALhydrogel ™ at 20% v/v or 12 µg AbiSCO Example 8

Combination of Peptide Immunogens on KLH

This study aimed to evaluate how efficacious a combination of peptides conjugated to KLH (as detailed in Example 4 above) were in inducing an antibody response that can bind to human IgE. Female Balb/c (6-8 weeks) were injected by the intramuscular route (50 microliter volume injected into each Tibialis anterior muscle) on days 0, 19 and 34. Necropsy took place on day 46. At necropsy 400-600 microliter blood was sampled from euthanised mice by cardiac puncture. Blood was left to coagulate overnight and the next day, serum was collected.

Antibody responses from immunized animals were investigated for using either all or some of the following assays: a) IgG titer determination, b) binding to serum free IgE, c) binding to FceRI bound IgE, d) degranulation assay, and e) IgE quantification assays. All assays are described in detail under Example 5.

A Summary of Data is Presented in Table 8.

This study showed that a combination of Yellow and Orange, Blue and Purple, Yellow and Purple are highly immunogenic and induce antibody responses that can efficiently bind free IgE, despite the low doses used in this study due to restricted amount of peptides available. These antibody responses were not able to bind receptor engaged IgE and did not cause degranulation of receptor expressing target cells.

Example 9

Efficacy of Conjugate Vaccine to Break Tolerance In Vivo (Animal Model)

The ability of IgE peptide vaccines to reduce IgE levels in vivo is evaluated in animal models, using species naturally expressing raised IgE levels (e.g. through allergies) or inducing raised IgE levels experimentally using model or real allergens to immunize animals. For example, mice are immunized with endotoxin-free ovalbumin (OVA) as a model antigen formulated with alum to induce an IgE response to OVA (example reference Lloyd C et al, J. Immunol 2001, 166, p 2033-2040). Post-induction of IgE responses, mice are vaccinated with antigenic peptides coupled to carrier and formulated with adjuvants. Peptides from homologous regions of mouse IgE can be used (in mice), homologous regions of other species in respective animal species, as well as human IgE peptides for non human primates. The efficacy of vaccinations at lowering IgE levels can then be monitored by measuring levels of IgE in sera pre- and post-vaccination. In addition, the ability of the peptides to decrease allergic inflammatory responses can be monitored by challenging mice with intra-nasal or intra-tracheal OVA (for example over 2-5 sequential days) and evaluating the allergic inflammatory response in the lungs by counting leukocyte subset infiltration in lung lavage samples and by histological assessment of eosinophil recruitment into the lung parenchyma as well as

TABLE 8

Summary of data from Example 8

|  | Reciprocal IgG titer | IgE binding titer Geomean (95% confidence interval) | IgE binding max (±std dev) | % Bidning to IgE-FceRI (±std dev) | % Degranuation (±std dev) |
|---|---|---|---|---|---|
| Yellow + Orange | 15063* | 60 (39-93) | 10793 (±6959) | 4 (±3) | 10 (±0.2) |
| Blue + Purple | 23670* | 220 (124-391) | 21928 (±11019) | 2 (±1) | 9 (±0.3) |
| Yellow + Purple | 22560* | 415 (307-561) | 35473 (±12824) | 3 (±2) | 9 (±0.7) |
| Blue + Orange | 8876* | 38 (31-46) | 6861 (±3428) | 3 (±1) | 9 (±0.2) |
| Peng peptides | 14229* | 107 (81-142) | 17931 (±5715) | 2 (±1) | 10 (±0.2) |
| Adjuvant control | 100* | 30 (30-30) | 1897 (±232) | 11 (±13) | 9 (±0.4) |

Yellow dose: 16 microgram per dose
Orange dose: 20.3 microgram per dose
Blue dose: 0.5 microgram per dose
Purple dose: 25.3 microgram per dose
Doses on days 0, 21
Conjugation partner = KLH
Adjuvant: 12 µg AbiSCO goblet cell metaplasia and mucus production (e.g. Coyle A. et al, 1996 J. Exp. Med. 183, 1303-1310.).

Example 10

Efficacy and Suitability of Linear and Chemically Constrained Peptides Conjugated to Qbeta or HBsAg at Inducing Antibodies that can Bind to Human IgE One of the challenges of using short linear peptides as immunogens for inducing anti-IgE responses is accurately representing the secondary structure of IgE, thus ensuring that antibodies generated by the vaccination efficiently recognise free, circulating IgE. Chemical constraining to introduce suitable secondary structure into the linear parental amino acid sequences can provide alternate immunogens for inducing antibody responses to IgE.

Analysis of the three dimensional structure of the Cϵ3ϵ4 domains of IgE present in PDB 1F6A (Garman et al, 2000 Nature 406: p 259-266) revealed that some of the target sequences at the interface between Cϵ3Cϵ4 and the FCϵRI receptor adopt non-linear arrangements that may not be well represented by the linear sequences detailed in table 9. Sequences were therefore identified that were candidates for chemical constraining in an attempt to evaluate the ability of constrained peptides to induce anti-IgE antibodies (following in vivo administration) detectable in a free IgE binding assay.

Variants of both the Yellow (SEQ ID NO: 220) and Orange+Cyst (SEQ ID NO: 436) sequences were separately constrained by two different methods: one method involved the use of Click chemistry to introduce a triazole moiety across two adjacent atoms of the peptide sequence. The degree of constraining exerted on the peptide sequence by this method can be adjusted by the addition of methylene groups to the triazole moiety (Orange046, Orange047, Yellow043, Yellow044 were produced by this method). The second method involved cyclising via the templating effect of a heterochiral Diproline unit (D-Pro-L-Pro) which are noted in the literature to have β-turn inducing potential (Spath et al, 1998, Helvetica Chimica Acta 81, p 1726-1738); (Orange044, Orange045, Yellow040, Yellow041, Yellow042 were produced by this method). Chemical structures of these constrained peptides are displayed in Table 9.

Several studies were performed to evaluate anti-human IgE immune responses induction by either linear or constrained peptides of different length conjugated to HBsAg and Qbeta (conjugations as detailed in Examples 2 and 3).

The constrained peptides Orange+Cyst (SEQ ID No: 436), Yellow (SEQ ID No: 220), Orange044, Orange045, Orange046, Orange047, Yellow040, Yellow041, Yellow042, Yellow043 and Yellow044 were conjugated to Qbeta virus-like particles using Succinimidyl-6-[β-maleimidopropionamido]hexanoate (SMPH) chemistry at 1.5× molar excess and used as immunogens in mice. Female Balb/c (6-8 weeks) were injected by the intramuscular route (50 μl injected into each Tibialis anterior muscle) with antigen and Alhydrogel plus CpG-24555 (all internucleotide linkages phosphorothioate linkages) adjuvants on days as described below in table 9. Sera prepared 1 week after the final boost were tested for anti-IgE antibody activity in the IgE binding assay as described in Example 5.

Data from these studies, which are summarized in Table 9, showed that linear peptides derived from purple, orange and yellow peptides conjugated to Qbeta and HBsAg and delivered with the combined adjuvants Alhydrogel and CpG24555 induced antibody responses that were capable of binding to free IgE.

Additionally, most constrained peptide immunogens induced antisera capable of binding free human IgE. Blue 003, 004 and 005 surprisingly only induced weak anti-IgE responses. Orange 047 and Orange 048 did not induce anti-IgE antibodies above background levels.

TABLE 9

Summary of data from Example 10

| Sequence | Name | IgE binding max Mean (±Std Dev) |
|---|---|---|
| ADSNPRGVSAYLSRPSPc* | PURPLE 001 | 12018 (±6900) |
| ADSNPRGVSAYLSRPSPc* | PURPLE 001 | 17809 (±8042) |
| ADSNPRGVSAYLSRPSPggc** | PURPLE 003 | 33548 (±19309) |
| cggADSNPRGVSAYLSRPSP** | PURPLE 004 | 30400 (±27654) |
| ADSNPRGVggc** | PURPLE 005 | 3707 (±286) |
| ADSNPRGVSAYLSRPSPggc | PURPLE 014 | 5737 (±1954) |
| ADSNPRGVSAYLSRPSggc* | PURPLE 015 | 9097 (±3135) |
| ADSNPRGVSAYLSRPSggc | PURPLE 015 | 7602 (±3104) |
| ADSNPRGVSAYLSRPggc | PURPLE 016 | 6087 (±1176) |
| ADSNPRGVSAYLSRggc* | PURPLE 017 | 9453 (±2650) |
| ADSNPRGVSAYLSRggc | PURPLE 017 | 19078 (±17703) |
| ADSNPRGVSAYLSggc | PURPLE 018 | 5717 (±2531) |
| ADSNPRGVSAYLggc | PURPLE 019 | 5507 (±273) |
| ADSNPRGVSAYggc | PURPLE 020 | 4742 (±601) |
| ADSNPRGVSAggc* | PURPLE 021 | 13890 (±9311) |
| ADSNPRGVSAggc | PURPLE 021 | 9028 (±10144) |
| ADSNPRGVSggc | PURPLE 022 | 4701 (±414) |
| ADSNPRGVggc | PURPLE 023 | 5169 (±494) |
| ADSNPRGggc | PURPLE 024 | 4256 (±480) |
| ADSNPRggc | PURPLE 025 | 4679 (±541) |
| ADSNPggc | PURPLE 026 | 4969 (±393) |
| DSNPRGVSAYLSRPSPggc* | PURPLE 027 | 10197 (±5102) |
| DSNPRGVSAYLSRPSPggc* | PURPLE 027 | 9047 (±1509) |
| SNPRGVSAYLSRPSPggc* | PURPLE 028 | 12685 (±5655) |
| NPRGVSAYLSRPSPggc* | PURPLE 029 | 19549 (±10976) |
| NPRGVSAYLSRPSPggc* | PURPLE 029 | 10323 (±7495) |
| PRGVSAYLSRPSPggc* | PURPLE 030 | 7485 (±1494) |
| RGVSAYLSRPSPggc* | PURPLE 031 | 29423 (±42261) |
| RGVSAYLSRPSPggc* | PURPLE 031 | 9595 (±3569) |

TABLE 9-continued

Summary of data from Example 10

| Sequence | Name | IgE binding max Mean (±Std Dev) |
|---|---|---|
| GVSAYLSRPSPggc* | PURPLE 032 | 9102 (±3114) |
| GVSAYLSRPSPggc* | PURPLE 032 | 9137 (±6945) |
| VSAYLSRPSPggc* | PURPLE 033 | 8901 (±2718) |
| VSAYLSRPSPggc* | PURPLE 033 | 8249 (±3741) |
| SAYLSRPSPggc* | PURPLE 034 | 11229 (±11683) |
| SAYLSRPSPggc* | PURPLE 034 | 9347 (±9239) |
| AYLSRPSPggc* | PURPLE 035 | 8132 (±652) |
| AYLSRPSPggc* | PURPLE 035 | 7360 (±1660) |
| YLSRPSPggc* | PURPLE 036 | 8139 (±1924) |
| YLSRPSPggc* | PURPLE 036 | 6872 (±1239) |
| cggDSNPRGVSAYLSRPSP* | PURPLE 037 | 6358 (±1702) |
| cggDSNPRGVSAYLSRPSP* | PURPLE 037 | 8767 (±3064) |
| cggSNPRGVSAYLSRPSP* | PURPLE 038 | 6470 (±1666) |
| cggNPRGVSAYLSRPSP* | PURPLE 039 | 7835 (±3446) |
| cggNPRGVSAYLSRPSP* | PURPLE 039 | 8783 (±3331) |
| cggPRGVSAYLSRPSP* | PURPLE 040 | 10233 (±7119) |
| cggRGVSAYLSRPSP* | PURPLE 041 | 11954 (±11540) |
| cggRGVSAYLSRPSP* | PURPLE 041 | 6544 (±1341) |
| cggGVSAYLSRPSP* | PURPLE 042 | 4931 (±1274) |
| cggGVSAYLSRPSP* | PURPLE 042 | 5392 (±1608) |
| cggVSAYLSRPS* | PURPLE 043 | 6418 (±816) |
| cggVSAYLSRPSP* | PURPLE 043 | 3447 (±970) |
| cggSAYLSRPSP* | PURPLE 044 | 6328 (±2224) |
| cggSAYLSRPSP* | PURPLE 044 | 5584 (±1328) |
| cggAYLSRPSP* | PURPLE 045 | 5870 (±1647) |
| cggAYLSRPSP* | PURPLE 045 | 5716 (±1510) |
| cggYLSRPSP* | PURPLE 046 | 6228 (±1102) |
| cggYLSRPSP* | PURPLE 046 | 5947 (±1042) |
| cggADSNPRGVSAYLSRPS* | PURPLE 047 | 9446 (±3755) |
| cggADSNPRGVSAYLSRPS* | PURPLE 047 | 6658 (±3006) |
| cggADSNPRGVSAYLSRP* | PURPLE 048 | 14972 (±16875) |
| cggADSNPRGVSAYLSRP* | PURPLE 048 | 10134 (±12441) |
| cggADSNPRGVSAYLSR* | PURPLE 049 | 4949 (±835) |
| cggADSNPRGVSAYLSR* | PURPLE 049 | 5183 (±615) |
| cggADSNPRGVSAYLS* | PURPLE 050 | 5903 (±1790) |
| cggADSNPRGVSAYLS* | PURPLE 050 | 4934 (±793) |
| cggADSNPRGVSAYL* | PURPLE 051 | 6060 (±479) |
| cggADSNPRGVSAYL* | PURPLE 051 | 4566 (±1162) |
| cggADSNPRGVSAY* | PURPLE 052 | 7496 (±5251) |
| cggADSNPRGVSA* | PURPLE 053 | 5406 (±1117) |
| cggADSNPRGVSA* | PURPLE 053 | 5534 (±527) |
| cggADSNPRGVS* | PURPLE 054 | 5952 (±722) |
| cggADSNPRGV* | PURPLE 055 | 6536 (±1019) |
| cggADSNPRGV* | PURPLE 055 | 8022 (±8108) |
| cggAYLSRPSPFDLFIRKS* | PURPLE 056 | 45475 (±18743) |
| cggAYLSRPSPFDLF* | PURPLE 057 | 5726 (±1757) |
| cggAYLSRPSPFDLF* | PURPLE 057 | 6185 (±1002) |
| QCRVTHPHLPRALMRS | YELLOW 001 | 7193 (±1900) |
| QCRVTHPHLPRALMRS | YELLOW 001 | 6482 (±1531) |
| QCRVTHPHLPRALMRS | YELLOW 001 | 8544 (±3058) |
| QCRVTHPHLPRALMRS^ | YELLOW 001 | 51567 (±32315) |
| QCRVTHPHLPRALMRS* | YELLOW 001 | 6449 (±3586) |
| QCRVTHPHLPRALMRS^ | YELLOW 001 | 46265 (±15556) |
| RVTHPHLPRALMRSggc** | YELLOW 002 | 60067 (±51724) |
| cggRVTHPHLPRALMRS ** | YELLOW 003 | 67569 (±22134) |
| RVTHPHLPRALMRggc | YELLOW 009 | 8350 (±4658) |
| RVTHPHLPRALMRggc* | YELLOW 009 | 29546 (±10133) |
| RVTHPHLPRALMggc | YELLOW 010 | 11706 (±8804) |
| RVTHPHLPRALMggc* | YELLOW 010 | 27517 (±13701) |
| RVTHPHLPRALggc | YELLOW 011 | 7570 (±1980) |
| RVTHPHLPRAggc | YELLOW 012 | 6695 (±601) |
| cggRVTHPHLPRALMR | YELLOW 013 | 7500 (±1440) |
| cggRVTHPHLPRALM | YELLOW 014 | 9790 (±3374) |
| cggRVTHPHLPRALM* | YELLOW 014 | 27898 (±8203) |
| cggRVTHPHLPRALM | YELLOW 014 | 25321 (±21324) |
| cggRVTHPHLPRAL | YELLOW 015 | 5312 (±890) |
| cggRVTHPHLPRA | YELLOW 016 | 8679 (±5297) |
| cggRVTHPHLPRA* | YELLOW 016 | 13419 (±4677) |
| RVTHPHLPRALMRSggc | YELLOW 017 | 12415 (±7279) |
| RVTHPHLPRALMRSggc* | YELLOW 017 | 15306 (±5774) |
| VTHPHLPRALMRSggc | YELLOW 018 | 4842 (±824) |
| THPHLPRALMRSggc | YELLOW 019 | 6766 (±2621) |
| cggRVTHPHLPRALMRS | YELLOW 020 | 12381 (±5181) |
| cggRVTHPHLPRALMRS* | YELLOW 020 | 21246 (±14412) |
| cggVTHPHLPRALMRS | YELLOW 021 | 7082 (±2453) |

TABLE 9-continued

Summary of data from Example 10

| Sequence | Name | IgE binding max Mean (±Std Dev) |
|---|---|---|
| cggTHPHLPRALMRS | YELLOW 022 | 4941 (±536) |
| VTHPHLPRALggc | YELLOW 024 | 4655 (±1022) |
| THPHLPRAggc | YELLOW 025 | 7201 (±4374) |
| cggVTHPHLPRAL | YELLOW 027 | 6952 (±2459) |
| cggVTHPHLPRA | YELLOW 028 | 6045 (±1431) |
| QCRVTHPHLPSALMSS* | YELLOW 029 | 5281 (±358) |
| QCRVTHPHLPRALMSS* | YELLOW 030 | 6486 (±1954) |
| QCRVTHPHLPSALMRS* | YELLOW 031 | 5637 (±1069) |
| QCRVTHPHLP-Cit-ALM-Cit-S* | YELLOW 032 | 5090 (±501) |
| QCRVTHPHLPRALM-Cit-S* | YELLOW 033 | 5641 (±801) |
| QCRVTHPHLP-Cit-ALMRS* | YELLOW 034 | 6528 (±1437) |
| cddddRVTHPHLPRALMRS^ | YELLOW 035 | 38979 (±20434) |
| cddddRVTHPHLPRALM^ | YELLOW 036 | 25851 (±15732) |
| cddddVTHPHLPRALMRS^ | YELLOW 037 | 18637 (±6978) |
| cddddVTHPHLPRALM^ | YELLOW 038 | 15365 (±2986) |
| Cyc-QCRVTHPHLPRALMRS-DPro-LPro-Cyc | YELLOW 040 | 35761 (±6293) |

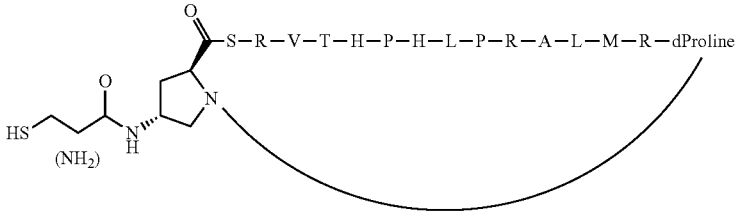

YELLOW 041    55855 (±19382)

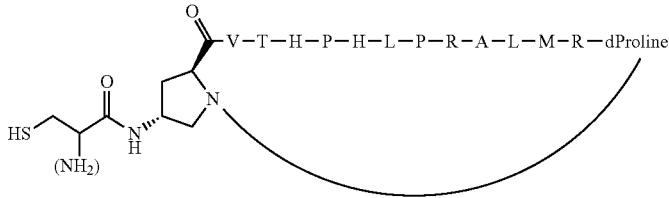

YELLOW 042    31595 (±9368)

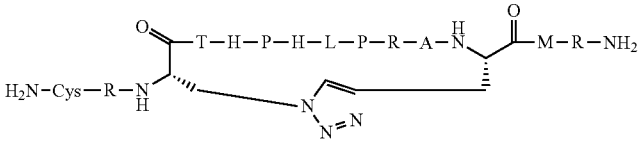

YELLOW 043    19465 (±14660)

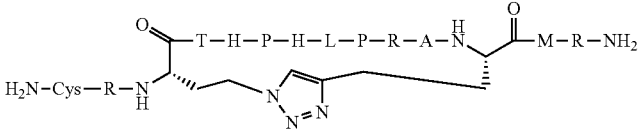

YELLOW 044    11435 (±8674)

| Sequence | Name | IgE binding max Mean (±Std Dev) |
|---|---|---|
| STRKEEKQRNGTLTVTSTLPc | ORANGE 001 | 5295 (±645) |
| STRKEEKQRNGTLTVTSTLPc | ORANGE 001 | 8754 (±2808) |
| STRKEEKQRNGTLTVTSTLPc | ORANGE 002 | 5074 (±336) |
| STRKEEKQRNGTLTVTSTLPggc^ | ORANGE 002 | 6715 (±1063) |
| STRKEEKQRNGTLTVTSTLPggc^ | ORANGE 002 | 8448 (±2700) |
| STRKEEKQRNGTLTVTSTLPggc** | ORANGE 002 | 14637 (±13062) |
| cggSTRKEEKQRNGTLTVTSTLP** | ORANGE 003 | 5747 (±3695) |
| kggCQRNGTC | ORANGE 004 | 6121 (±2590) |
| kggCQRNGTC** | ORANGE 004 | 3621 (±238) |
| kggCEE-Cit-QRNGTLTVC | ORANGE 005 | 6035 (±711) |
| kggCEE-Cit-QRNGTLTVC** | ORANGE 005 | 3807 (±681) |
| STRKEEKQRNGTLTVTSTggc | ORANGE 008 | 5778 (±1059) |
| STRKEEKQRNGTLTVTSggc | ORANGE 009 | 5822 (±953) |
| STRKEEKQRNGTLTVTggc | ORANGE 010 | 5493 (±860) |
| STRKEEKQRNGTLTVggc | ORANGE 011 | 5727 (±720) |
| STRKEEKQRNGTLTggc | ORANGE 012 | 5210 (±891) |
| STRKEEKQRNGTLggc | ORANGE 013 | 5854 (±861) |
| cggSTRKEEKQRNGTLTVTST | ORANGE 014 | 5661 (±770) |
| cggSTRKEEKQRNGTLTVTS | ORANGE 015 | 5613 (±962) |
| cggSTRKEEKQRNGTLTVT | ORANGE 016 | 5452 (±772) |

TABLE 9-continued

Summary of data from Example 10

| Sequence | Name | IgE binding max Mean (±Std Dev) |
|---|---|---|
| cggSTRKEEKQRNGTLTV | ORANGE 017 | 6362 (±1950) |
| cggSTRKEEKQRNGTLT | ORANGE 018 | 5277 (±578) |
| cggSTRKEEKQRNGTL | ORANGE 019 | 7611 (±4748) |
| TRKEEKQRNGTLTVTSTggc | ORANGE 021 | 5282 (±603) |
| RKEEKQRNGTLTVTSTggc | ORANGE 022 | 5262 (±575) |
| KEEKQRNGTLTVTSTggc | ORANGE 023 | 6344 (±1990) |
| EEKQRNGTLTVTSTggc | ORANGE 024 | 5005 (±773) |
| EKQRNGTLTVTSTggc | ORANGE 025 | 5173 (±882) |
| cggTRKEEKQRNGTLTVTST^ | ORANGE 027 | 7344 (+1926) |
| cggRKEEKQRNGTLTVTST^ | ORANGE 028 | 7768 (±1821) |
| cggKEEKQRNGTLTVTST^ | ORANGE 029 | 7374 (±1985) |
| cggEEKQRNGTLTVTST^ | ORANGE 030 | 7187 (±5429) |
| cggEKQRNGTLTVTST^ | ORANGE 031 | 8397 (±3778) |
| TRKEEKQRNGTLTVTSggc^ | ORANGE 033 | 9604 (±4122) |
| RKEEKQRNGTLTVTggc^ | ORANGE 034 | 9805 (±5228) |
| KEEKQRNGTLTVggc^ | ORANGE 035 | 7339 (±2516) |
| EEKQRNGTLTggc^ | ORANGE 036 | 9965 (±5327) |
| EKQRNGTLggc^ | ORANGE 037 | 4607 (±332) |
| cggTRKEEKQRNGTLTVTS^ | ORANGE 039 | 7214 (±1842) |
| cggRKEEKQRNGTLTVT^ | ORANGE 040 | 6500 (±2302) |
| cggKEEKQRNGTLTV^ | ORANGE 041 | 6973 (±2437) |
| cggEEKQRNGTLT^ | ORANGE 042 | 8758 (±3602) |
| Cyc-STRKEEKQRNGTLTVTSTLPC-DPro-LPro | ORANGE 044 | ND |
| [structure] | ORANGE 045 | 5826 (±2164) |
| [structure] | ORANGE 046 | 7991 (±4270) |
| [structure] | ORANGE 047 | 2528 (±656) |
| [structure] | ORANGE 048 | 2506 (±515) |
| LVVDLAPSKGTVNggc** | BLUE 003 | 4684 (±796) |
| cggLVVDLAPSKGTVN** | BLUE-004 | 8010 (±6572) |
| cggGGSDLAPSKGTVSGggc** | BLUE-005 | 3777 (±525) |
| N/A | NAKED Qb-VLP | 6132 (±491) |
| N/A | NAKED Qb-VLP | 3922 (±647) |

TABLE 9-continued

Summary of data from Example 10

| Sequence | Name | IgE binding max Mean (±Std Dev) |
|---|---|---|
| N/A | NAKED Qb-VLP | 4830 (±323) |
| N/A | NAKED Qb-VLP | 4935 (±540) |
| N/A^ | NAKED Qb-VLP | 7550 (±1723) |
| N/A* | NAKED Qb-VLP | 6393 (±830) |
| N/A | NAKED Qb-VLP | 3779 (±403) |
| N/A** | ALUM CpG 24555 | 5098 (±2925) |
| N/A ** | NAKED HBsAg | 3724 (±434) |

Total conjugate dose is 25 microgram per injection administered twice per the intramuscular route in female BALB/c mice on days 0 and 14 besides groups marked by * which were dosed with a conjugation dose of 50 microgram and groups marked with ^ which were dosed 3 times on days 0, 14, and 28. Constrained peptides and groups marked with ~ were dosed 3 times on days 0, 21 and 42.
Conjugation partner = Q beta or HBsAg VLP (marked with **)
Adjuvant: 20 μg CPG 24555 (all internucleotide linkages phosphorothioate linkages) + Alhydrogel™ at 20% v/v
ND = Not Done
Note-
c, cgg, gcc, cdddd and kgg are linkers added to IgE peptide sequences for conjugation purposes Example 11

Efficacy of Peptides Conjugated to Qbeta, HBsAg and DT at Inducing Antibody Response that can Bind to Human IgE This study aimed to evaluate how efficacious peptides conjugated to a variety of carriers such as DT, CRM197, *Pseudomonas aeruginosa* exotoxin A, HBsAg and Qbeta (as detailed in Examples above) were at inducing an antibody response that can bind to human IgE. For the generation of DT conjugates Diptheria toxoid (concentration 3 mg/ml) was derivatised with Succinimidyl-6-[β-maleimidopropionamido]hexanoate (SMPH, Thermo Fisher Scientific Inc) at a 10 fold molar excess. After this activation step, excess SMPH reagent was removed by using a NAP-25 desalting column (GE Healthcare) into Dulbeccos Phosphate Buffered Saline (DPBS) with 5 mM EDTA. Lyophilised peptide solid was then added directly to the maleimide activated Diptheria toxiod and incubated with gentle mixing for 90 minutes. Whereupon the sample was applied to a NAP-25 desalting column (GE Healthcare) and eluted in Dulbeccos Phosphate Buffered Saline (DPBS) to remove free peptide. Following this, the protein solution was concentrated using 10 kD spin microconcentrators and sterilised using a 0.22 μm filter and kept at −80° C. until use. Qb-peptide and HbsAg-peptide conjugates were produced as follows: VLPs (both Qβ and HBsAg) were activated using N-gamma-maleimido-butyryloxy-succinimide ester (GMBS) linking reagent or Succinimidyl-6-[β-maleimidopropionamido]hexanoate (SMPH) both of which were obtained from Thermo Fisher Scientific Inc. The GMBS or SMPH reagent was dissolved in dimethyl sulphoxide (DMSO) and added to the VLP solution at a ≥5-fold molar excess. The activation reaction was allowed to proceed for ≥30 minutes and the solution was then desalted using a NAP-25 desalting column (GE Healthcare) into Dulbeccos Phosphate Buffered Saline (DPBS) with 5 mM EDTA. Following this, an appropriate quantity of solid lyophilised peptide was added directly to maleimide activated VLP and the reaction between the VLPs and the peptides was allowed to proceed for at least thirty minutes with very gentle mixing. At the end of the reaction time each sample was desalted into Dulbeccos PBS (DPBS) using NAP-25 desalting columns (GE Healthcare). The desalted conjugated peptides were analysed for protein content using the Bradford (Coomassie Brilliant Blue, Thermo Fisher Scientific Inc.) assay or the BCA Protein Assay (bicinchoninic acid, Thermo Fisher Scientific Inc.) as well as by SDS-PAGE and size-exclusion chromatography.

Female Balb/c (6-8 weeks) were injected by the intramuscular route (50 μl injected into each Tibialis anterior muscle) with peptides conjugated to Qbeta, Hepatitis B surface antigen (HBsAg) or Diphtheria toxoid (DT) with Alhydrogel plus CpG adjuvants on days 0, 19 & 34 as described below in table 10. Sera prepared 1 week after the final boost were tested for anti-IgE antibody activity in the IgE binding assay as described in Example 5. Responses are shown in Table 10.

Results

This study (Table 10) showed that PURPLE 001 and YELLOW 001 peptides (sequences shown at table 9) could induce anti-human IgE antibodies when conjugated to DT, Qbeta or HBsAg. Anti-human IgE antibodies were induced using either the GMBS linker or the SMPH linker.

TABLE 10

Summary of data from Example 11

| Peptide Ag + Carrier | Total conjugate dose (microgram) | Epitope density (peptide per monomer or equivalent) | IgE binding max Mean (StDev) |
|---|---|---|---|
| YELLOW 001 Qbeta VLP (GMBS) | 50 | ~0.5 | 5421 (±624) |
| PURPLE 001 Qbeta VLP (GMBS) | 50 | ~0.5 | 4465 (±199) |
| YELLOW 001 Qbeta VLP (SMPH) | 50 | ~0.5 | 13792 (±5544) |
| YELLOW 001 Qbeta VLP (SMPH) | 50 | ~1.0 | 37108 (±13782) |
| YELLOW 001 Qbeta VLP (SMPH) | 5 | >1.5 | 37742 (±7018) |
| YELLOW 001 Qbeta VLP (SMPH) | 50 | >1.5 | 34802 (±13636) |
| PURPLE 001 Qbeta VLP (SMPH) | 50 | ~0.5 | 10653 (±2915) |
| PURPLE 001 Qbeta VLP (SMPH) | 50 | ~1.0 | 29546 (±10133) |

TABLE 10-continued

Summary of data from Example 11

| Peptide Ag + Carrier | Total conjugate dose (microgram) | Epitope density (peptide per monomer or equivalent) | IgE binding max Mean (StDev) |
|---|---|---|---|
| PURPLE 001 Qbeta VLP (SMPH) | 5 | >1.5 | 27517 (±13701) |
| PURPLE 001 Qbeta VLP (SMPH) | 50 | >1.5 | 27898 (±8203) |
| YELLOW 001 HBsAg (SMPH) | 5 | >1.5 | 13419 (±4677) |
| YELLOW 001 HBsAg (SMPH) | 50 | >1.5 | 15306 (±5774) |
| PURPLE 001 HBsAg (SMPH) | 5 | >1.5 | 21246 (±14412) |
| PURPLE 001 HBsAg (SMPH) | 50 | >1.5 | 11484 (±7349) |
| YELLOW 001 DT (SMPH) | 50 | >1.5 | 9038 (±2209) |
| YELLOW 001 DT (SMPH) | 50 | >1.5 | 11484 (±2097) |
| PURPLE 001 DT (SMPH) | 5 | >1.5 | 13052 (±4841) |
| PURPLE 001 DT (SMPH) | 50 | >1.5 | 17762 (±9906) |
| Qbeta control | 50 | N/A | 5646 (±105) |
| HbSAg control | 50 | N/A | 5781 (±346) |
| DT control | 50 | N/A | 5181 (±840) |

Female BALB/c mice were immunized on days 0 and 14. Sera was collected and analyzed on day 21.
Conjugation partner = Q beta, DT or HBsAg VLP (as per table above) using either SMPH and GMBS as outlined in table above.
Adjuvant: 20 μg CPG 24555 (all internucleotide linkages phosphorothioate linkages) + Alhydrogel™ at 20% v/v

Example 12

Efficacy of a Combination of Peptides is Greater than Using Single Peptides Conjugated to Qbeta at Inducing Antibody Responses that can Bind to Human IgE Several studies aimed to evaluate how peptides conjugated to Qbeta (as detailed in Examples above) were at inducing an antibody response that can bind to human IgE were performed. Female Balb/c (6-8 weeks) were immunized by the intramuscular route as described in Example 5, with specific timing details as indicated in the tables. Anti-IgE responses, degranulation-inducing activity and IgE depletion activity were measured as detailed in Example 5.

The results, which are presented in Table 11. show that conjugation of the peptides (see sequences at table 9) to Qbeta induced antibody responses that were capable of binding to free IgE without causing degranulation above the control value. Using Alhydrogel as single adjuvant is effective and a combination of purple peptides and yellow peptides induced higher IgE binding antibody responses. Furthermore, the combination of peptides induced antibody responses that were more potent at binding and depleting IgE. Adding CPG 24555 to the Alhydrogel formulation increased the anti-IgE antibody responses further without inducing degranulation activity.

TABLE 11

Summary of data from Example 12

| Peptide Ag (see sequences at table 9) | ADJUVANTS | Post $2^{nd}$ dose IgE binding max: Mean (±std dev) | Post $3^{rd}$ dose IgE binding max: Mean (±std dev) | Post $3^{rd}$ dose Percentage Degranuation (±std dev) | Post $3^{rd}$ dose Percentage decrease in IgE levels (±std dev) |
|---|---|---|---|---|---|
| PURPLE 014^ | ALUM | 25051 (±7485) | 40132 (±7125) | 9.5 (2.1) | −15.53 (13.27) |
| PURPLE 014* | ALUM | 35825 (±8690) | 39276 (±15943) | 9.7 (2) | −10.75 (12.32) |
| YELLOW 001^ | ALUM | 46380 (±15316) | 47442 (±8052) | 12.9 (5.6) | 0.619 (12.46) |
| YELLOW 001* | ALUM | 49695 (±13050) | 44900 (±13597) | 10.4 (2.5) | −8.27 (7.6) |
| YELLOW 014^ | ALUM | 22800 (±12361) | 47982 (±28244) | ND | ND |
| YELLOW 014* | ALUM | 24976 (±8424) | 28969 (±6456) | ND | ND |
| PURPLE 014^ + YELLOW 001^ | ALUM | 55655 (±20653) | 58342 (±14712) | 9.5 (1.5) | 33.23 (49.96) |
| PURPLE 014* + YELLOW 001* | ALUM | 79572 (±22961) | 71068 (±19829) | 10.1 (2.1) | 18.8 (31.9) |
| PURPLE 014^ + YELLOW 014^ | ALUM | 47695 (±10489) | 62932 (±13579) | ND | ND |
| PURPLE 014* + YELLOW 014* | ALUM | 44089 (±16271) | 45506 (±8253) | ND | ND |
| NAKED Qb-VLP** | ALUM | 2468 (±497) | 3018 (±270) | 11.4 (5.5) | −11.8 (8.03) |
| PURPLE 014^ | ALUM + CpG-24555 | 36667 (±13720) | 36947 (±15325) | 10.1 (2.7) | −0.108 (27.67) |
| PURPLE 014* | ALUM + CpG-24555 | 33429 (±9511) | 42935 (±19555) | 9.9 (2.7) | −10.42 (5.46) |
| YELLOW 001^ | ALUM + CpG-24555 | 74180 (±20978) | 80789 (±12783) | 9.3 (1.8) | 2.84 (19.68) |
| YELLOW 001* | ALUM + CpG-24555 | 75703 (±18385) | 65831 (±21843) | 9.8 (1.7) | −6.07 (10.1) |
| YELLOW 014^ | ALUM + CpG-24555 | 31477 (±13045) | 27621 (±9763) | ND | ND |
| YELLOW 014* | ALUM + CpG-24555 | 51564 (±30634) | 51346 (±22522) | ND | ND |
| PURPLE 014^ + YELLOW 001^ | ALUM + CpG-24555 | 78604 (±25881) | 68086 (±22146) | 10.7 (2.2) | 15.24 (34.44) |
| PURPLE 014* + YELLOW 001* | ALUM + CpG-24555 | 75617 (±26964) | 69765 (±19017) | 10 (1.5) | 23.31 (37.4) |
| PURPLE 014^ + YELLOW 014^ | ALUM + CpG-24555 | 63775 (±23432) | 42457 (±9704) | ND | ND |
| PURPLE 014* + YELLOW 014* | ALUM + CpG-24555 | 52660 (±27718) | 54023 (±26129) | ND | ND |
| NAKED Qb-VLP** | ALUM + CpG-24555 | 2932 (±336) | 3266 (±942) | 11.6 (1.9) | −17.61 (14.46) |

^= 20 microgram dose
*= 100 microgram dose
**= 200 microgram dose
Conjugation partner = Q beta VLP.
Dosing female BALB/c mice every 4 weeks at w 0, 4, 8. Samples taken for testing 7 days post $2^{nd}$ and $3^{rd}$ dose.
The dose of Alhydrogel equals vaccine dose as above
CpG-24555 (all internucleotide linkages phosphorothioate linkages) was dosed at 100 microgram
IgE depleting activity was testing using 1000 ng/ml human IgE spiked into normal BALB/c serum (see Example 5 for details)

Example 13

Induction of Anti-Self IgE Responses by a Murine Homologue of Purple 001 and Yellow 001

The ability of IgE peptide vaccines to induce IgG anti-self IgE antibodies and reduce IgE levels in vivo was evaluated in mice with raised IgE levels (induced by preimmunization with endotoxin-free ovalbumin (OVA) as a model antigen formulated with alum—example reference Lloyd C et al, J. Immunol 2001, 166, p 2033-2040). Post-induction of IgE anti-OVA responses, mice were vaccinated with antigenic peptides coupled to Qbeta carrier and formulated with adjuvants. Peptides from homologous regions of mouse IgE were used (murine yellow 001=QCIVDHPDFPKPIVRS(SEQ ID NO: 458); murine purple001=PDHEPRGVITYLIPPSPC (SEQ ID NO: 459)). The efficacy of vaccinations at lowering IgE levels were monitored by measuring levels of IgE anti-OVA in sera pre- and post-vaccination.

a) Ovalbumin Specific IgE Quantification Assay

Summary: An electrochemiluminescence (ECL) assay which determines a concentration of OVA-specific murine IgE. An OVA specific IgE monoclonal antibody (AbD Serotec Cat# PMP68) was used as a positive control, with quantitative 12 point ½ log dilutions of this standard (spiked at a top concentration of 30 µg/mL into Balb/c neg serum from Harlan Labs (pooled from 400 animals Harlan laboratories Code# R-0131D) tested in each assay. This pooled normal serum was also used alone as a negative control. Coating of assay plates: 384-well assay plates (Meso-Scale Diagnostics (MSD) standard bind Cat# L11XA-1, 0370PA) were coated with 12 µL/well of Rat pAb to mouse IgE—Invitrogen Cat#04700 diluted to 15 µg/mL with 0.01M PBS pH7.4, then incubated on a shaker at RT for 2 hours. After washing ×3 with 0.01 M PBS pH 7.4, plates were blocked using 25 µL/well of Pierce starting blocking buffer (Pierce Biotech. Cat#37538) and incubated on a shaker at RT for 40 mins, before a final wash ×3 with 0.01 M PBS pH 7.4. Sample preparation and assay: Each serum sample was diluted 1 in 200 and 1 in 500 (0.01M PBS pH 7.4/1% BSA diluent) and 124 of each dilution added, in triplicate, to the coated MSD plates, with dilutions of standard tested in parallel. After incubating on a shaker at RT for 2 hours, plates were washed ×3 with 0.01M PBS pH 7.4/0.05% Tween 20. Added 12 µL/well detection, SULFO tagged Ovalbumin, 1:300 with 0.01 M PBS pH 7.4/1% BSA, then incubated shaking at RT for 1 hour. After washing ×3 with 0.01 M PBS pH 7.4/0.05% Tween 20 added 50 µL/well MSD Read buffer T (4×) with surfactant (MSD Cat# R92TC) 1:2 with MQ Water. Plates were read using an MSD Sector Imager 6000. Data analysis: Raw data (Pixels) was logged, standard curve plotted (Log mouse IgE anti-OVA concentration ng/mL vs. Log Pixels) and an asymmetric 5-parameter curve fit applied. Log IgE concentrations of the test samples were predicted from the standard curve and subsequently anti-logged and multiplied by 200 or 500 to derive the actual IgE concentrations in ng/mL.

b) Anti Murine IgE Total IgG Titer Determination

Summary: A colorimetric ELISA that generates a reciprocal titer (RT) to represent the levels of total IgG molecules which are specific to murine IgE. Serial dilutions were prepared from sera samples and tested in the assay. Rat pAb to mouse IgE—Invitrogen Cat#04700 spiked into Balb/c neg serum from Harlan Labs at 10 µg/mL and titrated in an 8 point half log serial dilution was used as positive control. Balb/c neg serum from Harlan Labs was used as negative control (pooled from 400 animals Harlan laboratories Code# R-0131D) along with a pooled sample from the study negative group (treated same as samples). Coating of assay plates: 384-well high bind assay plates (Corning International Cat#3700) were coated with 25 µL/well of mouse IgE to OVA (AbD Serotec Cat# PMP68) stock diluted to 5 µg/mL with 0.01M PBS pH 7.4 and incubated on a shaker at RT for 2 hours. After washing ×2 with PBS pH 7.4, plates were blocked using 80 µL/well of 0.01M PBS/1% BSA, incubated at RT for 1 hour before a final wash ×3 with 0.01 M PBS pH 7.4/0.05% Tween 20. Sample preparation and assay: An 8 point 1/10 serial dilution of each sample was prepared starting at 1:10 dilution (PBS/1% BSA diluent), 25 µL/well of the serial dilution transferred in duplicate into the mouse IgE coated plate then incubated shaking at RT for 1.5 hours. After washing ×3 with 0.01 M PBS pH 7.4/0.05% Tween 20, 25 µL/well of Total IgG detection antibody was added (Rabbit anti-mu IgG-Fc, Cat# A90-130A Bethyl Laboratories) 1:6000 with 0.01 M PBS pH 7.4/1% BSA, then incubated shaking at RT for 1 hour. After washing ×5 with 0.01 M PBS pH 7.4/0.05% Tween 20, added 25 µL/well Bio-Rad kit goat anti-rabbit horseradish peroxidase conjugate (Bio-Rad Cat#172-1019) 1:3000 with 0.01M PBS pH 7.4/0.05% Tween 20 pH 7.4, then incubated shaking at RT for 1 hour. After washing ×4 with 0.01M PBS pH 7.4/0.05% Tween 20 then ×1 with 0.01M PBS pH 7.4 only, 25 µL/well Mouse Typer HRP Substrate (Bio-Rad Cat#172-1064) was added, then incubated at RT for 30 mins before adding 25 µL/well 2% oxalic acid to stop the reaction and reading Absorbance at 405 nm. Data analysis: Titration curves were plotted for each test sample (sample titer vs Abs 405 nm) and the sample titer (subsequently transformed into reciprocal titer) was predicted from a cut-off value of OD 1.

The results, which are presented in Table 12, show that a combination of the murine homologue of Yellow 001 (mYellow-001=QCIVDHPDFPKPIVRS (SEQ ID NO: 458)) and the murine homologue of Purple 001 (mPurple-001=PDHEPRGVITYLIPPSPC (SEQ ID NO: 459)) can induce anti-self IgE antibody responses that can efficiently lower endogenous levels of IgE (compared to levels in Qbeta VLP immunized controls). Proof of mechanism was hence achieved by showing that an IgE peptide conjugate can break B-cell tolerance to the endogenous IgE molecule and that this correlates with a reduction in the endogenous IgE levels.

TABLE 12

Summary of data from Example 13

| | Anti Mouse IgE IgG reciprocal titer (95% confidence interval) Post 3 vaccinations | Total ovalbumin specific IgE (ng/ml, (Std Dev)) Post 3 vaccinations |
|---|---|---|
| mPurple-001 and mYellow-001** | 237641 (15100-3740000) | ND |
| mPurple-001 and mYellow-001 | 540947 (225419-1298000) | 4425 (±3455) |
| Qbeta VLP control | 10 (10-10) | ND |
| Qbeta VLP control | 33 (15-75) | 15735 (±8212) |

BALB/c mice were sensitzed with ovalbumin on weeks 0 and 1 to raise endogenous levels of IgE.
Mice were vaccinated with 200 microgram of the murine purple 001 and yellow 001 (i.e. 100 microgram each) combination on weeks 3, 7 and 11, and tested 1 week post 3$^{rd}$ immunization.
Conjugation partner = Q beta VLP using SMPH.
Adjuvant: 20 µg CPG 24555 (all internucleotide linkages phosphorothioate linkages) + Alhydrogel ™ at 20% v/v
ND = not done

Example 14

Cynomolgus Macaque Vaccination with Purple 014 and Either Yellow 001 or Yellow 014

The ability of human IgE peptide vaccines to break tolerance against self IgE in vivo was evaluated in cynomolgus macaques vaccinated with antigenic peptides coupled to carrier (Q beta VLP) and formulated with adjuvants. Peptides from human IgE were used. The efficacy of vaccinations at inducing anti-self IgE immune responses were then monitored by measuring levels of IgG anti-IgE in sera pre- and post-vaccination.

Cynomolgus Macaque Assay a) Total IgG Titer Determination for IgG Specific for the Following Antigens/VLP: Cynomolgus Macaque IgE C$\epsilon$2-C$\epsilon$4 Domain, Human IgE C$\epsilon$3C$\epsilon$4 Domain, Individual Peptides (Yellow and Purple) Conjugated to KLH, and to Qbeta.

Summary: An electrochemiluminescence (ECL) assay that generates a reciprocal titer (RT) to represent the levels of total IgG molecules which are specific to the vaccine or VLP. Serial dilutions were prepared from sera samples and tested in the assay. Cynomolgus macaque serum spiked with humanized anti-IgE monoclonal antibody (E25, Xolair) was used at 40 µg/mL as a positive control. Unspiked cynomolgus macaques serum used as a negative control. Coating of assay plates: 384-well assay plates (Meso-Scale Diagnostics (MSD) streptavidin coated Cat# L21SA-1) were coated with 12 µL/well of biotinylated cynomolgus macaque IgE C$\epsilon$2-C$\epsilon$4 or human IgE C$\epsilon$3C$\epsilon$4 diluted to 1 µg/mL with 0.01M PBS pH 7.4/1% BSA. 384-well assay plates (Meso-Scale Diagnostics (MSD) standard bind Cat# L11XA-1, 0370PA) were coated with 12 µL/well of individual peptide (conjugated to KLH) diluted to to 1 µg/mL or Qbeta diluted to 2-5 ug/mL with 0.01 M PBS pH 7.4 (no BSA). Plates were then incubated on a shaker at RT for 1 hour. After washing ×3 with 0.01 M PBS pH 7.4, plates were blocked using 25 µL/well of Pierce starting blocking buffer (Pierce Biotech. Cat#37538) and incubated on a shaker at RT for 40 mins, before a final wash ×3 with 0.01 M PBS pH 7.4. Sample preparation and assay: An 8 point ½ log serial dilution of each sample including controls was prepared starting at 1:20 dilution (PBS/1% BSA diluent), 12 µL/well of the serial dilution was transferred into wells of plates coated with the test antigen/VLP then incubated shaking at RT for 1 hour. After washing ×3 with 0.01 M PBS pH 7.4/0.05% Tween 20, diluted SULFO-tagged Protein G to 0.02 µg/mL (PBS/1% BSA diluent) was added to the plates (12 µL/well). The plates were incubated with shaking at RT for 1 hour then washed ×3 with 0.01 M PBS pH 7.4/0.05% Tween 20. 50 µL/well MSD Read buffer T (4×) with surfactant (MSD Cat# R92TC) 1:2 with MQ Water was added. Plates were read using an MSD Sector Imager 6000. Data analysis: Titration curves were plotted for each test sample (sample titer vs Pixels) and the sample titer (subsequently transformed into reciprocal titer) was predicted from a cut off value (Pixels).

b) Cynomolgus Macaques Antibody Avidity Assay

Summary: A colorimetric ELISA that generates an Avidity Index (AI) to represent the binding strength of total IgG molecules which are specific to human C$\epsilon$3C$\epsilon$4. The humanized anti-IgE antibody Xolair (E25) was spiked into a pooled cynomolgus macaque serum (prepared from the Qb-VLP control group of this study) at 40 and 4 ug/mL and titrated in a 12 point half log serial dilution as positive control. Cynomolgus macaque serum from study Qb-VLP group was used as negative control along with commercial cynomolgus macaque serum. Coating of assay plates: Reacti-Bind™ Streptavidin Coated HBC Clear 384-Well Plates with SuperBlock Blocking Buffer (Fisher Scientific Co Ltd PI15504) were coated with 12 µL/well of biotinylated human C$\epsilon$3C$\epsilon$4 at 1 µg/mL in 0.01 M PBS pH 7.4 and incubated on a shaker at RT for 1 hour. After washing ×3 with PBS pH 7.4, plates were blocked using 25 µL/well of 0.01M PBS/1% BSA, incubated at RT for 40 mins before a final wash ×3 with 0.01M PBS pH 7.4/0.05% Tween 20. Sample preparation and assay: Samples were diluted with 0.01 M PBS/1% BSA. Each sample had a titration curve generated and from this curve a pixel value of 180,000 was used to calculate an individual reciprocal titer (RT) dilution to use for each sample. This RT was used to dilute each sample to ensure that similar levels of antibodies from each sample were used in the avidity assay. 12 uL of each diluted sample was added to 24 wells of the coated 384 well plates and incubated shaking at RT for 1 hour. After washing ×5 with 0.01 M PBS pH 7.4/0.05% Tween 20, ammonium thiocyanate was added to the plate at differing concentrations at 12 µL/well then incubated shaking for 15 minutes at RT. (12 concentrations of Ammonium thiocyanate were used: 12, 10, 8, 7, 6, 5, 4, 3, 2, 1, 0.5 and 0M were added to duplicate samples). After washing ×4 with 0.01M PBS pH 7.4/0.05% Tween 20, 12 µL/well Mouse anti-human IgG HRP-labeled (Southern Biotech 9042-05) with 0.01M PBS/1% BSA was added, then incubated shaking at RT for 1 hour. After washing ×5 with 0.01 M PBS pH 7.4/0.05% Tween 20, 25 µL/well TMB Substrate (Sigma P-8665) was added, then incubated at RT in the dark for 30 mins. To stop the reaction, 25 µL/well 2% oxalic acid was added and plates read at Abs 450 nm. Data analysis: % reduction for each sample for each ammonium thiocyanate concentration was calculated using the mean Abs 405 nm for 0M ammonium thiocyanate samples as 0% reduction. Titration curves were then plotted for each test sample (% reduction vs Abs 450 nm) and the AI was predicted from a cut-off value of 50% reduction.

The results, which are presented in Table 13, showed that a combination of the Yellow 001 or Yellow014 with Purple 014 (see sequence at table 9) is immunogenic and induced anti-self (cynomolgus macaque) IgE and anti-human IgE antibody responses which correlated with responses to the specific peptides. Further it shows that avidity of the antibody responses can be increased by repeated dosing in the cynomolgus macaque.

TABLE 13

Summary of data from Example 14

| | Reciprocal IgG titer to cynomolgus IgE (95% confidence interval) | Reciprocal IgG titer to Yellow sequence (95% confidence interval) | Reciprocal IgG titer to Purple sequence (95% confidence interval) | Reciprocal IgG titer to human IgE (95% confidence interval) | Avidity Index (mean and Std Dev) |
|---|---|---|---|---|---|
| Yellow-001 + Purple-014 2 wks post dose 1 | 20 | 400 (203-786) | 588 (313-1106) | 20 | 1.693 (±0.05636) |
| Yellow-001 + Purple-014 2 wks post dose 2 | 840 (374-1888) | 2013 (1052-3855) | 2145 (1469-3133) | 1521 (641-3610) | 5.191 (±1.305) |

TABLE 13-continued

Summary of data from Example 14

|  | Reciprocal IgG titer to cynomolgus IgE (95% confidence interval) | Reciprocal IgG titer to Yellow sequence (95% confidence interval) | Reciprocal IgG titer to Purple sequence (95% confidence interval) | Reciprocal IgG titer to human IgE (95% confidence interval) | Avidity Index (mean and Std Dev) |
|---|---|---|---|---|---|
| Yellow-001 + Purple-014 2 wks post dose 3 | 1139 (170-3507) | 1716 (1213-2429) | 2125 (1706-2647) | 1802 (980-3316) | 6.757 (±0.8725) |
| Yellow-014 + Purple-014 2 wks post dose 1 | 22 (16-32) | 400 (203-786) | 588 (313-1106) | 20 | 1.693 (±0.05636) |
| Yellow-014 + Purple-014 2 wks post dose 2 | 385 (98-1505) | ND | ND | 761 (205-2819) | 5.191 (±1.305) |
| Qbeta control 2 wks post dose post dose 1 | ND | 20 (20-20) | 20 (20-20) | 20 | ND |
| Qbeta control 2 wks post dose 2 | 34 (6-194) | 20 (20-20) | 20 (20-20) | 20 | ND |
| Qbeta control 2 wks post dose 3 | 33 (7-161) | 20 (20-20) | 20 (20-20) | 20 | ND |

Cynomolgus macaques were vaccinated with 600 microgram of the purple 014 and yellow 001 or yellow 014 (i.e. 300 microgram each) combination on weeks 0, 4 and 8, and tested week 12.
Conjugation partner = Q beta VLP using SMPH.
Adjuvant: 500 μg CPG 24555 (all internucleotide linkages phosphorothioate linkages) + Alhydrogel ™ at 600 microgram.
ND = not done Example 15

Conjugation of Human and Murine IgE Peptides to CRM197 Via BAANS and SMPH Conjugation Chemistries Human and murine IgE peptides were conjugated onto both CRM197 and Q-Beta, using either succinimidyl-6-[β-maleimidopropionamido]hexanoate (SMPH) or bromoacetic acid N-hydroxysuccinimide ester (BAANS) as bi-valent cross linkers. Conjugates were analysed prior to assessing their ability to induce anti-IgE antibodies in mice (subsequent examples).

IgE peptides used in these studies:

```
Human IgE peptides
Y001:
                              (SEQ ID NO: 220)
QCRVTHPHLPRALMRS P014:
                              (SEQ ID NO: 457)
ADSNPRGVSAYLSRPSPGGC (GGC is the added peptide linker)

Murine IgE Peptides
Y060:
                              (SEQ ID NO: 458)
QCIVDHPDFPKPIVRS P007:
                              (SEQ ID NO: 459)
PDHEPRGVITYLIPPSPGGC (GGC is the added peptide linker)
```

Conjugation of IgE Peptides on CRM197 Via BAANS Conjugation Chemistry

A 6 ml volume of CRM197 (35.46 mg at 5.91 mg/ml) was thawed and desalted into 100 mM Phosphate buffer, pH 8.0, using 10DG desalting columns (Pierce) (on: 3 ml, off: 4 ml). The desalted solution was then adjusted to a final concentration of 4 mg/ml using the same buffer. 8 ml of this 4 mg/ml solution was then taken and cooled to 2-8° C. for 30 mins. All further reaction steps were performed at 2-8° C.

Whilst the CRM197 was being cooled, 12 mg of BAANS was weighed out and dissolved in 600 μl of DMSO to a final concentration of 20 mg/ml.

Once the CRM197 solution had cooled, the 8 ml CRM197 solution was then activated by adding 600 μl of the 20 mg/ml BAANS solution. This BAANS solution was added slowly and with agitation. The solution was then left to react for 30 mins on a rotating platform. After this time, the 8 ml solution was desalted into cold 100 mM sodium carbonate/bicarbonate buffer, pH 9.1. using NAP25 desalting columns (Gibco). The final desalted solution was then split into four 3 ml aliquots.

5.6 mg of peptides Y001, Y007, P014 and P060 were each weighed out and dissolved separately in 280 μl DMSO per peptide to a final concentration of 20 mg/ml. Each peptide solution was then added slowly and drop-wise to one of the four 3 ml aliquots of desalted bromoacetylated CRM197. The reaction mixtures were reacted in the absence of light, with mixing, for 18 hours.

After this time, 2 μl N-acetyl cysteamine (NAC) was added to each reaction mixture and reacted, again in absence of light, for 3 hours with agitation (0.5 ml per g CRM197). Each reaction was then desalted into Dulbecco's phosphate buffered saline, pH 7.2 (dPBS) using 10DG columns to remove any un-reacted reagents or by-products (on: 3 ml, off: 4 ml). Finally the samples were sterile filtered through a 0.22 μm syringe filter and aseptically aliquoted. These aseptic aliquots were stored at 2-8° C.

A small 200 μl sample was kept for characterisation of the conjugate. This sample was used to determine protein content using the BCA (Pierce) assay via a BSA standard (final concentrations shown in table 14). The conjugate was also analysed by SDS-PAGE and for endotoxin content using the LAL assay. To quantify the average peptide load for each sample, the samples were analysed by the S-Carboxymethylcysteine/ S-Carboxymethylcysteamine (CMC/CMCA) assay (see FIG. 3) and MALDI-MS (average peptide load data for this method shown in table 15).

TABLE 14

| conjugate | protein conc. (mg/ml) |
|---|---|
| CRM197-Y001 | 0.85 |
| CRM197-Y007 | 1.96 |
| CRM197-P014 | 2.40 |
| CRM197-P060 | 2.27 |

TABLE 15

| conjugate | Ave. peptide load |
|---|---|
| CRM197-Y001 | 13.62 |
| CRM197-Y007 | ND |
| CRM197-P014 | ND |
| CRM197-P060 | ND |

Conjugation of IgE Peptides on CRM197 Via SMPH Conjugation Chemistry

A 6 ml volume of CRM197 (35.46 mg at 5.91 mg/ml) was thawed and desalted into dPBS using 10DG desalting columns (Pierce) (on: 3 ml, off: 4 ml). The desalted solution was then adjusted to a final concentration of 4 mg/ml using the same buffer A total of 9.5 mg of SMPH was weighed out and dissolved in 2.5 ml of DMSO to make 10 mM stock solution. 2.208 ml of this SMPH stock solution was then added drop-wise and with agitation to 8 ml of CRM197. This was then left to react on a rotating platform for 90 mins.

After this time, the activated CRM197 solution was desalted into dPBS using 10DG desalting columns to remove any unreacted reagent. The final desalted solution was then split into four 3 ml aliquots. 3 mg of peptides Y001, Y007, P014 and P060 were each weighed out and dissolved separately in 200 μL DMSO per peptide to a final concentration of 15 mg/ml. Each peptide solution was then added slowly and drop-wise to one of the four 3 ml aliquots of activated CRM197. The samples were then left to react for 2 hours on a rotating platform.

After this time, each individual reaction was desalted into Dulbecco's phosphate buffered saline, pH 7.2 (dPBS) using 10DG desalting columns to remove any un-reacted reagents or by-products (on: 3 ml, off: 4 ml). Finally the samples were sterile filtered through a 0.22 μm syringe filter and aseptically aliquoted. These aseptic aliquots were stored at 2-8° C.

A small 200 μl sample was kept for characterisation of the conjugate. This sample was used to determine protein content using the BCA (Pierce) assay via a BSA standard (final concentrations shown in table 16). The conjugate was also analysed by SDS-PAGE electrophoresis and for endotoxin content using the LAL assay. To quantify the average peptide load for each sample, the samples were analysed by MALDI-MS (average peptide load shown in table 17).

TABLE 16

| conjugate | protein conc. (mg/ml) |
|---|---|
| CRM197-Y001 | 1.21 |
| CRM197-Y007 | 1.64 |
| CRM197-P014 | 1.98 |
| CRM197-P060 | 1.86 |

TABLE 17

| conjugate | Ave. peptide load |
|---|---|
| CRM197-Y001 | 14.16 |
| CRM197-Y007 | 14.77 |
| CRM197-P014 | 13.86 |
| CRM197-P060 | 17.26 |

Quantitative Determination of S-Carboxymethylcysteine and S-Carboxymethylcysteamine as Evaluation of Degree of Conjugation and Capping of Peptide Immunogen-Protein/Polypeptide Conjugates (CMC/CMCA Assay)

Figure 3:
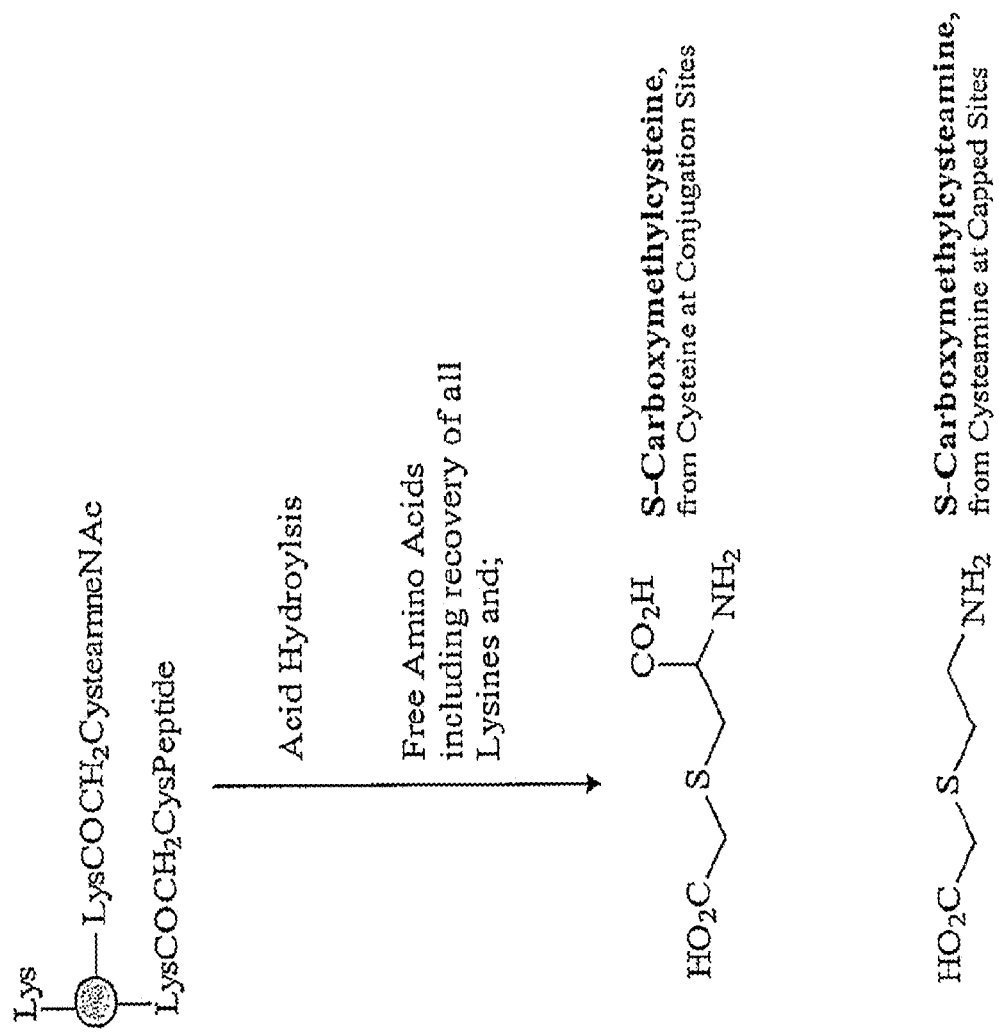
FIG. 3. An illustration of the method and chemical entities involved in the CMC/CMCA assay method for determining peptide conjugation densities following conjugation with the BAANS method FIG. 4. SDS-PAGE analysis of IgE peptides conjugated to CRM197 via SMPH (upper panel) or BAANS (lower panel). Conjugates of Y001, Y007, P014 and P060 (of two different peptide coupling densities—"high" and "intermediate") were run on SDS-PAGE gels, with unconjugated CRM197 as a comparator (Cont). The first and last lanes on the gel are molecular weight markers. Peptide conjugated CRM197 samples run with a higher apparent molecular weight than unconjugated material, with the "high" peptide loaded samples displaying the highest apparent molecular weight, indicating they have a higher average density of peptides per CRM 197 molecule.
Figure 5:
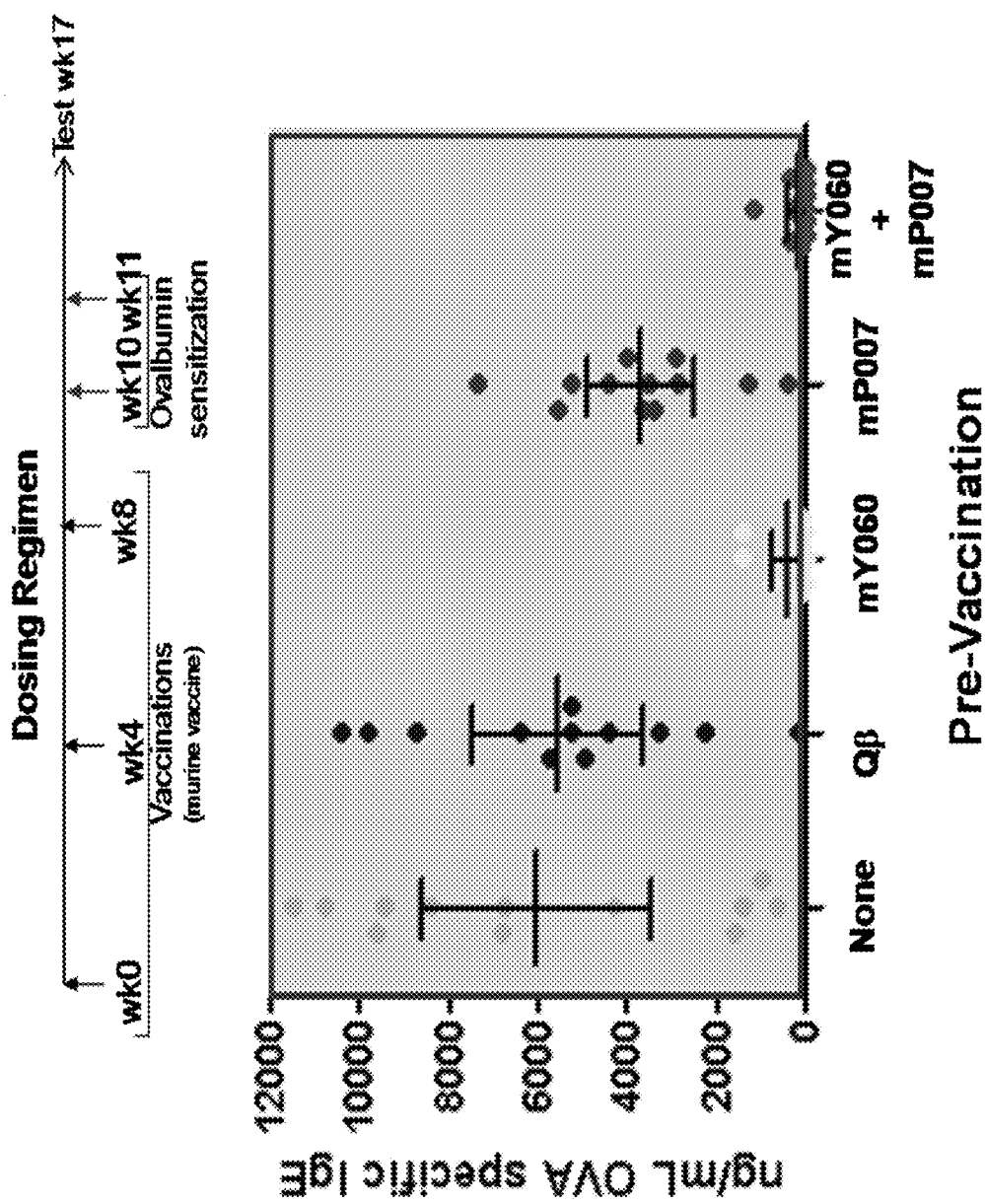
FIG. 5. Pre-vaccination with murine Y060 and P007 IgE peptide conjugates decreases circulating IgE levels. Mice were vaccinated with peptides conjugated to Qβ, singly or in combination, or unconjugated Qβ or left un-vaccinated (3 doses of vaccine, 4 weeks apart). Mice were then challenged twice, a week apart, with ovalbumin in Alum to elicit production of IgE. Mice vaccinated with IgE peptide conjugates developed lower IgE levels than control vaccinated or unvaccinated mice.
Figure 6:
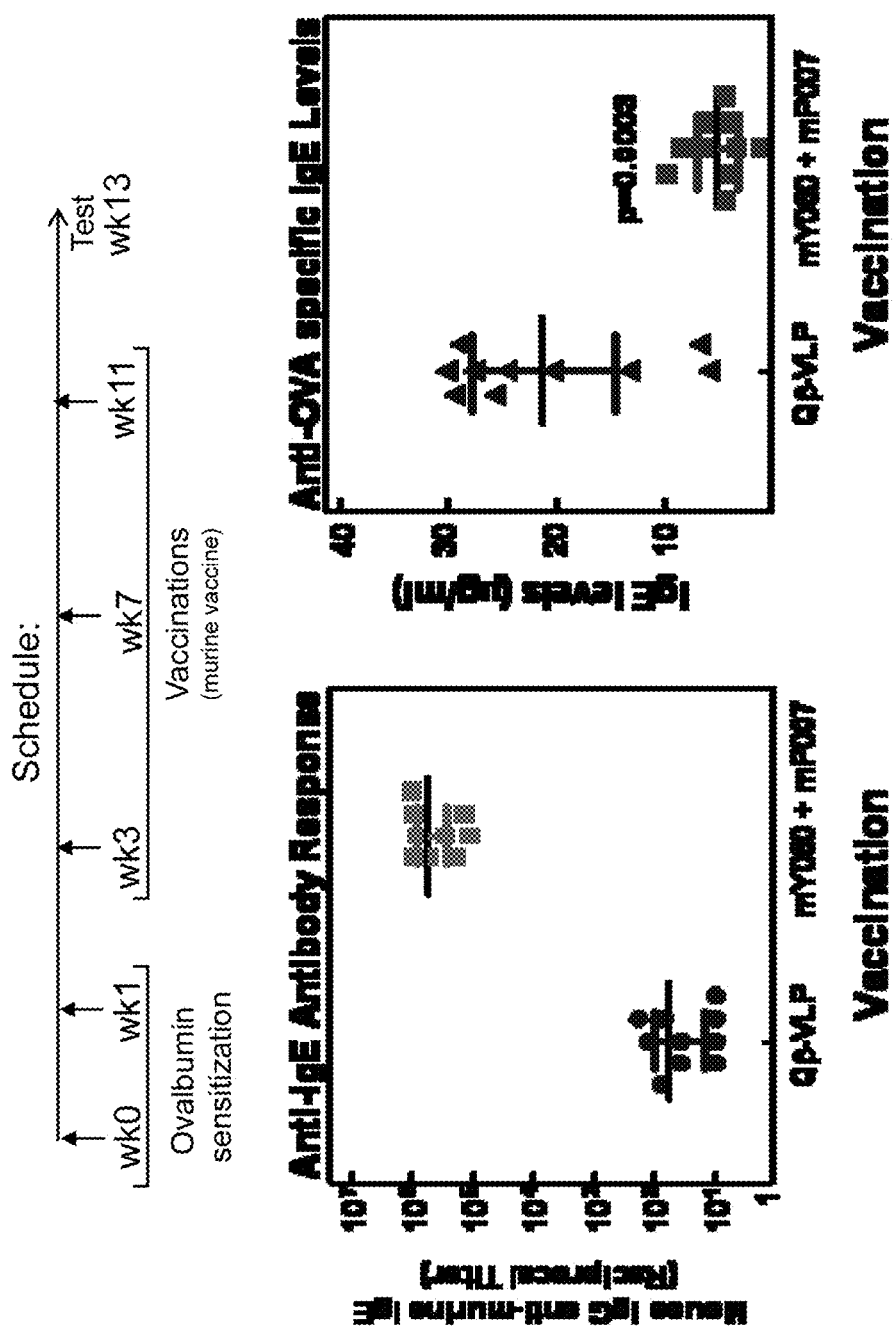
FIG. 6. Vaccination with murine Y060 and P007 IgE peptide conjugates decreases circulating IgE levels. Mice were challenged twice, a week apart, with ovalbumin in Alum to elicit production of IgE. They were then vaccinated with a combination of murine Y060 and P007 IgE peptide Qβ conjugates or control Qβ. Vaccination with a combination of Y060 and P007 IgE peptide conjugates lowered IgE levels compared to control (Qβ-VLP) vaccinated mice.

Acid hydrolysis of protein-peptide conjugates generated using bromoacetyl activation chemistry resulted in the formation of acid stable S-carboxymethylcysteine (CMC) from the cysteines at the conjugated sites and the formation of acid stable S-carboxymethylcysteamine (CMCA) from the cysteamine at the capped sites (FIG. 3). All of the conjugated and capped lysines were converted back to lysine and detected as such. All other amino acids were hydrolyzed back to free amino acids except for tryptophan and cysteine, which were destroyed by the hydrolysis conditions. Asparagine and glutamine were converted to aspartic acid and glutamic acid respectively.

Conjugate samples were diluted with deionized water to a total protein concentration of less than 1 mg/mL. Two 10 microgram aliquots of each conjugate were dried and resuspended in 100 μL of 6N HCl [Pierce], 5 μL of melted phenol [Sigma-Aldrich], and 1 μL of 2-mercaptoethanol [Sigma-Aldrich]. The samples were then incubated under vacuum (100 mT) at 110° C. for 22 hours. The resulting hydrolysates were dried, resuspended in 250 μL of Beckman Na—S sodium citrate sample dilution buffer (pH 2.2) [Beckman Instruments, Inc., Fullerton, Calif.], and filtered using Whatman 0.2 μm nylon syringe tip filters and 1 mL syringes.

Each sample was then loaded into a Beckman 6300 amino acid analyzer sample loop and placed in the analyzer. The amino acids of each hydrolyzed sample and control were separated using ion exchange chromatography followed by reaction with Beckman Ninhydrin NinRX solution at 135° C. The derivatized amino acids were then detected in the visible range at 570 nm and 440 nm. A standard set of amino acids [Pierce Amino Acid Standard H] containing 500 picomoles of each amino acid was run along with the samples and controls for each set of analysis. S-carboxymethylcysteine [Sigma-Aldrich] was added to the standard.

The areas of each standard peak were used as a quantitative equivalence for proportional evaluation of each sample. Proline was determined from 440 nm and was converted to an equivalence in 570 nm using Glutamic acid, the closest amino acid.

Each of these picomole values was converted to a molar ratio of amino acid residues using a comparison of picomoles of lysine to the theoretical lysine value present in the protein. Lysine was chosen for this evaluation based on its covalent attachment to Cysteine and Cysteamine and the expected similar hydrolysis. The resulting numbers of moles of amino acids were then compared to the amino acid composition of the protein and reported along with the values for CMC and CMCA. The CMC value was used directly for evaluation of the degree of conjugation and the CMCA value was used directly for evaluation of the degree of capping.

Quantitative Determination of Degree of Conjugation Peptide-Immunogen-Protein/Polypeptide Conjugates by MALDI-TOF Mass Spectrometry Method
Millipore C4 ZipTip Sample Preparation
1) wet with 2.5 uL MeOH×5
2) wash with 2.5 uL 0.1% formic acid (aq)×5
3) load 2.0 uL sample×5
4) wash ziptip with 2.5 uL 0.1% formic acid (aq)×5
5) elute with 0.5 uL 60% MeCN/40% H20+1% formic acid onto matrix plate
6) Add 0.5 uL of sinapinic acid onto matrix plate
MALDI-TOF Mass Spectrometry
MALDI Acquisition Parameters
  Linear mode
  25000 V accelerating voltage
  2000 shots/spectrum
  Low mass gate at 6000
  Epitope density calculation
  Assumes that the only mass addition is the peptide+spacer arm of cross-linker and no buffer complexation $$\text{Epitope density} = \frac{(\text{Mass } CRM\text{-peptide} - \text{Mass } CRM)}{\text{Mass peptide} + SMPH/BAANS \text{ spacer arm}}$$

Example 16

Conjugation of Human and Murine IgE Peptides to CRM197 Via BAANS and SMPH Conjugation Chemistries at Lower Conjugation Density Samples were also produced with a lower peptide load, to compare whether this had any impact on immunogenicity. The conjugates were made as shown in example 15 & 16 with the following changes.

For the BAANS intermediate load conjugates, the amount of BAANS added at the activation step was reduced to 4 mg, i.e. 200 µL of 20 mg/ml solution. The protein concentration as determined by the BCA assay for these conjugates is shown in Table 18.

TABLE 18

| conjugate | protein conc. (mg/ml) |
|---|---|
| CRM197-Y001 | 1.20 |
| CRM197-Y007 | 1.71 |
| CRM197-P014 | 2.34 |
| CRM197-P060 | 2.16 |

For the SMPH intermediate load conjugates, the amount of SMPH added at the activation step was reduced to adding 1.104 ml of the 10 mM stock solution. The protein concentration as determined by the BCA assay for these conjugates is shown in Table 19.

TABLE 19

| conjugate | protein conc. (mg/ml) |
|---|---|
| CRM197-Y001 | 1.84 |
| CRM197-Y007 | 1.52 |
| CRM197-P014 | 1.45 |
| CRM197-P060 | 1.45 |

FIG. 4 shows SDS-PAGE gels for CRM197 conjugates made at both "High" and "Intermediate" (Int) coupling density, compared to unconjugated CRM197 protein (Cont). As seen in the figure, the intermediate density conjugates migrated further on the gels than the high density conjugates, indicating they indeed had a lower peptide density.

Example 17

Efficacy of Peptides Conjugated to Qbeta and CRM197 at Inducing Antibody Response that can Bind to Human IgE This study aimed to evaluate the efficacy of peptides conjugated to Qbeta and CRM197 at inducing an antibody response that can bind to human IgE. SMPH or BAANS were used to conjugate the peptides to the carrier. Female Balb/c (6-8 weeks) were injected with formulated peptide conjugates by the intramuscular route (50 microliter volume injected into each Tibialis anterior muscle) on days 0, 21 and 42. All formulations were injected in adjuvant Alhydrogel 85 together with 20 µg CpG 24555 (wherein all internucleotide linkages of the oligonucleotide are phosphorothioate linkages). Alhydrogel 85 was used at a ratio of 1:1 with the total amount of protein. Necropsy took place on day 56. At necropsy 400-600 microliter blood was sampled from euthanised mice by cardiac puncture. Blood was left to coagulate overnight and the next day, serum was collected.
a) Free IgE Binding Titer
Summary: An electrochemiluminescence (ECL) assay was used that generates a reciprocal titer (RT) and max value. This represents the levels of mouse IgG:human IgE complexes formed after incubation of serial dilutions of test sera overnight with a high concentration of human IgE. Serum sample prepared from pooled Ce3-vaccinated mice sera samples was used as positive control, along with a mouse antibody to a region of the human IgE Ce3 domain (AbDserotec 0100-0413 (E411 (5H2)) spiked at 50 µg/mL and 1 mg/mL into Balb/c neg serum from Harlan Labs (pooled from 400 animals Harlan laboratories Code# R-0131D), which was also used alone as a negative control. Incubation of samples with Human IgE: An 8 point ½ log serial dilution of each sample, including controls, was prepared starting at 1:3 dilution (0.01M PBS pH 7.4/1% BSA diluent). 10 µL volumes of each sample concentration was mixed with 10 µL of 100 µg/mL Human IgE (diluted from stock using 0.01M PBS pH 7.4/1% BSA), then plates were sealed and incubated overnight at 4° C. Coating of assay plates: The following day, 384-well assay plates (Meso-Scale Diagnostics (MSD) standard bind Cat# L11XA-1, 0370PA) were coated with 12 µL/well of Sheep pAb to human IgE (Gentaur, ICL (Immunology Consultants Lab) Cat# SE-80A) diluted to 1 µg/mL with 0.01 M PBS pH 7.4, then incubated on a shaker at RT for 2 hours. After washing ×3 with 0.01M PBS pH 7.4, plates were blocked using 25 µL/well of Pierce starting blocking buffer (Pierce Biotech. Cat#37538) and incubated on a shaker at RT for 40 mins, before a final wash ×3 with 0.01 M PBS pH 7.4. Sample preparation and assay: Volumes of 20 µL of the overnight incubation mix of sera with human IgE were diluted 1:5 with 80 µL/well 0.01M PBS pH 7.4/1% BSA and then 12 µL/well transferred in duplicate into the coated MSD assay plates. After incubating on a shaker at RT for 2 hours, plates were washed ×3 with 0.01M PBS pH 7.4/0.05% Tween 20. Added 12 µL/well detection antibody (Donkey pAb to mouse IgG H+L Abcam Cat# ab6707, MSD SULFO-tagged using MSD Cat# R91AN-1) 1:5000 with 0.01M PBS pH 7.4/1% BSA, then incubated shaking at RT for 1 hour. After washing ×3 with 0.01 M PBS pH 7.4/0.05% Tween 20 added 50 µL/well MSD Read buffer T (4×) with surfactant (MSD Cat# R92TC) 1:2 with MQ Water. Plates were read using an MSD Sector Imager 6000.

Data analysis: A cut-off value (Pixels) was calculated by taking the mean of the duplicate reads generated by the lowest concentration of the appropriate study negative control group and multiplying this value by 5. Titration curves were plotted for each test sample (sample titer vs Pixels) and the sample titer (subsequently transformed into reciprocal titer) was predicted from the calculated cut off value. The max peak value of the titration curves was also recorded.

Results: The results, which are presented in Table 20, show that immunization with a combination of P014-CRM197 and Y001-CRM197 efficiently induced anti-human IgE antibodies. Anti-human IgE antibodies were induced using either the BAANS linker or the SMPH linker to couple the peptides to the carrier protein. Different conjugation densities (average number of peptides per carrier molecule) induced different levels of anti-IgE antibodies.

TABLE 20

| Conjugate | Conjugation density | IgE binding reciprocal titer geomean (95% confidence interval) | IgE binding max Mean (StDev) |
|---|---|---|---|
| CRM197 (BAANS) Y001 + P014 (50 μg each) | high | 1280 (935-1751) | 74110 (15651) |
| CRM197 (SMPH) Y001 + P014 (50 μg each) | high | 881 (562-1382) | 61128 (9357) |
| CRM197 (BAANS) Y001 + P014 (50 μg each) | intermediate | 715 (478-1070) | 56635 (15082) |
| CRM197 (SMPH) Y001 + P014 (50 μg each) | intermediate | 906 (458-1792) | 46917 (12649) |
| Qbeta Y001 + P0014 (50 μg each) | high | 1240 (896-1717) | 85377 (13652) |
| None (negative control) | — | 30 (30-30) | 5330 (99) |

Female BALB/c mice were immunized on days 0, 21 and 42. Sera was collected and analyzed on day 56.
Carrier protein = Q beta or CRM197 (as per table above) using either SMPH or BAANS to conjugate peptides as outlined in table above. The negative control group data represent the assay background.
Adjuvant: 20 μg CPG 24555 + 100 μg Alhydrogel85 ™

Example 18

Induction of Anti-Self IgE Responses by a Murine Homologue of P014 and Y001

The ability of IgE peptide vaccines to induce IgG anti-self IgE antibodies was evaluated in mice. Mice were vaccinated with antigenic peptides coupled to Qbeta and CRM197 carriers (BAANS and SMPH conjugation) and formulated with adjuvants, as described in Example 17. Peptides from homologous regions of mouse IgE were used (Y007 and P060)

a) Anti Murine IgE Total IgG Titer Determination

Summary: A colorimetric ELISA that generates a reciprocal titer (RT) to represent the levels of total IgG molecules which are specific to murine IgE. Serial dilutions were prepared from sera samples and tested in the assay. Rat pAb to mouse IgE—Invitrogen Cat#04700 spiked into Balb/c neg serum from Harlan Labs at 10 μg/mL and titrated in an 8 point half log serial dilution was used as positive control. Balb/c neg serum from Harlan Labs was used as negative control (pooled from 400 animals Harlan laboratories Code# R-0131D) along with a pooled sample from the study negative group (treated same as samples). Coating of assay plates: 384-well high bind assay plates (Corning International Cat#3700) were coated with 25 μL/well of mouse IgE to OVA (AbD Serotec Cat# PMP68) stock diluted to 5 μg/mL with 0.01M PBS pH 7.4 and incubated on a shaker at RT for 2 hours. After washing ×2 with PBS pH 7.4, plates were blocked using 80 μL/well of 0.01M PBS/1% BSA, incubated at RT for 1 hour before a final wash ×3 with 0.01 M PBS pH 7.4/0.05% Tween 20. Sample preparation and assay: An 8 point 1/10 serial dilution of each sample was prepared starting at 1:10 dilution (PBS/1% BSA diluent), 25 μL/well of the serial dilution transferred in duplicate into the mouse IgE coated plate then incubated shaking at RT for 1.5 hours. After washing ×3 with 0.01 M PBS pH 7.4/0.05% Tween 20, 25 μL/well of Total IgG detection antibody was added (Rabbit anti-mu IgG-Fc, Cat# A90-130A Bethyl Laboratories) 1:6000 with 0.01 M PBS pH 7.4/1% BSA, then incubated shaking at RT for 1 hour. After washing ×5 with 0.01 M PBS pH 7.4/0.05% Tween 20, added 25 μL/well Bio-Rad kit goat anti-rabbit horseradish peroxidase conjugate (Bio-Rad Cat#172-1019) 1:3000 with 0.01M PBS pH 7.4/0.05% Tween 20 pH 7.4, then incubated shaking at RT for 1 hour. After washing ×4 with 0.01M PBS pH 7.4/0.05% Tween 20 then ×1 with 0.01M PBS pH 7.4 only, 25 μL/well Mouse Typer HRP Substrate (Bio-Rad Cat#172-1064) was added, then incubated at RT for 30 mins before adding 25 μL/well 2% oxalic acid to stop the reaction and reading Absorbance at 405 nm. Data analysis: Titration curves were plotted for each test sample (sample titer vs Abs 405 nm) and the sample titer (subsequently transformed into reciprocal titer) was predicted from a cut-off value of OD 1.

Results: The results, which are presented in Table 21, show that a combination of CRM197 conjugates of Y007 and P060, the murine homologues of Y001 and P014, induced anti-self IgE antibody responses. As in example 17, different conjugation densities (average number of peptides per carrier molecule) induced different levels of anti-IgE antibodies.

TABLE 21

| Conjugate | Conjugation density | Anti Mouse IgE IgG reciprocal titer (95% confidence interval) |
|---|---|---|
| CRM (BAANS) Y007 + P060 (50 ug each) | high | 25090 (13464-46752) |
| CRM (SMPH) Y007 + P060 (50 ug each) | high | 3939 (1083-14330) |
| CRM (BAANS) Y007 + P060 (50 ug each) | intermediate | 11125 (4767-25965) |
| CRM (SMPH) Y007 + P060 (50 ug each) | intermediate | 516 (159-1682) |
| Qbeta Y007 + P060 (50 ug each) | high | 85032 (27570-262254) |
| Naive | | 10 (10-10) |

Female BALB/c mice were immunized on days 0, 21 and 42. Sera was collected and analyzed on day 56.
Conjugation partner = Q beta or CRM197 (as per table above) using either SMPH or BAANS as outlined in table above. The negative control group data represent the assay background.
Adjuvant: 20 μg CPG 24555 + 100 μg Alhydrogel85 ™

Example 19

Cynomolgus Macaque Vaccination with CRM197 Conjugates of Human IgE Peptides P014 and Y001

The ability of human IgE peptide vaccines to induce antibody responses against self IgE in vivo was evaluated in cynomolgus macaques vaccinated with antigenic peptides coupled to CRM197 carrier (via an SMPH linker) and formulated with adjuvants. The efficacy of vaccinations at inducing anti-self IgE immune responses was then monitored by measuring levels of IgG anti-IgE in sera pre- and post-vaccination. Individual macaques were immunized on days 0, 28, 84 and 168 with different doses of a 1:1 combination of CRM197 conjugated human P014 and Y001 IgE peptides (100 or 10 µg of each mixed in a 1:1 ratio to give a total of 200 or 20 µg of conjugate in the vaccine), formulated with or without different adjuvants (Alhydrogel 85, CpG, saponin-based adjuvant), as detailed at Table 22. One group of macaques were selected that had previously been immunized against the CRM197 carrier to evaluate the effect of pre-existing immunity to CRM197 on the induction of anti-IgE responses. Blood samples were collected from all groups every two weeks starting two weeks before Day 0.

TABLE 22

| Grp (n) | Antigen | Dose (µg) | Adjuvant |
|---|---|---|---|
| 1 (n = 6) | SMPH Crm Conjugates | 100 each | Alhydrogel/CpG |
| 2 (n = 6) | SMPH Crm Conjugates | 10 each | AlhydrogelCpG |
| 3 (n = 6) | SMPH Crm Conjugates | 100 each | Saponin Adjuvant |
| 4 (n = 6) | SMPH Crm Conjugates | 10 each | Saponin Adjuvant |
| 5 (n = 6) Crm-immune | SMPH Crm Conjugates | 10 each | Alhydrogel/CpG |
| 6 (n = 2) | Crm Assay Control | 200 | Alhydrogel/CpG |
| 7 (n = 2) | Crm Assay Control | 200 | Saponin Adjuvant | a) Total IgG antibody titers were determined for the following antigens: cynomolgus macaque IgE Cε2-Cε4 domain, human IgE Cε3Cε4 domain, human IgE peptide. The assay described at Example 14 a) was used to measure the levels of total IgG molecules induced by the vaccinations. The data in Table 23 show that immunization with the combination of CRM IgE peptide conjugates (CRM-Y001 and CRM-P014) induced strong antibody responses to both human and cynomolgus macaque IgE (samples tested 2 weeks after the third and 4th immunizations, weeks 14 and 26 respectively). Antibodies reacted to both human IgE and Cynomolgus IgE (Cε2-Cε4 fragment, also termed C2C4). Antibodies were induced by either Alum and CpG as adjuvant or with the Saponin-based adjuvant, and higher titers were found after the 4th dose than the 3rd. Macaques that had previously been immunized with an unrelated CRM197 conjugate, and thus were primed to the carrier, still responded to vaccination with the IgE peptide CRM conjugates. Unconjugated CRM controls do not induce anti-IgE antibodies (not shown).

b) Cynomolgus Macaques Antibody Avidity Assay

Figure 7:
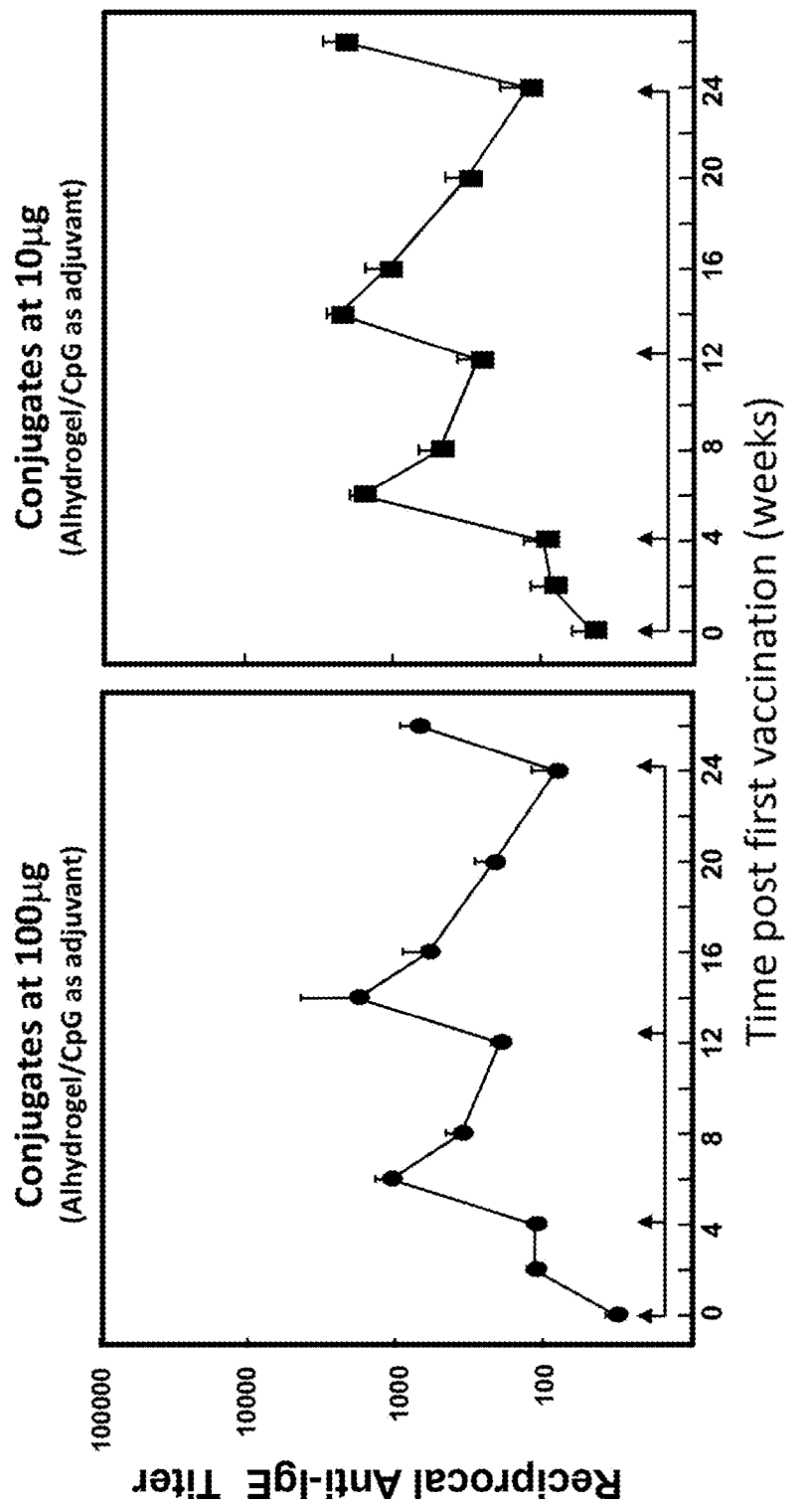
FIG. 7. Vaccination of cynomolgus monkeys with human peptide Y001 and P001 elicits antibodies to whole human IgE. Animals were vaccinated on weeks 0, 4, 12 and 24. Vaccinations were performed in the presence of alum/CpG. The kinetic and magnitude of the anti-IgE response were similar using 10 ug and 100 ug of the conjugates.
Figure 8:
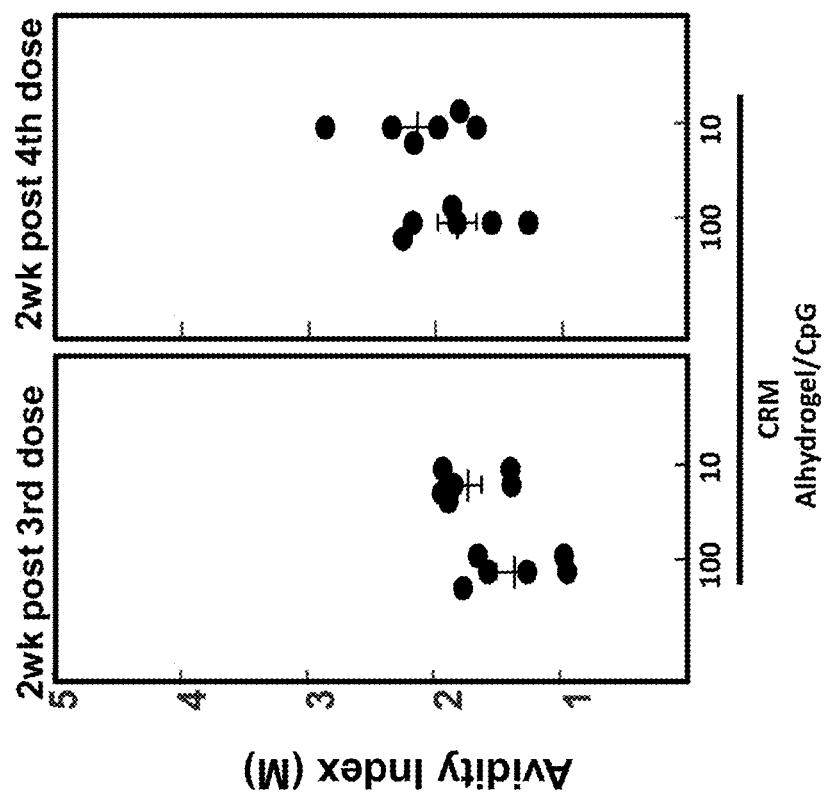
FIG. 8. Vaccination of cynomolgus monkeys with human peptide Y001 and P001 elicits antibodies to whole human IgE. Animals were vaccinated on weeks 0, 4, 12 and 24 using alum/CpG. The avidity of the anti-IgE antibody responses increased over time being higher following the $3^{rd}$ dose compared to the $4^{th}$ dose. There was no significant difference between the 10 ug and 100 ug dose.
Figure 9:
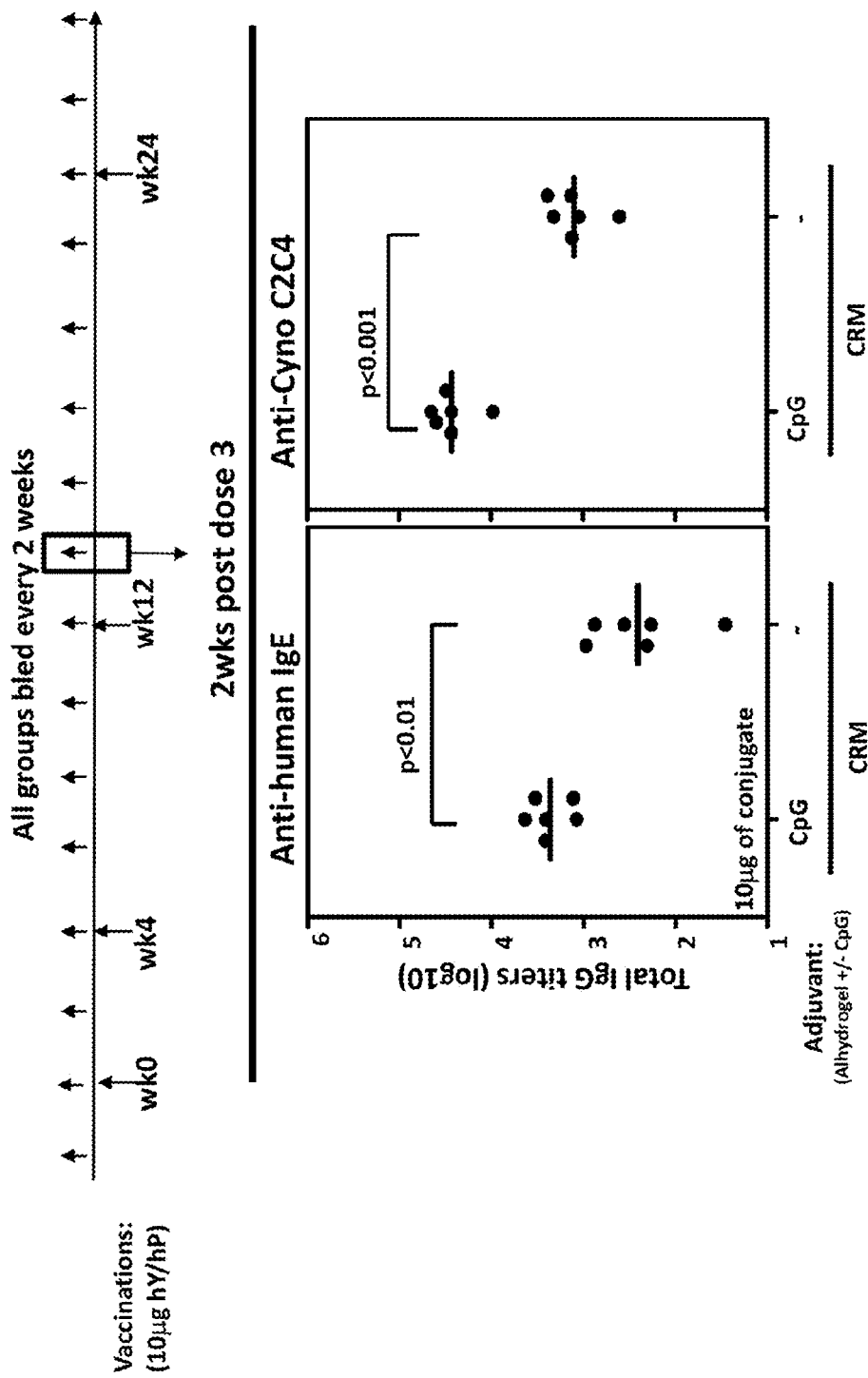
FIG. 9. Vaccination of cynomolgus monkeys with human peptide Y001 and P001 elicits antibodies to both whole human IgE and and C2C4 peptide of the cyno IgE. Animals were vaccinated on weeks 0, 4, 12 and 24 using alum with or without CpG. Responses to whole IgE as well as the cyno C2C4 peptide were significantly enhanced by CpG as shown by titer data 2 weeks following the $3^{rd}$ dose.

The assay described at Example 14 b) was used to measure the relative avidity of induced antibodies for IgE—as an Avidity Index (AI), which represents the binding strength of total IgG molecules which are specific to human IgE (using the Cε3Cε4 domain as antigen). The data in Table 23 show that different adjuvant formulations can differ in the average avidity of antibodies induced. FIG. 7 illustrates the anti-IgE levels at different times during the course of the vaccinations, showing the response is boosted following each vaccination time point and then titers decline over time. FIG. 8 shows that the average avidity of the responses is higher after the 4$^{th}$ vaccination than the third, and that a lower dose (10 µg) induced higher average avidity than the higher (100 µg) dose. The data in FIG. 9 show that adding CpG to the Alhydrogel formulation of the CRM conjugates enhances the anti-IgE antibody titers induced by the vaccinations when compared to vaccinations without CpG.

TABLE 23

Induction of anti-IgE responses in Cynomolgus macaques

|  | Titer anti-whole human IgE | Titer anti-Cyn-C2C4 | Avidity Index |
|---|---|---|---|
| | week 14 | | |
| 100 ug CRM ALUM CpG | 77.17 ± 57.55 | 285.4 ± 135.4 | 1.36 ± 0.32 |
| 10 ug CRM ALUM CpG | 160.5 ± 126.3 | 641.5 ± 501.7 | 1.73 ± 0.24 |
| 100 ug CRM Saponin | 97.44 ± 99.53 | 483.1 ± 417.6 | 2.02 ± 0.57 |
| 10 ug CRM Saponin | 68.86 ± 43.13 | 308.9 ± 179.7 | 2.25 ± 0.3 |
| 10 ug CRM ALUM CpG** | 125.5 ± 116.8 | 569.9 ± 624 | 1.85 ± 0.66 |
| | week 26 | | |
| 100 ug CRM ALUM CpG | 387.4 ± 358.2 | 688.8 ± 450.3 | 1.83 ± 0.34 |
| 10 ug CRM ALUM CpG | 851.6 ± 1069 | 1508 ± 1603 | 2.14 ± 0.39 |
| 100 ug CRM Saponin | 392.3 ± 443.7 | 789.4 ± 835 | 1.85 ± 0.51 |
| 10 ug CRM Saponin | 278.2 ± 134.7 | 710.4 ± 399.5 | 2.34 ± 0.6 |
| 10 ug CRM ALUM CpG** | 733.2 ± 1111 | 814.1 ± 1123 | 1.79 ± 0.59 |

Example 20

Cynomolgus Macaque Vaccination with CRM197 Conjugates of Human IgE Peptides P014 and Y001

The ability of human IgE peptide vaccines to induce antibody responses against self IgE in vivo was evaluated in cynomolgus macaques vaccinated with antigenic peptides coupled to CRM197 carrier (via either SMPH or BAANS linker chemistry) and formulated with adjuvants. The efficacy of vaccinations at inducing anti-self IgE immune responses was then monitored by measuring levels of IgG anti-IgE in sera pre- and post-vaccination. Individual macaques were immunized on days 0, 28, 84 and 168 with different doses of a combination of CRM197 conjugated P014 and Y001 IgE peptides, formulated with or without different adjuvants (Alhydrogel 85, CpG) as detailed in Table 24. Blood samples were collected from all groups every two weeks starting two weeks before Day 0.

TABLE 24

| Grp (n) | Antigen | Dose (µg) | Adjuvant |
|---|---|---|---|
| 1 (n = 6) | SMPH Crm Conjugates | 100 each | Alum/CpG |
| 2 (n = 6) | SMPH Crm Conjugates | 10 each | Alum/CpG |
| 3 (n = 6) | SMPH Crm Conjugates | 10 each | Alum |
| 4 (n = 3) | Unconjugated Crm | 200 | Alum/CpG |
| 5 (n = 6) | BAANS Crm Conjugates | 100 each | Alum/CpG |

Induced anti-IgE antibody responses were measured as described in Example 14:

a) Total IgG titer determination for IgG specific for the following antigens: cynomolgus macaque IgE Cε2-Cε4 domain, human IgE Cε3Cε4 domain, individual peptides (Y001 and P014) conjugated to KLH.

Figure 10:
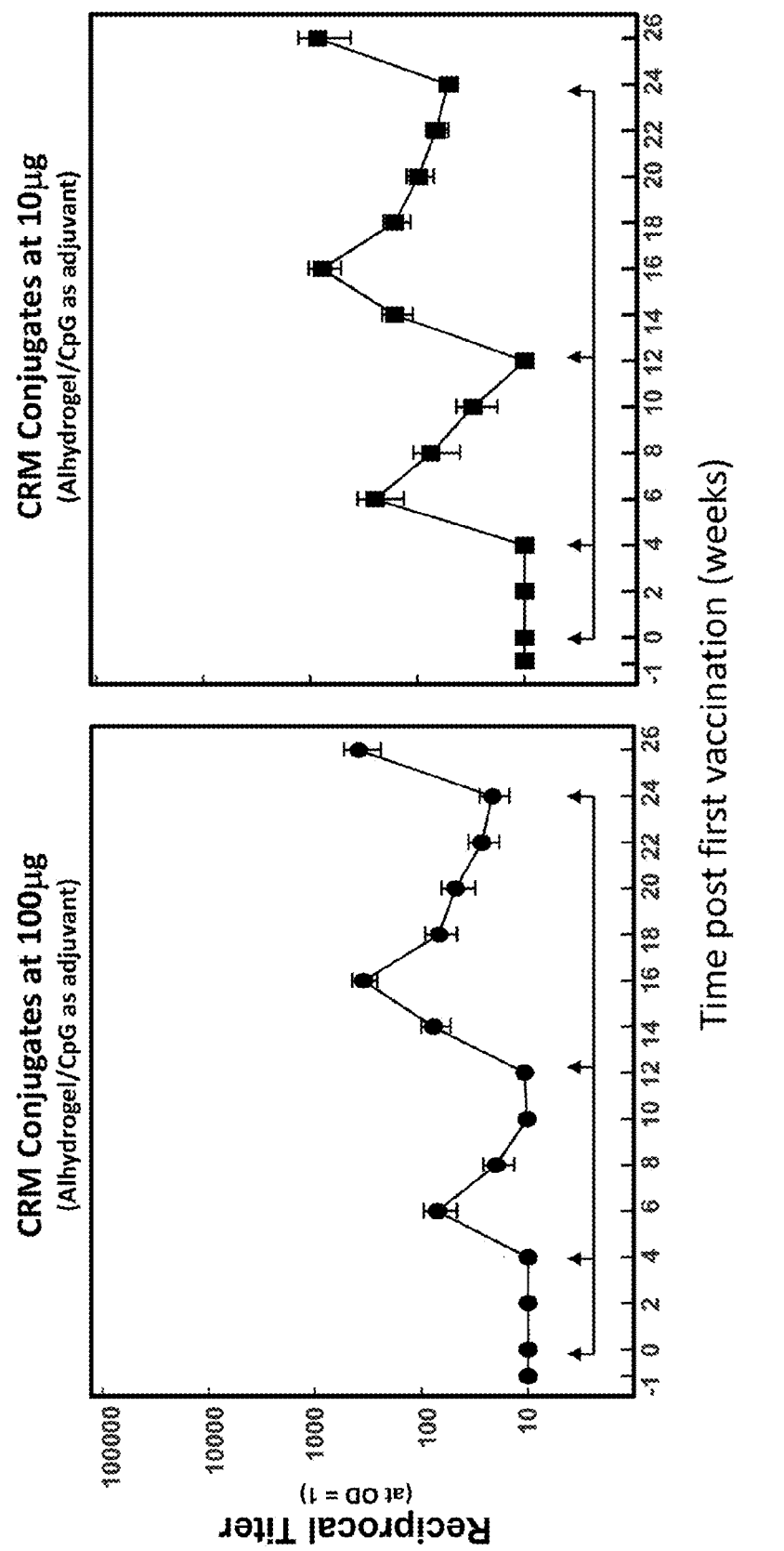
FIG. 10. Vaccination of cynomolgus monkeys with human peptide Y001 and P001 elicits antibodies to whole human IgE. Animals were vaccinated on weeks 0, 4, 12 and 24. Vaccinations were performed in the presence of alum/CpG. The kinetic and magnitude of the response were similar using 10 ug and 100 ug of the conjugates.

The assay described at Example 14 a) is used to measure the levels of total IgG molecules which are specific to the vaccine. The data in Table 25 show that CRM conjugates made with either an SMPH or a BAANS linker can induce anti-IgE antibodies, reactive with both human and cynomolgus IgE, and such antibodies can be induced with Alum/CpG as adjuvant or with Alum without CpG, Without CpG, the titers were lower than in with CpG. FIG. 10 illustrates the anti-IgE levels at different times during the course of the vaccinations, showing the response is boosted following each vaccination time point and then titers decline over time.

b) Cynomolgus Macaques Antibody Avidity Assay

The assay described at Example 14 b) is used to measure Avidity Index (AI) which represents the binding strength of total IgG molecules which are specific to human Cε3Cε4. As shown in Table 25, similar avidity indices were induced by conjugates prepared with either SMPH or with BAANS linkers, and inclusion of CpG with Alum as adjuvant induced antibody responses of overall higher avidity.

TABLE 25

Induction of anti-IgE antibodies in Cynomolgus macaques

|  | Titer anti-whole human IgE | Titer anti-Cyn-C2C4 | Avidity |
|---|---|---|---|
| week 14 | | | |
| SMPH CRM 100 ug + Alum/CpG | 1799 ± 6359 | 17747 ± 58094 | 0.94 ± 0.27 |
| SMPH CRM 10 ug + Alum/CpG | 2314 ± 1206 | 26884 ± 12157 | 1.14 ± 0.26 |
| SMPH CRM 10 ug + Alum | 256 ± 359 | 1270 ± 728 | 0.90 ± 0.47 |
| BANNS CRM 100 ug + Alum/CpG | 2729 ± 559 | 22561 ± 11173 | 0.97 ± 0.34 |
| week 26 | | | |
| SMPH CRM 100 ug + Alum/CpG | 695 ± 517 | 7813 ± 10769 | 0.94 ± 0.34 |
| SMPH CRM 10 ug + Alum/CpG | 2160 ± 2006 | 23820 ± 20915 | 1.39 ± 0.30 |
| SMPH CRM 10 ug + Alum | 194 ± 358 | 537 ± 260 | 0.90 ± 0.47 |
| BANNS CRM 100 ug + Alum/CpG | 2842 ± 1016 | 19458 ± 11332 | 1.05 ± 0.34 |

Example 21

Selection of Optimal Conjugation Density of IgE Peptides on CRM197

As linear IgE peptides will be required to adopt the appropriate 3-dimensional conformation in order to efficiently induce antibodies that react with fully folded, intact IgE molecules, optimal conjugation densities can be identified by generating a range of peptide conjugation densities and evaluating their ability to induce anti-IgE antibodies as described in earlier examples. The amount of peptide loading on CRM197 protein can be controlled by varying the amount (ratio to protein or peptide) of BAANS or SMPH linkers used in the reactions. (e.g. in Examples 15 and 16, the higher BAANS conjugates used 90× molar excess, the intermediate used 30× molar excess BAANS; the higher SMPH conjugates used 30× molar excess, and the intermediate used 10× molar excess SMPH).

Figure 11:
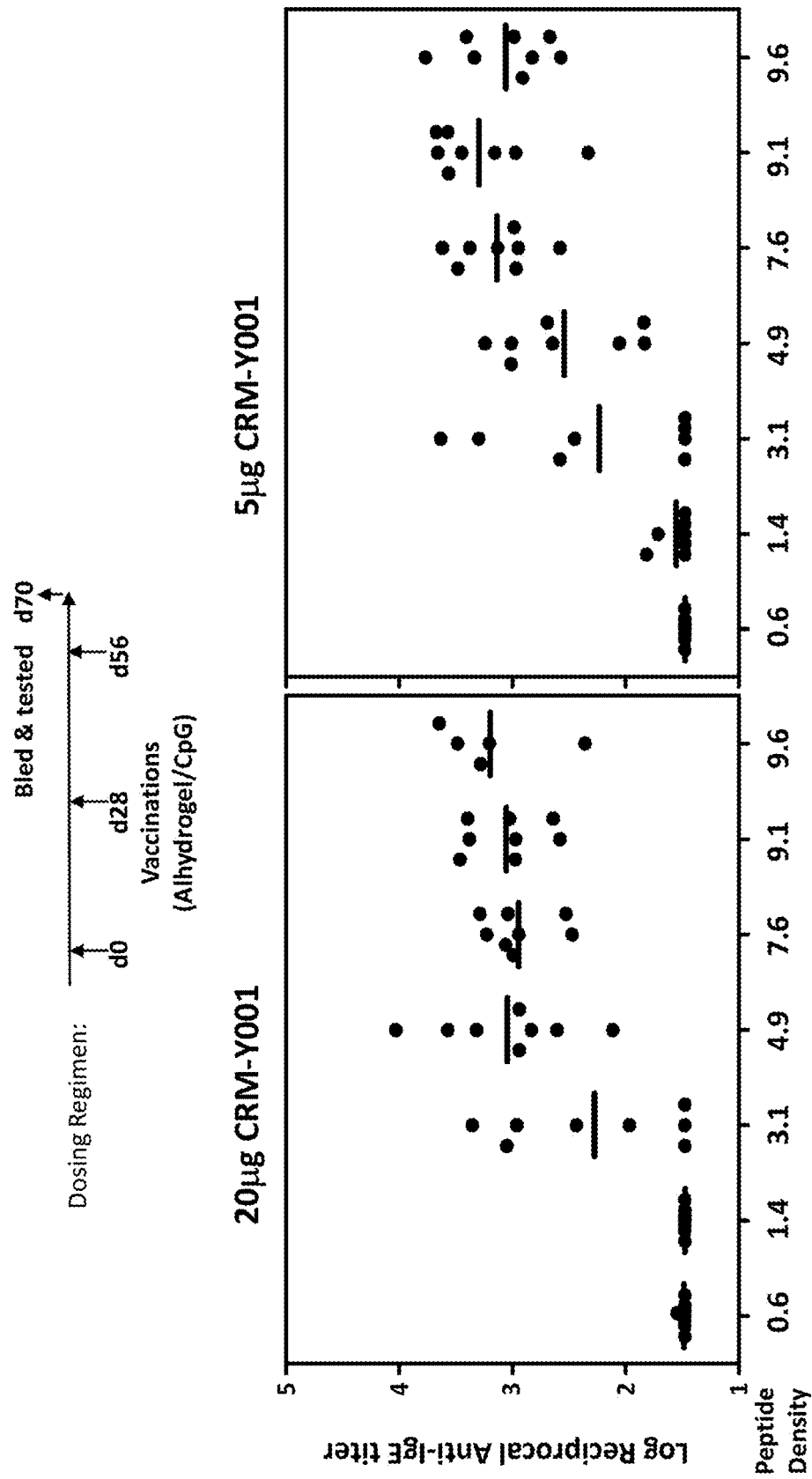
FIG. 11. Vaccination with human IgE peptide Y001 CRM-conjugates of different peptide densities suggest that low densities (0.6, 1.4 & 3.1 peptides per CRM197 molecule) are suboptimal for induction of anti-IgE responses in mice. Peptide densities ranging from 4.9 to 9.6 peptides per CRM molecule, all elicited similar responses. Animals were vaccinated on day 0, 28 and 56, and bled for anti-IgE titers on day 70.

A range of CRM197 conjugates varying in density of Y001 IgE peptides were generated and characterized as described in examples 15 and 16 and evaluated for their ability to induce anti-IgE antibodies in mice as described in examples 17 and 18. The results, which are presented in Table 26 and FIG. 11, show that suboptimal anti-IgE responses are induced at low conjugation densities (0.6, 1.4 & 3.1 peptides per CRM197 molecule under these immunization conditions) and also that conjugation densities can also be too high to be optimal at anti-IgE induction (9.6 peptides per CRM197 when vaccinated at lower 5 µg dose under these immunization conditions). High conjugation densities may also be too high for optimal conjugate production characteristics, such as solubility or avoiding aggregation.

TABLE 26

Effect of Density of IgE Peptides on Antibody Induction

| peptide density (average number of peptides per CRM197 molecule) | Anti-IgE titer | |
|---|---|---|
| | 5 µg dose | 20 µg dose |
| 0.6 | 30 ± 0 | 30.65 ± 1.8 |
| 1.4 | 37.45 ± 13.52 | 30 ± 0 |
| 3.1 | 881.8 ± 1528 | 594 ± 798.9 |
| 4.9 | 621.8 ± 597.3 | 2426 ± 3528 |
| 7.6 | 1760 ± 1303 | 1046 ± 576 |
| 9.1 | 2746 ± 1698 | 1441 ± 995.4 |
| 9.6 | 1734 ± 1851 | 2244 ± 1583 |

Example 22

Optimizing Dose of CRM197-IgE Peptide Conjugates for Effective Induction of Anti-IgE Responses Different doses (1-15 µg) of CRM197 conjugates of human IgE peptides, formulated with adjuvants (Alhydrogel 85 and CpG) were used to immunize mice and sera tested for levels of induced anti-IgE antibodies. The results, which are presented in Table 27, show that anti-IgE titers induced by CRM197 peptide conjugates (dosed in a 1:1 combination) are dependent on dose used, and that higher doses do not equate with higher titers, rather an optimal dose needs to be determined by testing.

TABLE 27

| Dose of each conjugate in 1:1 combination vaccine | Anti-IgE titer | |
|---|---|---|
| | Day 70 | Day 98 |
| 15 µg CRM197-Y001 and P014 | 151.1 ± 277 | 2285 ± 2516 |
| 8 µg CRM197-Y001 and P014 | 948.8 ± 948.3 | 3662 ± 1581 |
| 4 µg CRM197-Y001 and P014 | 445.4 ± 476.7 | 4505 ± 6278 |
| 2 µg CRM197-Y001 and P014 | 723.1 ± 856.8 | 2692 ± 1355 |
| 1 µg CRM197-Y001 and P014 | 454.3 ± 511 | 3822 ± 3195 |

Example 23

Reducing IgE Responses in Mice by Vaccinating with CRM197-Conjugated IgE Peptides Mice were immunized with endotoxin-free ovalbumin (OVA) as a model antigen formulated with alum to induce an IgE response to OVA (example reference Lloyd C et al, J. Immunol 2001, 166, p 2033-2040). Pre- or post-induction of IgE responses, mice were vaccinated with IgE peptides coupled to CRM197 and formulated with Alhydrogel and CpG as adjuvants. Peptides Y007 (SEQ ID 458) and P060 (SEQ ID 459), from homologous regions of mouse IgE to Y001 and P001 peptides from human IgE were used. The efficacy of vaccinations at inducing anti-mouse IgE antibody responses and at lowering IgE levels was then monitored by measuring levels of anti-IgE antibody and IgE in sera pre- and/or post-vaccination.

Figure 12:
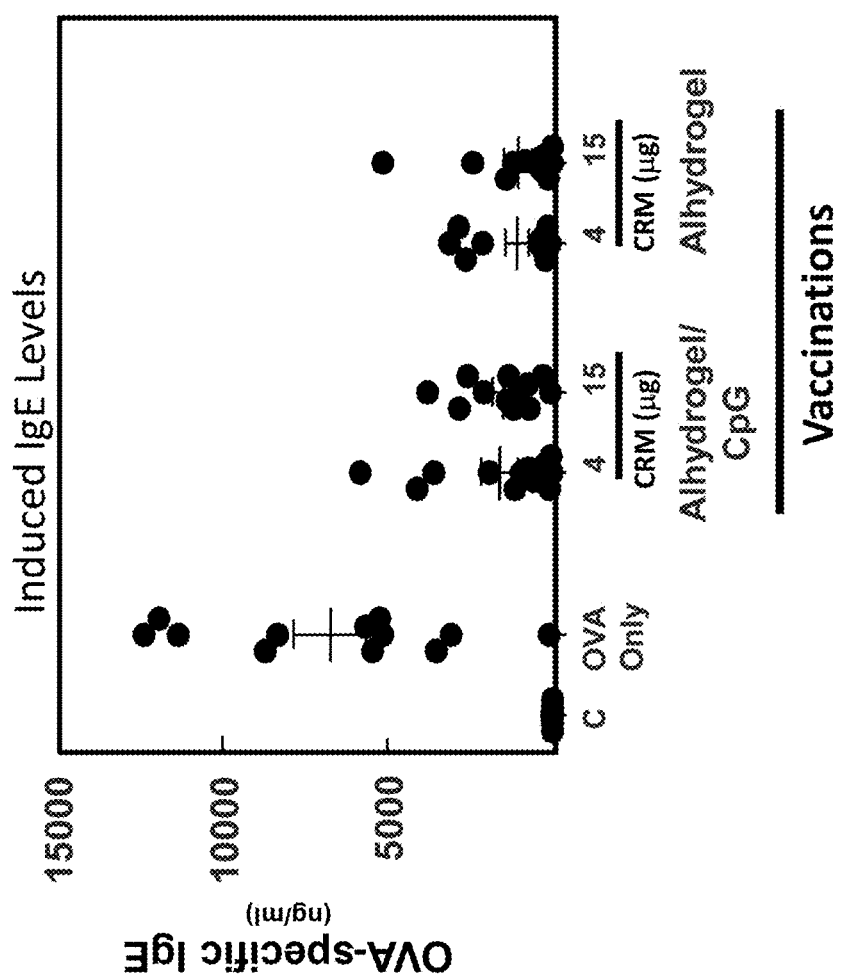
FIG. 12. Mice pre-vaccinated with 15 μg or 4 μg of a combination of CRM197 conjugated Y060 and P007 murine IgE peptides reduced the levels of OVA specific serum IgE in mice subsequently challenged with OVA/Alum. Vaccinations were performed using Alhydrogel 85 with or without CpG, The IgE levels were suppressed both in the presence and absence of CpG in the formulations.

The data, presented in Table 28 and FIG. 12, show that mice that were pre-vaccinated with a combination of CRM197 conjugated Y060 and P007 murine IgE peptides (15 μg or 4 μg of each conjugate formulated with Alhydrogel 85 plus or minus CpG and dosed as described in examples 17 and 18) clearly induced anti-IgE titers and in parallel reduced the levels of serum IgE in mice subsequently challenged with OVA/Alum.

TABLE 28

| Vaccination | Day 105 | |
| --- | --- | --- |
| | ng/mL OVA specific IgE | Titer anti-murine IgE Total IgG |
| PBS | 16.89 ± 9.814 | 9 ± 0 |
| OVA PBS | 6735 ± 3834 | 9 ± 0 |
| 4 + 4 ug CRM Alum/CpG | 1605 ± 1895 | 735.6 ± 943.2 |
| 15 + 15 ug CRM ALUM CpG | 1500 ± 1108 | 309.7 ± 356.4 |
| 4 + 4 ug CRM ALUM | 1065 ± 1215 | 232.4 ± 203.1 |
| 15 + 15 ug CRM ALUM | 1039 ± 1472 | 157.3 ± 103.6 |

In a similar study, vaccinations that were given therapeutically (i.e. after the induction of IgE responses by challenging mice with OVA/Alum) were also able to lower the levels of IgE in the serum (Tables 29 and 30E). In this study, mice were dosed with OVA/Alum on days 0 & 7 and then once IgE levels were high, they were vaccinated (days 63, 91 and 119) with murine IgE peptide conjugates (1:1 ratio in Alum plus or minus CpG) and anti-IgE and OVA-specific IgE levels monitored at different time points (one group of mice were tested on days 84 and 105, Table 29 while the other group were tested on days 140 and 176, Table 30). The data, which are presented in Tables 29 and 30, show that CRM197 conjugates of mouse IgE peptides can stimulate anti-mouse IgE responses and that this is associated with lower levels of OVA-specific IgE. IgE lowering was better when vaccines included CpG in the formulation. When analyzed at an individual mouse level, comparing IgE amounts pre- and post-vaccination similar reductions in IgE were apparent.

TABLE 29

| | Y007/P060 CRM197-conjugate | Anti-IgE Titer | OVA specific IgE (ng/mL) |
| --- | --- | --- | --- |
| Day 84 | PBS | 10 ± 0 | 14267 ± 4705 |
| | 4 ug + Alum/CpG | 37.97 ± 51.29 | 6216 ± 5071 |
| | 15 ug + Alum/CpG | 22.3 ± 12.8 | 7116 ± 5922 |
| | 4 ug + Alum | 10 ± 0 | 11996 ± 3038 |
| | 15 ug + Alum | 10 ± 0 | 15150 ± 11147 |
| Day 105 | PBS | 9 ± 0 | 13647 ± 2966 |
| | 4 ug + Alum/CpG | 4084 ± 6662 | 3545 ± 3417 |
| | 15 ug + Alum/CpG | 871.2 ± 767.4 | 4705 ± 4942 |
| | 4 ug + Alum | 306.1 ± 186.5 | 9683 ± 3198 |
| | 15 ug + Alum | 192.5 ± 147.3 | 13547 ± 10387 |

TABLE 30

| | Y007/P060 CRM197-conjugate | Anti-IgE Titer | OVA specific IgE (ng/mL) |
| --- | --- | --- | --- |
| Day 140 | PBS | 10 ± 0 | 28516 ± 6582 |
| | 4 ug + Alum/CpG | 860 ± 790.3 | 7396 ± 4128 |
| | 15 ug + Alum/CpG | 456.8 ± 373.1 | 9488 ± 7651 |
| | 4 ug + Alum | 209.9 ± 75.38 | 15353 ± 3397 |
| | 15 ug + Alum | 99.3 ± 82.45 | 19013 ± 10921 |

TABLE 30-continued

| | Y007/P060 CRM197-conjugate | Anti-IgE Titer | OVA specific IgE (ng/mL) |
| --- | --- | --- | --- |
| Day 176 | PBS | 10 ± 0 | 18006 ± 3750 |
| | 4 ug + Alum/CpG | 836.7 ± 754.5 | 4588 ± 2734 |
| | 15 ug + Alum/CpG | 430.3 ± 479.1 | 9138 ± 6473 |
| | 4 ug + Alum | 430.2 ± 152.3 | 10366 ± 3204 |
| | 15 ug + Alum | 268.6 ± 207.3 | 13169 ± 8616 |

SEQUENCE LISTING

SEQ ID NO:1    STRKEEKQRNGTLTVTSTLP

SEQ ID NO:2    TRKEEKQRNGTLTVTSTLP

SEQ ID NO:3    RKEEKQRNGTLTVTSTLP

SEQ ID NO:4    KEEKQRNGTLTVTSTLP

SEQ ID NO:5    EEKQRNGTLTVTSTLP

SEQ ID NO:6    EKQRNGTLTVTSTLP

SEQ ID NO:7    KQRNGTLTVTSTLP

SEQ ID NO:8    QRNGTLTVTSTLP

SEQ ID NO:9    RNGTLTVTSTLP

SEQ ID NO:10   NGTLTVTSTLP

SEQ ID NO:11   GTLTVTSTLP

SEQ ID NO:12   TLTVTSTLP

SEQ ID NO:13   LTVTSTLP

SEQ ID NO:14   TVTSTLP

SEQ ID NO:15   VTSTLP

SEQ ID NO:16   TSTLP

SEQ ID NO:17   STLP

SEQ ID NO:18   STRKEEKQRNGTLTVTSTL

SEQ ID NO:19   TRKEEKQRNGTLTVTSTL

SEQ ID NO:20   RKEEKQRNGTLTVTSTL

SEQ ID NO:21   KEEKQRNGTLTVTSTL

SEQ ID NO:22   EEKQRNGTLTVTSTL

SEQ ID NO:23   EKQRNGTLTVTSTL

SEQUENCE LISTING

| SEQ ID NO: 24 | KQRNGTLTVTSTL |
| SEQ ID NO: 25 | QRNGTLTVTSTL |
| SEQ ID NO: 26 | RNGTLTVTSTL |
| SEQ ID NO: 27 | NGTLTVTSTL |
| SEQ ID NO: 28 | GTLTVTSTL |
| SEQ ID NO: 29 | TLTVTSTL |
| SEQ ID NO: 30 | LTVTSTL |
| SEQ ID NO: 31 | TVTSTL |
| SEQ ID NO: 32 | VTSTL |
| SEQ ID NO: 33 | TSTL |
| SEQ ID NO: 34 | STRKEEKQRNGTLTVTST |
| SEQ ID NO: 35 | TRKEEKQRNGTLTVTST |
| SEQ ID NO: 36 | RKEEKQRNGTLTVTST |
| SEQ ID NO: 37 | KEEKQRNGTLTVTST |
| SEQ ID NO: 38 | EEKQRNGTLTVTST |
| SEQ ID NO: 39 | EKQRNGTLTVTST |
| SEQ ID NO: 40 | KQRNGTLTVTST |
| SEQ ID NO: 41 | QRNGTLTVTST |
| SEQ ID NO: 42 | RNGTLTVTST |
| SEQ ID NO: 43 | NGTLTVTST |
| SEQ ID NO: 44 | GTLTVTST |
| SEQ ID NO: 45 | TLTVTST |
| SEQ ID NO: 46 | LTVTST |
| SEQ ID NO: 47 | TVTST |
| SEQ ID NO: 48 | VTST |
| SEQ ID NO: 49 | STRKEEKQRNGTLTVTS |
| SEQ ID NO: 50 | TRKEEKQRNGTLTVTS |
| SEQ ID NO: 51 | RKEEKQRNGTLTVTS |
| SEQ ID NO: 52 | KEEKQRNGTLTVTS |
| SEQ ID NO: 53 | EEKQRNGTLTVTS |
| SEQ ID NO: 54 | EKQRNGTLTVTS |
| SEQ ID NO: 55 | KQRNGTLTVTS |
| SEQ ID NO: 56 | QRNGTLTVTS |
| SEQ ID NO: 57 | RNGTLTVTS |
| SEQ ID NO: 58 | NGTLTVTS |
| SEQ ID NO: 59 | GTLTVTS |
| SEQ ID NO: 60 | TLTVTS |
| SEQ ID NO: 61 | LTVTS |
| SEQ ID NO: 62 | TVTS |
| SEQ ID NO: 63 | STRKEEKQRNGTLTVT |
| SEQ ID NO: 64 | TRKEEKQRNGTLTVT |
| SEQ ID NO: 65 | RKEEKQRNGTLTVT |
| SEQ ID NO: 66 | KEEKQRNGTLTVT |
| SEQ ID NO: 67 | EEKQRNGTLTVT |
| SEQ ID NO: 68 | EKQRNGTLTVT |
| SEQ ID NO: 69 | KQRNGTLTVT |
| SEQ ID NO: 70 | QRNGTLTVT |
| SEQ ID NO: 71 | RNGTLTVT |
| SEQ ID NO: 72 | NGTLTVT |
| SEQ ID NO: 73 | GTLTVT |
| SEQ ID NO: 74 | TLTVT |

SEQUENCE LISTING

SEQ ID NO: 75 LTVT

SEQ ID NO: 76 STRKEEKQRNGTLTV

SEQ ID NO: 77 TRKEEKQRNGTLTV

SEQ ID NO: 78 RKEEKQRNGTLTV

SEQ ID NO: 79 KEEKQRNGTLTV

SEQ ID NO: 80 EEKQRNGTLTV

SEQ ID NO: 81 EKQRNGTLTV

SEQ ID NO: 82 KQRNGTLTV

SEQ ID NO: 83 QRNGTLTV

SEQ ID NO: 84 RNGTLTV

SEQ ID NO: 85 NGTLTV

SEQ ID NO: 86 GTLTV

SEQ ID NO: 87 TLTV

SEQ ID NO: 88 STRKEEKQRNGTLT

SEQ ID NO: 89 TRKEEKQRNGTLT

SEQ ID NO: 90 RKEEKQRNGTLT

SEQ ID NO: 91 KEEKQRNGTLT

SEQ ID NO: 92 EEKQRNGTLT

SEQ ID NO: 93 EKQRNGTLT

SEQ ID NO: 94 KQRNGTLT

SEQ ID NO: 95 QRNGTLT

SEQ ID NO: 96 RNGTLT

SEQ ID NO: 97 NGTLT

SEQ ID NO: 98 GTLT

SEQ ID NO: 99 STRKEEKQRNGTL

SEQ ID NO: 100 TRKEEKQRNGTL

SEQ ID NO: 101 RKEEKQRNGTL

SEQ ID NO: 102 KEEKQRNGTL

SEQ ID NO: 103 EEKQRNGTL

SEQ ID NO: 104 EKQRNGTL

SEQ ID NO: 105 KQRNGTL

SEQ ID NO: 106 QRNGTL

SEQ ID NO: 107 RNGTL

SEQ ID NO: 108 NGTL

SEQ ID NO: 109 STRKEEKQRNGT

SEQ ID NO: 110 TRKEEKQRNGT

SEQ ID NO: 111 RKEEKQRNGT

SEQ ID NO: 112 KEEKQRNGT

SEQ ID NO: 113 EEKQRNGT

SEQ ID NO: 114 EKQRNQT

SEQ ID NO: 115 KQRNGT

SEQ ID NO: 116 QRNGT

SEQ ID NO: 117 RNGT

SEQ ID NO: 118 STRKEEKQRNG

SEQ ID NO: 119 TRKEEKQRNG

SEQ ID NO: 120 RKEEKQRNG

SEQ ID NO: 121 KEEKQRNG

SEQ ID NO: 122 EEKQRNG

SEQ ID NO: 123 EKQRNG

SEQ ID NO: 124 KQRNG

SEQ ID NO: 125 QRNG

SEQUENCE LISTING

| SEQ ID NO: 126 | STRKEEKQRN |
| --- | --- |
| SEQ ID NO: 127 | TRKEEKQRN |
| SEQ ID NO: 128 | RKEEKQRN |
| SEQ ID NO: 129 | KEEKQKN |
| SEQ ID NO: 130 | EEKQRN |
| SEQ ID NO: 131 | EKQRN |
| SEQ ID NO: 132 | KQRN |
| SEQ ID NO: 133 | STRKEEKQR |
| SEQ ID NO: 134 | TRKEEKQR |
| SEQ ID NO: 135 | RKEEKQR |
| SEQ ID NO: 136 | KEEKQR |
| SEQ ID NO: 137 | EEKQR |
| SEQ ID NO: 138 | EKQR |
| SEQ ID NO: 139 | STRKEEKQ |
| SEQ ID NO: 140 | TRKEEKQ |
| SEQ ID NO: 141 | RKEEKQ |
| SEQ ID NO: 142 | KEEKQ |
| SEQ ID NO: 143 | EEKQ |
| SEQ ID NO: 144 | STRKEEK |
| SEQ ID NO: 145 | TRKREEK |
| SEQ ID NO: 146 | RKEEK |
| SEQ ID NO: 147 | KEEK |
| SEQ ID NO: 148 | STRKEE |
| SEQ ID NO: 149 | TRKEE |
| SEQ ID NO: 150 | RKEE |
| SEQ ID NO: 151 | STRKE |
| SEQ ID NO: 152 | TRKE |
| SEQ ID NO: 153 | STRK |
| SEQ ID NO: 154 | CLVVDLAPSKGTVN |
| SEQ ID NO: 155 | CLVVDLAPSKGTV |
| SEQ ID NO: 156 | CLVVDLAPSKGT |
| SEQ ID NO: 157 | CLVVDLAPSKG |
| SEQ ID NO: 158 | CLVVDLAPSK |
| SEQ ID NO: 159 | CLVVDLAPS |
| SEQ ID NO: 160 | CLVVDLAP |
| SEQ ID NO: 161 | CLVVDLA |
| SEQ ID NO: 162 | CLVVDL |
| SEQ ID NO: 163 | CLVVD |
| SEQ ID NO: 164 | CLVV |
| SEQ ID NO: 165 | LVVDLAPSKGTVN |
| SEQ ID NO: 166 | LVVDLAPSKGTV |
| SEQ ID NO: 167 | LVVDLAPSKGT |
| SEQ ID NO: 168 | LVVDLAPSKG |
| SEQ ID NO: 169 | LVVDLAPSK |
| SEQ ID NO: 170 | LVVDLAPS |
| SEQ ID NO: 171 | LVVDLAP |
| SEQ ID NO: 172 | LVVDLA |
| SEQ ID NO: 173 | LVVDL |
| SEQ ID NO: 174 | LVVD |
| SEQ ID NO: 175 | VVDLAPSKGTVN |
| SEQ ID NO: 176 | VVDLAPSKGTV |

SEQUENCE LISTING

| SEQ ID NO: 177 | VVDLAPSKGT |
| SEQ ID NO: 178 | VVDLAPSKG |
| SEQ ID NO: 179 | VVDLAPSK |
| SEQ ID NO: 180 | VVDLAPS |
| SEQ ID NO: 181 | VVDLAP |
| SEQ ID NO: 182 | VVDLA |
| SEQ ID NO: 183 | VVDL |
| SEQ ID NO: 184 | VDLAPSKGTVN |
| SEQ ID NO: 185 | VDLAPSKGTV |
| SEQ ID NO: 186 | VDLAPSKGT |
| SEQ ID NO: 187 | VDLAPSKG |
| SEQ ID NO: 188 | VDLAPSK |
| SEQ ID NO: 189 | VDLAPS |
| SEQ ID NO: 190 | VDLAP |
| SEQ ID NO: 191 | VDLA |
| SEQ ID NO: 192 | DLAPSKGTVN |
| SEQ ID NO: 193 | DLAPSKGTV |
| SEQ ID NO: 194 | DLAPSKGT |
| SEQ ID NO: 195 | DLAPSKG |
| SEQ ID NO: 196 | DLAPSK |
| SEQ ID NO: 197 | DLAPS |
| SEQ ID NO: 198 | DLAP |
| SEQ ID NO: 199 | LAPSKGTVN |
| SEQ ID NO: 200 | LAPSKGTV |
| SEQ ID NO: 201 | LAPSKGT |
| SEQ ID NO: 202 | LAPSKG |
| SEQ ID NO: 203 | LAPSK |
| SEQ ID NO: 204 | LAPS |
| SEQ ID NO: 205 | APSKGTVN |
| SEQ ID NO: 206 | APSKGTV |
| SEQ ID NO: 207 | APSKGT |
| SEQ ID NO: 208 | APSKG |
| SEQ ID NO: 209 | APSK |
| SEQ ID NO: 210 | PSKGTVN |
| SEQ ID NO: 211 | PSKGTV |
| SEQ ID NO: 212 | PSKGT |
| SEQ ID NO: 213 | PSKG |
| SEQ ID NO: 214 | SKGTVN |
| SEQ ID NO: 215 | SKGTV |
| SEQ ID NO: 216 | SKGT |
| SEQ ID NO: 217 | KGTVN |
| SEQ ID NO: 218 | KGTV |
| SEQ ID NO: 219 | GTVN |
| SEQ ID NO: 220 | QCRVTHPHLPRALMRS |
| SEQ ID NO: 221 | CRVTHPHLPRALMRS |
| SEQ ID NO: 222 | RVTHPHLPRALMRS |
| SEQ ID NO: 223 | VTHPHLPRALMRS |
| SEQ ID NO: 224 | THPHLPRALMRS |
| SEQ ID NO: 225 | HPHLPRALMRS |
| SEQ ID NO: 226 | PHLPRALMRS |
| SEQ ID NO: 227 | HLPRALMRS |

SEQUENCE LISTING

SEQ ID NO: 228  LPRALMRS

SEQ ID NO: 229  PRALMRS

SEQ ID NO: 230  RALMRS

SEQ ID NO: 231  ALMRS

SEQ ID NO: 232  LMRS

SEQ ID NO: 233  QCRVTHPHLPRALMR

SEQ ID NO: 234  CRVTHPHLPRALMR

SEQ ID NO: 235  RVTHPHLPRALMR

SEQ ID NO: 236  VTHPHLPRALMR

SEQ ID NO: 237  THPHLPRALMR

SEQ ID NO: 238  HPHLPRALMR

SEQ ID NO: 239  PHLPRALMR

SEQ ID NO: 240  HLPRALMR

SEQ ID NO: 241  LPRALMR

SEQ ID NO: 242  PRALMR

SEQ ID NO: 243  RALMR

SEQ ID NO: 244  ALMR

SEQ ID NO: 245  QCRVTHPHLPRALM

SEQ ID NO: 246  CRVTHPHLPRALM

SEQ ID NO: 247  RVTHPHLPRALM

SEQ ID NO: 248  VTHPHLPRALM

SEQ ID NO: 249  THPHLPRALM

SEQ ID NO: 250  HPHLPRALM

SEQ ID NO: 251  PHLPRALM

SEQ ID NO: 252  HLPRALM

SEQ ID NO: 253  LPRALM

SEQ ID NO: 254  PRALM

SEQ ID NO: 255  RALM

SEQ ID NO: 256  QCRVTHPHLPRAL

SEQ ID NO: 257  CRVTHPHLPRAL

SEQ ID NO: 258  RVTHPHLPRAL

SEQ ID NO: 259  VTHPHLPRAL

SEQ ID NO: 260  THPHLPRAL

SEQ ID NO: 261  HPHLPRAL

SEQ ID NO: 262  PHLPRAL

SEQ ID NO: 263  HLPRAL

SEQ ID NO: 264  LPRAL

SEQ ID NO: 265  PRAL

SEQ ID NO: 266  QCRVTHPHLPRA

SEQ ID NO: 267  CRVTHPHLPRA

SEQ ID NO: 268  RVTHPHLPRA

SEQ ID NO: 269  VTHPHLPRA

SEQ ID NO: 270  THPHLPRA

SEQ ID NO: 271  HPHLPRA

SEQ ID NO: 272  PHLPRA

SEQ ID NO: 273  HLPRA

SEQ ID NO: 274  LPRA

SEQ ID NO: 275  QCRVTHPHLPR

SEQ ID NO: 276  CRVTHPHLPR

SEQ ID NO: 277  RVTHPHLPR

SEQ ID NO: 278  VTHPHLPR

SEQUENCE LISTING

SEQ ID NO: 279  THPHLPR

SEQ ID NO: 280  HPHLPR

SEQ ID NO: 281  PHLPR

SEQ ID NO: 282  HLPR

SEQ ID NO: 283  QCRVTHPHLP

SEQ ID NO: 284  CRVTHPHLP

SEQ ID NO: 285  RVTHPHLP

SEQ ID NO: 286  VTHPHLP

SEQ ID NO: 287  THPHLP

SEQ ID NO: 288  HPHLP

SEQ ID NO: 289  PHLP

SEQ ID NO: 290  QCRVTHPHL

SEQ ID NO: 291  CRVTHPHL

SEQ ID NO: 292  RVTHPHL

SEQ ID NO: 293  VTHPHL

SEQ ID NO: 294  THPHL

SEQ ID NO: 295  HPHL

SEQ ID NO: 296  QCRVTHPH

SEQ ID NO: 297  CRVTHPH

SEQ ID NO: 298  RVTHPH

SEQ ID NO: 299  VTHPH

SEQ ID NO: 300  THPH

SEQ ID NO: 301  QCRVTHP

SEQ ID NO: 302  CRVTHP

SEQ ID NO: 303  RVTHP

SEQ ID NO: 304  VTHP

SEQ ID NO: 305  QCRVTH

SEQ ID NO: 306  CRVTH

SEQ ID NO: 307  RVTH

SEQ ID NO: 308  QCRVT

SEQ ID NO: 309  CRVT

SEQ ID NO: 310  QCRV

SEQ ID NO: 311  CADSNPRGVSAYLSRPSP

SEQ ID NO: 312  ADSNPRGVSAYLSRPSP

SEQ ID NO: 313  DSNPRGVSAYLSRPSP

SEQ ID NO: 314  SNPRGVSAYLSRPSP

SEQ ID NO: 315  NPRGVSAYLSRPSP

SEQ ID NO: 316  PRGVSAYLSRPSP

SEQ ID NO: 317  RGVSAYLSRPSP

SEQ ID NO: 318  GVSAYLSRPSP

SEQ ID NO: 319  VSAYLSRPSP

SEQ ID NO: 320  SAYLSRPSP

SEQ ID NO: 321  AYLSRPSP

SEQ ID NO: 322  YLSRPSP

SEQ ID NO: 323  LSRPSP

SEQ ID NO: 324  SRPSP

SEQ ID NO: 325  RPSP

SEQ ID NO: 326  CADSNPRGVSAYLSRPS

SEQ ID NO: 327  ADSNPRGVSAYLSRPS

SEQ ID NO: 328  DSNPRGVSAYLSRPS

SEQ ID NO: 329  SNPRGVSAYLSRPS

SEQUENCE LISTING

| SEQ ID NO: 330 | NPRGVSAYLSRPS |
| SEQ ID NO: 331 | PRGVSAYLSRPS |
| SEQ ID NO: 332 | RGVSAYLSRPS |
| SEQ ID NO: 333 | GVSAYLSRPS |
| SEQ ID NO: 334 | VSAYLSRPS |
| SEQ ID NO: 335 | SAYLSRPS |
| SEQ ID NO: 336 | AYLSRPS |
| SEQ ID NO: 337 | YLSRPS |
| SEQ ID NO: 338 | LSRPS |
| SEQ ID NO: 339 | SRPS |
| SEQ ID NO: 340 | CADSNPRGVSAYLSRP |
| SEQ ID NO: 341 | ADSNPRGVSAYLSRP |
| SEQ ID NO: 342 | DSNPRGVSAYLSRP |
| SEQ ID NO: 343 | SNPRGVSAYLSRP |
| SEQ ID NO: 344 | NPRGVSAYLSRP |
| SEQ ID NO: 345 | PRGVSAYLSRP |
| SEQ ID NO: 346 | RGVSAYLSRP |
| SEQ ID NO: 347 | GVSAYLSRP |
| SEQ ID NO: 348 | VSAYLSRP |
| SEQ ID NO: 349 | SAYLSRP |
| SEQ ID NO: 350 | AYLSRP |
| SEQ ID NO: 351 | YLSRP |
| SEQ ID NO: 352 | LSRP |
| SEQ ID NO: 353 | CADSHPRGVSAYLSR |
| SEQ ID NO: 354 | ADSNPRGVSAYLSR |
| SEQ ID NO: 355 | DSNPRGVSAYLSR |
| SEQ ID NO: 356 | SNPRGVSAYLSR |
| SEQ ID NO: 357 | NPRGVSAYLSR |
| SEQ ID NO: 358 | PRGVSAYLSR |
| SEQ ID NO: 359 | RGVSAYLSR |
| SEQ ID NO: 360 | GVSAYLSR |
| SEQ ID NO: 361 | VSAYLSR |
| SEQ ID NO: 362 | SAYLSR |
| SEQ ID NO: 363 | AYLSR |
| SEQ ID NO: 364 | YLSR |
| SEQ ID NO: 365 | CADSNPRGVSAYLS |
| SEQ ID NO: 366 | ADSNPRGVSAYLS |
| SEQ ID NO: 367 | DSNPRGVSAYLS |
| SEQ ID NO: 368 | SNPRGVSAYLS |
| SEQ ID NO: 369 | NPRGVSAYLS |
| SEQ ID NO: 370 | PRGVSAYLS |
| SEQ ID NO: 371 | RGVSAYLS |
| SEQ ID NO: 372 | GVSAYLS |
| SEQ ID NO: 373 | VSAYLS |
| SEQ ID NO: 374 | SAYLS |
| SEQ ID NO: 375 | AYLS |
| SEQ ID NO: 376 | CADSNPRGVSAYL |
| SEQ ID NO: 377 | ADSNPRGVSAYL |
| SEQ ID NO: 378 | DSNPRGVSAYL |
| SEQ ID NO: 379 | SNPRGVSAYL |
| SEQ ID NO: 380 | NPRGVSAYL |

SEQUENCE LISTING

SEQ ID NO: 381  PRGVSAYL

SEQ ID NO: 382  RGVSAYL

SEQ ID NO: 383  GVSAYL

SEQ ID NO: 384  VSAYL

SEQ ID NO: 385  SAYL

SEQ ID NO: 386  CADSNPRGVSAY

SEQ ID NO: 387  ADSNPRGVSAY

SEQ ID NO: 388  DSNPRGVSAY

SEQ ID NO: 389  SNPRGVSAY

SEQ ID NO: 390  NPRGVSAY

SEQ ID NO: 391  PRGVSAY

SEQ ID NO: 392  RGVSAY

SEQ ID NO: 393  GVSAY

SEQ ID NO: 394  VSAY

SEQ ID NO: 395  CADSNPRGVSA

SEQ ID NO: 396  ADSNPRGVSA

SEQ ID NO: 397  DSNPRGVSA

SEQ ID NO: 398  SNPRGVSA

SEQ ID NO: 399  NPRGVSA

SEQ ID NO: 400  PRGVSA

SEQ ID NO: 401  RGVSA

SEQ ID NO: 402  GVSA

SEQ ID NO: 403  CADSNPRGVS

SEQ ID NO: 404  ADSNPRGVS

SEQ ID NO: 405  DSNPRGVS

SEQ ID NO: 406  SNPRGVS

SEQ ID NO: 407  NPRGVS

SEQ ID NO: 408  PRGVS

SEQ ID NO: 409  RGVS

SEQ ID NO: 410  CADSNPRGV

SEQ ID NO: 411  ADSNPRGV

SEQ ID NO: 412  DSNPRGV

SEQ ID NO: 413  SNPRGV

SEQ ID NO: 414  NPRGV

SEQ ID NO: 415  PRGV

SEQ ID NO: 416  CADSNPRG

SEQ ID NO: 417  ADSNPRG

SEQ ID NO: 418  DSNPRG

SEQ ID NO: 419  SNPRG

SEQ ID NO: 420  NPRG

SEQ ID NO: 421  CADSNPR

SEQ ID NO: 422  ADSNPR

SEQ ID NO: 423  DSNPR

SEQ ID NO: 424  SNPR

SEQ ID NO: 425  CADSNP

SEQ ID NO: 426  ADSNP

SEQ ID NO: 427  DSNP

SEQ ID NO: 428  CADSN

SEQ ID NO: 429  ADSN

SEQ ID NO: 430  CADS

SEQ ID NO: 431  TCGTCGTTTTCGGTGCTTTT

| SEQUENCE LISTING | |
|---|---|
| SEQ ID NO: 432 | TCGTCGTTTTCGGTCGTTTT |
| SEQ ID NO: 433 | TCGTCGTTTGTCGTTTTGTCGTT |
| SEQ ID NO: 434 | ADSNPRGVSAYLSRPSPC |
| SEQ ID NO: 435 | MAKLETVTLGNIGKDGKQTLVLNPRGVNPTNGVASLS QAGAVPALEKRVTVSVSQP SRNRKNYKVQVKIQNPTACTANGSCDPSVTRQAYADV TFSFTQYSTDEERAFVRT ELAALLASPLLIDAIDQLNPAY |
| SEQ ID NO: 436 | STRKEEKQRNGTLTVTSTLPC |
| SEQ ID NO: 437 | LVVDLAPSKGTVNC |
| SEQ ID NO: 438 | CLVVDLAPSKGTVNGGGGGC |
| SEQ ID NO: 439 | CADSNPRGVSAYLSRPSPC |
| SEQ ID NO: 440 | GGGGACGACGTCGTGGGGGGG |
| SEQ ID NO: 441 | TCGTCGTTTCGTCGTTTTGTCGTT |
| SEQ ID NO: 442 | TCGTCGTTTTGTCGTTTTTTTCGA |
| SEQ ID NO: 443 | TCGCGTCGTTCGGCGCGCGCCG |
| SEQ ID NO: 444 | TCGTCGACGTTCGGCGCGCGCCG |
| SEQ ID NO: 445 | TCGGACGTTCGGCGCGCGCCG |
| SEQ ID NO: 446 | TCGGACGTTCGGCGCGCCG |
| SEQ ID NO: 447 | TCGCGTCGTTCGGCGCGCCG |
| SEQ ID NO: 448 | TCGACGTTCGGCGCGCGCCG |
| SEQ ID NO: 449 | TCGACGTTCGGCGCGCCG |
| SEQ ID NO: 450 | TCGCGTCGTTCGGCGCCG |
| SEQ ID NO: 451 | TCGCGACGTTCGGCGCGCGCCG |
| SEQ ID NO: 452 | TCGTCGTTTTCGGCGCGCGCCG |
| SEQ ID NO: 453 | TCGTCGTTTTCGGCGGCCGCCG |
| SEQ ID NO: 454 | TCGTCGTTTTACGGCGCCGTGCCG |
| SEQ ID NO: 455 | TCGTCGTTTTCGGCGCGCCGT |
| SEQ ID NO: 456 | TCGTCGACGATCGGCGCGCGCCG |
| SEQ ID NO: 457 | ADSNPRGVSAYLSRPSPGGC |
| SEQ ID NO: 458 | QCIVDHPDFPKPIVRS |
| SEQ ID NO: 459 | PDHEPRGVITYLIPPSPGGC |

The invention claimed is:

1. A method for inducing an immune response against self-IgE in a subject, comprising administering to the subject an immunogenically effective amount of an immunogen, wherein the immunogen comprises an antigenic IgE peptide, a peptide linker, and an immunogenic carrier, and wherein:
   (i) said antigenic IgE peptide consists of the amino acid sequence of SEQ ID NO:312;
   (ii) said peptide linker is joined at the C-terminus of the antigenic IgE peptide and is selected from GGC or GC;
   (iii) said immunogenic carrier is CRM197;
   (iv) said antigenic IgE peptide is individually chemically cross-linked to said immunogenic carrier via a thioether linkage using SMPH (Succinimidyl-6-[β-maleimidopropionamido]hexanoate) or BAANS (bromoacetic acid N-hydroxysuccinimide ester) as cross linker, wherein the linkage is between a lysine residue of the immunogenic carrier and the cysteine residue of the peptide linker; and
   (v) the molar ratio of said antigenic IgE peptide to said immunogenic carrier is in the range of 5:1 and 10:1.

2. The method according to claim 1, further comprising administering to the subject an adjuvant.

3. The method according to claim 2, wherein the adjuvant is an aluminium salt.

4. The method according to claim 2, wherein the adjuvant is a saponin-based adjuvant.

5. The method according to claim 2, wherein the adjuvant is a CpG-containing nucleioligonucleotide selected from the group consisting of CpG7909 (SEQ ID NO:433), CpG10103 (SEQ ID NO:432), and CpG24555 (SEQ ID NO:431).

6. The method according to claim 1, wherein the subject is a human.

7. A method for alleviating or treating an IgE-related disorder in a human, comprising administering to the human a therapeutically effective amount of an immunogen, wherein the immunogen comprises an antigenic IgE peptide, a peptide linker, and an immunogenic carrier, and wherein:
 (i) said antigenic IgE peptide consists of the amino acid sequence of SEQ ID NO:312;
 (ii) said peptide linker is joined at the C-terminus of the antigenic IgE peptide and is selected from GGC or GC;
 (iii) said immunogenic carrier is CRM197;
 (iv) said antigenic IgE peptide is individually chemically cross-linked to said immunogenic carrier via a thioether linkage using SMPH (Succinimidyl-6-[β-maleimidopropionamido]hexanoate) or BAANS (bromoacetic acid N-hydroxysuccinimide ester) as cross linker, wherein the linkage is between a lysine residue of the immunogenic carrier and the cysteine residue of the peptide linker; and
 (v) the molar ratio of said antigenic IgE peptide to said immunogenic carrier is in the range of 5:1 and 10:1.

8. The method according to claim 7, further comprising administering to the human an adjuvant.

9. The method according to claim 8, wherein the adjuvant is an aluminium salt.

10. The method according to claim 8, wherein the adjuvant is a saponin-based adjuvant.

11. The method according to claim 8, wherein the adjuvant is a CpG-containing oligonucleotide.

12. The method according to claim 11, wherein the CpG-containing oligonucleotide is CpG7909 (SEQ ID NO:433).

13. The method according to claim 11, wherein the CpG-containing oligonucleotide is CpG10103 (SEQ ID NO:432).

14. The method according to claim 11, wherein the CpG-containing oligonucleotide is CpG24555 (SEQ ID NO:431).

15. The method according to claim 7, wherein the IgE-related disorder is asthma.

16. The method according to claim 7, wherein the IgE-related disorder is allergic rhinitis.

17. The method according to claim 7, wherein the IgE-related disorder is food allergy.

* * * * *